US009713639B2

(12) United States Patent
Lawrence et al.

(10) Patent No.: US 9,713,639 B2
(45) Date of Patent: Jul. 25, 2017

(54) RECOMBINANT SPIKE PROTEIN SUBUNIT BASED VACCINE FOR PORCINE EPIDEMIC DIARRHEA VIRUS (PEDV)

(71) Applicant: MERIAL, INC., Duluth, GA (US)

(72) Inventors: Paulraj Lawrence, Arden Hills, MN (US); Russell Bey, Alexandria, MN (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/716,481

(22) Filed: May 19, 2015

(65) Prior Publication Data

US 2015/0328307 A1 Nov. 19, 2015

Related U.S. Application Data

(60) Provisional application No. 62/000,240, filed on May 19, 2014.

(51) Int. Cl.

| | |
|---|---|
| ***A61K 39/215*** | (2006.01) |
| ***A61K 39/295*** | (2006.01) |
| ***A61K 39/12*** | (2006.01) |
| ***A61K 39/225*** | (2006.01) |
| ***C12N 7/00*** | (2006.01) |
| *A61K 39/00* | (2006.01) |

(52) U.S. Cl.

CPC .......... *A61K 39/215* (2013.01); *A61K 39/225* (2013.01); *C12N 7/00* (2013.01); *A61K 2039/5256* (2013.01); *A61K 2039/552* (2013.01); *A61K 2039/70* (2013.01); *C12N 2710/14041* (2013.01); *C12N 2770/20034* (2013.01)

(58) Field of Classification Search

None

See application file for complete search history.

(56) References Cited

U.S. PATENT DOCUMENTS

| | | | | |
|---|---|---|---|---|
| 7,897,744 B2 * | 3/2011 | Plummer | ............. | C07K 14/005 435/235.1 |
| 8,541,003 B2 * | 9/2013 | Anderson | ............ | A61K 39/215 424/199.1 |
| 2006/0257852 A1 * | 11/2006 | Rappuoli | ............. | C07K 14/005 435/5 |

(Continued)

FOREIGN PATENT DOCUMENTS

| | | | | |
|---|---|---|---|---|
| CN | 103756974 A * | 4/2014 | | |
| WO | WO 2013152083 A2 * | 10/2013 | ........... | A61K 39/295 |

OTHER PUBLICATIONS

Google English Translation of CN103756974 (2014).*

(Continued)

*Primary Examiner* — Janet L Andres

*Assistant Examiner* — M. Franco Salvoza

(74) *Attorney, Agent, or Firm* — Judy Jarecki-Black; Ruoying Chen; Merial Inc.

(57) ABSTRACT

The present invention encompasses porcine epidemic diarrhea virus (PEDV) vaccines or compositions. The vaccine or composition may be a vaccine or composition containing PEDV antigens. The invention also encompasses recombinant vectors encoding and expressing PEDV antigens, epitopes or immunogens which can be used to protect porcine animals against PEDV.

5 Claims, 53 Drawing Sheets

(56) References Cited

U.S. PATENT DOCUMENTS

2015/0283229 A1* 10/2015 Hernandez ............ C07K 16/10
424/186.1

OTHER PUBLICATIONS

Duarte et al., "Sequence of the spike protein of the porcine epidemic diarrhea virus," Journal of General Virology 75: 1195-1200 (1994).*
Lawson et al., "Development of an 8-plex Luminex assay to detect swine cytokines for vaccine development: Assessment of immunity after porcine reproductive and respiratory syndrome virus (PRRSV) vaccination," Vaccine, vol. 28, Issue 32: 5356-5364 (2010).*
Alvarez et al., "Quantification of the impact of swine disease in growing pig production," SDEC Partners Research Update, University of Minnesota Swine Disease Eradication Center, Voo. 3, Issue 6 (2014).*
Shi et al., "Protein N-Glycosylation in the Baculovirus—Insect Cell System," Curr Drug Targets 8(10):1116-1125 (2007).*
Kulakosky et al., "N-Linked glycosylation of a baculovirus-expressed recombinant glycoprotein in insect larvae and tissue culture cells," Glycobiology vol. 8, No. 7:741-745 (1998).*

* cited by examiner

Figure 1A

1-292-5'UTR nt – SEQ ID NO: 1

ACTTAAAAAGATTTTCTATCTACGGATAGTTAGCTCTTTTTCTAGACTCTTGTCTACTCAATTCAACTAAACGAAATT
TTGTCCTTCCGGCCGCATGTCCATGCTGCTGGAAGCTGACGTGGAATTTCATTAGGTTTGCTTAAGTAGCCATCGCA
AGTGCTGTGCTGTCCTCTAGTTCCTGGTTGGCGTTCCGTCGCCTTCTACATACTAGACAAACAGCCTTCCTCCGGTT
CCGTCTGGGGGTTGTGTGGATAACTAGTTCCGTCTAGTTTGAAACCAGTAACTGTCGGCT 293-20,638-Polyprotein nt, ORF1a and ORF1b – SEQ ID NO: 2

ATGGCTAGCAACCATGTTACATTGGCTTTTGCCAATGATGCAGAAATTTCAGCTTTTGGCTTTTGCACTGCTAGTGA
AGCCGTCTCATACTATTCTGAGGCCGCCGCTAGTGGATTTATGCAATGCCGTTTCGTGTCCTTCGATCTCGCTGACA
CTGTTGAGGGATTGCTTCCCGAAGACTATGTCATGGTGGTGGTCGGCACTACCAAGCTTAGTGCGTATGTGGACA
CTTTTGGTAGCCGCCCCAAAAACATTTGTGGTTGGCTGTTATTTTCTAACTGTAATTACTTCCTCGAAGAGTTAGAG
CTTACTTTTGGTCGTCGTGGTGGTAACATCGTGCCAGTTGACCAATACATGTGTGGCGCTGACGGTAAACCTGTTC
TTCAGGAATCCGAATGGGAGTATACAGATTTCTTTGCTGACTCCGAAGACGGTCAACTCAACATTGCTGGTATCAC
TTATGTGAAGGCCTGGATTGTAGAGCGATCGGATGTCTCTTATGCGAGTCAGAATTTAACATCTATTAAGTCTATTA
CTTACTGTTCAACCTATGAGCATACTTTTCCTGATGGTACTGCCATGAAGGTTGCACGTACTCCAAAGATTAAGAAG
ACTGTTGTCTTGTCTGAGCCACTTGCTACTATCTACAGGGAAATTGGTTCTCCTTTTGTGGATAATGGGAGCGATGC
TCGTTCTATCATTAAGAGACCAGTGTTCCTCCACGCTTTTGTTAAGTGTAAGTGTGGTAGTTATCATTGGACTGTTG
GTGATTGGACTTCCTATGTCTCCACTTGCTGTGGCTTTAAGTGTAAGCCAGTCCTTGTGGCTTCATGCTCTGCTACG
CCTGGTTCTGTTGTGGTTACGCGCGCTGGTGCTGGCACTGGTGTTAAGTATTACAACAACATGTTCCTGCGCCATG
TGGCAGACATTGATGGGTTGGCATTCTGGCGAATTCTCAAGGTGCAGTCCAAAGACGACCTCGCTTGCTCTGGTAA
ATTCCTTGAACACCATGAGGAAGGTTTCACAGATCCTTGCTACTTTTTGAATGACTCGAGCATTGCTACTAAGCTCA
AGTTTGACATCCTTAGTGGCAAGTTTTCTGATGAAGTCAAACAAGCTATCTTTGCTGGTCATGTTGTTGTTGGCAGC
GCGCTCGTTGACATTGTTGACGATGCACTGGGACAGCCTTGGTTTATACGTAAGCTTGGTGACCTTGCAAGTGCAG
CTTGGGAGCAGCTTAAGGCTGTCGTTAGAGGCCTTAACCTCCTGTCTGATGAGGTCGTGCTCTTTGGCAAAAGACT
TAGCTGTGCCACTCTTAGTATCGTTAACGGTGTTTTTGAGTTCATCGCCGAAGTGCCTGAGAAGTTGGCTGCGGCT
GTTACAGTTTTTGTCAACTTCTTGAATGAGCTTTTTGAGTCTGCCTGTGACTGCTTAAAGGTCGGAGGTAAAACCTT
TAACAAGGTTGGCTCTTATGTTCTTTTTGACAACGCATTGGTTAAGCTTGTCAAGGCAAAAGTTCGCGGCCCACGA
CAGGCAGGTGTTTGTGAAGTTCGTTACACAAGCCTTGTTATTGGGAGTACTACCAAGGTGGTTTCCAAGCGCGTTG
AAAATGCCAATGTGAATCTCGTCGTCGTTGACGAGGATGTGACCCTCAACACCACTGGTCGTACAGTTGTTGTTGA

Figure 1B

CGGACTTGCATTCTTCGAGAGTGACGGGTTTTACAGACATCTTGCTGATGCTGACGTTGTCATTGAACATCCTGTTT
ATAAGTCTGCTTGTGAGCTCAAGCCAGTTTTTGAGTGTGACCCAATACCTGATTTTCCTATGCCTGTGGCCGCTAGT
GTTGCAGAGCTTTGTGTGCAAACTGATCTGTTGCTTAAAAATTACAACACTCCTTATAAAACTTACAGCTGCGTTGT
GAGAGGTGATAAGTGTTGCATCACTTGCACCTTACATATCACAGCACCAAGTTATATGGAGGATGCTGCTAATTTT
GTAGACCTCTGTACCAAGAACATTGGTACTGCTGGTTTTCATGAGTTTTACATTACGGCCCATGAACAACAGGATCT
GCAAGGGTTCGTAACCACTTGTTGCACGATGTCAGGTTTTGAGTGTTTTATGCCTATAATCCCACAGTGTCCAGCA
GTGCTTGAAGAGATTGATGGTGGTAGCATCTGGCGGTCTTTTATCACTGGTCTTAATACAATGTGGGATTTTTGCA
AGCATCTTAAAGTCAGCTTTGGACTAGATGGCATTGTTGTCACTGTAGCACGCAAATTTAAACGACTTGGTGCTCTC
TTGGCAGAAATGTATAACACTTACCTTTCAACTGTGGTGGAAAACTTGGTACTGGCCGGTGTTAGCTTCAAGTATT
ATGCCACCAGTGTCCCAAAAATTGTTTTGGGCTGTTGTTTTCACAGTGTTAAAAGTGTTCTTGCAAGTGCCTTCCAG
ATTCCTGTCCAGGCAGGCGTTGAGAAGTTTAAAGTCTTCCTTAACTGTGTTCACCCTGTTGTACCACGTGTCATTGA
AACTTCTTTTGTGGAATTAGAAGAGACGACATTTAAACCACCAGCACTCAATGGTAGTATTGCTATTGTTGATGGCT
TTGCTTTCTATTATGATGGAACACTATACTATCCCACCGATGGTAATAGCGTTGTTCCTATCTGCTTTAAGAAGAAA
GGTGGTGGTGATGTCAAATTCTCTGATGAAGTCTCTGTTAAAACCATTGACCCAGTTTATAAGGTCTCCCTTGAATT
TGAGTTCGAGTCTGAGACTATTATGGCTGTGCTTAATAAGGCTGTTGGTAATTGTATCAAGGTTACAGGTGGTTGG
GACGATGTTGTTGAGTATATCAATGTTGCCATTGAGGTTCTTAAAGATCACATCGATGTGCCTAAGTACTACATCTA
TGATGAGGAAGGTGGCACCGATCCTAATCTGCCCGTAATGGTTTCTCAGTGGCCGTTGAATGATGACACGATCTCA
CAGGATCTGCTTGATGTTGAAGTTGTTACTGATGCGCCAGTTGATTTCGAGGGTGATGAAGTAGACTCCTCTGACC
CTGATAAGGTGGCAGACGTGGCTAACTCTGAGCCTGAGGATGACGGTCTTAATGTAGCTCCTGAAACAAATGTAG
AGTCTGAAGTTGAGGAAGTTGCCGCAACCTTGTCCTTTATTAAAGATACACCTTCCACAGTTACTAAGGATCCTTTT
GCTTTTGACTTTGCaagctatgGAGGACTTAAGGTTTTAAGACAATCTCATAACAACTGCTGGGTTACTTCTACCTTGG
TGCAGCTACAATTGCTTGGCATCGTTGATGACCCTGCAATGGAGCTTTTTAGTGCTGGTAGAGTTGGTCCAATGGT
TCGCAAATGCTATGAGTCACAAAAGGCTATCTTGGGATCTTTGGGTGATGTGTCGGCTTGCCTAGAGTCTCTGACT
AAGGACCTACACACACTTAAGATTACCTGTTCTGTAGTCTGTGGTTGTGGTACTGGTGAACGTATCTATGATGGTT
GTGCTTTTCGTATGACGCCAACTTTGGAACCGTTCCCATATGGTGCTTGTGCTCAGTGTGCTCAAGTTTTGATGCAC
ACTTTTAAAAGTATTGTTGGCACCGGCATCTTTTGTCGAGATACTACTGCTCTCTCCTTGGATTCTTTGGTTGTAAAA
CCTCTTTGTGCGGCTGCTTTTATAGGCAAGGATAGTGGTCATTATGTCACTAACTTTTATGATGCTGCTATGGCTAT
TGATGGTTATGGTCGTCATCAGATAAAGTATGACACACTGAACACTATTTGTGTTAAAGACGTTAATTGGACAGCA
CCTTTTGTCCCAGACGTTGAGCCTGTATTGGAGCCTGTTGTCAAACCTTTCTATTCTTATAAGAATGTTGATTTTTAC

Figure 1C

CAAGGAGATTTTAGTGACCTTGTTAAACTTCCATGTGATTTTGTTGTTAATGCTGCAAATGAGAATTTGTCTCACGG
TGGCGGCATAGCAAAGGCCATTGATGTTTATACCAAGGGCATGTTGCAGAAGTGCTCGAATGATTACATTAAAGC
ACACGGTCCCATTAAAGTTGGACGTGGTGTCATGTTGGAGGCATTAGGTCTTAAGGTCTTTAATGTTGTTGGTCCA
CGTAAGGGTAAGCATGCACCTGAGCTTCTTGTTAAGGCTTATAAGTCCGTTTTTGCTAATTCAGGTGTTGCTCTTAC
ACCTTTGATTAGTGTTGGAATTTTTAGTGTTCCTTTGGAAGAATCTTTATCTGCTTTTCTTGCATGTGTTGGTGATCG
CCACTGTAAGTGCTTTTGTTATAGTGACAAAGAGCGCGAGGCGATCATTAATTACATGGATGGCTTGGTAGATGCT
ATTTTCAAAGATGCACTTGTTGATACTACTCCTGTCCAGGAAGATGTTCAACAAGTTTCACAAAAACCAGTTTTGCC
TAATTTTGAACCTTTCAGGATTGAAGGTGCTCATGCTTTCTATGAGTGCAACCCTGAAGGTTTGATGTCATTAGGTG
CTGACAAGCTGGTGTTGTTTACAAATTCCAATTTGGATTTTTGTAGCGTTGGTAAGTGTCTTAACAATGTGACTGGC
GGTGCATTGCTTGAAGCCATAAATGTATTTAAAAAGAGTAACAAAACAGTGCCTGCTGGCAACTGTGTTACTTTTG
AGTGTGCAGATATGATTTCTATTACTATGGTAGTATTGCCATCTGACGGTGATGCTAATTATGACAAAAATTATGCA
CGCGCCGTCGTCAAGGTATCTAAGCTTAAAGGCAAGTTATTGCTTGCTGTTGGTGATGCCATGTTGTATTCCAAGTT
GTCCCACCTCAGCGTGTTAGGTTTCGTATCCACACCTGATGATGTGGAGCGTTTCTACGCAAATAAGAGTGTGGTT
ATTAAAGTTACTGAGGATACACGTAGTGTTAAGACTGTTAAAGTAGAATCCACTGTTACTTATGGACAACAAATTG
GACCTTGTCTTGTTAATGACACCGTTGTCACAGACAACAAACCTGTTGTTGCTGATGTTGTAGCTAAGGTTGTACCA
AGTGCTAATTGGGATTCACATTATGGTTTTGATAAGGCTGGTGAGTTCCACATGCTAGACCATACTGGGTTTGCCTT
TCCTAGTGAAGTTGTTAACGGTAGGCGTGTGCTTAAAACCACAGATAATAACTGTTGGGTTAATGTTACATGTTTA
CAATTACAGTTTGCTAGATTTAGGTTCAAGTCAGCAGGTCTACAGGCTATGTGGGAGTCCTATTGTACTGGTGATG
TTGCTATGTTTGTGCATTGGTTGTACTGGCTTACTGGTGTTGACAAAGGTCAGCCTAGTGATTCAGAAAATGCACTT
AACATGTTGTCTAAGTACATTGTTCCTGCTGGTTCTGTCACTATTGAACGTGTCACGCATGACGGTTGTTGTTGTAG
TAAGCGTGTTGTCACTGCACCAGTTGTGAATGCTAGCGTGTTGAAGCTTGGCGTCGAGGATGGTCTTTGTCCACAT
GGTCTTAACTACATTGACAAAGTTGTTGTAGTTAAAGGTACTACAATTGTTGTCAATGTTGGAAAACCTGTAGTGG
CACCATCGCACCTCTTTCTTAAGGGTGTTTCCTACACAACATTCCTAGATAATGGTAACGGTGTTGCCGGCCATTAT
ACTGTTTTTGATCATGACACTGGTATGGTGCATGATGGAGATGTTTTTGTACCAGGTGATCTCAATGTGTCTCCTGT
TACAAATGTTGTCGTCTCAGAGCAGACGGCTGTTGTGATTAAAGACCCTGTGAAGAAAGTAGAGTTAGACGCTAC
AAAGCTGTTAGACACTATGAATTATGCATCGGAAAGATTCTTTTCCTTTGGTGATTTTATGTCACGTAATTTAATTAC
AGTGTTTTTGTACATCCTTAGTATTTTGGGTCTCTGTTTTAGGGCCTTTCGTAAGAGGGATGTTAAAGTTCTAGCTG
GTGTACCCCAACGTACTGGTATTATATTGCGTAAAAGTGTGCGCTATAATGCAAAGGCTTTGGGTGTCTTCTTCAA
GCTAAAACTTTATTGGTTCAAAGTTCTTGGTAAGTTTAGTTTGGGTATTTATGCATTGTATGCATTACTATTCATGAC

Figure 1D

AATACGCTTTACACCTATAGGTGGCCCTGTTTGTGATGATGTTGTTGCTGGTTATGCTAATTCTAGTTTTGACAAGA

ATGAGTATTGCAACAGTGTTATTTGTAAGGTCTGTCTCTATGGGTACCAGGAACTTTCGGACTTCTCTCACACACAG
GTAGTATGGCAACACCTTAGAGACCCATTAATTGGTAATGTGATGCCTTTCTTTTATTTGGCATTTCTGGCAATTTTT
GGGGGTGTTTATGTAAAGGCTATTACTCTCTATTTTATTTTCCAGTATCTTAACATACTTGGTGTGTTTTTGGGCCTA
CAACAGTCCATTTGGTTTTTGCAGCTTGTGCCTTTTGATGTCTTTGGTGACGAGATCGTCGTCTTTTTCATCGTTACA
CGCGTATTGATGTTCCTTAAGCATGTTTTCCTTGGCTGCGATAAGGCATCTTGTGTGGCTTGCTCTAAGAGTGCTCG
CCTTAAGCGCGTTCCTGTCCAGACTATTTTTCAGGGTACTAGCAAATCCTTCTACGTACATGCCAATGGTGGTTCTA
AGTTCTGTAAGAAGCACAATTTCTTTTGTTTAAATTGTGATTCTTATGGTCCAGGCTGCACTTTTATTAATGACGTCA
TTGCAACTGAAGTTGGTAATGTTGTCAAACTTAATGTGCAACCGACAGGTCCTGCCACTATTCTTATTGACAAGGTT
GAATTCAGTAATGGTTTTTACTATCTTTATAGTGGTGACACATTTTGGAAGTACAACTTTGACATAACAGATAACAA
ATACACTTGCAAAGAGTCACTTAAAAATTGTAGCATAATCACAGACTTTATTGTTTTTAACAATAATGGTTCCAATG
TAAATCAGGTTAAGAATGCATGTGTGTATTTTTCACAGATGCTTTGTAAACCTGTTAAGTTAGTGGACTCAGCGTTG
TTGGCCAGTTTGTCTGTTGATTTTGGTGCAAGCTTACATAGTGCTTTTGTTAGTGTGTTGTCGAATAGTTTTGGCAA
AGACCTGTCAAGTTGTAATGACATGCAGGATTGCAAGAGCACATTGGGTTTTGATGATGTACCATTGGATACCTTT
AATGCTGCTGTTGCTGAGGCTCATCGTTACGATGTCCTCTTGACTGACATGTCGTTCAACAATTTTACCACCAGTTA
TGCAAAACCAGAGGAAAAACTTCCCGTCCATGACATTGCCACGTGTATGCGTGTAGGTGCCAAGATTGTTAATCAT
AACGTTCTTGTCAAGGATAGTATACCTGTGGTGTGGCTTGTACGTGATTTCATTGCCCTTTCTGAAGAAACTAGGA
AGTACATTATTCGTACGACTAAAGTTAAGGGTATAACCTTCATGTTGACCTTTAATGATTGTCGTATGCATACTACC
ATACCTACTGTTTGCATTGCAAATAAGAAGGGTGCAGGTCTTCCTAGTTTTTCAAAGGTTAAGAAATTCTTCTGGTT
TTTGTGTCTGTTCATAGTTGCTGTTTTCTTTGCACTAAGCTTTTTTGATTTTAGTACTCAGGTTAGCAGTGATAGTGA
TTATGACTTCAAGTATATTGAGAGTGGCCAGTTGAAGACTTTTGACAATCCACATAGTTGTGTGCATAATGTCTTTA
GTAACTTCGACCAGTGGCATGATGCCAAGTTTGGTTTCACCCCCGTCAACAATCCTAGTTGTCCTATAGTCGTTGGT
GTATCAGACGAAGCGCGCACTGTTCCAGGTATCCCAGCAGGTGTTTATTTAGCTGGTAAAACACTTGTTTTTGCTAT
TAACACCATTTTTGGTACATCTGGTTTGTGCTTTGATGCTAGTGGCGTTGCTGATAAGGGCGCTTGCATTTTTAATT
CGGCTTGCACCACATTATCTGGTTTGGGTGGAACTGCTGTCTACTGTTATAAGAATGGTCTAGTTGAAGGTGCTAA
ACTTTATAGTGAGTTGGCACCTCATAGCTACTATAAAATGGTAGATGGTAATGCTGTGTCTTTACCTGAAATTATCT
CACGCGGCTTTGGCATCCGTACTATCCGTACAAAGGCTATGACCTACTGTCGCGTTGGCCAGTGTGTGCAATCTGC
AGAAGGTGTTTGTTTTGGCGCCGATAGATTCTTTGTCTATAATGCAGAATCTGGTTCTGACTTTGTTTGTGGCACAG

Figure 1E

GGCTCTTTACATTGTTGATGAACGTTATTAGTGTTTTTTCCAAGACAGTACCAGTAACTGTGTTGTCTGGTCAAATA
CTTTTTAATTGCATTATTGCTTTTGCTGCTGTTGCGGTGTGTTTCTTATTTACAAAGTTTAAGCGCATGTTCGGTGAT
ATGTCTGTTGGCGTTTTCACTGTCGGTGCTTGTACTTTGTTGAACAATGTTTCCTACATTGTAACACAGAACACACTT
GGCATGTTGGGCTATGCAACTTTGTACTTTTTGTGCACTAAAGGTGTTAGATATATGTGGATTTGGCATTTGGGATT
TTTGATCTCATATATACTTATTGCACCATGGTGGGTTTTGATGGTTTATGCCTTTTCAGCCATTTTTGAGTTTATGCCT
AACCTTTTTAAGCTTAAGGTTTCAACACAACTTTTTGAGGGTGACAAGTTCGTAGGCTCTTTTGAAAATGCTGCAGC
AGGTACATTTGTGCTTGATATGCATGCCTATGAGAGACTTGCCAACTCTATCTCAACTGAAAAACTGCGTCAGTAT
GCTAGTACTTACAATAAGTACAAGTATTATTCAGGCAGTGCTTCAGAGGCTGATTACAGGCTTGCTTGTTTTGCCCA
TTTGGCCAAGGCTATGATGGATTATGCTTCTAATCACAACGACACGTTATACACACCACCCACTGTGAGTTACAATT
CAACTCTACAGGCTGGCTTGCGTAAGATGGCACAACCATCTGGTGTTGTTGAGAAGTGCATAGTTCGTGTTTGCTA
TGGTAATATGGCTCTTAATGGCCTATGGCTTGGTGATACTGTTATCTGCCCACGCCATGTTATAGCGTCTAGTACTA
CTAGCACTATAGATTATGACTATGCCCTTTCTGTTTTACGCCTCCACAACTTCTCCATTTCATCTGGTAATGTTTTCCT
AGGTGTTGTGGGTGTAACCATGCGAGGTGCTTTGTTGCAGATAAAGGTTAATCAAAACAATGTCCACACGCCTAA
GTACACCTATCGCACAGTTAGACCGGGTGAATCTTTTAATATCTTGGCGTGCTATGATGGTTCTGCCAGTGGTGTTT
ACGGCGTTAACATGCGCTCTAATTACACTATTAGAGGCTCGTTCATTAATGGCGCTTGTGGTTCACCTGGTTATAAC
ATTAACAATGGTACCGTTGAGTTTTGCTATTTACACCAGCTTGAACTTGGTTCAGGCTGTCATGTTGGTAGCGACTT
AGATGGTGTTATGTATGGTGGTTATGAGGACCAACCTACTTTGCAAGTTGAAGGCGCTAGTAGTCTGTTTACAGAG
AATGTGTTGGCATTTCTTTATGCAGCACTCATTAATGGTTCTACCTGGTGGCTTAGTTCTTCTAGGATTGCTGTAGA
CAGGTTTAATGAGTGGGCTGTTCATAATGGTATGACAACAGTAGTTAATACTGATTGCTTTTCTATTCTTGCTGCTA
AGACTGGTGTTGATGTACAACGTTTGTTGGCCTCAATCCAGTCTCTGCATAAGAATTTTGGTGGAAAGCAAATTCTT
GGCTATACCTCGTTGACAGATGAGTTTACTACAGGTGAAGTTATACGTCAAATGTATGGCGTTAATCTTCAGAGTG
GTTATGTTTCACGCGCCTGTAGAAATGTCTTGCTGGTTGGTTCTTTTCTGACTTTCTTTTGGTCAGAATTAGTTTCCT
ACACTAAGTTCTTTTGGGTAAATCCTGGTTATGTCACACCTATGTTTGCGTGTTTGTCATTGCTGTCCTCACTTTTGA
TGTTCACACTCAAGCATAAGACATTGTTTTTCCAGGTCTTTCTAATACCTGCTCTGATTGTTACATCTTGCATTAATTT
GGCATTTGATGTTGAAGTCTACAACTATTTGGCAGAGCATTTTGATTACCATGTTTCTCTCATGGGTTTTAATGCAC
AAGGTCTTGTTAACATCTTTGTCTGCTTTGTTGTTACCATTTTACACGGCACATACACATGGCGCTTTTTTAACACAC
CTGTGAGTTCTGTCACTTATGTGGTAGCTTTGCTGACTGCGGCATATAACTATTTTTACGCTAGTGACATTCTTAGTT
GTGCTATGACACTATTTGCTAGTGTGACTGGCAACTGGTTCGTTGGTGCTGTTTGTTATAAAGCTGCTGTTTATATG
GCCTTGAGATTTCCTACTTTTGTGGCTATTTTTGGTGATATTAAGAGTGTTATGTTCTGTTACCTTGTGTTGGGTTAT

Figure 1F

TTTACCTGTTGCTTCTACGGTATTCTCTACTGGTTCAACAGGTTTTTTAAGGTTAGTGTAGGTGTCTATGACTATACT
GTTAGTGCTGCTGAGTTTAAGTATATGGTTGCTAACGGCCTACGTGCACCAACTGGAACACTTGATTCACTACTTCT
GTCTGCCAAATTGATTGGTATTGGTGGTGAGCGGAATATTAAGATTTCTTCCGTTCAGTCTAAACTGACTGATATTA
AGTGTAGTAACGTTGTGCTTTTAGGCTGTCTCTCTAGCATGAATGTCTCAGCAAATTCAACAGAATGGGCCTATTGT
GTTGACTTGCATAACAAGATCAACTTGTGTAATGACCCAGAAAAAGCGCAGGAAATGCTACTTGCTTTGTTGGCAT
TTTTCCTTAGTAAGAATAGTGCTTTTGGTTTAGATGACTTATTGGAATCCTATTTTAATGACAATAGTATGTTGCAGA
GTGTTGCATCTACTTATGTCGGTTTGCCTTCTTATGTCATTTATGAAAATGCACGCCAACAGTATGAAGATGCTGTT
AATAATGGTTCTCCACCTCAGTTGGTTAAGCAATTGCGCCATGCCATGAATGTAGCAAAGAGCGAATTTGACCGTG
AGGCTTCTACTCAGCGTAAGCTTGATAGAATGGCGGAACAGGCTGCAGCACAGATGTACAAAGAGGCACGAGCA
GTTAATAGGAAGTCCAAAGTTGTAAGTGCTATGCATTCACTGCTTTTTGGTATGTTGAGACGTTTGGACATGTCTTC
TGTAGACACCATTCTCAACTTGGCAAAGGATGGGGTTGTACCTCTGTCTGTCATACCGGCAGTCAGTGCTACTAAG
CTTAACATTGTTACTTCTGATATCGATTCTTATAATCGTATCCAGCGTGAGGGATGTGTCCACTACGCTGGTACCAT
TTGGAATATAATTGATATCAAGGACAATGATGGCAAGGTGGTACACGTTAAGGAGGTAACCGCACAGAATGCTGA
GTCCCTGTCATGGCCCCTGGTCCTTGGGTGTGAGCGTATTGTCAAGCTCCAGAATAATGAAATTATTCCTGGTAAG
CTGAAGCAGCGCTCCATTAAGGCAGAAGGAGATGGCATAGTTGGAGAAGGTAAGGCACTTTACAATAATGAGGG
TGGACGTACTTTTATGTATGCTTTCATCTCGGACAAACCGGACCTGCGTGTAGTCAAGTGGGAGTTCGATGGTGGT
TGTAACACTATTGAGCTAGAACCACCACGTAAGTTCTTGGTGGATTCTCCTAATGGTGCACAGATCAAGTATCTCTA
CTTTGTTCGTAACCTTAACACGTTACGTAGGGGTGCTGTTCTCGGCTACATAGGTGCCACTGTACGCTTGCAGGCT
GGTAAACAAACAGAACAGGCTATTAACTCTTCATTGTTGACACTTTGCGCTTTCGCTGTGGATCCTGCTAAGACCTA
CATCGATGCTGTCAAAAGTGGTCACAAACCAGTAGGTAACTGTGTTAAGATGTTGGCCAATGGTTCTGGTAATGG
ACAAGCTGTTACTAATGGTGTGGAGGCTAGTACTAACCAGGATTCATACGGTGGTGCGTCCGTGTGTCTATATTGT
AGAGCACATGTTGAGCATCCATCTATGGATGGTTTTTGCAGACTGAAAGGCAAGTACGTACAGGTTCCACTAGGT
ACAGTGGATCCTATACGTTTTGTACTTGAGAATGACGTTTGCAAGGTTTGTGGTTGTTGGCTGGCTAATGGCTGCA
CTTGTGACAGATCCATTATGCAAAGCACTGATTATGGCTTATTTAAACGAGTACGGGGCTCTAGTGCAGCTCGACT
AGAGCCCTGTAACGGTACTGATACACAACATGTGTATCGTGCTTTTGACATCTACAACAAGGATGTTGCTTGTCTA
GGTAAATTCCTCAAGGTGAACTGTGTTCGCCTGAAGAATTTGGATAAGCATGATGCATTCTATGTTGTCAAAAGAT
GTACCAAGTCTGCGATGGAACACGAGCAATCCATCTATAGCAGACTTGAAAAGTGTGGAGCCGTAGCCGAACACG
ATTTCTTCACTTGGAAGGATGGTCGTGCCATCTATGGTAACGTTTGTAGAAAGGATCTTACCGAGTATACTATGAT
GGATTTGTGTTACGCTTTACGTAACTTTGATGAAAACAATTGCGATGTTCTTAAGAGCATTTTAATTAAGGTAGGCG

Figure 1G

CTTGTGAGGAGTCCTACTTCAATAATAAAGTCTGGTTTGACCCTGTTGAAAATGAAGACATTCATCGTGTCTATGCA
TTGTTAGGTACCATTGTTTCACGTGCTATGCTTAAATGCGTTAAGTTCTGTGATGCAATGGTTGAACAAGGTATAGT
TGGTGTTGTCACATTAGATAATCAGGATCTTAATGGTGATTTTTATGATTTTGGTGATTTTACTTGTAGCATCAAGG
GAATGGGTATACCCATTTGCACATCATATTACTCTTATATGATGCCTGTTATGGGTATGACTAATTGCCTTGCTAGT
GAGTGTTTTGTTAAGAGTGATATATTTGGTGAGGATTTCAAGTCATATGACCTGCTGGAATATGATTTCACGGAGC
ATAAGACAGCACTCTTCAACAAGTATTTCAAGTATTGGGGACTGCAATACCACCCTAACTGTGTGGACTGCAGTGA
TGAGCAGTGCATAGTTCACTGTGCCAACTTCAATACGTTGTTTTCCACTACTATACCTATTACGGCATTTGGACCTTT
GTGTCGCAAGTGTTGGATTGATGGTGTTCCACTGGTAACTACAGCTGGTTATCATTTTAAACAGTTAGGTATAGTTT
GGAACAATGACCTCAACTTACACTCTAGCAGGCTCTCTATTAACGAATTACTCCAGTTTTGTAGTGATCCTGCATTG
CTTATAGCATCATCACCAGCCCTTGTTGATCAGCGTACTGTTTGCTTTTCAGTTGCAGCGCTAGGTACAGGTATGAC
TAACCAGACTGTTAAACCTGGCCATTTCAATAAGGAGTTTTATGACTTCTTACTTGAGCAAGGTTTCTTTTCTGAGG
GCTCTGAGCTTACTTTAAAGCACTTCTTCTTTGCACAGAAGGGTGATGCAGCTGTTAAGGATTTTGACTACTATAGG
TATAATAGACCTACTGTTCTGGACATTTGCCAAGCTCGCGTCGTGTATCAAATAGTGCAACGCTATTTTGATATTTA
CGAAGGTGGTTGTATCACTGCTAAAGAGGTGGTTGTTACAAACCTTAACAAGAGCGCAGGTTATCCTTTGAACAA
GTTTGGTAAAGCTGGTCTTTACTATGAGTCTTTATCCTATGAGGAACAGGATGAACTTTATGCTTATACTAAGCGTA
ACATCCTGCCCACTATGACACAGCTCAACCTTAAATATGCTATAAGTGGCAAAGAACGTGCACGCACAGTGGGTG
GTGTTTCGCTTTTGTCAACCATGACTACTCGGCAGTATCATCAGAAACACCTTAAGTCCATAGTTAATACTAGGGGC
GCTTCGGTTGTTATTGGTACTACTAAGTTTTATGGTGGTTGGGACAATATGCTTAAGAACCTTATTGATGGTGTTGA
AAATCCGTGTCTTATGGGTTGGGACTACCCAAAGTGCGACAGAGCACTGCCCAATATGATACGTATGATTTCAGCC
ATGATTTTAGGCTCTAAGCACACCACATGCTGCAGTTCCACTGACCGCTTTTTCAGGTTGTGCAATGAATTGGCTCA
AGTCCTTACTGAGGTTGTTTATTCTAATGGAGGTTTTTATTTGAAGCCAGGTGGTACTACCTCTGGTGATGCAACCA
CCGCATATGCAAACTCAGTTTTTAATATCTTCCAAGCAGTAAGTGCCAATGTTAACAAACTTCTTAGTGTTGACAGC
AATGTCTGTCATAATTTAGAAGTTAAGCAATTGCAGCGTAAGCTTTATGAGTGCTGTTATAGATCAACTACCGTCG
ATGACCAGTTCGTCGTTGAGTATTATGGTTACTTGCGTAAACATTTTTCAATGATGATTCTTTCTGATGATGGCGTT
GTTTGTTATAACAATGACTATGCATCACTTGGTTATGTCGCTGATCTTAACGCATTCAAGGCTGTTTTGTATTACCAG
AACAATGTCTTCATGAGCGCCTCTAAATGTTGGATCGAGCCTGACATTAATAAAGGTCCTCATGAATTTTGCTCGCA
GCATACTATGCAGATTGTCGATAAAGATGGTACTTATTACCTTCCTTACCCTGATCCTTCAAGAATTCTCTCTGCAG
GTGTGTTTGTTGATGACGTTGTTAAAACTGATGCAGTTGTATTGCTTGAACGTTATGTGTCATTGGCTATAGATGCC
TACCCGTTATCTAAGCATGAAAACCCTGAATATAAGAAGGTGTTTTATGTGCTTTTGGATTGGGTTAAGCATCTGTA

Figure 1H

CAAAACTCTTAATGCTGGTGTGTTAGAGTCTTTTTCTGTCACACTTTTGGAAGATTCTACTGCTAAATTCTGGGATG
AGAGCTTTTATGCCAACATGTATGAGAAATCTGCAGTTTTACAATCTGCAGGGCTTTGTGTTGTTTGTGGCTCTCAA
ACTGTTTTACGTTGTGGTGATTGTCTACGGCGTCCTATGCTTTGTACTAAGTGTGCTTATGATCATGTCATTGGAAC
AACTCACAAGTTCATTTTGGCCATCACTCCATATGTGTGTTGTGCTTCAGATTGTGGTGTCAATGATGTAACTAAGC
TCTACTTAGGTGGTCTTAGTTATTGGTGTCATGACCACAAGCCACGTCTTGCATTCCCGTTGTGCTCTGCTGGTAAT
GTTTTTGGCTTGTACAAAAATTCTGCTACCGGCTCACCCGATGTTGAAGACTTTAATCGCATTGCTACATCCGATTG
GACTGATGTTTCTGACTACAGGTTGGCAAATGATGTCAAGGACTCATTGCGTCTGTTTGCAGCGGAAACTATCAAG
GCCAAGGAGGAGAGCGTTAAGTCATCCTATGCTTGTGCAACACTACATGAGGTTGTAGGACCTAAAGAGTTGTTG
CTCAAATGGGAAGTCGGCAGACCCAAACCACCCCTTAATAGAAATTCGGTTTTCACTTGTTATCATATAACGAAGA
ACACCAAATTTCAAATCGGTGAGTTTGTGTTTGAGAAGGCAGAATATGATAATGATGCTGTAACATATAAAACTAC
CGCCACAACAAAACTTGTTCCTGGCATGGTTTTTGTGCTTACCTCACATAATGTTCAGCCATTGCGCGCACCGACCA
TTGCTAATCAAGAACGTTATTCCACTATACATAAGTTGCATCCTGCTTTTAACATACCTGAAGCTTATTCTAGCTTAG
TGCCCTATTACCAATTGATTGGTAAGCAGAAGATTACAACTATTCAGGGACCTCCCGGTAGTGGTAAATCTCACTG
TGTTATAGGGCTAGGTTTGTACTATCCAGGTGCACGTATAGTGTTTACAGCTTGTTCTCATGCAGCGGTCGATTCAC
TTTGTGTGAAAGCTTCCACTGCTTATAGCAATGACAAATGTTCACGCATCATACCACAGCGCGCTCGTGTTGAGTGT
TATGATGGTTTCAAGTCTAATAATACTAGTGCTCAGTACCTTTTCTCTACTGTCAATGCTTTGCCAGAGTGCAATGC
GGACATTGTTGTGGTGGATGAGGTCTCTATGTGCACTAATTATGACTTGTCTGTCATAAATCAGCGCATCAGCTAT
AGGCATGTAGTCTATGTTGGTGACCCTCAACAGCTGCCTGCACCACGTGTTATGATTTCACGTGGTACTTTGGAAC
CAAAGGACTACAACGTTGTCACTCAACGCATGTGTGCCCTTAAGCCTGATGTTTTCTTGCACAAGTGTTATCGCTGT
CCTGCTGAGATAGTGCGTACTGTGTCTGAGATGGTCTATGAAAACCAATTCATTCCTGTGCACCCAGATAGCAAGC
AGTGTTTTAAAATCTTTTGCAAGGGTAATGTTCAGGTTGATAATGGTTCAAGCATTAATCGCAGGCAATTGGATGT
TGTGCGTATGTTTTTGGCTAAAAATCCTAGGTGGTCAAAGGCTGTTTTTATTTCTCCTTATAACAGCCAGAATTATG
TTGCCAGCCGCATGCTAGGTCTACAAATTCAGACAGTTGATTCATCCCAGGGTAGTGAGTATGACTATGTCATTTA
CACACAAACTTCAGATACTGCCCATGCCTGTAATGTTAACAGGTTTAATGTTGCCATCACAAGGGCCAAGAAAGGC
ATATTATGTATAATGTGCGATAGGTCCCTTTTTGATGTGCTTAAATTCTTTGAGCTTAAATTGTCTGATTTGCAGGCT
AATGAGGGTTGTGGTCTTTTTAAAGACTGTAGCAGAGGTGATGATCTGTTGCCACCATCTCACGCTAACACCTTCA
TGTCTTTAGCGGACAATTTTAAGACTGATCAAGATCTTGCTGTTCAAATAGGTGTTAATGGACCCATTAAATATGAG
CATGTTATCTCGTTTATGGGTTTCCGTTTTGATATCAACATACCCAACCATCATACTCTCTTTTGCACACGCGACTTT
GCCATGCGCAATGTTAGAGGTTGGTTAGGCTTTGACGTTGAAGGAGCACATGTTGTTGGCTCTAACGTCGGTACA

Figure 1I

AATGTCCCATTGCAATTAGGGTTTTCTAACGGTGTTGATTTTGTTGTCAGACCTGAAGGTTGCGTTGTAACAGAGTC
TGGTGACTACATTAAACCCGTCAGAGCTCGTGCTCCACCAGGGGAACAATTCGCACACCTTTTGCCTTTACTTAAAC
GCGGCCAACCATGGGATGTTGTCCGCAAACGTATAGTGCAGATGTGTAGTGACTACCTGGCCAACCTATCAGACA
TACTAATTTTTGTGTTGTGGGCTGGTGGTTTGGAGTTGACAACTATGCGTTATTTTGTCAAGATTGGACCAAGTAA
GAGTTGTGATTGTGGTAAGGTTGCTACTTGTTACAATAGTGCGCTGCATACGTACTGTTGTTTCAAACATGCCCTTG
GTTGTGATTATCTGTATAACCCATACTGTATTGATATACAGCAGTGGGGATACAAGGGATCACTTAGCCTTAACCA
CCATGAGCATTGTAATGTACATAGAAACGAGCATGTGGCTTCTGGTGATGCCATAATGACTCGCTGTCTGGCCATA
CATGATTGCTTTGTCAAGAACGTTGACTGGTCCATCACATACCCATTTATTGGTAATGAGGCTGTTATTAATAAGAG
CGGCCGAATTGTGCAATCACACACTATGCGGTCAGTTCTTAAGTTATACAATCCGAAAGCCATATATGATATTGGC
AATCCTAAGGGCATTAGATGTGCCGTAACGGATGCTAAGTGGTTTTGCTTTGACAAGAATCCTACTAATTCTAATG
TCAAGACATTGGAGTATGACTATATAACACATGGCCAATTTGATGGGTTGTGCTTGTTTTGGAATTGCAATGTAGA
CATGTATCCAGAATTTTCTGTGGTCTGTCGTTTTGATACTCGCTGTAGGTCACCACTCAACTTGGAGGGTTGTAATG
GTGGTTCACTGTATGTTAATAATCATGCATTCCATACACCGGCTTTTGACAAGCGTGCTTTTGCTAAGTTGAAGCCA
ATGCCATTTTTCTTTTATGATGATACTGAGTGTGACAAGTTACAGGACTCCATAAACTATGTTCCTCTTAGGGCTAG
TAACTGCATTACTAAATGTAATGTTGGTGGTGCTGTCTGTAGTAAGCATTGTGCTATGTATCATAGCTATGTTAATG
CTTACAACACTTTTACGTCGGCGGGCTTTACTATTTGGGTGCCTACTTCGTTTGACACCTATAATCTGTGGCAGACA
TTTAGTAACAATTTGCAAGGTCTTGAGAACATTGCTTTCAATGTCGTAAAGAAAGGATCTTTTGTTGGTGCCGAAG
GTGAACTTCCTGTAGCTGTGGTTAATGACAAAGTGCTCGTTAGAGATGGTACTGTTGATACTCTTGTTTTTACAAAC
AAGACATCACTACCCACTAACGTAGCTTTTGAGTTGTATGCCAAGCGTAAGGTAGGACTCACCCCACCCATTACGA
TCCTACGTAACTTGGGTGTAGTTTGTACATCTAAGTGTGTCATTTGGGACTATGAAGCCGAACGTCCACTTACTACT
TTTACAAAGGATGTTTGTAAATATACCGACTTTGAGGGTGACGTCTGTACACTCTTTGATAACAGCATTGTTGGTTC
ATTAGAGCGATTCTCCATGACCCAAAATGCTGTGCTTATGTCACTTACAGCTGTTAAAAAGCTTACTGGCATAAAGT
TAACTTATGGTTATCTTAATGGTGTCCCAGTTAACACACATGAAGATAAACCTTTTACTTGGTATATTTACACTAGG
AAGAACGGCAAGTTCGAGGACCATCCTGATGGCTATTTTACCCAAGGTAGAACAACCGCTGATTTTAGCCCTCGTA
GCGACATGGAAAAGGACTTCCTAAGTATGGATATGGGTCTGTTTATTAACAAGTACGGACTTGAAGATTACGGCTT
TGAGCACGTTGTGTATGGTGATGTTTCAAAAACCACCCTTGGTGGTTTGCATCTACTAATTTCGCAGGTGCGTCTG
GCCTGTATGGGTGTGCTCAAAATAGACGAGTTTGTGTCTAGTAATGATAGCACGTTAAAGTCTTGTACTGTTACAT
ATGCTGATAACCCTAGTAGTAAGATGGTTTGTACGTATATGGATCTCCTGCTTGACGATTTTGTCAGCATTCTTAAA
TCTTTGGATTTGGGCGTTGTATCTAAAGTTCATGAAGTTATGGTCGATTGTAAAATGTGGAGGTGGATGTTGTGGT

Figure 1J

GTAAGGATCATAAACTCCAGACATTTTATCCGCAACTTCAGGCCAGTGAATGGAAGTGTGGTTATTCCATGCCTTCT
ATTTACAAGATACAACGTATGTGTTTAGAACCTTGCAATCTCTACAACTATGGTGCTGGTATTAAGTTACCTGATGG
CATTATGTTTAACGTAGTTAAATACACACAGCTTTGTCAATATCTCAATAGCACCACAATGTGTGTACCCCATCACA
TGCGTGTGCTACATCTTGGTGCTGGCTCCGACAAGGGTGTTGCACCTGGCACGGCTGTCTTACGACGTTGGTTGCC
ACTGGATGCCATTATAGTTGACAATGATAGTGTGGATTACGTTAGCGATGCTGATTATAGTGTTACAGGAGATTGC
TCTACCTTATACCTGTCAGATAAGTTTGATTTAGTTATATCTGATATGTATGATGGTAAGATTAAAAGTTGTGATGG
GGAGAACGTGTCTAAAGAAGGCTTCTTTCCCTATATTAATGGTGTCATCACCGAAAAGTTGGCACTTGGTGGTACT
GTAGCTATTAAGGTGACGGAGTTTAGTTGGAATAAGAAGTTGTATGAACTCATTCAGAGGTTTGAGTATTGGACA
ATGTTCTGTACCAGTGTTAACACGTCATCGTCAGAGGCATTCTTAATTGGTGTTCACTATTTAGGTGATTTTGCAAG
TGGCGCTGTGATTGACGGCAACACTATGCATGCCAATTATATCTTCTGGCGTAATTCCACAATTATGACTATGTCTT
ACAATAGTGTACTTGATTTAAGCAAGTTCAATTGTAAGCATAAGGCTACAGTTGTCATTAATTTAAAAGATTCATCC
ATTAGTGATGTTGTGTTAGGTTTGTTGAAGAATGGTAAGTTGCTAGTGCGTAATAATGACGCCATTTGTGGTTTTTC
TAATCATTTGGTCAACGTAAACAAATGA 20,639-24,799- Spike Protein nt – SEQ ID NO: 3

ATGAAGTCTTTAACCTACTTCTGGTTGTTCTTACCAGTACTTTCAACACTTAGCCTACCACAAGATGTCACCAGGTGC
TCAGCTAACACTAATTTTAGGCGGTTCTTTTCAAAATTTAATGTTCAGGCGCCTGCAGTTGTTGTACTGGGCGGTTA
TCTACCTATTGGTGAAAACCAGGGTGTCAATTCAACTTGGTACTGTGCTGGCCAACATCCAACTGCTAGTGGCGTT
CATGGTATCTTTGTTAGCCATATTAGAGGTGGTCATGGCTTTGAGATTGGCATTTCGCAAGAGCCTTTTGACCCTAG
TGGTTACCAGCTTTATTTACATAAGGCTACTAACGGTAACACTAATGCTACTGCGCGACTGCGCATTTGCCAGTTTC
CTAGCATTAAAACATTGGGCCCCACTGCTAATAATGATGTTACAACAGGTCGTAATTGCCTATTTAACAAAGCCATC
CCAGCTCATATGAGTGAACATAGTGTTGTCGGCATAACATGGGATAATGATCGTGTCACTGTCTTTTCTGACAAGA
TCTATTATTTTTATTTTAAAAATGATTGGTCCCGTGTTGCGACAAAGTGTTACAACAGTGGAGGTTGTGCTATGCAA
TATGTTTACGAACCCACCTATTACATGCTTAATGTTACTAGTGCTGGTGAGGATGGTATTTCTTATCAACCCTGTAC
AGCTAATTGCATTGGTTATGCTGCCAATGTATTTGCTACTGAGCCCAATGGCCACATACCAGAAGGTTTTAGTTTTA
ATAATTGGTTTCTTTTGTCCAATGATTCCACTTTGGTGCATGGTAAGGTGGTTTCCAACCAACCATTGTTGGTCAATT
GTCTTTTGGCCATTCCTAAGATTTATGGACTAGGCCAATTTTTCTCCTTTAATCAAACGATCGATGGTGTTTGTAATG
GAGCTGCTGTGCAGCGTGCACCAGAGGCTCTGAGGTTTAATATTAATGACACCTCTGTCATTCTTGCTGAAGGCTC
AATTGTACTTCATACTGCTTTAGGAACAAATTTTTCTTTTGTTTGCAGTAATTCCTCAAATCCTCACTTAGCCACCTTC

Figure 1K

GCCATACCTCTGGGTGCTACCCAAGTACCTTATTATTGTTTTCTTAAAGTGGATACTTACAACTCCACTGTTTATAAA
TTTTTGGCTGTTTTACCTCCTACCGTCAGGGAAATTGTCATCACCAAGTATGGTGATGTTTATGTCAATGGGTTTGG
ATACTTGCATCTCGGTTTGTTGGATGCTGTCACAATTAATTTCACTGGTCATGGCACTGACGATGATGTTTCTGGTT
TTTGGACCATAGCATCGACTAATTTTGTTGATGCACTCATCGAAGTTCAAGGAACCGCCATTCAGCGTATTCTTTAT
TGTGATGATCCTGTTAGCCAACTCAAGTGTTCTCAGGTTGCTTTTGACCTTGACGATGGTTTTTACCCTATTTCTTCT
AGAAACCTTCTGAGTCATGAACAGCCAATTTCTTTTGTTACTCTGCCATCATTTAATGATCATTCTTTTGTTAACATTA
CTGTATCTGCTTCCTTTGGTGGTCATAGTGGTGCCAACCTTATTGCATCTGACACTACTATCAATGGGTTTAGTTCTT
TCTGTGTTGACACTAGACAATTTACCATTTCACTGTTTTATAACGTTACAAACAGTTATGGTTATGTGTCTAAATCAC
AGGACAGTAATTGCCCTTTCACCTTGCAATCTGTTAATGATTACCTGTCTTTTAGCAAATTTTGTGTTTCCACCAGCC
TTTTGGCTAGTGCCTGTACCATAGATCTTTTTGGTTACCCTGAGTTTGGTAGTGGTGTTAAGTTTACGTCCCTTTACT
TTCAATTCACAAAGGGTGAGTTGATTACTGGCACGCCTAAACCACTTGAAGGTGTCACGGACGTTTCTTTTATGACT
CTGGATGTGTGTACCAAGTATACTATCTATGGCTTTAAAGGTGAGGGTATCATTACCCTTACAAATTCTAGCTTTTT
GGCAGGTGTTTATTACACATCTGATTCTGGACAGTTGTTAGCCTTTAAGAATGTCACTAGTGGTGCTGTTTATTCTG
TTACGCCATGTTCTTTTTCAGAGCAGGCTGCATATGTTGATGATGATATAGTGGGTGTTATTTCTAGTTTGTCTAGC
TCCACTTTTAACAGTACTAGGGAGTTGCCTGGTTTCTTCTACCATTCTAATGATGGCTCTAATTGTACAGAGCCTGT
GTTGGTGTATAGTAACATAGGTGTTTGTAAATCTGGCAGTATTGGCTACGTCCCATCTCAGTCTGGCCAAGTCAAG
ATTGCACCCACGGTTACTGGGAATATTAGTATTCCCACCAACTTTAGTATGAGTATTAGGACAGAATATTTACAGCT
TTACAACACGCCTGTTAGTGTTGATTGTGCCACATATGTTTGTAATGGTAACTCTCGTTGTAAACAATTACTCACCC
AGTACACTGCAGCATGTAAGACCATAGAGTCAGCATTACAACTCAGCGCTAGGCTTGAGTCTGTTGAAGTTAACTC
TATGCTTACTATTTCTGAAGAGGCTCTACAGTTAGCTACCATTAGTTCGTTTAATGGTGATGGATATAATTTTACTAA
TGTGCTGGGTGTTTCTGTGTATGATCCTGCAAGTGGCAGGGTGGTACAAAAAAGGTCTTTTATTGAAGACCTGCTT
TTTAATAAAGTGGTTACTAATGGCCTTGGTACTGTTGATGAAGACTATAAGCGCTGTTCTAATGGTCGCTCTGTGG
CAGATCTAGTCTGTGCACAGTATTACTCTGGTGTCATGGTACTACCTGGTGTTGTTGACGCTGAGAAGCTTCACAT
GTATAGTGCGTCTCTCATCGGTGGTATGGTGCTAGGAGGTTTTACTTCTGCAGCGGCATTGCCTTTTAGCTATGCTG
TTCAAGCTAGACTCAATTATCTTGCTCTACAGACGGATGTTCTACAGCGGAACCAGCAATTGCTTGCTGAGTCTTTT
AACTCTGCTATTGGTAATATAACTTCAGCCTTTGAGAGTGTTAAAGAGGCTATTAGTCAAACTTCCAAGGGTTTGA
ACACTGTGGCTCATGCGCTTACTAAGGTTCAAGAGGTTGTTAACTCGCAGGGTGCAGCTTTGACTCAACTTACCGT
ACAGCTGCAACACAACTTCCAAGCCATTTCTAGTTCTATTGATGACATTTACTCTCGACTGGACATTCTTTCAGCCGA
TGTTCAGGTTGACCGTCTCATCACCGGCAGATTATCAGCACTTAATGCTTTTGTTTCTCAAACCCTCACTAAGTATAC

Figure 1L

TGAGGTTCAGGCTAGCAGGAAGTTAGCACAGCAAAAGGTTAATGAGTGCGTTAAATCGCAATCTCAGCGTTATGG
TTTTTGTGGTGGTGATGGCGAGCACATTTTCTCTCTGGTACAGGCAGCACCTCAGGGCCTGCTGTTTTTACATACAG
TACTTGTACCGAGTGATTTTGTAGATGTTATTGCCATCGCTGGCTTATGCGTTAACGATGAAATTGCCTTGACTCTA
CGTGAGCCTGGCTTAGTCTTGTTTACGCATGAACTTCAAAATCATACTGCGACGGAATATTTTGTTTCATCGCGACG
TATGTTTGAACCTAGAAAACCTACCGTTAGTGATTTTGTTCAAATTGAGAGTTGTGTGGTCACCTATGTCAATTTGA
CTAGAGACCAACTACCAGATGTAATCCCAGATTACATCGATGTTAACAAAACACTTGATGAGATTTTAGCTTCTCTG
CCCAATAGAACTGGTCCAAGTCTTCCTTTAGATGTTTTTAATGCCACTTATCTTAATCTCACTGGTGAAATTGCAGAT
TTAGAGCAGCGTTCAGAGTCTCTCCGTAATACTACAGAGGAGCTCCAAAGTCTTATATATAATATCAACAACACACT
AGTTGACCTTGAGTGGCTCAACCGAGTTGAGACATATATCAAGTGGCCGTGGTGGGTTTGGTTGATTATTTTCATT
GTTCTCATCTTTGTTGTGTCATTACTAGTGTTCTGCTGCATTTCCACGGGTTGTTGTGGATGCTGCGGCTGCTGCTGT
GCTTGTTTCTCAGGTTGTTGTAGGGGTCCTAGACTTCAACCTTACGAAGTTTTTGAAAAGGTCCACGTGCAGTGA 24,800-25,474- Coronavirus NS3b nt – SEQ ID NO: 4

ATGTTTCTTGGACTTTTTCAATACACGATTGACACAGTTGTCAAAGATGTCTCAAAGTCTGCTAACTTGTCTTTGGAT
GCTGTCCAAGAGTTGGAGCTCAATGTAGTTCCAATTAGACAAGCTTCAAATGTGACGGGTTTTCTTTTCACCAGTGT
TTTTATCTACTTCTTTGCACTGTTTAAAGCGTCTTCTTTGAGGCGCAATTATATTATGTTGGCAGCGCGTTTTGCTGT
CATTGTTCTTTATTGCCCACTTTTATATTATTGTGGTGCATTTTTAGATGCAACTATTATTTGTTGCACACTTATTGGC
AGGCTTTGTTTAGTCTGCTTTTACTCCTGGCGCTATAAAAATGCGCTCTTTATTATTTTTAATACTACGACACTTTCTT
TCCTCAATGGTAAAGCAGCTTATTATGACGGCAAATCCATTGTGATTTTAGAAGGTGGTGACCATTACATCACTTTT
GGCAACTCTTTTGTTGCTTTTGTTAGTAGCATCGACTTGTATCTAGCTATACGTGGGCGGCAAGAAGCTGACCTACA
GCTGTTGCGAACTGTTGAGCTTCTTGATGGCAAGAAGCTTTATGTCTTTTCGCAACATCAAATTGTTGGCATTACTA
ATGCTGCATTTGACTCAATTCAACTAGACGAGTATGCTACAATTAGTGAATGA 25,474-25,705-Envelope protein nt – SEQ ID NO: 5

ATGCTACAATTAGTGAATGATAATGGTCTAGTAGTTAATGTTATACTTTGGCTTTTCGTACTCTTTTTCCTGCTTATT
ATAAGCATTACTTTCGTCCAATTGGTTAATCTGTGCTTCACTTGTCACCGGTTGTGTAATAGCGCAGTTTACACACCT
ATAGGGCGTTTGTATAGAGTTTATAAGTCTTACATGCAAATAGACCCCCTCCCTAGTACTGTTATTGACGTATAA

Figure 1M

Intergenic region A – SEQ ID NO: 6

ACGAAAT 25,713-26,393-Membrane protein nt – SEQ ID NO: 7

ATGTCTAACGGTTCTATTCCCGTTGATGAGGTGATTCAACACCTTAGAAACTGGAATTTCACATGGAATATCATACT
GACGATACTACTTGTAGTGCTTCAGTATGGCCATTACAAGTACTCTGCGTTCTTGTATGGTGTCAAGATGGCTATTC
TATGGATACTTTGGCCTCTTGTGTTAGCACTGTCACTTTTTGATGCATGGGCTAGCTTTCAGGTCAATTGGGTCTTTT
TTGCTTTCAGCATCCTTATGGCTTGCATCACTCTTATGCTGTGGATAATGTACTTTGTCAATAGCATTCGGTTGTGGC
GCAGGACACATTCTTGGTGGTCTTTCAATCCTGAAACAGACGCGCTTCTCACTACTTCTGTGATGGGCCGACAGGT
CTGCATTCCAGTGCTTGGAGCACCAACTGGTGTAACGCTAACACTCCTTAGTGGTACATTGCTTGTAGAGGGCTAT
AAGGTTGCTACTGGCGTACAGGTAAGTCAATTACCTAATTTCGTCACAGTCGCCAAGGCCACTACAACAATTGTCT
ACGGACGTGTTGGTCGTTCAGTCAATGCTTCATCTGGCACTGGTTGGGCTTTCTATGTCCGGTCCAAACACGGCGA
CTACTCAGCTGTGAGTAATCCGAGTTCGGTTCTCACAGATAGTGAGAAAGTGCTTCATTTAGTCTAA

Intergenic region B – SEQ ID NO: 8

ACAGAAACTTT 26,405-27,730-Nucleoprotein nt – SEQ ID NO: 9

ATGGCTTCTGTCAGTTTTCAGGATCGTGGCCGCAAACGGGTGCCATTATCCCTCTATGCCCCTCTTAGGGTTACTAA
TGACAAACCCCTTTCTAAGGTACTTGCAAATAATGCTGTACCCACTAATAAAGGAAATAAGGACCAGCAAATTGGA
TACTGGAATGAGCAAATTCGCTGGCGCATGCGCCGTGGTGAGCGAATTGAACAACCTTCCAATTGGCATTTCTACT
ACCTCGGAACAGGACCTCACGCCGACCTCCGCTATAGGACTCGTACTGAGGGTGTTTTCTGGGTTGCTAAAGAAG
GCGCAAAGACTGAACCCACTAACCTGGGTGTCAGAAAGGCGTCTGAAAAGCCAATTATTCCAAATTTCTCTCAACA
GCTTCCCAGCGTAGTTGAGATTGTTGAACCTAACACACCTCCTACTTCACGTGCAAATTCACGTAGCAGGAGTCGT
GGTAATGGCAACAACAGGTCCAGATCTCCAAGTAACAACAGAGGCAATAACCAGTCCCGCGGTAATTCACAGAAT
CGTGGAAATAACCAGGGTCGTGGAGCTTCTCAGAACAGAGGAGGCAATAATAATAACAATAACAAGTCTCGTAAC
CAGTCCAAGAACAGAAACCAGTCAAATGACCGTGGTGGTGTAACATCACGCGATGATCTGGTGGCTGCTGTCAAG
GATGCCCTTAAATCTTTGGGTATTGGCGAAAACCCTGACAAGCTTAAGCAACAGCAGAAGCCCAAACAGGAAAGG

Figure 1N

TCTGACAGCAGCGGCAAAAATACACCTAAGAAGAACAAATCCAGAGCCACTTCGAAAGAACGTGACCTCAAAGAC
ATCCCAGAGTGGAGGAGAATTCCCAAGGGCGAAAATAGCGTAGCAGCTTGCTTCGGACCCAGGGGAGGCTTCAA
AAATTTTGGAGATGCGGAATTTGTCGAAAAAGGTGTTGATGCCTCAGGCTATGCTCAGATCGCCAGTTTAGCACCA
AATGTTGCAGCATTGCTCTTTGGTGGTAATGTGGCTGTTCGTGAGCTAGCGGACTCTTACGAGATTACATATAATT
ATAAAATGACTGTGCCAAAGTCTGATCCAAATGTAGAGCTTCTTGTTTCACAGGTGGATGCATTTAAAACTGGGAA
TGCAAAACCCCAGAGAAAGAAGGAAAAGAAGAACAAGCGTGAAACCACGCAGCAGCTGAATGAAGAGGCCATCT
ACGATGATGTGGGTGTGCCATCTGATGTGACTCATGCCAATTTGGAATGGGACACAGCTGTTGATGGTGGTGACA
CGGCCGTTGAAATTATCAACGAGATCTTCGACACAGGAAATTAA 27,731-28,064-3'UTR nt – SEQ ID NO: 10

ACAATGTTTGACTGGCTTATCCTGGCTATGTCCCAGGGTAGTGCCATTACACTGTTATTACTGAGTGTTTTTCTAGC
GACTTGGCTGCTGGGCTATGGCTTTGCCCTCTAACTAGCGGTCTTGGTCTTGCACACAACGGTAAGCCAGTGGTAA
TGTCAGTGCAAGAAGGATATTACCATAGCACTGTCATGAGGGGAACGCAGTACCTTTTCATCTAAACCTTTGCACG
AGTAATCAAAGATCCGCTTGACGAGCCTATATGGAAGAGCGTGCCAGGTATTTGACTCAAGGACTGTTAGTAACT
GAAGACCTGACGGTGTTGATATGGATACAC

FIGURE 1O

ORF1a/ORF1b aa – SEQ ID NO: 11

MASNHVTLAFANDAEISAFGFCTASEAVSYYSEAAASGFMQCRF
VSFDLADTVEGLLPEDYVMVVVGTTKLSAYVDTFGSRPKNICGWLLFSNCNYFLEELE
LTFGRRGGNIVPVDQYMCGADGKPVLQESEWEYTDFFADSEDGQLNIAGITYVKAWIV
ERSDVSYASQNLTSIKSITYCSTYEHTFPDGTAMKVARTPKIKKTVVLSEPLATIYRE
IGSPFVDNGSDARSIIKRPVFLHAFVKCKCGSYHWTVGDWTSYVSTCCGFKCKPVLVA
SCSATPGSVVVTRAGAGTGVKYYNNMFLRHVADIDGLAFWRILKVQSKDDLACSGKFL
EHHEEGFTDPCYFLNDSSIATKLKFDILSGKFSDEVKQAIFAGHVVVGSALVDIVDDA
LGQPWFIRKLGDLASAAWEQLKAVVRGLNLLSDEVVLFGKRLSCATLSIVNGVFEFIA
EVPEKLAAAVTVFVNFLNELFESACDCLKVGGKTFNKVGSYVLFDNALVKLVKAKVRG
PRQAGVCEVRYTSLVIGSTTKVVSKRVENANVNLVVVDEDVTLNTTGRTVVVDGLAFF
ESDGFYRHLADADVVIEHPVYKSACELKPVFECDPIPDFPMPVAASVAELCVQTDLLL
KNYNTPYKTYSCVVRGDKCCITCTLHFTAPSYMEAAANFVDLCTKNIGTAGFHEFYIT
AHEQQDLQGFVTTCCTMSGFECFMPIIPQCPAVLEEIDGGSIWRSFITGLNTMWDFCK
HLKVSFGLDGIVVTVARKFKRLGALLAEMYNTYLSTVVENLVLAGVSFKYYATSVPKI
VLGCCFHSVKSVLASAFQIPVQAGVEKFKVFLNCVHPVVPRVIETSFVELEETTFKPP
ALNGSIAIVDGFAFYYDGTLYYPTDGNSVVPICFKKKGGGDVKFSDEVSVKTIDPVYK
VSLEFEFESETIMAVLNKAVGNCIKVTGGWDDVVEYINVAIEVLKDHIDVPKYYIYDE
EGGTDPNLPVMVSQWPLNDDTISQDLLDVEVVTDAPVDFEGDEVDSSDPDKVADVANS
EPEDDGLNVAPETNVESEVEEVAATLSFIKDTPSTVTKDPFAFDFASYGGLKVLRQSH
NNCWVTSTLVQLQLLGIVDDPAMELFSAGRVGPMVRKCYESQKAILGSLGDVSACLES
LTKDLHTLKITCSVVCGCGTGERIYDGCAFRMTPTLEPFPYGACAQCAQVLMHTFKSI
VGTGIFCRDTTALSLDSLVVKPLCAAAFIGKDSGHYVTNFYDAAMAIDGYGRHQIKYD
TLNTICVKDVNWTAPFVPDVEPVLEPVVKPFYSYKNVDFYQGDFSDLVKLPCDFVVNA
ANENLSHGGGIAKAIDVYTKGMLQKCSNDYIKAHGPIKVGRGVMLEALGLKVFNVVGP
RKGKHAPELLVKAYKSVFANSGVALTPLISVGIFSVPLEESLSAFLACVGDRHCKCFC
YSDKEREAIINYMDGLVDAIFKDALVDTTPVQEDVQQVSQKPVLPNFEPFRIEGAHAF
YECNPEGLMSLGADKLVLFTNSNLDFCSVGKCLNNVTGGALLEAINVFKKSNKTVPAG
NCVTFECADMISITMVVLPSDGDANYDKNYARAVVKVSKLKGKLLLAVGDAMLYSKLS
HLSVLGFVSTPDDVERFYANKSVVIKVTEDTRSVKTVKVESTVTYGQQIGPCLVNDTV
VTDNKPVVADVVAKVVPSANWDSHYGFDKAGEFHMLDHTGFAFPSEVVNGRRVLKTTD
NNCWVNVTCLQLQFARFRFKSAGLQAMWESYCTGDVAMFVHWLYWLTGVDKGQPSDSE
NALNMLSKYIVPAGSVTIERVTHDGCCCSKRVVTAPVVNASVLKLGVEDGLCPHGLNY
IDKVVVVKGTTIVVNVGKPVVAPSHLFLKGVSYTTFLDNGNGVAGHYTVFDHDTGMVH
DGDVFVPGDLNVSPVTNVVVSEQTAVVIKDPVKKVELDATKLLDTMNYASERFFSFGD
FMSRNLITVFLYILSILGLCFRAFRKRDVKVLAGVPQRTGIILRKSVRYNAKALGVFF
KLKLYWFKVLGKFSLGIYALYALLFMTIRFTPIGGPVCDDVVAGYANSSFDKNEYCNS
VICKVCLYGYQELSDFSHTQVVWQHLRDPLIGNVMPFFYLAFLAIFGGVYVKAITLYF
IFQYLNILGVFLGLQQSIWFLQLVPFDVFGDEIVVFFIVTRVLMFLKHVFLGCDKASC
VACSKSARLKRVPVQTIFQGTSKSFYVHANGGSKFCKKHNFFCLNCDSYGPGCTFIND
VIATEVGNVVKLNVQPTGPATILIDKVEFSNGFYYLYSGDTFWKYNFDITDNKYTCKE
SLKNCSIITDFIVFNNNGSNVNQVKNACVYFSQMLCKPVKLVDSALLASLSVDFGASL
HSAFVSVLSNSFGKDLSSCNDMQDCKSTLGFDDVPLDTFNAAVAEAHRYDVLLTDMSF

Figure 1P

NNFTTSYAKPEEKLPVHDIATCMRVGAKIVNHNVLVKDSIPVVWLVRDFIALSEETRK
YIIRTTKVKGITFMLTFNDCRMHTTIPTVCIANKKGAGLPSFSKVKKFFWFLCLFIVA
VFFALSFFDFSTQVSSDSDYDFKYIESGQLKTFDNPLSCVHNVFSNFDQWHDAKFGFT
PVNNPSCPIVVGVSDEARTVPGIPAGVYLAGKTLVFAINTIFGTSGLCFDASGVADKG
ACIFNSACTTLSGLGGTAVYCYKNGLVEGAKLYSELAPHSYYKMVDGNAVSLPEIISR
GFGIRTIRTKAMTYCRVGQCVQSAEGVCFGADRFFVYNAESGSDFVCGTGLFTLLMNV
ISVFSKTVPVTVLSGQILFNCIIAFAAVAVCFLFTKFKRMFGDMSVGVFTVGACTLLN
NVSYIVTQNTLGMLGYATLYFLCTKGVRYMWIWHLGFLISYILIAPWWVLMVYAFSAI
FEFMPNLFKLKVSTQLFEGDKFVGSFENAAAGTFVLDMHAYERLANSISTEKLRQYAS
TYNKYKYYSGSASEADYRLACFAHLAKAMMDYASNHNDTLYTPPTVSYNSTLQAGLRK
MAQPSGVVEKCIVRVCYGNMALNGLWLGDTVICPRHVIASSTTSTIDYDYALSVLRLH
NFSISSGNVFLGVVGVTMRGALLQIKVNQNNVHTPKYTYRTVRPGESFNILACYDGSA
AGVYGVNMRSNYTIRGSFINGACGSPGYNINNGTVEFCYLHQLELGSGCHVGSDLDGV
MYGGYEDQPTLQVEGASSLFTENVLAFLYAALINGSTWWLSSSRIAVDRFNEWAVHNG
MTTVVNTDCFSILAAKTGVDVQRLLASIQSLHKNFGGKQILGYTSLTDEFTTGEVIRQ
MYGVNLQSGYVSRACRNVLLVGSFLTFFWSELVSYTKFFWVNPGYVTPMFACLSLLSS
LLMFTLKHKTLFFQVFLIPALIVTSCINLAFDVEVYNYLAEHFDYHVSLMGFNAQGLV
NIFVCFVVTILHGTYTWRFFNTPVSSVTYVVALLTAAYNYFYASDILSCAMTLFASVT
GNWFVGAVCYKAAVYMALRFPTFVAIFGDIKSVMFCYLVLGYFTCCFYGILYWFNRFF
KVSVGVYDYTVSAAEFKYMVANGLRAPTGTLDSLLLSAKLIGIGGERNIKISSVQSKL
TDIKCSNVVLLGCLSSMNVSANSTEWAYCVDLHNKINLCNDPEKAQEMLLALLAFFLS
KNSAFGLDDLLESYFNDNSMLQSVASTYVGLPSYVIYENARQQYEDAVNNGSPPQLVK
QLRHAMNVAKSEFDREASTQRKLDRMAEQAAAQMYKEARAVNRKSKVVSAMHSLLFGM
LRRLDMSSVDTILNLAKDGVVPLSVIPAVSATKLNIVTSDIDSYNRIQREGCVHYAGT
IWNIIDIKDNDGKVVHVKEVTAQNAESLSWPLVLGCERIVKLQNNEIIPGKLKQRSIK
AEGDGIVGEGKALYNNEGGRTFMYAFISDKPDLRVVKWEFDGGCNTIELEPPRKFLVD
SPNGAQIKYLYFVRNLNTLRRGAVLGYIGATVRLQAGKQTEQAINSSLLTLCAFAVDP
AKTYIDAVKSGHKPVGNCVKMLANGSGNGQAVTNGVEASTNQDSYGGASVCLYCRAHV
EHPSMDGFCRLKGKYVQVPLGTVDPIRFVLENDVCKVCGCWLANGCTCDRSIMQSTDY
GLFKRVRGSSAARLEPCNGTDTQHVYRAFDIYNKDVACLGKFLKVNCVRLKNLDKHDA
FYVVKRCTKSAMEHEQSIYSRLEKCGAVAEHDFFTWKDGRAIYGNVCRKDLTEYTMMD
LCYALRNFDENNCDVLKSILIKVGACEESYFNNKVWFDPVENEDIHRVYALLGTIVSR
AMLKCVKFCDAMVEQGIVGVVTLDNQDLNGDFYDFGDFTCSIKGMGIPICTSYYSYMM
PVMGMTNCLASECFVKSDIFGEDFKSYDLLEYDFTEHKTALFNKYFKYWGLQYHPNCV
DCSDEQCIVHCANFNTLFSTTIPITAFGPLCRKCWIDGVPLVTTAGYHFKQLGIVWNN
DLNLHSSRLSINELLQFCSDPALLIASSPALVDQRTVCFSVAALGTGMTNQTVKPGHF
NKEFYDFLLEQGFFSEGSELTLKHFFFAQKGDAAVKDFDYYRYNRPTVLDICQARVVY
QIVQRYFDIYEGGCITAKEVVVTNLNKSAGYPLNKFGKAGLYYESLSYEEQDELYAYT
KRNILPTMTQLNLKYAISGKERARTVGGVSLLSTMTTRQYHQKHLKSIVNTRGASVVI
GTTKFYGGWDNMLKNLIDGVENPCLMGWDYPKCDRALPNMIRMISAMILGSKHTTCCS
STDRFFRLCNELAQVLTEVVYSNGGFYLKPGGTTSGDATTAYANSVFNIFQAVSANVN
KLLSVDSNVCHNLEVKQLQRKLYECCYRSTTVDDQFVVEYYGYLRKHFSMMILSDDGV
VCYNNDYASLGYVADLNAFKAVLYYQNNVFMSASKCWIEPDINKGPHEFCSQHTMQIV
DKDGTYYLPYPDPSRILSAGVFVDDVVKTDAVVLLERYVSLAIDAYPLSKHENPEYKK

Figure 1Q

VFYVLLDWVKHLYKTLNAGVLESFSVTLLEDSTAKFWDESFYANMYEKSAVLQSAGLC
VVCGSQTVLRCGDCLRRPMLCTKCAYDHVIGTTHKFILAITPYVCCASDCGVNDVTKL
YLGGLSYWCHDHKPRLAFPLCSAGNVFGLYKNSATGSPDVEDFNRIATSDWTDVSDYR
LANDVKDSLRLFAAETIKAKEESVKSSYACATLHEVVGPKELLLKWEVGRPKPPLNRN
SVFTCYHITKNTKFQIGEFVFEKAEYDNDAVTYKTTATTKLVPGMVFVLTSHNVQPLR
APTIANQERYSTIHKLHPAFNIPEAYSSLVPYYQLIGKQKITTIQGPPGSGKSHCVIG
LGLYYPGARIVFTACSHAAVDSLCVKASTAYSNDKCSRIIPQRARVECYDGFKSNNTS
AQYLFSTVNALPECNADIVVVDEVSMCTNYDLSVINQRISYRHVVYVGDPQQLPAPRV
MISRGTLEPKDYNVVTQRMCALKPDVFLHKCYRCPAEIVRTVSEMVYENQFIPVHPDS
KQCFKIFCKGNVQVDNGSSINRRQLDVVRMFLAKNPRWSKAVFISPYNSQNYVASRML
GLQIQTVDSSQGSEYDYVIYTQTSDTAHACNVNRFNVAITRAKKGILCIMCDRSLFDV
LKFFELKLSDLQANEGCGLFKDCSRGDDLLPPSHANTFMSLADNFKTDQDLAVQIGVN
GPIKYEHVISFMGFRFDINIPNHHTLFCTRDFAMRNVRGWLGFDVEGAHVVGSNVGTN
VPLQLGFSNGVDFVVRPEGCVVTESGDYIKPVRARAPPGEQFAHLLPLLKRGQPWDVV
RKRIVQMCSDYLANLSDILIFVLWAGGLELTTMRYFVKIGPSKSCDCGKVATCYNSAL
HTYCCFKHALGCDYLYNPYCIDIQQWGYKGSLSLNHHEHCNVHRNEHVASGDAIMTRC
LAIHDCFVKNVDWSITYPFIGNEAVINKSGRIVQSHTMRSVLKLYNPKAIYDIGNPKG
IRCAVTDAKWFCFDKNPTNSNVKTLEYDYITHGQFDGLCLFWNCNVDMYPEFSVVCRF
DTRCRSPLNLEGCNGGSLYVNNHAFHTPAFDKRAFAKLKPMPFFFYDDTECDKLQDSI
NYVPLRASNCITKCNVGGAVCSKHCAMYHSYVNAYNTFTSAGFTIWVPTSFDTYNLWQ
TFSNNLQGLENIAFNVVKKGSFVGAEGELPVAVVNDKVLVRDGTVDTLVFTNKTSLPT
NVAFELYAKRKVGLTPPITILRNLGVVCTSKCVIWDYEAERPLTTFTKDVCKYTDFEG
DVCTLFDNSIVGSLERFSMTQNAVLMSLTAVKKLTGIKLTYGYLNGVPVNTHEDKPFT
WYIYTRKNGKFEDHPDGYFTQGRTTADFSPRSDMEKDFLSMDMGLFINKYGLEDYGFE
HVVYGDVSKTTLGGLHLLISQVRLACMGVLKIDEFVSSNDSTLKSCTVTYADNPSSKM
VCTYMDLLLDDFVSILKSLDLGVVSKVHEVMVDCKMWRWMLWCKDHKLQTFYPQLQAS
EWKCGYSMPSIYKIQRMCLEPCNLYNYGAGIKLPDGIMFNVVKYTQLCQYLNSTTMCV
PHHMRVLHLGAGSDKGVAPGTAVLRRWLPLDAIIVDNDSVDYVSDADYSVTGDCSTLY
LSDKFDLVISDMYDGKIKSCDGENVSKEGFFPYINGVITEKLALGGTVAIKVTEFSWN
KKLYELIQRFEYWTMFCTSVNTSSSEAFLIGVHYLGDFASGAVIDGNTMHANYIFWRN
STIMTMSYNSVLDLSKFNCKHKATVVINLKDSSISDVVLGLLKNGKLLVRNNDAICGF
SNHLVNVNK

Spike (S domain) protein aa – SEQ ID NO: 12

MKSLTYFWLFLPVLSTLSLPQDVTRCSANTNFRRFFSKFNVQAPAVVVLGGYLPIGENQG
VNSTWYCAGQHPTASGVHGIFVSHIRGGHGFEIGISQEPFDPSGYQLYLHKATNGNTNAT
ARLRICQFPSIKTLGPTANNDVTTGRNCLFNKAIPAHMSEHSVVGITWDNDRVTVFSDKI
YYFYFKNDWSRVATKCYNSGGCAMQYVYEPTYYMLNVTSAGEDGISYQPCTANCIGYAAN
VFATEPNGHIPEGFSFNNWFLLSNDSTLVHGKVVSNQPLLVNCLLAIPKIYGLGQFFSFN

Figure 1R

QTIDGVCNGAAVQRAPEALRFNINDTSVILAEGSIVLHTALGTNFSFVCSNSSNPHLATF
AIPLGATQVPYYCFLKVDTYNSTVYKFLAVLPPTVREIVITKYGDVYVNGFGYLHLGLLD
AVTINFTGHGTDDDVSGFWTIASTNFVDALIEVQGTAIQRILYCDDPVSQLKCSQVAFDL
DDGFYPISSRNLLSHEQPISFVTLPSFNDHSFVNITVSASFGGHSGANLIASDTTINGFS
SFCVDTRQFTISLFYNVTNSYGYVSKSQDSNCPFTLQSVNDYLSFSKFCVSTSLLASACT
IDLFGYPEFGSGVKFTSLYFQFTKGELITGTPKPLEGVTDVSFMTLDVCTKYTIYGFKGE
GIITLTNSSFLAGVYYTSDSGQLLAFKNVTSGAVYSVTPCSFSEQAAYVDDDIVGVISSL
SSSTFNSTRELPGFFYHSNDGSNCTEPVLVYSNIGVCKSGSIGYVPSQSGQVKIAPTVTG
NISIPTNFSMSIRTEYLQLYNTPVSVDCATYVCNGNSRCKQLLTQYTAACKTIESALQLS
ARLESVEVNSMLTISEEALQLATISSFNGDGYNFTNVLGVSVYDPASGRVVQKRSFIEDL
LFNKVVTNGLGTVDEDYKRCSNGRSVADLVCAQYYSGVMVLPGVVDAEKLHMYSASLIGG
MVLGGFTSAAALPFSYAVQARLNYLALQTDVLQRNQQLLAESFNSAIGNITSAFESVKEA
ISQTSKGLNTVAHALTKVQEVVNSQGAALTQLTVQLQHNFQAISSSIDDIYSRLDILSAD
VQVDRLITGRLSALNAFVSQTLTKYTEVQASRKLAQQKVNECVKSQSQRYGFCGGDGEHI
FSLVQAAPQGLLFLHTVLVPSDFVDVIAIAGLCVNDEIALTLREPGLVLFTHELQNHTAT
EYFVSSRRMFEPRKPTVSDFVQIESCVVTYVNLTRDQLPDVIPDYIDVNKTLDEILASLP
NRTGPSLPLDVFNATYLNLTGEIADLEQRSESLRNTTEELQSLIYNINNTLVDLEWLNRV
ETYIKWPWWVWLIIFIVLIFVVSLLVFCCISTGCCGCCGCCCACFSGCCRGPRLQPYEVF
EKVHVQ

ORF3 Coronavirus NS3b Protein aa – SEQ ID NO: 13

MFLGLFQYTIDTVVKDVSKSANLSLDAVQELELNVVPIRQASNVTGFLFTSVFIYFFALF
KASSLRRNYIMLAARFAVIVLYCPLLYYCGAFLDATIICCTLIGRLCLVCFYSWRYKNAL
FIIFNTTTLSFLNGKAAYYDGKSIVILEGGDHYITFGNSFVAFVSSIDLYLAIRGRQEAD
LQLLRTVELLDGKKLYVFSQHQIVGITNAAFDSIQLDEYATISE

Envelope protein aa – SEQ ID NO: 14

MLQLVNDNGLVVNVILWLFVLFFLLIISITFVQLVNLCFTCHRLCNSAVYTPIGRLYRVY
KSYMQIDPLPSTVIDV

Membrane protein aa – SEQ ID NO: 15

MSNGSIPVDEVIQHLRNWNFTWNIILTILLVVLQYGHYKYSAFLYGVKMAILWILWPLVL
ALSLFDAWASFQVNWVFFAFSILMACITLMLWIMYFVNSIRLWRRTHSWWSFNPETDALL
TTSVMGRQVCIPVLGAPTGVTLTLLSGTLLVEGYKVATGVQVSQLPNFVTVAKATTTIVY
GRVGRSVNASSGTGWAFYVRSKHGDYSAVSNPSSVLTDSEKVLHLV

Figure 1S

Nucleoprotein aa – SEQ ID NO: 16

MASVSFQDRGRKRVPLSLYAPLRVTNDKPLSKVLANNAVPTNKGNKDQQIGYWNEQIRWR
MRRGERIEQPSNWHFYYLGTGPHADLRYRTRTEGVFWVAKEGAKTEPTNLGVRKASEKPI
IPNFSQQLPSVVEIVEPNTPPTSRANSRSRSRGNGNNRSRSPSNNRGNNQSRGNSQNRGN
NQGRGASQNRGGNNNNNNKSRNQSKNRNQSNDRGGVTSRDDLVAAVKDALKSLGIGENPD
KLKQQQKPKQERSDSSGKNTPKKNKSRATSKERDLKDIPEWRRIPKGENSVAACFGPRGG
FKNFGDAEFVEKGVDASGYAQIASLAPNVAALLFGGNVAVRELADSYEITYNYKMTVPKS
DPNVELLVSQVDAFKTGNAKPQRKKEKKNKRETTQQLNEEAIYDDVGVPSDVTHANLEWD
TAVDGGDTAVEIINEIFDTGN

Figure 2A nt = SEQ ID NO: 3 aa = SEQ ID NO: 12

```
atgaagtctttaacctacttctggttgttcttaccagtactttcaacacttagcctacca
 M  K  S  L  T  Y  F  W  L  F  L  P  V  L  S  T  L  S  L  P
caagatgtcaccaggtgctcagctaacactaattttaggcggttcttttcaaaatttaat
 Q  D  V  T  R  C  S  A  N  T  N  F  R  R  F  F  S  K  F  N
gttcaggcgcctgcagttgttgtactgggcggttatctacctattggtgaaaaccagggt
 V  Q  A  P  A  V  V  V  L  G  G  Y  L  P  I  G  E  N  Q  G
gtcaattcaacttggtactgtgctggccaacatccaactgctagtggcgttcatggtatc
 V  N  S  T  W  Y  C  A  G  Q  H  P  T  A  S  G  V  H  G  I
tttgttagccatattagaggtggtcatggctttgagattggcatttcgcaagagcctttt
 F  V  S  H  I  R  G  G  H  G  F  E  I  G  I  S  Q  E  P  F
gaccctagtggttaccagctttatttacataaggctactaacggtaacactaatgctact
 D  P  S  G  Y  Q  L  Y  L  H  K  A  T  N  G  N  T  N  A  T
gcgcgactgcgcatttgccagtttcctagcattaaaacattgggccccactgctaataat
 A  R  L  R  I  C  Q  F  P  S  I  K  T  L  G  P  T  A  N  N
gatgttacaacaggtcgtaattgcctatttaacaaagccatcccagctcatatgagtgaa
 D  V  T  T  G  R  N  C  L  F  N  K  A  I  P  A  H  M  S  E
catagtgttgtcggcataacatgggataatgatcgtgtcactgtcttttctgacaagatc
 H  S  V  V  G  I  T  W  D  N  D  R  V  T  V  F  S  D  K  I
tattatttttattttaaaaatgattggtcccgtgttgcgacaaagtgttacaacagtgga
 Y  Y  F  Y  F  K  N  D  W  S  R  V  A  T  K  C  Y  N  S  G
ggttgtgctatgcaatatgtttacgaacccacctattacatgcttaatgttactagtgct
 G  C  A  M  Q  Y  V  Y  E  P  T  Y  Y  M  L  N  V  T  S  A
Ggtgaggatggtatttcttatcaaccctgtacagctaattgcattggttatgctgccaat
 G  E  D  G  I  S  Y  Q  P  C  T  A  N  C  I  G  Y  A  A  N
gtatttgctactgagcccaatggccacataccagaaggttttagttttaataattggttt
 V  F  A  T  E  P  N  G  H  I  P  E  G  F  S  F  N  N  W  F
cttttgtccaatgattccactttggtgcatggtaaggtggtttccaaccaaccattgttg
 L  L  S  N  D  S  T  L  V  H  G  K  V  V  S  N  Q  P  L  L
gtcaattgtcttttggccattcctaagatttatggactaggccaatttttctcctttaat
 V  N  C  L  L  A  I  P  K  I  Y  G  L  G  Q  F  F  S  F  N
caaacgatcgatggtgtttgtaatggagctgctgtgcagcgtgcaccagaggctctgagg
 Q  T  I  D  G  V  C  N  G  A  A  V  Q  R  A  P  E  A  L  R
tttaatattaatgacacctctgtcattcttgctgaaggctcaattgtacttcatactgct
 F  N  I  N  D  T  S  V  I  L  A  E  G  S  I  V  L  H  T  A
ttaggaacaaatttttcttttgtttgcagtaattcctcaaatcctcacttagccaccttc
 L  G  T  N  F  S  F  V  C  S  N  S  S  N  P  H  L  A  T  F
gccatacctctgggtgctacccaagtaccttattattgtttcttaaagtggatacttac
 A  I  P  L  G  A  T  Q  V  P  Y  Y  C  F  L  K  V  D  T  Y
aactccactgtttataaatttttggctgttttacctcctaccgtcagggaaattgtcatc
 N  S  T  V  Y  K  F  L  A  V  L  P  P  T  V  R  E  I  V  I
accaagtatggtgatgtttatgtcaatgggtttggatacttgcatctcggtttgttggat
 T  K  Y  G  D  V  Y  V  N  G  F  G  Y  L  H  L  G  L  L  D
gctgtcacaattaatttcactggtcatggcactgacgatgatgtttctggtttttggacc
 A  V  T  I  N  F  T  G  H  G  T  D  D  D  V  S  G  F  W  T
atagcatcgactaattttgttgatgcactcatcgaagttcaaggaaccgccattcagcgt
 I  A  S  T  N  F  V  D  A  L  I  E  V  Q  G  T  A  I  Q  R
attctttattgtgatgatcctgttagccaactcaagtgttctcaggttgcttttgacctt
 I  L  Y  C  D  D  P  V  S  Q  L  K  C  S  Q  V  A  F  D  L
```

Figure 2B

```
gacgatggtttttaccctatttcttctagaaaccttctgagtcatgaacagccaatttct
 D   D   G   F   Y   P   I   S   S   R   N   L   L   S   H   E   Q   P   I   S
tttgttactctgccatcatttaatgatcattcttttgttaacattactgtatctgcttcc
 F   V   T   L   P   S   F   N   D   H   S   F   V   N   I   T   V   S   A   S
tttggtggtcatagtggtgccaaccttattgcatctgacactactatcaatgggtttagt
 F   G   G   H   S   G   A   N   L   I   A   S   D   T   T   I   N   G   F   S
tctttctgtgttgacactagacaatttaccatttcactgttttataacgttacaaacagt
 S   F   C   V   D   T   R   Q   F   T   I   S   L   F   Y   N   V   T   N   S
tatggttatgtgtctaaatcacaggacagtaattgccctttcaccttgcaatctgttaat
 Y   G   Y   V   S   K   S   Q   D   S   N   C   P   F   T   L   Q   S   V   N
gattacctgtctttttagcaaatttgtgtttccaccagcctttttggctagtgcctgtacc
 D   Y   L   S   F   S   K   F   C   V   S   T   S   L   L   A   S   A   C   T
atagatctttttggttaccctgagtttggtagtggtgttaagtttacgtccctttacttt
 I   D   L   F   G   Y   P   E   F   G   S   G   V   K   F   T   S   L   Y   F
caattcacaaagggtgagttgattactggcacgcctaaaccacttgaaggtgtcacggac
 Q   F   T   K   G   E   L   I   T   G   T   P   K   P   L   E   G   V   T   D
gtttcttttatgactctggatgtgtgtaccaagtatactatctatggctttaaaggtgag
 V   S   F   M   T   L   D   V   C   T   K   Y   T   I   Y   G   F   K   G   E
ggtatcattacccttacaaattctagcttttttggcaggtgtttattacacatctgattct
 G   I   I   T   L   T   N   S   S   F   L   A   G   V   Y   Y   T   S   D   S
ggacagttgttagcctttaagaatgtcactagtggtgctgtttattctgttacgccatgt
 G   Q   L   L   A   F   K   N   V   T   S   G   A   V   Y   S   V   T   P   C
tctttttcagagcaggctgcatatgttgatgatgatatagtgggtgttatttctagtttg
 S   F   S   E   Q   A   A   Y   V   D   D   D   I   V   G   V   I   S   S   L
tctagctccacttttaacagtactagggagttgcctggtttcttctaccattctaatgat
 S   S   S   T   F   N   S   T   R   E   L   P   G   F   F   Y   H   S   N   D
ggctctaattgtacagagcctgtgttggtgtatagtaacataggtgtttgtaaatctggc
 G   S   N   C   T   E   P   V   L   V   Y   S   N   I   G   V   C   K   S   G
agtattggctacgtcccatctcagtctggccaagtcaagattgcacccacggttactggg
 S   I   G   Y   V   P   S   Q   S   G   Q   V   K   I   A   P   T   V   T   G
aatattagtattcccaccaactttagtatgagtattaggacagaatatttacagctttac
 N   I   S   I   P   T   N   F   S   M   S   I   R   T   E   Y   L   Q   L   Y
aacacgcctgttagtgttgattgtgccacatatgtttgtaatggtaactctcgttgtaaa
 N   T   P   V   S   V   D   C   A   T   Y   V   C   N   G   N   S   R   C   K
caattactcacccagtacactgcagcatgtaagaccatagagtcagcattacaactcagc
 Q   L   L   T   Q   Y   T   A   A   C   K   T   I   E   S   A   L   Q   L   S
gctaggcttgagtctgttgaagttaactctatgcttactatttctgaagaggctctacag
 A   R   L   E   S   V   E   V   N   S   M   L   T   I   S   E   E   A   L   Q
ttagctaccattagttcgtttaatggtgatggatataattttactaatgtgctgggtgtt
 L   A   T   I   S   S   F   N   G   D   G   Y   N   F   T   N   V   L   G   V
tctgtgtatgatcctgcaagtggcagggtggtacaaaaaaggtcttttattgaagacctg
 S   V   Y   D   P   A   S   G   R   V   V   Q   K   R   S   F   I   E   D   L
ctttttaataaagtggttactaatggccttggtactgttgatgaagactataagcgctgt
 L   F   N   K   V   V   T   N   G   L   G   T   V   D   E   D   Y   K   R   C
tctaatggtcgctctgtggcagatctagtctgtgcacagtattactctggtgtcatggta
 S   N   G   R   S   V   A   D   L   V   C   A   Q   Y   Y   S   G   V   M   V
ctacctggtgttgttgacgctgagaagcttcacatgtatagtgcgtctctcatcggtggt
 L   P   G   V   V   D   A   E   K   L   H   M   Y   S   A   S   L   I   G   G
atggtgctaggaggttttacttctgcagcggcattgcctttttagctatgctgttcaagct
 M   V   L   G   G   F   T   S   A   A   A   L   P   F   S   Y   A   V   Q   A
```

Figure 2C

```
agacccaattatcttgctctacagacggatgttctacagcggaaccagcaattgcttgct
 R  L  N  Y  L  A  L  Q  T  D  V  L  Q  R  N  Q  Q  L  L  A
gagtcttttaactctgctattggtaatataacttcagcctttgagagtgttaaagaggct
 E  S  F  N  S  A  I  G  N  I  T  S  A  F  E  S  V  K  E  A
attagtcaaacttccaagggtttgaacactgtggctcatgcgcttactaaggttcaagag
 I  S  Q  T  S  K  G  L  N  T  V  A  H  A  L  T  K  V  Q  E
gttgttaactcgcagggtgcagctttgactcaacttaccgtacagctgcaacacaacttc
 V  V  N  S  Q  G  A  A  L  T  Q  L  T  V  Q  L  Q  H  N  F
caagccatttctagttctattgatgacatttactctcgactggacattctttcagccgat
 Q  A  I  S  S  S  I  D  D  I  Y  S  R  L  D  I  L  S  A  D
gttcaggttgaccgtctcatcaccggcagattatcagcacttaatgcttttgttgctcaa
 V  Q  V  D  R  L  I  T  G  R  L  S  A  L  N  A  F  V  A  Q
accctcactaagtatactgaggttcaggctagcaggaagttagcacagcaaaaggttaat
 T  L  T  K  Y  T  E  V  Q  A  S  R  K  L  A  Q  Q  K  V  N
gagtgcgttaaatcgcaatctcagcgttatggtttttgtggtggtgatggcgagcacatt
 E  C  V  K  S  Q  S  Q  R  Y  G  F  C  G  G  D  G  E  H  I
ttctctctggtacaggcagcacctcagggcctgctgtttttacatacagtacttgtaccg
 F  S  L  V  Q  A  A  P  Q  G  L  L  F  L  H  T  V  L  V  P
agtgattttgtagatgttattgccatcgctggcttatgcgttaacgatgaaattgccttg
 S  D  F  V  D  V  I  A  I  A  G  L  C  V  N  D  E  I  A  L
actctacgtgagcctggcttagtcttgtttacgcatgaacttcaaaatcatactgcgacg
 T  L  R  E  P  G  L  V  L  F  T  H  E  L  Q  N  H  T  A  T
gaatattttgtttcatcgcgacgtatgtttgaacctagaaaacctaccgttagtgatttt
 E  Y  F  V  S  S  R  R  M  F  E  P  R  K  P  T  V  S  D  F
gttcaaattgagagttgtgtggtcacctatgtcaatttgactagagaccaactaccagat
 V  Q  I  E  S  C  V  V  T  Y  V  N  L  T  R  D  Q  L  P  D
gtaatcccagattacatcgatgttaacaaaacacttgatgagattttagcttctctgccc
 V  I  P  D  Y  I  D  V  N  K  T  L  D  E  I  L  A  S  L  P
aatagaactggtccaagtcttcctttagatgtttttaatgccacttatcttaatctcact
 N  R  T  G  P  S  L  P  L  D  V  F  N  A  T  Y  L  N  L  T
ggtgaaattgcagatttagagcagcgttcagagtctctccgtaatactacagaggagctc
 G  E  I  A  D  L  E  Q  R  S  E  S  L  R  N  T  T  E  E  L
caaagtcttatatataatatcaacaacacactagttgaccttgagtggctcaaccgagtt
 Q  S  L  I  Y  N  I  N  N  T  L  V  D  L  E  W  L  N  R  V
gagacatatatcaagtggccgtggtgggtttggttgattattttcattgttctcatcttt
 E  T  Y  I  K  W  P  W  W  V  W  L  I  I  F  I  V  L  I  F
gttgtgtcattactagtgttctgctgcatttccacgggttgttgtggatgctgcggctgc
 V  V  S  L  L  V  F  C  C  I  S  T  G  C  C  G  C  C  G  C
tgctgtgcttgtttctcaggttgttgtaggggtcctagacttcaaccttacgaagttttt
 C  C  A  C  F  S  G  C  C  R  G  P  R  L  Q  P  Y  E  V  F
gaaaaggtccacgtgcagtga
 E  K  V  H  V  Q  -
```

S1 domain; S2 domain

Figure 3A

Antigenicity Index of Native spike (S domain) sequences

```
Max_score_pos at "*"

(1) SEQ ID NO: 22
Score 1.227 length 18 at residues 38->55
                       *
 Sequence: KFNVQAPAVVVLGGYLPI
            |                 |
           38                 55
 Max_score_pos: 46

(2) SEQ ID NO: 23
Score 1.224 length 38 at residues 259->296
                                    *
 Sequence: WFLLSNDSTLVHGKVVSNQPLLVNCLLAIPKIYGLGQF
            |                                    |
          259                                    296
 Max_score_pos: 282

(3) SEQ ID NO: 24
Score 1.217 length 71 at residues 355->425
                              *
Sequence:PHLATFAIPLGATQVPYYCFLKVDTYNSTVYKFLAVLPPTVREIVI
TKYGDVYVNGFGYLHLGLLDAVTIN
        |
       355             |
                      425

Max_score_pos: 372

(4) SEQ ID NO: 25
Score 1.189 length 33 at residues 691->723
                     *
 Sequence: SGAVYSVTPCSFSEQAAYVDDDIVGVISSLSSS
            |                               |
          691                               723
 Max_score_pos: 697
```

Figure 3B

```
 (5) SEQ ID NO: 26
Score 1.186 length 23 at residues 4->26
                  *
 Sequence: LTYFWLFLPVLSTLSLPQDVTRC
           |                      |
           4                      26
 Max_score_pos: 12

(6) SEQ ID NO: 27
Score 1.179 length 33 at residues 745->777
            *
 Sequence: TEPVLVYSNIGVCKSGSIGYVPSQSGQVKIAPT
           |                                |
         745                                777
 Max_score_pos: 747

(7) SEQ ID NO: 28
Score 1.175 length 39 at residues 569->607
                                *
 Sequence: DSNCPFTLQSVNDYLSFSKFCVSTSLLASACTIDLFGYP
           |                                      |
         569                                      607
 Max_score_pos: 592

(8) SEQ ID NO: 29
Score 1.159 length 15 at residues 326->340
                    *
 Sequence: TSVILAEGSIVLHTA
           |              |
         326              340
 Max_score_pos: 338

(9) SEQ ID NO: 30
Score 1.152 length 22 at residues 458->479
                    *
 Sequence: IQRILYCDDPVSQLKCSQVAFD
           |                     |
         458                     479
 Max_score_pos: 470
```

Figure 3C

```
(10) SEQ ID NO: 31
Score 1.146 length 17 at residues 202->218
                *
 Sequence: CAMQYVYEPTYYMLNVT
           |               |
          202             218
 Max_score_pos: 205

(11) SEQ ID NO: 32
Score 1.143 length 23 at residues 63->85
                              *
 Sequence: STWYCAGQHPTASGVHGIFVSHI
           |                     |
           63                    85
 Max_score_pos: 80

(12) SEQ ID NO: 33
Score 1.141 length 10 at residues 668->677
                  *
 Sequence: SSFLAGVYYT
           |        |
          668      677
 Max_score_pos: 673

(13) SEQ ID NO: 34
Score 1.137 length 15 at residues 304->318
                  *
 Sequence: DGVCNGAAVQRAPEA
           |             |
          304           318
 Max_score_pos: 309

(14) SEQ ID NO: 35
Score 1.136 length 13 at residues 444->456
                   *
 Sequence: TNFVDALIEVQGT
           |           |
          444         456
 Max_score_pos: 450
```

Figure 3D

```
(15) SEQ ID NO: 36
Score 1.130 length 13 at residues 643->655
                 *
 Sequence: FMTLDVCTKYTIY
           |           |
          643         655
 Max_score_pos: 649

(16) SEQ ID NO: 37
Score 1.128 length 14 at residues 122->135
                 *
 Sequence: RLRICQFPSIKTLG
           |            |
          122          135
 Max_score_pos: 128

(17) SEQ ID NO: 38
Score 1.125 length 9 at residues 539->547
             *
 Sequence: FSSFCVDTR
           |       |
          539     547
 Max_score_pos: 541

(18) SEQ ID NO: 39
Score 1.125 length 10 at residues 102->111
                 *
 Sequence: PSGYQLYLHK
           |        |
          102      111
 Max_score_pos: 108

(19) SEQ ID NO: 40
Score 1.123 length 23 at residues 483->505
                             *
 Sequence: GFYPISSRNLLSHEQPISFVTLP
           |                     |
          483                   505
 Max_score_pos: 501
```

Figure 3E

```
(20) SEQ ID NO: 41
Score 1.118 length 9 at residues 550->558
                *
 Sequence: TISLFYNVT
           |       |
          550      558
 Max_score_pos: 554

(21) SEQ ID NO: 42
Score 1.117 length 7 at residues 160->166
                *
 Sequence: EHSVVGI
           |     |
          160    166
 Max_score_pos: 164

(22) SEQ ID NO: 43
Score 1.113 length 19 at residues 226->244
                  *
 Sequence: SYQPCTANCIGYAANVFAT
           |                 |
          226                244
 Max_score_pos: 232

(23) SEQ ID NO: 44
Score 1.111 length 9 at residues 344->352
               *
 Sequence: NFSFVCSNS
           |       |
          344      352
 Max_score_pos: 347

(24) SEQ ID NO: 45
Score 1.107 length 14 at residues 172->185
                      *
 Sequence: RVTVFSDKIYYFYF
           |            |
          172           185
 Max_score_pos: 182
```

Figure 3F

```
(25) SEQ ID NO: 46
Score 1.106 length 8 at residues 681->688
                  *
 Sequence: GQLLAFKN
           |      |
         681      688
 Max_score_pos: 686

(26) SEQ ID NO: 47
Score 1.105 length 13 at residues 610->622
                   *
 Sequence: GSGVKFTSLYFQF
           |           |
         610           622
 Max_score_pos: 616

(27) SEQ ID NO: 48
Score 1.105 length 10 at residues 191->200
                *
 Sequence: RVATKCYNSG
           |        |
         191        200
 Max_score_pos: 194

(28) SEQ ID NO: 49
Score 1.101 length 13 at residues 510->522
                 *
 Sequence: HSFVNITVSASFG
           |           |
         510           522
 Max_score_pos: 514

(29) SEQ ID NO: 50
Score 1.096 length 14 at residues 145->158
                   *
 Sequence: GRNCLFNKAIPAHM
           |            |
         145            158
 Max_score_pos: 151
```

Figure 3G

```
(30) SEQ ID NO: 51
Score 1.091 length 6 at residues 732->737
             *
 Sequence: PGFFYH
           |    |
        732    737
 Max_score_pos: 734

(31) SEQ ID NO: 52
Score 1.076 length 8 at residues 560->567
              *
 Sequence: SYGYVSKS
           |      |
        560      567
 Max_score_pos: 563

(32) SEQ ID NO: 53
Score 1.074 length 7 at residues 635->641
                *
 Sequence: LEGVTDV
           |     |
        635     641
 Max_score_pos: 640

(33) SEQ ID NO: 54
Score 1.033 length 7 at residues 527->533
           *
 Sequence: ANLIASD
           |     |
        527     533
 Max_score_pos: 527
```

Figure 3H

```
Max_score_pos at "*"

(1) SEQ ID NO: 55
Score 1.285 length 55 at residues 540->594

                                             *
Sequence:WVWLIIFIVLIFVVSLLVFCCISTGCCGCCGCCCACFSGCCRGPRL
QPYEVFEKV
          |
         540
         |
        594

 Max_score_pos: 571

(2) SEQ ID NO: 56
Score 1.235 length 21 at residues 425->445
                            *
 Sequence: KPTVSDFVQIESCVVTYVNLT
            |                    |
          425                  445
 Max_score_pos: 439

(3) SEQ ID NO: 57
Score 1.207 length 11 at residues 86->96
                  *
 Sequence: TNVLGVSVYDP
            |         |
           86        96
 Max_score_pos: 91

(4) SEQ ID NO: 58
Score 1.207 length 23 at residues 137->159
                   *
 Sequence: VADLVCAQYYSGVMVLPGVVDAE
            |                      |
          137                    159
 Max_score_pos: 143
```

Figure 3I

```
(5) SEQ ID NO: 59
Score 1.196 length 38 at residues 351->388
                           *
 Sequence: IFSLVQAAPQGLLFLHTVLVPSDFVDVIAIAGLCVNDE
           |                                    |
         351                                    388
 Max_score_pos: 367

(6) SEQ ID NO: 60
Score 1.172 length 23 at residues 5->27
                           *
 Sequence: TEYLQLYNTPVSVDCATYVCNGN
           |                     |
           5                     27
 Max_score_pos: 21

(7) SEQ ID NO: 61
Score 1.152 length 12 at residues 108->119
                 *
 Sequence: IEDLLFNKVVTN
           |          |
         108          119
 Max_score_pos: 114

(8) SEQ ID NO: 62
Score 1.146 length 35 at residues 179->213
                  *
 Sequence: SAAALPFSYAVQARLNYLALQTDVLQRNQQLLAES
           |                                 |
         179                                 213
 Max_score_pos: 186
```

Figure 3J

```
(9) SEQ ID NO: 63
Score 1.139 length 59 at residues 239->297


Sequence:LNTVAHALTKVQEVVNSQGAALTQLTVQLQHNFQAISSSIDDIYSR
      *
LDILSADVQVDRL
         |
       239 |
          297
 Max_score_pos: 291

(10) SEQ ID NO: 64
Score 1.131 length 16 at residues 476->491
                  *
 Sequence: PSLPLDVFNATYLNLT
           |              |
         476             491
 Max_score_pos: 480

(11) SEQ ID NO: 65
Score 1.123 length 14 at residues 390->403
                       *
 Sequence: ALTLREPGLVLFTH
           |            |
         390           403
 Max_score_pos: 400

(12) SEQ ID NO: 66
Score 1.113 length 12 at residues 449->460
              *
 Sequence: LPDVIPDYIDVN
           |          |
         449         460
 Max_score_pos: 451
```

Figure 3K

```
(13) SEQ ID NO: 67
Score 1.112 length 33 at residues 30->62
              *
 Sequence: CKQLLTQYTAACKTIESALQLSARLESVEVNSM
           |                                |
          30                               62
 Max_score_pos: 33

(14) SEQ ID NO: 68
Score 1.111 length 23 at residues 316->338
                               *
 Sequence: YTEVQASRKLAQQKVNECVKSQS
           |                      |
         316                     338
 Max_score_pos: 336

(15) SEQ ID NO: 69
Score 1.111 length 16 at residues 299->314
                      *
 Sequence: TGRLSALNAFVAQTLT
           |              |
         299             314
 Max_score_pos: 310

(16) SEQ ID NO: 70
Score 1.106 length 7 at residues 520->526
                *
 Sequence: NTLVDLE
           |     |
         520    526
 Max_score_pos: 525

(17) SEQ ID NO: 71
Score 1.101 length 11 at residues 66->76
                 *
 Sequence: SEEALQLATIS
           |         |
          66        76
 Max_score_pos: 72
```

Figure 3L

```
(18) SEQ ID NO: 72
Score 1.099 length 7 at residues 511->517
              *
 Sequence: LQSLIYN
           |     |
         511     517
 Max_score_pos: 513

(19) SEQ ID NO: 73
Score 1.098 length 8 at residues 98->105
                  *
 Sequence: SGRVVQKR
           |      |
          98      105
 Max_score_pos: 104

(20) SEQ ID NO: 74
Score 1.092 length 7 at residues 464->470
                *
 Sequence: DEILASL
           |     |
         464     470
 Max_score_pos: 468

(21) SEQ ID NO: 75
Score 1.087 length 12 at residues 161->172
                      *
 Sequence: LHMYSASLIGGM
           |          |
         161          172
 Max_score_pos: 171

(22) SEQ ID NO: 76
Score 1.067 length 8 at residues 411->418
              *
 Sequence: TEYFVSSR
           |      |
         411      418
 Max_score_pos: 413
```

Figure 3M

```
(23) SEQ ID NO: 77
Score 1.058 length 8 at residues 224->231
                  *
 Sequence: AFESVKEA
             |      |
           224      231
Max_score_pos: 231
```

S1S2 = SEQ ID NO: 17

Full = SEQ ID NO: 12

```
S1S2        ------------------------------------------------------------
Full        MKSLTYFWLFLPVLSTLSLPQDVTRCSANTNFRRFFSKFNVQAPAVVVLGGYLPIGENQG
60

S1S2        ------------------------------------------------------------
Full        VNSTWYCAGQHPTASGVHGIFVSHIRGGHGFEIGISQEPFDPSGYQLYLHKATNGNTNAT
120

S1S2        ------------------------------------------------------------
Full        ARLRICQFPSIKTLGPTANNDVTTGRNCLFNKAIPAHMSEHSVVGITWDNDRVTVFSDKI
180

S1S2        ----------------------------------------GEDGISYQPCTANCIGYAAN
20
Full        YYFYFKNDWSRVATKCYNSGGCAMQYVYEPTYYMLNVTSAGEDGISYQPCTANCIGYAAN
240
                                                    ********************

S1S2        VFATEPNGHIPEGFSFNNWFLLSNDSTLVHGKVVSNQPLLVNCLLAIPKIYGLGQFFSFN
80
Full        VFATEPNGHIPEGFSFNNWFLLSNDSTLVHGKVVSNQPLLVNCLLAIPKIYGLGQFFSFN
300
            ************************************************************

S1S2        QTIDGVCNGAAVQRAPEALRFNINDTSVILAEGSIVLHTALGTNFSFVCSNSSNPHLATF
140
Full        QTIDGVCNGAAVQRAPEALRFNINDTSVILAEGSIVLHTALGTNFSFVCSNSSNPHLATF
360
            ************************************************************

S1S2        AIPLGATQVPYYCFLKVDTYNSTVYKFLAVLPPTVREIVITKYGDVYVNGFGYLHLGLLD
200
Full        AIPLGATQVPYYCFLKVDTYNSTVYKFLAVLPPTVREIVITKYGDVYVNGFGYLHLGLLD
420
            ************************************************************

S1S2        AVTINFTGHGTDDDVSGFWTIASTNFVDALIEVQGTAIQRILYCDDPVSQLKCSQVAFDL
260
Full        AVTINFTGHGTDDDVSGFWTIASTNFVDALIEVQGTAIQRILYCDDPVSQLKCSQVAFDL
480
            ************************************************************

S1S2        DDGFYPISSRNLLSHEQPISFVTLPSFNDHSFVNITVSASFGGHSGANLIASDTTINGFS
320
Full        DDGFYPISSRNLLSHEQPISFVTLPSFNDHSFVNITVSASFGGHSGANLIASDTTINGFS
540
            ************************************************************
```

Figure 3O

```
S1S2    SFCVDTRQFTISLFYNVTNSYGYVSKSQDSNCPFTLQSVNDYLSFSKFCVSTSLLASACT
380
Full    SFCVDTRQFTISLFYNVTNSYGYVSKSQDSNCPFTLQSVNDYLSFSKFCVSTSLLASACT
600
        ************************************************************

S1S2    IDLFGYPEFGSGVKFTSLYFQFTKGELITGTPKPLEGVTDVSFMTLDVCTKYTIYGFKGE
440
Full    IDLFGYPEFGSGVKFTSLYFQFTKGELITGTPKPLEGVTDVSFMTLDVCTKYTIYGFKGE
660
        ************************************************************

S1S2    GIITLTNSSFLAGVYYTSDSGQLLAFKNVTSGAVYSVTPCSFSEQAAYVDDDIVGVISSL
500
Full    GIITLTNSSFLAGVYYTSDSGQLLAFKNVTSGAVYSVTPCSFSEQAAYVDDDIVGVISSL
720
        ************************************************************

S1S2    SSSTFNSTRELPGFFYHSNDGSNCTEPVLVYSNIGVCKSGSIGYVPSQSGQVKIAPTVTG
560
Full    SSSTFNSTRELPGFFYHSNDGSNCTEPVLVYSNIGVCKSGSIGYVPSQSGQVKIAPTVTG
780
        ************************************************************

S1S2    NISIPTNFS---------------------------------------------------
569
Full    NISIPTNFSMSIRTEYLQLYNTPVSVDCATYVCNGNSRCKQLLTQYTAACKTIESALQLS
840
        *********

S1S2    ------------------------------------------------------------
Full    ARLESVEVNSMLTISEEALQLATISSFNGDGYNFTNVLGVSVYDPASGRVVQKRSFIEDL
900

S1S2    --------------------SNGRSVADLVCAQYYSGVMVLPGVVDAEKLHMYSASLIGG
609
Full    LFNKVVTNGLGTVDEDYKRCSNGRSVADLVCAQYYSGVMVLPGVVDAEKLHMYSASLIGG
960
                            ****************************************

S1S2    MVLGGFTSAAALPFSYAVQARLNYLALQTDVLQRNQQLLAESFNSAIGNITSAFESVKEA
669
Full    MVLGGFTSAAALPFSYAVQARLNYLALQTDVLQRNQQLLAESFNSAIGNITSAFESVKEA
1020
        ************************************************************

S1S2    ISQTSKGLNTVAHALTKVQEVVNSQGAALTQLTVQLQHNFQAISSSIDDIYSRLDILSAD
729
Full    ISQTSKGLNTVAHALTKVQEVVNSQGAALTQLTVQLQHNFQAISSSIDDIYSRLDILSAD
1080
        ************************************************************
```

Figure 3P

```
S1S2        VQVDRLITGRLSALNAFVAQTLTKYTEVQASRKLAQQKVNECVKSQSQRYGFCGGDGEHI
789
Full        VQVDRLITGRLSALNAFVAQTLTKYTEVQASRKLAQQKVNECVKSQSQRYGFCGGDGEHI
1140
            ************************************************************

S1S2        FSLVQAAPQGLLFLHTVLVPSDFVDVIAIAGLCVNDEIALTLREPGLVLFTHELQNHTAT
849
Full        FSLVQAAPQGLLFLHTVLVPSDFVDVIAIAGLCVNDEIALTLREPGLVLFTHELQNHTAT
1200
            ************************************************************

S1S2        EYFVSSRRMFEPRKPTVSDFVQIESCVVTYVNLTRDQLPDVIPDYIDVNKTLDEILASLP
909
Full        EYFVSSRRMFEPRKPTVSDFVQIESCVVTYVNLTRDQLPDVIPDYIDVNKTLDEILASLP
1260
            ************************************************************

S1S2        NRTGPSLPLDVFNATYLNLTGEIADLEQRSESLRNTTEELQSLIYNINNTLVDLEWLNRV
969
Full        NRTGPSLPLDVFNATYLNLTGEIADLEQRSESLRNTTEELQSLIYNINNTLVDLEWLNRV
1320
            ************************************************************

S1S2        ETYIKWPWWVWLIIFIVLIFVVSLLVFCCISTGCCGCCGCCCACFSGCCRGPRLQPYEVF
1029
Full        ETYIKWPWWVWLIIFIVLIFVVSLLVFCCISTGCCGCCGCCCACFSGCCRGPRLQPYEVF
1380
            ************************************************************

S1S2        EKVHVQ- 1035
Full        EKVHVQ- 1386
            ******
```

Figure 3Q = SEQ ID NO: 17

S1S2

MGEDGISYQPCTANCIGYAAN
VFATEPNGHIPEGFSFNNWFLLSNDSTLVHGKVVSNQPLLVNCLLAIPKIYGLGQFFSFN
QTIDGVCNGAAVQRAPEALRFNINDTSVILAEGSIVLHTALGTNFSFVCSNSSNPHLATF
AIPLGATQVPYYCFLKVDTYNSTVYKFLAVLPPTVREIVITKYGDVYVNGFGYLHLGLLD
AVTINFTGHGTDDDVSGFWTIASTNFVDALIEVQGTAIQRILYCDDPVSQLKCSQVAFDL
DDGFYPISSRNLLSHEQPISFVTLPSFNDHSFVNITVSASFGGHSGANLIASDTTINGFS
SFCVDTRQFTISLFYNVTNSYGYVSKSQDSNCPFTLQSVNDYLSFSKFCVSTSLLASACT
IDLFGYPEFGSGVKFTSLYFQFTKGELITGTPKPLEGVTDVSFMTLDVCTKYTIYGFKGE
GIITLTNSSFLAGVYYTSDSGQLLAFKNVTSGAVYSVTPCSFSEQAAYVDDDIVGVISSL
SSSTFNSTRELPGFFYHSNDGSNCTEPVLVYSNIGVCKSGSIGYVPSQSGQVKIAPTVTG
NISIPTNFSSNGRSVADLVCAQYYSGVMVLPGVVDAEKLHMYSASLIGGMVLGGFTSAAA
LPFSYAVQARLNYLALQTDVLQRNQQLLAESFNSAIGNITSAFESVKEAISQTSKGLNTV
AHALTKVQEVVNSQGAALTQLTVQLQHNFQAISSSIDDIYSRLDILSADVQVDRLITGRL
SALNAFVAQTLTKYTEVQASRKLAQQKVNECVKSQSQRYGFCGGDGEHIFSLVQAAPQGL
LFLHTVLVPSDFVDVIAIAGLCVNDEIALTLREPGLVLFTHELQNHTATEYFVSSRRMFE
PRKPTVSDFVQIESCVVTYVNLTRDQLPDVIPDYIDVNKTLDEILASLPNRTGPSLPLDV
FNATYLNLTGEIADLEQRSESLRNTTEELQSLIYNINNTLVDLEWLNRVETYIKWPHHHHHH

Figure 4A – nt

Optimized = SEQ ID NO: 18

Original = SEQ ID NO: 78

```
Optimized    1   ATGGGTGAAGACGGAATCTCCTACCAACCTTGTACTGCTAACTGCATCGGATACGCTGCC
Original     1   ATGGGTGAGGATGGTATTTCTTATCAACCCTGTACAGCTAATTGCATTGGTTATGCTGCC

Optimized   61   AACGTGTTCGCCACTGAGCCAAACGGACACATCCCCGAGGGATTCTCTTTCAACAACTGG
Original    61   AATGTATTTGCTACTGAGCCCAATGGCCACATACCAGAAGGTTTTAGTTTTAATAATTGG

Optimized  121   TTCCTGCTCAGCAACGACTCAACCCTCGTGCACGGCAAGGTGGTCAGCAACCAACCCTTG
Original   121   TTTCTTTTGTCCAATGATTCCACTTTGGTGCATGGTAAGGTGGTTTCCAACCAACCATTG

Optimized  181   CTGGTCAACTGTCTCTTGGCTATCCCTAAGATCTACGGACTGGGCCAGTTCTTCTCCTTC
Original   181   TTGGTCAATTGTCTTTTGGCCATTCCTAAGATTTATGGACTAGGCCAATTTTTCTCCTTT

Optimized  241   AACCAAACTATCGACGGAGTTTGCAACGGTGCTGCTGTGCAGAGGGCTCCTGAGGCTTTG
Original   241   AATCAAACGATCGATGGTGTTTGTAATGGAGCTGCTGTGCAGCGTGCACCAGAGGCTCTG

Optimized  301   AGATTCAACATCAACGATACCTCTGTGATCCTGGCTGAAGGAAGCATCGTCTTGCACACC
Original   301   AGGTTTAATATTAATGACACCTCTGTCATTCTTGCTGAAGGCTCAATTGTACTTCATACT

Optimized  361   GCCCTGGGTACTAACTTCTCATTCGTGTGTTCGAACTCCTCTAACCCACACTTGGCCACA
Original   361   GCTTTAGGAACAAATTTTTCTTTTGTTTGCAGTAATTCCTCAAATCCTCACTTAGCCACC

Optimized  421   TTCGCTATCCCACTGGGTGCTACCCAGGTTCCGTACTACTGCTTCCTGAAGGTGGACACA
Original   421   TTCGCCATACCTCTGGGTGCTACCCAAGTACCTTATTATTGTTTTCTTAAAGTGGATACT

Optimized  481   TACAACTCCACCGTCTACAAGTTCTTGGCCGTTCTGCCCCCTACTGTCCGTGAGATCGTT
Original   481   TACAACTCCACTGTTTATAAATTTTTGGCTGTTTTACCTCCTACCGTCAGGGAAATTGTC

Optimized  541   ATCACAAAGTACGGAGACGTCTACGTTAACGGCTTCGGATACTTGCACCTGGGTCTGCTC
Original   541   ATCACCAAGTATGGTGATGTTTATGTCAATGGGTTTGGATACTTGCATCTCGGTTTGTTG

Optimized  601   GATGCTGTGACTATCAACTTCACAGGTCACGGCACCGACGATGACGTCTCAGGCTTCTGG
Original   601   GATGCTGTCACAATTAATTTCACTGGTCATGGCACTGACGATGATGTTTCTGGTTTTTGG

Optimized  661   ACTATCGCTTCGACAAACTTCGTGGACGCCCTGATCGAGGTCCAGGGAACCGCTATCCAA
Original   661   ACCATAGCATCGACTAATTTTGTTGATGCACTCATCGAAGTTCAAGGAACCGCCATTCAG
```

Figure 4B

| | | |
|---|---|---|
| Optimized | 721 | AGGATCCTGTACTGTGATGACCCAGTCTCGCAGCTCAAGTGCTCCCAAGTTGCCTTCGAC |
| Original | 721 | CGTATTCTTTATTGTGATGATCCTGTTAGCCAACTCAAGTGTTCTCAGGTTGCTTTTGAC |
| Optimized | 781 | TTGGATGACGGCTTCTACCCGATCAGCTCAAGAAACTTGCTGTCCCACGAACAGCCCATC |
| Original | 781 | CTTGACGATGGTTTTTACCCTATTTCTTCTAGAAACCTTCTGAGTCATGAACAGCCAATT |
| Optimized | 841 | TCTTTCGTGACACTGCCTTCTTTCAACGATCACAGCTTCGTGAACATCACTGTCTCCGCC |
| Original | 841 | TCTTTTGTTACTCTGCCATCATTTAATGATCATTCTTTTGTTAACATTACTGTATCTGCT |
| Optimized | 901 | TCCTTCGGTGGCCACTCCGGTGCTAACCTCATCGCCTCTGACACCACTATCAACGGCTTC |
| Original | 901 | TCCTTTGGTGGTCATAGTGGTGCCAACCTTATTGCATCTGACACTACTATCAATGGGTTT |
| Optimized | 961 | TCGTCCTTCTGTGTCGATACCCGCCAGTTCACTATCTCCCTGTTCTACAACGTCACCAAC |
| Original | 961 | AGTTCTTTCTGTGTTGACACTAGACAATTTACCATTTCACTGTTTTATAACGTTACAAAC |
| Optimized | 1021 | TCTTACGGTTACGTTAGCAAGTCACAAGACAGCAACTGCCCATTCACTCTCCAGTCAGTG |
| Original | 1021 | AGTTATGGTTATGTGTCTAAATCACAGGACAGTAATTGCCCTTTCACCTTGCAATCTGTT |
| Optimized | 1081 | AACGATTACTTGTCGTTCTCCAAGTTCTGTGTCTCCACTAGCCTCTTGGCCAGCGCTTGC |
| Original | 1081 | AATGATTACCTGTCTTTTAGCAAATTTTGTGTTTCCACCAGCCTTTTGGCTAGTGCCTGT |
| Optimized | 1141 | ACAATCGACTTGTTCGGCTACCCCGAGTTCGGAAGCGGTGTGAAGTTCACCTCACTGTAC |
| Original | 1141 | ACCATAGATCTTTTTGGTTACCCTGAGTTTGGTAGTGGTGTTAAGTTTACGTCCCTTTAC |
| Optimized | 1201 | TTCCAGTTCACTAAGGGCGAGCTCATCACTGGAACACCAAAGCCGTTGGAAGGTGTCACA |
| Original | 1201 | TTTCAATTCACAAAGGGTGAGTTGATTACTGGCACGCCTAAACCACTTGAAGGTGTCACG |
| Optimized | 1261 | GACGTCTCCTTCATGACCCTGGATGTCTGCACCAAGTACACCATCTACGGCTTCAAGGGC |
| Original | 1261 | GACGTTTCTTTTATGACTCTGGATGTGTGTACCAAGTATACTATCTATGGCTTTAAAGGT |
| Optimized | 1321 | GAGGGAATCATCACCTTGACTAACTCTAGCTTCCTGGCTGGCGTGTACTACACCTCAGAC |
| Original | 1321 | GAGGGTATCATTACCCTTACAAATTCTAGCTTTTTGGCAGGTGTTTATTACACATCTGAT |
| Optimized | 1381 | TCGGGACAACTGCTCGCTTTCAAGAACGTCACCTCAGGAGCCGTTTACTCGGTGACTCCC |
| Original | 1381 | TCTGGACAGTTGTTAGCCTTTAAGAATGTCACTAGTGGTGCTGTTTATTCTGTTACGCCA |
| Optimized | 1441 | TGCTCCTTCTCTGAACAGGCTGCCTACGTGGATGACGATATCGTGGGTGTCATCTCATCG |
| Original | 1441 | TGTTCTTTTTCAGAGCAGGCTGCATATGTTGATGATGATATAGTGGGTGTTATTTCTAGT |

Figure 4C

Optimized 1501 CTCTCCTCTAGCACATTCAACTCCACCAGGGAGTTGCCCGGTTTCTTCTACCACTCCAAC
Original 1501 TTGTCTAGCTCCACTTTTAACAGTACTAGGGAGTTGCCTGGTTTCTTCTACCATTCTAAT Optimized 1561 GACGGCTCTAACTGTACTGAACCTGTTCTGGTGTACTCTAACATCGGGGTTTGCAAGAGC
Original 1561 GATGGCTCTAATTGTACAGAGCCTGTGTTGGTGTATAGTAACATAGGTGTTTGTAAATCT Optimized 1621 GGTTCAATCGGCTACGTGCCTTCCCAGTCCGGCCAAGTTAAGATCGCTCCAACAGTGACC
Original 1621 GGCAGTATTGGCTACGTCCCATCTCAGTCTGGCCAAGTCAAGATTGCACCCACGGTTACT Optimized 1681 GGAAACATCTCCATCCCGACCAACTTCTCATCCAACGGAAGATCTGTTGCTGACCTGGTC
Original 1681 GGGAATATTAGTATTCCCACCAACTTTAGTTCTAATGGTCGCTCTGTGGCAGATCTAGTC Optimized 1741 TGCGCCCAGTACTACAGCGGTGTCATGGTTCTGCCCGGCGTTGTGGATGCTGAGAAGCTC
Original 1741 TGTGCACAGTATTACTCTGGTGTCATGGTACTACCTGGTGTTGTTGACGCTGAGAAGCTT Optimized 1801 CACATGTACTCTGCCAGCCTCATCGGTGGTATGGTGTTGGGCGGATTCACCAGCGCTGCC
Original 1801 CACATGTATAGTGCGTCTCTCATCGGTGGTATGGTGCTAGGAGGTTTTACTTCTGCAGCG Optimized 1861 GCCTTGCCTTTCTCATACGCCGTGCAGGCTCGTCTGAACTACCTCGCCTTGCAGACTGAC
Original 1861 GCATTGCCTTTTAGCTATGCTGTTCAAGCTAGACTCAATTATCTTGCTCTACAGACGGAT Optimized 1921 GTCCTCCAACGCAACCAGCAATTGCTGGCTGAGTCGTTCAACTCCGCCATCGGAAACATC
Original 1921 GTTCTACAGCGGAACCAGCAATTGCTTGCTGAGTCTTTTAACTCTGCTATTGGTAATATA Optimized 1981 ACCAGCGCTTTCGAGTCAGTGAAGGAAGCCATCTCTCAGACTAGCAAGGGTCTGAACACA
Original 1981 ACTTCAGCCTTTGAGAGTGTTAAAGAGGCTATTAGTCAAACTTCCAAGGGTTTGAACACT Optimized 2041 GTGGCCCACGCTCTCACCAAGGTCCAGGAAGTCGTTAACTCCCAAGGCGCCGCTCTCACT
Original 2041 GTGGCTCATGCGCTTACTAAGGTTCAAGAGGTTGTTAACTCGCAGGGTGCAGCTTTGACT Optimized 2101 CAGTTGACAGTCCAGCTGCAACACAACTTCCAAGCTATCTCCTCTAGCATCGACGATATC
Original 2101 CAACTTACCGTACAGCTGCAACACAACTTCCAAGCCATTTCTAGTTCTATTGATGACATT Optimized 2161 TACTCGAGGCTGGACATCCTCTCCGCCGACGTGCAGGTCGATAGGCTGATCACCGGTAGA
Original 2161 TACTCTCGACTGGACATTCTTTCAGCCGATGTTCAGGTTGACCGTCTCATCACCGGCAGA Optimized 2221 TTGTCAGCCCTGAACGCTTTCGTCGCCCAAACTCTGACAAAGTACACTGAGGTTCAGGCT
Original 2221 TTATCAGCACTTAATGCTTTTGTTGCTCAAACCCTCACTAAGTATACTGAGGTTCAGGCT

Figure 4D

```
Optimized  2281  TCTAGGAAGCTCGCCCAGCAAAAGGTCAACGAATGTGTTAAGTCACAGTCGCAAAGATAC
Original   2281  AGCAGGAAGTTAGCACAGCAAAAGGTTAATGAGTGCGTTAAATCGCAATCTCAGCGTTAT

Optimized  2341  GGATTCTGCGGTGGCGACGGCGAGCACATCTTCAGCCTGGTGCAGGCCGCTCCACAAGGC
Original   2341  GGTTTTTGTGGTGGTGATGGCGAGCACATTTTCTCTCTGGTACAGGCAGCACCTCAGGGC

Optimized  2401  CTCTTGTTCCTCCACACCGTTTTGGTGCCGTCCGACTTCGTCGATGTTATCGCCATCGCT
Original   2401  CTGCTGTTTTTACATACAGTACTTGTACCGAGTGATTTTGTAGATGTTATTGCCATCGCT

Optimized  2461  GGCCTCTGCGTGAACGACGAGATCGCTCTGACACTCTGCGAACCTGGATTGGTCCTGTTC
Original   2461  GGCTTATGCGTTAACGATGAAATTGCCTTGACTCTACGTGAGCCTGGCTTAGTCTTGTTT

Optimized  2521  ACCCACGAGCTGCAGAACCACACCGCCACTGAATACTTCGTGTCATCGCGTCGCATGTTC
Original   2521  ACGCATGAACTTCAAAATCATACTGCGACGGAATATTTTGTTTCATCGCGACGTATGTTT

Optimized  2581  GAGCCCCGTAAGCCTACCGTGTCGGACTTCGTCCAAATCGAATCATGCGTGGTCACTTAC
Original   2581  GAACCTAGAAAACCTACCGTTAGTGATTTTGTTCAAATTGAGAGTTGTGTGGTCACCTAT

Optimized  2641  GTCAACCTGACACGCGACCAGCTCCCCGATGTTATCCCTGACTACATCGATGTGAACAAG
Original   2641  GTCAATTTGACTAGAGACCAACTACCAGATGTAATCCCAGATTACATCGATGTTAACAAA

Optimized  2701  ACTCTGGACGAGATCCTCGCTTCCTTGCCCAAACGTACAGGTCCATCTCTCCCGTTGGAC
Original   2701  ACACTTGATGAGATTTTAGCTTCTCTGCCCAATAGAACTGGTCCAAGTCTTCCTTTAGAT

Optimized  2761  GTGTTCAACGCTACCTACCTGAACCTCACTGGCGAAATCGCCGATTTGGAGCAACGTTCC
Original   2761  GTTTTTAATGCCACTTATCTTAATCTCACTGGTGAAATTGCAGATTTAGAGCAGCGTTCA

Optimized  2821  GAATCTCTGCGCAACACAACCGAGGAACTGCAGTCTCTCATCTACAACATCAACAACACC
Original   2821  GAGTCTCTCCGTAATACTACAGAGGAGCTCCAAAGTCTTATATATAATATCAACAACACA

Optimized  2881  TTGGTGGACCTGGAGTGGCTCAACCGCGTCGAAACTTACATCAAGTGGCCTTGGTGGGTC
Original   2881  CTAGTTGACCTTGAGTGGCTCAACCGAGTTGAGACATATATCAAGTGGCCGTGGTGGGTT

Optimized  2941  TGGCTGATCATCTTCATCGTTCTCATCTTCGTTGTGAGCCTGCTCGTCTTCTGCTGCATC
Original   2941  TGGTTGATTATTTTCATTGTTCTCATCTTTGTTGTGTCATTACTAGTGTTCTGCTGCATT
```

Figure 4E

```
Optimized  3001  TCAACCGGATGCTGTGGTTGCTGTGGCTGCTGTTGCGCTTGCTTCTCCGGTTGTTGTAGA
Original   3001  TCCACGGGTTGTTGTGGATGCTGCGGCTGCTGCTGTGCTTGTTTCTCAGGTTGTTGTAGG

Optimized  3061  GGTCCCAGACTCCAGCCATACGAGGTGTTCGAGAAGGTCCACGTCCAATAA
Original   3061  GGTCCTAGACTTCAACCTTACGAAGTTTTTGAAAAGGTCCACGTGCAGTGA
```

Figure 4F - aa

Optimized = SEQ ID NO: 19

Original = SEQ ID NO: 79

```
Optimized     1    MGEDGISYQPCTANCIGYAANVFATEPNGHIPEGFSFNNWFLLSNDSTLVHGKVVSNQPL
Original      1    MGEDGISYQPCTANCIGYAANVFATEPNGHIPEGFSFNNWFLLSNDSTLVHGKVVSNQPL

Optimized    61    LVNCLLAIPKIYGLGQFFSFNQTIDGVCNGAAVQRAPEALRFNINDTSVILAEGSIVLHT
Original     61    LVNCLLAIPKIYGLGQFFSFNQTIDGVCNGAAVQRAPEALRFNINDTSVILAEGSIVLHT

Optimized   121    ALGTNFSFVCSNSSNPHLATFAIPLGATQVPYYCFLKVDTYNSTVYKFLAVLPPTVREIV
Original    121    ALGTNFSFVCSNSSNPHLATFAIPLGATQVPYYCFLKVDTYNSTVYKFLAVLPPTVREIV

Optimized   181    ITKYGDVYVNGFGYLHLGLLDAVTINFTGHGTDDDVSGFWTIASTNFVDALIEVQGTAIQ
Original    181    ITKYGDVYVNGFGYLHLGLLDAVTINFTGHGTDDDVSGFWTIASTNFVDALIEVQGTAIQ

Optimized   241    RILYCDDPVSQLKCSQVAFDLDDGFYPISSRNLLSHEQPISFVTLPSFNDHSFVNITVSA
Original    241    RILYCDDPVSQLKCSQVAFDLDDGFYPISSRNLLSHEQPISFVTLPSFNDHSFVNITVSA

Optimized   301    SFGGHSGANLIASDTTINGFSSFCVDTRQFTISLFYNVTNSYGYVSKSQDSNCPFTLQSV
Original    301    SFGGHSGANLIASDTTINGFSSFCVDTRQFTISLFYNVTNSYGYVSKSQDSNCPFTLQSV

Optimized   361    NDYLSFSKFCVSTSLLASACTIDLFGYPEFGSGVKFTSLYFQFTKGELITGTPKPLEGVT
Original    361    NDYLSFSKFCVSTSLLASACTIDLFGYPEFGSGVKFTSLYFQFTKGELITGTPKPLEGVT

Optimized   421    DVSFMTLDVCTKYTIYGFKGEGIITLTNSSFLAGVYYTSDSGQLLAFKNVTSGAVYSVTP
Original    421    DVSFMTLDVCTKYTIYGFKGEGIITLTNSSFLAGVYYTSDSGQLLAFKNVTSGAVYSVTP

Optimized   481    CSFSEQAAYVDDDIVGVISSLSSSTFNSTRELPGFFYHSNDGSNCTEPVLVYSNIGVCKS
Original    481    CSFSEQAAYVDDDIVGVISSLSSSTFNSTRELPGFFYHSNDGSNCTEPVLVYSNIGVCKS

Optimized   541    GSIGYVPSQSGQVKIAPTVTGNISIPTNFSSNGRSVADLVCAQYYSGVMVLPGVVDAEKL
Original    541    GSIGYVPSQSGQVKIAPTVTGNISIPTNFSSNGRSVADLVCAQYYSGVMVLPGVVDAEKL

Optimized   601    HMYSASLIGGMVLGGFTSAAALPFSYAVQARLNYLALQTDVLQRNQQLLAESFNSAIGNI
Original    601    HMYSASLIGGMVLGGFTSAAALPFSYAVQARLNYLALQTDVLQRNQQLLAESFNSAIGNI

Optimized   661    TSAFESVKEAISQTSKGLNTVAHALTKVQEVVNSQGAALTQLTVQLQHNFQAISSSIDDI
Original    661    TSAFESVKEAISQTSKGLNTVAHALTKVQEVVNSQGAALTQLTVQLQHNFQAISSSIDDI
```

Figure 4G

```
Optimized  721    YSRLDILSADVQVDRLITGRLSALNAFVAQTLTKYTEVQASRKLAQQKVNECVKSQSQRY
Original   721    YSRLDILSADVQVDRLITGRLSALNAFVAQTLTKYTEVQASRKLAQQKVNECVKSQSQRY

Optimized  781    GFCGGDGEHIFSLVQAAPQGLLFLHTVLVPSDFVDVIAIAGLCVNDEIALTLREPGLVLF
Original   781    GFCGGDGEHIFSLVQAAPQGLLFLHTVLVPSDFVDVIAIAGLCVNDEIALTLREPGLVLF

Optimized  841    ------------------------------------------------------------
Original   841    THELQNHTATEYFVSSRRMFEPRKPTVSDFVQIESCVVTYVNLTRDQLPDVIPDYIDVNK

Optimized  901    TLDEILASLPNRTGPSLPLDVFNATYLNLTGEIADLEQRSESLRNTTEELQSLIYNINNT
Original   901    TLDEILASLPNRTGPSLPLDVFNATYLNLTGEIADLEQRSESLRNTTEELQSLIYNINNT

Optimized  961    LVDLEWLNRVETYIKWPWWVWLIIFIVLIFVVSLLVFCCISTGCCGCCGCCCACFSGCCR
Original   961    LVDLEWLNRVETYIKWPWWVWLIIFIVLIFVVSLLVFCCISTGCCGCCGCCCACFSGCCR

Optimized 1021    GPRLQPYEVFEKVHVQ*
Original  1021    GPRLQPYEVFEKVHVQ*
```

FIGURE 5A – nt

SEQ ID NO: 20

```
1     ATGCTACTAG TAAATCAGTC ACACCAAGGC TTCAATAAGG AACACACAAG CAAGATGGTA
61    AGCGCTATTG TTTTATATGT GCTTTTGGCG GCGGCGGCGC ATTCTGCCTT TGCGGCGGAT
121   CTTGGATCTG AATTCATGGG TGAAGACGGA ATCTCCTACC AACCTTGTAC TGCTAACTGC
181   ATCGGATACG CCGCCAACGT GTTCGCCACT GAGCCAAACG GACACATCCC CGAGGGATTC
241   TCTTTCAACA ACTGGTTCCT GCTCAGCAAC GACTCAACCC TCGTGCACGG CAAGGTGGTC
301   AGCAACCAAC CCTTGCTGGT CAACTGTCTC TTGGCTATCC CTAAGATCTA CGGACTGGGC
361   CAGTTCTTCT CCTTCAACCA AACTATCGAC GGAGTTTGCA ACGGTGCTGC TGTGCAGAGG
421   GCTCCTGAGG CTTTGAGATT CAACATCAAC GATACCTCTG TGATCCTGGC TGAAGGAAGC
481   ATCGTCTTGC ACACCGCCCT GGGTACTAAC TTCTCATTCG TGTGTTCGAA CTCCTCTAAC
541   CCACACTTGG CCACATTCGC TATCCCACTG GGTGCTACCC AGGTTCCGTA CTACTGCTTC
601   CTGAAGGTGG ACACATACAA CTCCACCGTC TACAAGTTCT TGGCCGTTCT GCCCCCTACT
661   GTCCGTGAGA TCGTTATCAC AAAGTACGGA GACGTCTACG TTAACGGCTT CGGATACTTG
721   CACCTGGGTC TGCTCGATGC TGTGACTATC AACTTCACAG GTCACGGCAC CGACGATGAC
781   GTCTCAGGCT TCTGGACTAT CGCTTCGACA AACTTCGTGG ACGCCCTGAT CGAGGTCCAG
841   GGAACCGCTA TCCAAAGGAT CCTGTACTGT GATGACCCAG TCTCGCAGCT CAAGTGCTCC
901   CAAGTTGCCT TCGACTTGGA TGACGGCTTC TACCCGATCA GCTCAAGAAA CTTGCTGTCC
961   CACGAACAGC CCATCTCTTT CGTGACACTG CCTTCTTTCA ACGATCACAG CTTCGTGAAC
1021  ATCACTGTCT CCGCCTCTTT CGGTGGCCAC TCCGGTGCTA ACCTCATCGC CTCTGACACC
1081  ACTATCAACG GCTTCTCGTC CTTCTGTGTC GATACCCGCC AGTTCACTAT CTCCCTGTTC
1141  TACAACGTCA CCAACTCTTA CGGTTACGTT AGCAAGTCAC AAGACAGCAA CTGCCCATTC
1201  ACTCTCCAGT CAGTGAACGA TTACTTGTCG TTCTCCAAGT TCTGTGTCTC TACTAGCCTC
1261  TTGGCCAGCG CTTGCACAAT CGACTTGTTC GGCTACCCCG AGTTCGGAAG CGGTGTGAAG
1321  TTCACCTCAC TGTACTTCCA GTTCACTAAG GGCGAGCTCA TCACTGGAAC ACCAAAGCCG
1381  TTGGAAGGTG TGACAGACGT CTCCTTCATG ACCCTGGATG TCTGCACAAA GTACACCATC
1441  TACGGCTTCA AGGGCGAGGG AATCATCACC TTGACTAACT CTAGCTTCCT GGCTGGCGTG
1501  TACTACACCT CAGACTCGGG ACAACTGCTC GCTTTCAAGA ACGTCACCTC AGGAGCCGTT
1561  TACTCGGTGA CTCCCTGCTC CTTCTCTGAA CAGGCTGCCT ACGTGGATGA CGATATCGTG
1621  GGTGTCATCT CATCGCTCTC CTCTAGCACA TTCAACTCCA CCAGGGAGTT GCCCGGTTTC
1681  TTCTACCACT CCAACGACGG CTCTAACTGT ACTGAACCTG TTCTGGTGTA CTCTAACATC
1741  GGCGTTTGCA AGAGCGGTTC AATCGGCTAC GTGCCTTCGC AGTCCGGCCA AGTTAAGATC
1801  GCTCCAACAG TGACCGGAAA CATCTCCATC CCGACCAACT TCTCATCGAA CGGAAGATCT
1861  GTTGCTGACC TGGTGTGCGC CCAGTACTAC AGCGGTGTCA TGGTTCTGCC CGGCGTTGTG
1921  GATGCTGAGA AGCTCCACAT GTACTCTGCC AGCCTCATCG GTGGTATGGT GTTGGGCGGA
```

FIGURE 5B

```
1981  TTCACCAGCG CTGCCGCTTT GCCTTTCTCA TACGCCGTGC AGGCTCGTCT GAACTACCTC
2041  GCCTTGCAGA CTGACGTCCT CCAACGCAAC CAGCAATTGC TGGCTGAGTC GTTCAACTCC
2101  GCCATCGGAA ACATCACCAG CGCTTTCGAG TCAGTGAAGG AAGCCATCTC TCAGACTAGC
2161  AAGGGTCTGA ACACAGTGGC CCACGCTCTC ACCAAGGTCC AGGAAGTCGT TAACTCCCAA
2221  GGCGCCGCTC TCACTCAGTT GACAGTCCAG CTGCAACACA ACTTCCAAGC TATCTCCTCT
2281  AGCATCGACG ATATCTACTC GAGGCTGGAC ATCCTCTCCG CCGACGTGCA GGTCGATAGG
2341  CTGATCACCG GTAGATTGTC AGCCCTGAAC GCTTTCGTCG CCCAAACTCT GACAAAGTAC
2401  ACTGAGGTTC AGGCTTCTAG GAAGCTCGCC CAGCAAAAGG TCAACGAATG TGTTAAGTCA
2461  CAGTCGCAAA GATACGGATT CTGCGGTGGC GACGGCGAGC ACATCTTCAG CCTGGTGCAG
2521  GCCGCTCCAC AAGGCCTCTT GTTCCTCCAC ACCGTTTTGG TGCCGTCCGA CTTCGTCGAT
2581  GTTATCGCCA TCGCTGGCCT CTGCGTGAAC GACGAGATCG CTCTGACACT CCGCGAACCT
2641  GGATTGGTCC TGTTCACCCA CGAGCTGCAG AACCACACCG CCACTGAATA CTTCGTGTCA
2701  TCGCGTCGCA TGTTCGAGCC CCGTAAGCCT ACCGTGTCGG ACTTCGTCCA AATCGAATCA
2761  TGCGTGGTCA CTTACGTCAA CCTGACACGC GACCAGCTCC CCGATGTTAT CCCTGACTAC
2821  ATCGATGTGA ACAAGACTCT GGACGAGATC CTCGCTTCCT TGCCAAACCG TACAGGTCCA
2881  TCTCTCCCGT TGGACGTGTT CAACGCTACC TACCTGAACC TCACTGGCGA AATCGCCGAT
2941  TTGGAGCAAC GTTCCGAATC TCTGCGCAAC ACAACCGAGG AACTGCAGTC TCTCATCTAC
3001  AACATCAACA ACACCTTGGT GGACCTGGAG TGGCTCAACC GCGTCGAAAC TTACATCAAG
3061  TGGCCTCACC ACCACCACCA CCACTAATGA AAGCTT
```

gp67 signal peptide

FIGURE 5C – aa

SEQ ID NO: 21

```
1     MLLVNQSHQG FNKEHTSKMV SAIVLYVLLA AAAHSAFA/AD LGSEFMGEDG ISYQPCTANC
61    IGYAANVFAT EPNGHIPEGF SFNNWFLLSN DSTLVHGKVV SNQPLLVNCL LAIPKIYGLG
121   QFFSFNQTID GVCNGAAVQR APEALRFNIN DTSVILAEGS IVLHTALGTN FSFVCSNSSN
181   PHLATFAIPL GATQVPYYCF LKVDTYNSTV YKFLAVLPPT VREIVITKYG DVYVNGFGYL
241   HLGLLDAVTI NFTGHGTDDD VSGFWTIAST NFVDALIEVQ GTAIQRILYC DDPVSQLKCS
301   QVAFDLDDGF YPISSRNLLS HEQPISFVTL PSFNDHSFVN ITVSASFGGH SGANLIASDT
361   TINGFSSFCV DTRQFTISLF YNVTNSYGYV SKSQDSNCPF TLQSVNDYLS FSKFCVSTSL
421   LASACTIDLF GYPEFGSGVK FTSLYFQFTK GELITGTPKP LEGVTDVSFM TLDVCTKYTI
481   YGFKGEGIIT LTNSSFLAGV YYTSDSGQLL AFKNVTSGAV YSVTPCSFSE QAAYVDDDIV
541   GVISSLSSST FNSTRELPGF FYHSNDGSNC TEPVLVYSNI GVCKSGSIGY VPSQSGQVKI
601   APTVTGNISI PTNFSSNGRS VADLVCAQYY SGVMVLPGVV DAEKLHMYSA SLIGGMVLGG
661   FTSAAALPFS YAVQARLNYL ALQTDVLQRN QQLLAESFNS AIGNITSAFE SVKEAISQTS
721   KGLNTVAHAL TKVQEVVNSQ GAALTQLTVQ LQHNFQAISS SIDDIYSRLD ILSADVQVDR
781   LITGRLSALN AFVAQTLTKY TEVQASRKLA QQKVNECVKS QSQRYGFCGG DGEHIFSLVQ
841   AAPQGLLFLH TVLVPSDFVD VIAIAGLCVN DEIALTLREP GLVLFTHELQ NHTATEYFVS
901   SRRMFEPRKP TVSDFVQIES CVVTYVNLTR DQLPDVIPDY IDVNKTLDEI LASLPNRTGP
961   SLPLDVFNAT YLNLTGEIAD LEQRSESLRN TTEELQSLIY NINNTLVDLE WLNRVETYIK
1021  WPHHHHHH
```

gp67 signal peptide / = potential signal-peptide cleavage site

6H = 6xHis tag

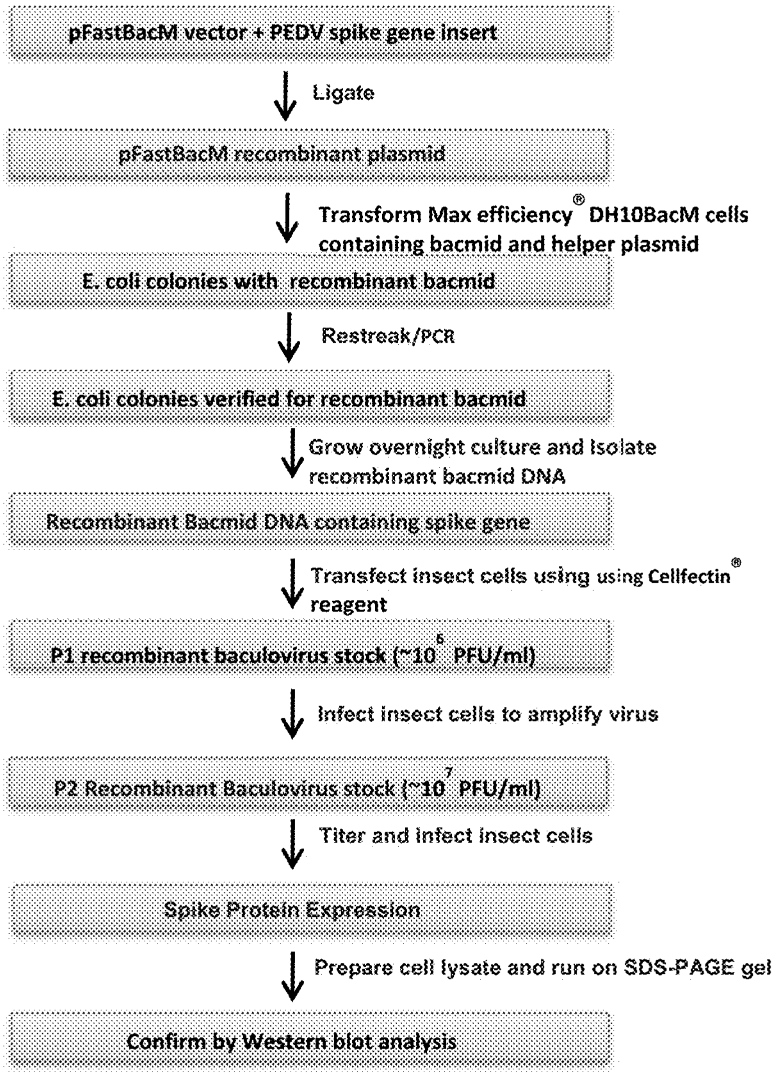

Figure 6A pFastBacM vector + PEDV spike gene insert
↓ Ligate
pFastBacM recombinant plasmid
↓ Transform Max efficiency® DH10BacM cells containing bacmid and helper plasmid
E. coli colonies with recombinant bacmid
↓ Restreak/PCR
E. coli colonies verified for recombinant bacmid
↓ Grow overnight culture and isolate recombinant bacmid DNA
Recombinant Bacmid DNA containing spike gene
↓ Transfect insect cells using using Cellfectin® reagent
P1 recombinant baculovirus stock (~$10^6$ PFU/ml)
↓ Infect insect cells to amplify virus
P2 Recombinant Baculovirus stock (~$10^7$ PFU/ml)
↓ Titer and infect insect cells
Spike Protein Expression
↓ Prepare cell lysate and run on SDS-PAGE gel
Confirm by Western blot analysis

Western Blot analysis using Anti-His antibody. The SDS-PAGE was run on 4%~20% gradient gel.
Lane 1: Medium of PEDV S protein; P2 generation
Lane 2: Whole cell of PEDV S protein; P2 generation
Protein Marker M: Genscript, Cat. No. MM0908
Anti-His Antibody: Genscript, Cat.No. A00612

SEQUENCE LISTING

<160> NUMBER OF SEQ ID NOS: 180

<210> SEQ ID NO 1
<211> LENGTH: 292
<212> TYPE: DNA
<213> ORGANISM: artificial sequence
<220> FEATURE:
<223> OTHER INFORMATION: 5' UTR nucleotide sequence of Newport Labs PEDV isolate

<400> SEQUENCE: 1

```
acttaaaaag attttctatc tacggatagt tagctctttt tctagactct tgtctactca     60

attcaactaa acgaaatttt gtccttccgg ccgcatgtcc atgctgctgg aagctgacgt    120

ggaatttcat taggtttgct taagtagcca tcgcaagtgc tgtgctgtcc tctagttcct    180

ggttggcgtt ccgtcgcctt ctacatacta gacaaacagc cttcctccgg ttccgtctgg    240

gggttgtgtg gataactagt tccgtctagt ttgaaaccag taactgtcgg ct            292
```

<210> SEQ ID NO 2
<211> LENGTH: 20346
<212> TYPE: DNA
<213> ORGANISM: artificial sequence
<220> FEATURE:
<223> OTHER INFORMATION: Polyprotein nucleotide sequence ORF1a and ORF 1b

<400> SEQUENCE: 2

```
atggctagca accatgttac attggctttt gccaatgatg cagaaatttc agcttttggc     60

ttttgcactg ctagtgaagc cgtctcatac tattctgagg ccgccgctag tggatttatg    120

caatgccgtt tcgtgtcctt cgatctcgct gacactgttg agggattgct tcccgaagac    180

tatgtcatgg tggtggtcgg cactaccaag cttagtgcgt atgtggacac ttttggtagc    240

cgccccaaaa acatttgtgg ttggctgtta ttttctaact gtaattactt cctcgaagag    300

ttagagctta cttttggtcg tcgtggtggt aacatcgtgc cagttgacca atacatgtgt    360

ggcgctgacg gtaaacctgt tcttcaggaa tccgaatggg agtatacaga tttctttgct    420

gactccgaag acggtcaact caacattgct ggtatcactt atgtgaaggc ctggattgta    480

gagcgatcgg atgtctctta tgcgagtcag aatttaacat ctattaagtc tattacttac    540

tgttcaacct atgagcatac ttttcctgat ggtactgcca tgaaggttgc acgtactcca    600

aagattaaga agactgttgt cttgtctgag ccacttgcta ctatctacag ggaaattggt    660

tctcctttttg tggataatgg gagcgatgct cgttctatca ttaagagacc agtgttcctc    720

cacgcttttg ttaagtgtaa gtgtggtagt tatcattgga ctgttggtga ttggacttcc    780

tatgtctcca cttgctgtgg ctttaagtgt aagccagtcc ttgtggcttc atgctctgct    840

acgcctggtt ctgttgtggt tacgcgcgct ggtgctggca ctggtgttaa gtattacaac    900

aacatgttcc tgcgccatgt ggcagacatt gatgggttgg cattctggcg aattctcaag    960

gtgcagtcca aagacgacct cgcttgctct ggtaaattcc ttgaacacca tgaggaaggt   1020

ttcacagatc cttgctactt tttgaatgac tcgagcattg ctactaagct caagtttgac   1080

atccttagtg gcaagttttc tgatgaagtc aaacaagcta tctttgctgg tcatgttgtt   1140

gttggcagcg cgctcgttga cattgttgac gatgcactgg gacagccttg gtttatacgt   1200

aagcttggtg accttgcaag tgcagcttgg gagcagctta aggctgtcgt tagaggcctt   1260

aacctcctgt ctgatgaggt cgtgctcttt ggcaaaagac ttagctgtgc cactcttagt   1320

atcgttaacg gtgtttttga gttcatcgcc gaagtgcctg agaagttggc tgcggctgtt   1380
```

-continued

```
acagtttttg tcaacttctt gaatgagctt tttgagtctg cctgtgactg cttaaaggtc   1440
ggaggtaaaa cctttaacaa ggttggctct tatgttcttt ttgacaacgc attggttaag   1500
cttgtcaagg caaaagttcg cggcccacga caggcaggtg tttgtgaagt tcgttacaca   1560
agccttgtta ttgggagtac taccaaggtg gtttccaagc gcgttgaaaa tgccaatgtg   1620
aatctcgtcg tcgttgacga ggatgtgacc ctcaacacca ctggtcgtac agttgttgtt   1680
gacggacttg cattcttcga gagtgacggg ttttacagac atcttgctga tgctgacgtt   1740
gtcattgaac atcctgttta taagtctgct tgtgagctca agccagtttt tgagtgtgac   1800
ccaatacctg attttcctat gcctgtggcc gctagtgttg cagagctttg tgtgcaaact   1860
gatctgttgc ttaaaaatta caacactcct tataaaactt acagctgcgt tgtgagaggt   1920
gataagtgtt gcatcacttg caccttacat atcacagcac caagttatat ggaggatgct   1980
gctaattttg tagacctctg taccaagaac attggtactg ctggttttca tgagttttac   2040
attacggccc atgaacaaca ggatctgcaa gggttcgtaa ccacttgttg cacgatgtca   2100
ggttttgagt gttttatgcc tataatccca cagtgtccag cagtgcttga agagattgat   2160
ggtggtagca tctggcggtc ttttatcact ggtcttaata caatgtggga tttttgcaag   2220
catcttaaag tcagctttgg actagatggc attgttgtca ctgtagcacg caaatttaaa   2280
cgacttggtg ctctcttggc agaaatgtat aacacttacc tttcaactgt ggtggaaaac   2340
ttggtactgg ccggtgttag cttcaagtat tatgccacca gtgtcccaaa aattgttttg   2400
ggctgttgtt ttcacagtgt taaaagtgtt cttgcaagtg ccttccagat tcctgtccag   2460
gcaggcgttg agaagtttaa agtcttcctt aactgtgttc accctgttgt accacgtgtc   2520
attgaaactt cttttgtgga attagaagag acgacattta aaccaccagc actcaatggt   2580
agtattgcta ttgttgatgg ctttgctttc tattatgatg gaacactata ctatcccacc   2640
gatggtaata gcgttgttcc tatctgcttt aagaagaaag gtggtggtga tgtcaaattc   2700
tctgatgaag tctctgttaa aaccattgac ccagtttata aggtctccct tgaatttgag   2760
ttcgagtctg agactattat ggctgtgctt aataaggctg ttggtaattg tatcaaggtt   2820
acaggtggtt gggacgatgt tgttgagtat atcaatgttg ccattgaggt tcttaaagat   2880
cacatcgatg tgcctaagta ctacatctat gatgaggaag gtggcaccga tcctaatctg   2940
cccgtaatgg tttctcagtg gccgttgaat gatgacacga tctcacagga tctgcttgat   3000
gttgaagttg ttactgatgc gccagttgat ttcgagggtg atgaagtaga ctcctctgac   3060
cctgataagg tggcagacgt ggctaactct gagcctgagg atgacggtct taatgtagct   3120
cctgaaacaa atgtagagtc tgaagttgag gaagttgccg caaccttgtc ctttattaaa   3180
gatacacctt ccacagttac taaggatcct tttgcttttg actttgcaag ctatggagga   3240
cttaaggttt taagacaatc tcataacaac tgctgggtta cttctacctt ggtgcagcta   3300
caattgcttg gcatcgttga tgaccctgca atggagcttt ttagtgctgg tagagttggt   3360
ccaatggttc gcaaatgcta tgagtcacaa aaggctatct tgggatcttt gggtgatgtg   3420
tcggcttgcc tagagtctct gactaaggac ctacacacac ttaagattac ctgttctgta   3480
gtctgtggtt gtggtactgg tgaacgtatc tatgatggtt gtgcttttcg tatgacgcca   3540
actttggaac cgttcccata tggtgcttgt gctcagtgtg ctcaagtttt gatgcacact   3600
tttaaaagta ttgttggcac cggcatcttt tgtcgagata ctactgctct ctccttggat   3660
tctttggttg taaaacctct ttgtgcggct gcttttatag gcaaggatag tggtcattat   3720
```

-continued

```
gtcactaact tttatgatgc tgctatggct attgatggtt atggtcgtca tcagataaag   3780
tatgacacac tgaacactat ttgtgttaaa gacgttaatt ggacagcacc ttttgtccca   3840
gacgttgagc ctgtattgga gcctgttgtc aaacctttct attcttataa gaatgttgat   3900
ttttaccaag gagattttag tgaccttgtt aaacttccat gtgattttgt tgttaatgct   3960
gcaaatgaga atttgtctca cggtggcggc atagcaaagg ccattgatgt ttataccaag   4020
ggcatgttgc agaagtgctc gaatgattac attaaagcac acggtcccat taaagttgga   4080
cgtggtgtca tgttggaggc attaggtctt aaggtcttta atgttgttgg tccacgtaag   4140
ggtaagcatg cacctgagct tcttgttaag gcttataagt ccgtttttgc taattcaggt   4200
gttgctctta cacctttgat tagtgttgga atttttagtg ttcctttgga agaatcttta   4260
tctgcttttc ttgcatgtgt tggtgatcgc cactgtaagt gcttttgtta tagtgacaaa   4320
gagcgcgagg cgatcattaa ttacatggat ggcttggtag atgctatttt caaagatgca   4380
cttgttgata ctactcctgt ccaggaagat gttcaacaag tttcacaaaa accagttttg   4440
cctaattttg aacctttcag gattgaaggt gctcatgctt tctatgagtg caaccctgaa   4500
ggtttgatgt cattaggtgc tgacaagctg gtgttgttta caaattccaa tttggatttt   4560
tgtagcgttg gtaagtgtct taacaatgtg actggcggtg cattgcttga agccataaat   4620
gtatttaaaa agagtaacaa aacagtgcct gctggcaact gtgttacttt tgagtgtgca   4680
gatatgattt ctattactat ggtagtattg ccatctgacg gtgatgctaa ttatgacaaa   4740
aattatgcac gcgccgtcgt caaggtatct aagcttaaag gcaagttatt gcttgctgtt   4800
ggtgatgcca tgttgtattc caagttgtcc cacctcagcg tgttaggttt cgtatccaca   4860
cctgatgatg tggagcgttt ctacgcaaat aagagtgtgg ttattaaagt tactgaggat   4920
acacgtagtg ttaagactgt taaagtagaa tccactgtta cttatggaca acaaattgga   4980
ccttgtcttg ttaatgacac cgttgtcaca gacaacaaac ctgttgttgc tgatgttgta   5040
gctaaggttg taccaagtgc taattgggat tcacattatg gttttgataa ggctggtgag   5100
ttccacatgc tagaccatac tgggtttgcc tttcctagtg aagttgttaa cggtaggcgt   5160
gtgcttaaaa ccacagataa taactgttgg gttaatgtta catgtttaca attacagttt   5220
gctagattta ggttcaagtc agcaggtcta caggctatgt gggagtccta ttgtactggt   5280
gatgttgcta tgtttgtgca ttggttgtac tggcttactg gtgttgacaa aggtcagcct   5340
agtgattcag aaaatgcact taacatgttg tctaagtaca ttgttcctgc tggttctgtc   5400
actattgaac gtgtcacgca tgacggttgt tgttgtagta agcgtgttgt cactgcacca   5460
gttgtgaatg ctagcgtgtt gaagcttggc gtcgaggatg gtctttgtcc acatggtctt   5520
aactacattg acaaagttgt tgtagttaaa ggtactacaa ttgttgtcaa tgttggaaaa   5580
cctgtagtgg caccatcgca cctctttctt aagggtgttt cctacacaac attcctagat   5640
aatggtaacg gtgttgccgg ccattatact gtttttgatc atgacactgg tatggtgcat   5700
gatggagatg tttttgtacc aggtgatctc aatgtgtctc ctgttacaaa tgttgtcgtc   5760
tcagagcaga cggctgttgt gattaaagac cctgtgaaga aagtagagtt agacgctaca   5820
aagctgttag acactatgaa ttatgcatcg gaaagattct tttcctttgg tgattttatg   5880
tcacgtaatt taattacagt gtttttgtac atccttagta ttttgggtct ctgttttagg   5940
gcctttcgta agagggatgt taaagttcta gctggtgtac cccaacgtac tggtattata   6000
ttgcgtaaaa gtgtgcgcta taatgcaaag gctttgggtg tcttcttcaa gctaaaactt   6060
tattggttca aagttcttgg taagtttagt ttgggtattt atgcattgta tgcattacta   6120
```

-continued

```
ttcatgacaa tacgctttac acctataggt ggccctgttt gtgatgatgt tgttgctggt   6180
tatgctaatt ctagttttga caagaatgag tattgcaaca gtgttatttg taaggtctgt   6240
ctctatgggt accaggaact ttcggacttc tctcacacac aggtagtatg gcaacacctt   6300
agagacccat taattggtaa tgtgatgcct ttcttttatt tggcatttct ggcaattttt   6360
gggggtgttt atgtaaaggc tattactctc tattttattt tccagtatct taacatactt   6420
ggtgtgtttt tgggcctaca acagtccatt tggtttttgc agcttgtgcc ttttgatgtc   6480
tttggtgacg agatcgtcgt ctttttcatc gttacacgcg tattgatgtt ccttaagcat   6540
gttttccttg gctgcgataa ggcatcttgt gtggcttgct ctaagagtgc tcgccttaag   6600
cgcgttcctg tccagactat tttcagggt actagcaaat ccttctacgt acatgccaat   6660
ggtggttcta agttctgtaa gaagcacaat ttcttttgtt taaattgtga ttcttatggt   6720
ccaggctgca cttttattaa tgacgtcatt gcaactgaag ttggtaatgt tgtcaaactt   6780
aatgtgcaac cgacaggtcc tgccactatt cttattgaca aggttgaatt cagtaatggt   6840
ttttactatc tttatagtgg tgacacattt tggaagtaca actttgacat aacagataac   6900
aaatacactt gcaaagagtc acttaaaaat tgtagcataa tcacagactt tattgttttt   6960
aacaataatg gttccaatgt aaatcaggtt aagaatgcat gtgtgtattt ttcacagatg   7020
ctttgtaaac ctgttaagtt agtggactca gcgttgttgg ccagtttgtc tgttgatttt   7080
ggtgcaagct tacatagtgc ttttgttagt gtgttgtcga atagttttgg caaagacctg   7140
tcaagttgta atgacatgca ggattgcaag agcacattgg gttttgatga tgtaccattg   7200
gataccttta atgctgctgt tgctgaggct catcgttacg atgtcctctt gactgacatg   7260
tcgttcaaca attttaccac cagttatgca aaaccagagg aaaaacttcc cgtccatgac   7320
attgccacgt gtatgcgtgt aggtgccaag attgttaatc ataacgttct tgtcaaggat   7380
agtatacctg tggtgtggct tgtacgtgat ttcattgccc tttctgaaga aactaggaag   7440
tacattattc gtacgactaa agttaagggt ataaccttca tgttgacctt taatgattgt   7500
cgtatgcata ctaccatacc tactgtttgc attgcaaata agaagggtgc aggtcttcct   7560
agtttttcaa aggttaagaa attcttctgg tttttgtgtc tgttcatagt tgctgttttc   7620
tttgcactaa gctttttga ttttagtact caggttagca gtgatagtga ttatgacttc   7680
aagtatattg agagtggcca gttgaagact tttgacaatc cacatagttg tgtgcataat   7740
gtctttagta acttcgacca gtggcatgat gccaagtttg gtttcacccc cgtcaacaat   7800
cctagttgtc ctatagtcgt tggtgtatca gacgaagcgc gcactgttcc aggtatccca   7860
gcaggtgttt atttagctgg taaaacactt gtttttgcta ttaacaccat ttttggtaca   7920
tctggtttgt gctttgatgc tagtggcgtt gctgataagg gcgcttgcat tttttaattcg   7980
gcttgcacca cattatctgg tttgggtgga actgctgtct actgttataa gaatggtcta   8040
gttgaaggtg ctaaacttta tagtgagttg gcacctcata gctactataa aatggtagat   8100
ggtaatgctg tgtctttacc tgaaattatc tcacgcggct ttggcatccg tactatccgt   8160
acaaaggcta tgacctactg tcgcgttggc cagtgtgtgc aatctgcaga aggtgtttgt   8220
tttggcgccg atagattctt tgtctataat gcagaatctg gttctgactt tgtttgtggc   8280
acagggctct ttacattgtt gatgaacgtt attagtgttt tttccaagac agtaccagta   8340
actgtgttgt ctggtcaaat actttttaat tgcattattg cttttgctgc tgttgcggtg   8400
tgtttcttat ttacaaagtt taagcgcatg ttcggtgata tgtctgttgg cgttttcact   8460
```

-continued

```
gtcggtgctt gtactttgtt gaacaatgtt tcctacattg taacacagaa cacacttggc   8520
atgttgggct atgcaacttt gtactttttg tgcactaaag gtgttagata tatgtggatt   8580
tggcatttgg gatttttgat ctcatatata cttattgcac catggtgggt tttgatggtt   8640
tatgcctttt cagccatttt tgagtttatg cctaaccttt ttaagcttaa ggtttcaaca   8700
caactttttg agggtgacaa gttcgtaggc tcttttgaaa atgctgcagc aggtacattt   8760
gtgcttgata tgcatgccta tgagagactt gccaactcta tctcaactga aaaactgcgt   8820
cagtatgcta gtacttacaa taagtacaag tattattcag gcagtgcttc agaggctgat   8880
tacaggcttg cttgttttgc ccatttggcc aaggctatga tggattatgc ttctaatcac   8940
aacgacacgt tatacacacc acccactgtg agttacaatt caactctaca ggctggcttg   9000
cgtaagatgg cacaaccatc tggtgttgtt gagaagtgca tagttcgtgt ttgctatggt   9060
aatatggctc ttaatggcct atggcttggt gatactgtta tctgcccacg ccatgttata   9120
gcgtctagta ctactagcac tatagattat gactatgccc tttctgtttt acgcctccac   9180
aacttctcca tttcatctgg taatgttttc ctaggtgttg tgggtgtaac catgcgaggt   9240
gctttgttgc agataaaggt taatcaaaac aatgtccaca cgcctaagta cacctatcgc   9300
acagttagac cgggtgaatc ttttaatatc ttggcgtgct atgatggttc tgccagtggt   9360
gtttacggcg ttaacatgcg ctctaattac actattagag gctcgttcat taatggcgct   9420
tgtggttcac ctggttataa cattaacaat ggtaccgttg agttttgcta tttacaccag   9480
cttgaacttg gttcaggctg tcatgttggt agcgacttag atggtgttat gtatggtggt   9540
tatgaggacc aacctacttt gcaagttgaa ggcgctagta gtctgtttac agagaatgtg   9600
ttggcatttc tttatgcagc actcattaat ggttctacct ggtggcttag ttcttctagg   9660
attgctgtag acaggtttaa tgagtgggct gttcataatg gtatgacaac agtagttaat   9720
actgattgct tttctattct tgctgctaag actggtgttg atgtacaacg tttgttggcc   9780
tcaatccagt ctctgcataa gaattttggt ggaaagcaaa ttcttggcta tacctcgttg   9840
acagatgagt ttactacagg tgaagttata cgtcaaatgt atggcgttaa tcttcagagt   9900
ggttatgttt cacgcgcctg tagaaatgtc ttgctggttg gttcttttct gactttcttt   9960
tggtcagaat tagtttccta cactaagttc ttttgggtaa atcctggtta tgtcacacct  10020
atgtttgcgt gtttgtcatt gctgtcctca cttttgatgt tcacactcaa gcataagaca  10080
ttgtttttcc aggtctttct aatacctgct ctgattgtta catcttgcat taatttggca  10140
tttgatgttg aagtctacaa ctatttggca gagcattttg attaccatgt ttctctcatg  10200
ggttttaatg cacaaggtct tgttaacatc tttgtctgct ttgttgttac cattttacac  10260
ggcacataca catggcgctt ttttaacaca cctgtgagtt ctgtcactta tgtggtagct  10320
ttgctgactg cggcatataa ctatttttac gctagtgaca ttcttagttg tgctatgaca  10380
ctatttgcta gtgtgactgg caactggttc gttggtgctg tttgttataa agctgctgtt  10440
tatatggcct tgagatttcc tacttttgtg gctatttttg gtgatattaa gagtgttatg  10500
ttctgttacc ttgtgttggg ttattttacc tgttgcttct acggtattct ctactggttc  10560
aacaggtttt ttaaggttag tgtaggtgtc tatgactata ctgttagtgc tgctgagttt  10620
aagtatatgg ttgctaacgg cctacgtgca ccaactggaa cacttgattc actacttctg  10680
tctgccaaat tgattggtat tggtggtgag cggaatatta agatttcttc cgttcagtct  10740
aaactgactg atattaagtg tagtaacgtt gtgcttttag gctgtctctc tagcatgaat  10800
gtctcagcaa attcaacaga atgggcctat tgtgttgact tgcataacaa gatcaacttg  10860
```

-continued

```
tgtaatgacc cagaaaaagc gcaggaaatg ctacttgctt tgttggcatt tttccttagt  10920
aagaatagtg cttttggttt agatgactta ttggaatcct attttaatga caatagtatg  10980
ttgcagagtg ttgcatctac ttatgtcggt ttgccttctt atgtcattta tgaaaatgca  11040
cgccaacagt atgaagatgc tgttaataat ggttctccac ctcagttggt taagcaattg  11100
cgccatgcca tgaatgtagc aaagagcgaa tttgaccgtg aggcttctac tcagcgtaag  11160
cttgatagaa tggcggaaca ggctgcagca cagatgtaca aagaggcacg agcagttaat  11220
aggaagtcca aagttgtaag tgctatgcat tcactgcttt ttggtatgtt gagacgtttg  11280
gacatgtctt ctgtagacac cattctcaac ttggcaaagg atggggttgt acctctgtct  11340
gtcataccgg cagtcagtgc tactaagctt aacattgtta cttctgatat cgattcttat  11400
aatcgtatcc agcgtgaggg atgtgtccac tacgctggta ccatttggaa tataattgat  11460
atcaaggaca atgatggcaa ggtggtacac gttaaggagg taaccgcaca gaatgctgag  11520
tccctgtcat ggcccctggt ccttgggtgt gagcgtattg tcaagctcca gaataatgaa  11580
attattcctg gtaagctgaa gcagcgctcc attaaggcag aaggagatgg catagttgga  11640
gaaggtaagg cactttacaa taatgagggt ggacgtactt ttatgtatgc tttcatctcg  11700
gacaaaccgg acctgcgtgt agtcaagtgg gagttcgatg gtggttgtaa cactattgag  11760
ctagaaccac cacgtaagtt cttggtggat tctcctaatg gtgcacagat caagtatctc  11820
tactttgttc gtaaccttaa cacgttacgt aggggtgctg ttctcggcta cataggtgcc  11880
actgtacgct tgcaggctgg taaacaaaca gaacaggcta ttaactcttc attgttgaca  11940
ctttgcgctt tcgctgtgga tcctgctaag acctacatcg atgctgtcaa aagtggtcac  12000
aaaccagtag gtaactgtgt taagatgttg gccaatggtt ctggtaatgg acaagctgtt  12060
actaatggtg tggaggctag tactaaccag gattcatacg gtggtgcgtc cgtgtgtcta  12120
tattgtagag cacatgttga gcatccatct atggatggtt tttgcagact gaaaggcaag  12180
tacgtacagg ttccactagg tacagtggat cctatacgtt ttgtacttga gaatgacgtt  12240
tgcaaggttt gtggttgttg gctggctaat ggctgcactt gtgacagatc cattatgcaa  12300
agcactgatt atggcttatt taaacgagta cggggctcta gtgcagctcg actagagccc  12360
tgtaacggta ctgatacaca acatgtgtat cgtgcttttg acatctacaa caaggatgtt  12420
gcttgtctag gtaaattcct caaggtgaac tgtgttcgcc tgaagaattt ggataagcat  12480
gatgcattct atgttgtcaa aagatgtacc aagtctgcga tggaacacga gcaatccatc  12540
tatagcagac ttgaaaagtg tggagccgta gccgaacacg atttcttcac ttggaaggat  12600
ggtcgtgcca tctatggtaa cgtttgtaga aaggatctta ccgagtatac tatgatggat  12660
ttgtgttacg ctttacgtaa ctttgatgaa aacaattgcg atgttcttaa gagcatttta  12720
attaaggtag gcgcttgtga ggagtcctac ttcaataata aagtctggtt tgaccctgtt  12780
gaaaatgaag acattcatcg tgtctatgca ttgttaggta ccattgtttc acgtgctatg  12840
cttaaatgcg ttaagttctg tgatgcaatg gttgaacaag gtatagttgg tgttgtcaca  12900
ttagataatc aggatcttaa tggtgatttt tatgattttg gtgattttac ttgtagcatc  12960
aagggaatgg gtatacccat ttgcacatca tattactctt atatgatgcc tgttatgggt  13020
atgactaatt gccttgctag tgagtgtttt gttaagagtg atatatttgg tgaggatttc  13080
aagtcatatg acctgctgga atatgatttc acggagcata agacagcact cttcaacaag  13140
tatttcaagt attggggact gcaataccac cctaactgtg tggactgcag tgatgagcag  13200
```

-continued

```
tgcatagttc actgtgccaa cttcaatacg ttgttttcca ctactatacc tattacggca  13260
tttggacctt tgtgtcgcaa gtgttggatt gatggtgttc cactggtaac tacagctggt  13320
tatcatttta aacagttagg tatagtttgg aacaatgacc tcaacttaca ctctagcagg  13380
ctctctatta acgaattact ccagttttgt agtgatcctg cattgcttat agcatcatca  13440
ccagcccttg ttgatcagcg tactgtttgc ttttcagttg cagcgctagg tacaggtatg  13500
actaaccaga ctgttaaacc tggccatttc aataaggagt tttatgactt cttacttgag  13560
caaggtttct tttctgaggg ctctgagctt actttaaagc acttcttctt tgcacagaag  13620
ggtgatgcag ctgttaagga ttttgactac tataggtata atagacctac tgttctggac  13680
atttgccaag ctcgcgtcgt gtatcaaata gtgcaacgct attttgatat ttacgaaggt  13740
ggttgtatca ctgctaaaga ggtggttgtt acaaacctta acaagagcgc aggttatcct  13800
ttgaacaagt ttggtaaagc tggtctttac tatgagtctt tatcctatga ggaacaggat  13860
gaactttatg cttatactaa gcgtaacatc ctgcccacta tgacacagct caaccttaaa  13920
tatgctataa gtggcaaaga acgtgcacgc acagtgggtg gtgtttcgct tttgtcaacc  13980
atgactactc ggcagtatca tcagaaacac cttaagtcca tagttaatac taggggcgct  14040
tcggttgtta ttggtactac taagttttat ggtggttggg acaatatgct taagaacctt  14100
attgatggtg ttgaaaatcc gtgtcttatg ggttgggact acccaaagtg cgacagagca  14160
ctgcccaata tgatacgtat gatttcagcc atgattttag gctctaagca caccacatgc  14220
tgcagttcca ctgaccgctt tttcaggttg tgcaatgaat tggctcaagt ccttactgag  14280
gttgtttatt ctaatggagg tttttatttg aagccaggtg gtactacctc tggtgatgca  14340
accaccgcat atgcaaactc agtttttaat atcttccaag cagtaagtgc caatgttaac  14400
aaacttctta gtgttgacag caatgtctgt cataatttag aagttaagca attgcagcgt  14460
aagctttatg agtgctgtta tagatcaact accgtcgatg accagttcgt cgttgagtat  14520
tatggttact tgcgtaaaca tttttcaatg atgattcttt ctgatgatgg cgttgtttgt  14580
tataacaatg actatgcatc acttggttat gtcgctgatc ttaacgcatt caaggctgtt  14640
ttgtattacc agaacaatgt cttcatgagc gcctctaaat gttggatcga gcctgacatt  14700
aataaaggtc ctcatgaatt ttgctcgcag catactatgc agattgtcga taaagatggt  14760
acttattacc ttccttaccc tgatccttca agaattctct ctgcaggtgt gtttgttgat  14820
gacgttgtta aaactgatgc agttgtattg cttgaacgtt atgtgtcatt ggctatagat  14880
gcctacccgt tatctaagca tgaaaaccct gaatataaga aggtgtttta tgtgcttttg  14940
gattgggtta agcatctgta caaaactctt aatgctggtg tgttagagtc tttttctgtc  15000
acacttttgg aagattctac tgctaaattc tgggatgaga gcttttatgc caacatgtat  15060
gagaaatctg cagttttaca atctgcaggg ctttgtgttg tttgtggctc tcaaactgtt  15120
ttacgttgtg gtgattgtct acggcgtcct atgctttgta ctaagtgtgc ttatgatcat  15180
gtcattggaa caactcacaa gttcattttg gccatcactc catatgtgtg ttgtgcttca  15240
gattgtggtg tcaatgatgt aactaagctc tacttaggtg gtcttagtta ttggtgtcat  15300
gaccacaagc cacgtcttgc attcccgttg tgctctgctg gtaatgtttt tggcttgtac  15360
aaaaattctg ctaccggctc acccgatgtt gaagacttta atcgcattgc tacatccgat  15420
tggactgatg tttctgacta caggttggca aatgatgtca aggactcatt gcgtctgttt  15480
gcagcggaaa ctatcaaggc caaggaggag agcgttaagt catcctatgc ttgtgcaaca  15540
ctacatgagg ttgtaggacc taaagagttg ttgctcaaat gggaagtcgg cagacccaaa  15600
```

```
ccacccctta atagaaattc ggttttcact tgttatcata taacgaagaa caccaaattt    15660

caaatcggtg agtttgtgtt tgagaaggca gaatatgata atgatgctgt aacatataaa    15720

actaccgcca caacaaaact tgttcctggc atggttttg tgcttacctc acataatgtt    15780

cagccattgc gcgcaccgac cattgctaat caagaacgtt attccactat acataagttg    15840

catcctgctt ttaacatacc tgaagcttat tctagcttag tgccctatta ccaattgatt    15900

ggtaagcaga agattacaac tattcaggga cctcccggta gtggtaaatc tcactgtgtt    15960

ataggctag gtttgtacta tccaggtgca cgtatagtgt ttacagcttg ttctcatgca    16020

gcggtcgatt cactttgtgt gaaagcttcc actgcttata gcaatgacaa atgttcacgc    16080

atcataccac agcgcgctcg tgttgagtgt tatgatggtt tcaagtctaa taatactagt    16140

gctcagtacc ttttctctac tgtcaatgct ttgccagagt gcaatgcgga cattgttgtg    16200

gtggatgagg tctctatgtg cactaattat gacttgtctg tcataaatca gcgcatcagc    16260

tataggcatg tagtctatgt tggtgaccct caacagctgc ctgcaccacg tgttatgatt    16320

tcacgtggta ctttggaacc aaaggactac aacgttgtca ctcaacgcat gtgtgccctt    16380

aagcctgatg ttttcttgca caagtgttat cgctgtcctg ctgagatagt gcgtactgtg    16440

tctgagatgg tctatgaaaa ccaattcatt cctgtgcacc cagatagcaa gcagtgtttt    16500

aaaatctttt gcaagggtaa tgttcaggtt gataatggtt caagcattaa tcgcaggcaa    16560

ttggatgttg tgcgtatgtt tttggctaaa atcctaggt ggtcaaaggc tgtttttatt    16620

tctcctttata acagccagaa ttatgttgcc agccgcatgc taggtctaca aattcagaca    16680

gttgattcat cccagggtag tgagtatgac tatgtcattt acacacaaac ttcagatact    16740

gcccatgcct gtaatgttaa caggtttaat gttgccatca aagggccaa gaaaggcata    16800

ttatgtataa tgtgcgatag gtcccttttt gatgtgctta aattctttga gcttaaattg    16860

tctgatttgc aggctaatga gggttgtggt cttttttaaag actgtagcag aggtgatgat    16920

ctgttgccac catctcacgc taacaccttc atgtctttag cggacaattt taagactgat    16980

caagatcttg ctgttcaaat aggtgttaat ggacccatta aatatgagca tgttatctcg    17040

tttatgggtt tccgttttga tatcaacata cccaaccatc atactctctt ttgcacacgc    17100

gactttgcca tgcgcaatgt tagaggttgg ttaggctttg acgttgaagg agcacatgtt    17160

gttggctcta acgtcggtac aaatgtccca ttgcaattag ggttttctaa cggtgttgat    17220

tttgttgtca gacctgaagg ttgcgttgta acagagtctg gtgactacat taaacccgtc    17280

agagctcgtg ctccaccagg ggaacaattc gcacaccttt tgccttact aaacgcggc    17340

caaccatggg atgttgtccg caaacgtata gtgcagatgt gtagtgacta cctggccaac    17400

ctatcagaca tactaatttt tgtgttgtgg gctggtggtt tggagttgac aactatgcgt    17460

tattttgtca agattggacc aagtaagagt tgtgattgtg gtaaggttgc tacttgttac    17520

aatagtgcgc tgcatacgta ctgttgtttc aaacatgccc ttggttgtga ttatctgtat    17580

aacccatact gtattgatat acagcagtgg ggatacaagg gatcacttag ccttaaccac    17640

catgagcatt gtaatgtaca tagaaacgag catgtggctt ctggtgatgc cataatgact    17700

cgctgtctgg ccatacatga ttgctttgtc aagaacgttg actggtccat cacataccca    17760

tttattggta atgaggctgt tattaataag agcggccgaa ttgtgcaatc acacactatg    17820

cggtcagttc ttaagttata caatccgaaa gccatatatg atattggcaa tcctaagggc    17880

attagatgtg ccgtaacgga tgctaagtgg ttttgctttg acaagaatcc tactaattct    17940
```

-continued aatgtcaaga cattggagta tgactatata acacatggcc aatttgatgg gttgtgcttg 18000
ttttggaatt gcaatgtaga catgtatcca gaattttctg tggtctgtcg ttttgatact 18060
cgctgtaggt caccactcaa cttggagggt tgtaatggtg gttcactgta tgttaataat 18120
catgcattcc atacaccggc ttttgacaag cgtgcttttg ctaagttgaa gccaatgcca 18180
tttttctttt atgatgatac tgagtgtgac aagttacagg actccataaa ctatgttcct 18240
cttagggcta gtaactgcat tactaaatgt aatgttggtg gtgctgtctg tagtaagcat 18300
tgtgctatgt atcatagcta tgttaatgct tacaacactt ttacgtcggc gggctttact 18360
atttgggtgc ctacttcgtt tgacacctat aatctgtggc agacatttag taacaatttg 18420
caaggtcttg agaacattgc tttcaatgtc gtaaagaaag gatcttttgt tggtgccgaa 18480
ggtgaacttc ctgtagctgt ggttaatgac aaagtgctcg ttagagatgg tactgttgat 18540
actcttgttt ttacaaacaa gacatcacta cccactaacg tagcttttga gttgtatgcc 18600
aagcgtaagg taggactcac cccacccatt acgatcctac gtaacttggg tgtagtttgt 18660
acatctaagt gtgtcatttg ggactatgaa gccgaacgtc cacttactac ttttacaaag 18720
gatgtttgta aatataccga ctttgagggt gacgtctgta cactctttga taacagcatt 18780
gttggttcat tagagcgatt ctccatgacc caaaatgctg tgcttatgtc acttacagct 18840
gttaaaaagc ttactggcat aaagttaact tatggttatc ttaatggtgt cccagttaac 18900
acacatgaag ataaaccttt tacttggtat atttacacta ggaagaacgg caagttcgag 18960
gaccatcctg atggctattt tacccaaggt agaacaaccg ctgattttag ccctcgtagc 19020
gacatggaaa aggacttcct aagtatggat atgggtctgt ttattaacaa gtacggactt 19080
gaagattacg gctttgagca cgttgtgtat ggtgatgttt caaaaaccac ccttggtggt 19140
ttgcatctac taatttcgca ggtgcgtctg gcctgtatgg gtgtgctcaa aatagacgag 19200
tttgtgtcta gtaatgatag cacgttaaag tcttgtactg ttacatatgc tgataaccct 19260
agtagtaaga tggtttgtac gtatatggat ctcctgcttg acgattttgt cagcattctt 19320
aaatctttgg atttgggcgt tgtatctaaa gttcatgaag ttatggtcga ttgtaaaatg 19380
tggaggtgga tgttgtggtg taaggatcat aaactccaga cattttatcc gcaacttcag 19440
gccagtgaat ggaagtgtgg ttattccatg ccttctattt acaagataca acgtatgtgt 19500
ttagaacctt gcaatctcta caactatggt gctggtatta agttacctga tggcattatg 19560
tttaacgtag ttaaatacac acagctttgt caatatctca atagcaccac aatgtgtgta 19620
ccccatcaca tgcgtgtgct acatcttggt gctggctccg acaagggtgt tgcacctggc 19680
acggctgtct tacgacgttg gttgccactg gatgccatta tagttgacaa tgatagtgtg 19740
gattacgtta gcgatgctga ttatagtgtt acaggagatt gctctacctt atacctgtca 19800
gataagtttg atttagttat atctgatatg tatgatggta agattaaaag ttgtgatggg 19860
gagaacgtgt ctaaagaagg cttctttccc tatattaatg gtgtcatcac cgaaaagttg 19920
gcacttggtg gtactgtagc tattaaggtg acggagttta gttggaataa gaagttgtat 19980
gaactcattc agaggtttga gtattggaca atgttctgta ccagtgttaa cacgtcatcg 20040
tcagaggcat tcttaattgg tgttcactat ttaggtgatt ttgcaagtgg cgctgtgatt 20100
gacggcaaca ctatgcatgc caattatatc ttctggcgta attccacaat tatgactatg 20160
tcttacaata gtgtacttga tttaagcaag ttcaattgta agcataaggc tacagttgtc 20220
attaatttaa aagattcatc cattagtgat gttgtgttag gtttgttgaa gaatggtaag 20280
ttgctagtgc gtaataatga cgccatttgt ggtttttcta atcatttggt caacgtaaac 20340
aaatga 20346

<210> SEQ ID NO 3
<211> LENGTH: 4161
<212> TYPE: DNA
<213> ORGANISM: artificial sequence
<220> FEATURE:
<223> OTHER INFORMATION: Spike (S domain) nucleotide sequence

<400> SEQUENCE: 3
atgaagtctt taacctactt ctggttgttc ttaccagtac tttcaacact tagcctacca 60
caagatgtca ccaggtgctc agctaacact aattttaggc ggttcttttc aaaatttaat 120
gttcaggcgc ctgcagttgt tgtactgggc ggttatctac ctattggtga aaaccagggt 180
gtcaattcaa cttggtactg tgctggccaa catccaactg ctagtggcgt tcatggtatc 240
tttgttagcc atattagagg tggtcatggc tttgagattg gcatttcgca agagcctttt 300
gaccctagtg gttaccagct ttatttacat aaggctacta acggtaacac taatgctact 360
gcgcgactgc gcatttgcca gtttcctagc attaaaacat tgggccccac tgctaataat 420
gatgttacaa caggtcgtaa ttgcctattt aacaaagcca tcccagctca tatgagtgaa 480
catagtgttg tcggcataac atgggataat gatcgtgtca ctgtcttttc tgacaagatc 540
tattattttt attttaaaaa tgattggtcc cgtgttgcga caaagtgtta caacagtgga 600
ggttgtgcta tgcaatatgt ttacgaaccc acctattaca tgcttaatgt tactagtgct 660
ggtgaggatg gtatttctta tcaaccctgt acagctaatt gcattggtta tgctgccaat 720
gtatttgcta ctgagcccaa tggccacata ccagaaggtt ttagttttaa taattggttt 780
cttttgtcca atgattccac tttggtgcat ggtaaggtgg tttccaacca accattgttg 840
gtcaattgtc ttttggccat tcctaagatt tatggactag gccaattttt ctcctttaat 900
caaacgatcg atggtgtttg taatggagct gctgtgcagc gtgcaccaga ggctctgagg 960
tttaatatta atgacacctc tgtcattctt gctgaaggct caattgtact tcatactgct 1020
ttaggaacaa atttttcttt tgtttgcagt aattcctcaa atcctcactt agccaccttc 1080
gccatacctc tgggtgctac ccaagtacct tattattgtt ttcttaaagt ggatacttac 1140
aactccactg tttataaatt tttggctgtt ttacctccta ccgtcaggga aattgtcatc 1200
accaagtatg gtgatgttta tgtcaatggg tttggatact tgcatctcgg tttgttggat 1260
gctgtcacaa ttaatttcac tggtcatggc actgacgatg atgtttctgg tttttggacc 1320
atagcatcga ctaattttgt tgatgcactc atcgaagttc aaggaaccgc cattcagcgt 1380
attctttatt gtgatgatcc tgttagccaa ctcaagtgtt ctcaggttgc ttttgacctt 1440
gacgatggtt tttaccctat ttcttctaga aaccttctga gtcatgaaca gccaatttct 1500
tttgttactc tgccatcatt taatgatcat tcttttgtta acattactgt atctgcttcc 1560
tttggtggtc atagtggtgc caaccttatt gcatctgaca ctactatcaa tgggtttagt 1620
tctttctgtg ttgacactag acaatttacc atttcactgt tttataacgt tacaaacagt 1680
tatggttatg tgtctaaatc acaggacagt aattgccctt tcaccttgca atctgttaat 1740
gattacctgt cttttagcaa attttgtgtt tccaccagcc ttttggctag tgcctgtacc 1800
atagatcttt ttggttaccc tgagtttggt agtggtgtta agtttacgtc cctttacttt 1860
caattcacaa agggtgagtt gattactggc acgcctaaac cacttgaagg tgtcacggac 1920
gtttctttta tgactctgga tgtgtgtacc aagtatacta tctatggctt taaaggtgag 1980

-continued

```
ggtatcatta cccttacaaa ttctagcttt ttggcaggtg tttattacac atctgattct   2040
ggacagttgt tagcctttaa gaatgtcact agtggtgctg tttattctgt tacgccatgt   2100
tctttttcag agcaggctgc atatgttgat gatgatatag tgggtgttat ttctagtttg   2160
tctagctcca cttttaacag tactagggag ttgcctggtt tcttctacca ttctaatgat   2220
ggctctaatt gtacagagcc tgtgttggtg tatagtaaca taggtgtttg taaatctggc   2280
agtattggct acgtcccatc tcagtctggc caagtcaaga ttgcacccac ggttactggg   2340
aatattagta ttcccaccaa ctttagtatg agtattagga cagaatattt acagctttac   2400
aacacgcctg ttagtgttga ttgtgccaca tatgtttgta atggtaactc tcgttgtaaa   2460
caattactca cccagtacac tgcagcatgt aagaccatag agtcagcatt acaactcagc   2520
gctaggcttg agtctgttga agttaactct atgcttacta tttctgaaga ggctctacag   2580
ttagctacca ttagttcgtt taatggtgat ggatataatt ttactaatgt gctgggtgtt   2640
tctgtgtatg atcctgcaag tggcagggtg gtacaaaaaa ggtcttttat tgaagacctg   2700
ctttttaata aagtggttac taatggcctt ggtactgttg atgaagacta taagcgctgt   2760
tctaatggtc gctctgtggc agatctagtc tgtgcacagt attactctgg tgtcatggta   2820
ctacctggtg ttgttgacgc tgagaagctt cacatgtata gtgcgtctct catcggtggt   2880
atggtgctag gaggttttac ttctgcagcg gcattgcctt ttagctatgc tgttcaagct   2940
agactcaatt atcttgctct acagacggat gttctacagc ggaaccagca attgcttgct   3000
gagtctttta actctgctat tggtaatata acttcagcct ttgagagtgt taaagaggct   3060
attagtcaaa cttccaaggg tttgaacact gtggctcatg cgcttactaa ggttcaagag   3120
gttgttaact cgcagggtgc agctttgact caacttaccg tacagctgca acacaacttc   3180
caagccattt ctagttctat tgatgacatt tactctcgac tggacattct ttcagccgat   3240
gttcaggttg accgtctcat caccggcaga ttatcagcac ttaatgcttt tgtttctcaa   3300
accctcacta agtatactga ggttcaggct agcaggaagt tagcacagca aaaggttaat   3360
gagtgcgtta aatcgcaatc tcagcgttat ggtttttgtg gtggtgatgg cgagcacatt   3420
ttctctctgg tacaggcagc acctcagggc ctgctgtttt tacatacagt acttgtaccg   3480
agtgattttg tagatgttat tgccatcgct ggcttatgcg ttaacgatga aattgccttg   3540
actctacgtg agcctggctt agtcttgttt acgcatgaac ttcaaaatca tactgcgacg   3600
gaatattttg tttcatcgcg acgtatgttt gaacctagaa aacctaccgt tagtgatttt   3660
gttcaaattg agagttgtgt ggtcacctat gtcaatttga ctagagacca actaccagat   3720
gtaatcccag attacatcga tgttaacaaa acacttgatg agattttagc ttctctgccc   3780
aatagaactg gtccaagtct tcctttagat gtttttaatg ccacttatct taatctcact   3840
ggtgaaattg cagatttaga gcagcgttca gagtctctcc gtaatactac agaggagctc   3900
caaagtctta tatataatat caacaacaca ctagttgacc ttgagtggct caaccgagtt   3960
gagacatata tcaagtggcc gtggtgggtt tggttgatta ttttcattgt tctcatcttt   4020
gttgtgtcat tactagtgtt ctgctgcatt tccacgggtt gttgtggatg ctgcggctgc   4080
tgctgtgctt gtttctcagg ttgttgtagg ggtcctagac ttcaacctta cgaagttttt   4140
gaaaaggtcc acgtgcagtg a                                               4161
```

<210> SEQ ID NO 4
<211> LENGTH: 675
<212> TYPE: DNA
<213> ORGANISM: artificial sequence
<220> FEATURE:
<223> OTHER INFORMATION: ORF3 Coronavirus NS3b nucleotide sequence

<400> SEQUENCE: 4
atgtttcttg gactttttca atacacgatt gacacagttg tcaaagatgt ctcaaagtct 60
gctaacttgt ctttggatgc tgtccaagag ttggagctca atgtagttcc aattagacaa 120
gcttcaaatg tgacgggttt tcttttcacc agtgttttta tctacttctt tgcactgttt 180
aaagcgtctt ctttgaggcg caattatatt atgttggcag cgcgttttgc tgtcattgtt 240
ctttattgcc cacttttata ttattgtggt gcatttttag atgcaactat tatttgttgc 300
acacttattg gcaggctttg tttagtctgc ttttactcct ggcgctataa aaatgcgctc 360
tttattattt ttaatactac gacactttct ttcctcaatg gtaaagcagc ttattatgac 420
ggcaaatcca ttgtgatttt agaaggtggt gaccattaca tcacttttgg caactctttt 480
gttgcttttg ttagtagcat cgacttgtat ctagctatac gtgggcggca agaagctgac 540
ctacagctgt tgcgaactgt tgagcttctt gatggcaaga agctttatgt cttttcgcaa 600
catcaaattg ttggcattac taatgctgca tttgactcaa ttcaactaga cgagtatgct 660
acaattagtg aatga 675

<210> SEQ ID NO 5
<211> LENGTH: 231
<212> TYPE: DNA
<213> ORGANISM: artificial sequence
<220> FEATURE:
<223> OTHER INFORMATION: DNA for Envelope protein

<400> SEQUENCE: 5
atgctacaat tagtgaatga taatggtcta gtagttaatg ttatactttg gcttttcgta 60
ctctttttcc tgcttattat aagcattact ttcgtccaat tggttaatct gtgcttcact 120
tgtcaccggt tgtgtaatag cgcagtttac acacctatag ggcgtttgta tagagtttat 180
aagtcttaca tgcaaataga ccccctccct agtactgtta ttgacgtata a 231

<210> SEQ ID NO 6
<211> LENGTH: 21
<212> TYPE: DNA
<213> ORGANISM: artificial sequence
<220> FEATURE:
<223> OTHER INFORMATION: Reseq19R primer

<400> SEQUENCE: 6
tcatcaacgg gaatagaacc g 21

<210> SEQ ID NO 7
<211> LENGTH: 681
<212> TYPE: DNA
<213> ORGANISM: artificial sequence
<220> FEATURE:
<223> OTHER INFORMATION: Membrane protein nucleotide sequence

<400> SEQUENCE: 7
atgtctaacg gttctattcc cgttgatgag gtgattcaac accttagaaa ctggaatttc 60
acatggaata tcatactgac gatactactt gtagtgcttc agtatggcca ttacaagtac 120
tctgcgttct tgtatggtgt caagatggct attctatgga tactttggcc tcttgtgtta 180
gcactgtcac tttttgatgc atgggctagc tttcaggtca attgggtctt ttttgctttc 240
agcatcctta tggcttgcat cactcttatg ctgtggataa tgtactttgt caatagcatt 300

-continued cggttgtggc gcaggacaca ttcttggtgg tctttcaatc ctgaaacaga cgcgcttctc 360
actacttctg tgatgggccg acaggtctgc attccagtgc ttggagcacc aactggtgta 420
acgctaacac tccttagtgg tacattgctt gtagagggct ataaggttgc tactggcgta 480
caggtaagtc aattacctaa tttcgtcaca gtcgccaagg ccactacaac aattgtctac 540
ggacgtgttg gtcgttcagt caatgcttca tctggcactg gttgggcttt ctatgtccgg 600
tccaaacacg gcgactactc agctgtgagt aatccgagtt cggttctcac agatagtgag 660
aaagtgcttc atttagtcta a 681

<210> SEQ ID NO 8
<211> LENGTH: 11
<212> TYPE: DNA
<213> ORGANISM: artificial sequence
<220> FEATURE:
<223> OTHER INFORMATION: Intergenic region B

<400> SEQUENCE: 8
acagaaactt t 11

<210> SEQ ID NO 9
<211> LENGTH: 1326
<212> TYPE: DNA
<213> ORGANISM: artificial sequence
<220> FEATURE:
<223> OTHER INFORMATION: Nucleoprotein nucleotide sequence

<400> SEQUENCE: 9
atggcttctg tcagttttca ggatcgtggc cgcaaacggg tgccattatc cctctatgcc 60
cctcttaggg ttactaatga caaacccctt tctaaggtac ttgcaaataa tgctgtaccc 120
actaataaag gaaataagga ccagcaaatt ggatactgga atgagcaaat tcgctggcgc 180
atgcgccgtg gtgagcgaat tgaacaacct tccaattggc atttctacta cctcggaaca 240
ggacctcacg ccgacctccg ctataggact cgtactgagg gtgttttctg ggttgctaaa 300
gaaggcgcaa agactgaacc cactaacctg ggtgtcagaa aggcgtctga aaagccaatt 360
attccaaatt tctctcaaca gcttcccagc gtagttgaga ttgttgaacc taacacacct 420
cctacttcac gtgcaaattc acgtagcagg agtcgtggta atggcaacaa caggtccaga 480
tctccaagta acaacagagg caataaccag tcccgcggta attcacagaa tcgtggaaat 540
aaccagggtc gtggagcttc tcagaacaga ggaggcaata ataataacaa taacaagtct 600
cgtaaccagt ccaagaacag aaaccagtca aatgaccgtg gtggtgtaac atcacgcgat 660
gatctggtgg ctgctgtcaa ggatgccctt aaatctttgg gtattggcga aaaccctgac 720
aagcttaagc aacagcagaa gcccaaacag gaaaggtctg acagcagcgg caaaaataca 780
cctaagaaga acaaatccag agccacttcg aaagaacgtg acctcaaaga catcccagag 840
tggaggagaa ttcccaaggg cgaaaatagc gtagcagctt gcttcggacc caggggaggc 900
ttcaaaaatt ttggagatgc ggaatttgtc gaaaaaggtg ttgatgcctc aggctatgct 960
cagatcgcca gtttagcacc aaatgttgca gcattgctct ttggtggtaa tgtggctgtt 1020
cgtgagctag cggactctta cgagattaca tataattata aaatgactgt gccaaagtct 1080
gatccaaatg tagagcttct tgtttcacag gtggatgcat ttaaaactgg gaatgcaaaa 1140
ccccagagaa agaaggaaaa gaagaacaag cgtgaaacca cgcagcagct gaatgaagag 1200
gccatctacg atgatgtggg tgtgccatct gatgtgactc atgccaattt ggaatgggac 1260
acagctgttg atggtggtga cacggccgtt gaaattatca acgagatctt cgacacagga 1320
aattaa 1326

<210> SEQ ID NO 10
<211> LENGTH: 334
<212> TYPE: DNA
<213> ORGANISM: artificial sequence
<220> FEATURE:
<223> OTHER INFORMATION: 3' UTR nucleotide sequence of Newport Labs PEDV isolate

<400> SEQUENCE: 10
acaatgtttg actggcttat cctggctatg tcccagggta gtgccattac actgttatta 60
ctgagtgttt ttctagcgac ttggctgctg ggctatggct ttgccctcta actagcggtc 120
ttggtcttgc acacaacggt aagccagtgg taatgtcagt gcaagaagga tattaccata 180
gcactgtcat gaggggaacg cagtaccttt tcatctaaac ctttgcacga gtaatcaaag 240
atccgcttga cgagcctata tggaagagcg tgccaggtat ttgactcaag gactgttagt 300
aactgaagac ctgacggtgt tgatatggat acac 334

<210> SEQ ID NO 11
<211> LENGTH: 6781
<212> TYPE: PRT
<213> ORGANISM: artificial sequence
<220> FEATURE:
<223> OTHER INFORMATION: ORF1a/ORF1b aa

<400> SEQUENCE: 11

Met Ala Ser Asn His Val Thr Leu Ala Phe Ala Asn Asp Ala Glu Ile
1 5 10 15

Ser Ala Phe Gly Phe Cys Thr Ala Ser Glu Ala Val Ser Tyr Tyr Ser
20 25 30

Glu Ala Ala Ala Ser Gly Phe Met Gln Cys Arg Phe Val Ser Phe Asp
35 40 45

Leu Ala Asp Thr Val Glu Gly Leu Leu Pro Glu Asp Tyr Val Met Val
50 55 60

Val Val Gly Thr Thr Lys Leu Ser Ala Tyr Val Asp Thr Phe Gly Ser
65 70 75 80

Arg Pro Lys Asn Ile Cys Gly Trp Leu Leu Phe Ser Asn Cys Asn Tyr
85 90 95

Phe Leu Glu Glu Leu Glu Leu Thr Phe Gly Arg Arg Gly Gly Asn Ile
100 105 110

Val Pro Val Asp Gln Tyr Met Cys Gly Ala Asp Gly Lys Pro Val Leu
115 120 125

Gln Glu Ser Glu Trp Glu Tyr Thr Asp Phe Phe Ala Asp Ser Glu Asp
130 135 140

Gly Gln Leu Asn Ile Ala Gly Ile Thr Tyr Val Lys Ala Trp Ile Val
145 150 155 160

Glu Arg Ser Asp Val Ser Tyr Ala Ser Gln Asn Leu Thr Ser Ile Lys
165 170 175

Ser Ile Thr Tyr Cys Ser Thr Tyr Glu His Thr Phe Pro Asp Gly Thr
180 185 190

Ala Met Lys Val Ala Arg Thr Pro Lys Ile Lys Lys Thr Val Val Leu
195 200 205

Ser Glu Pro Leu Ala Thr Ile Tyr Arg Glu Ile Gly Ser Pro Phe Val
210 215 220

Asp Asn Gly Ser Asp Ala Arg Ser Ile Ile Lys Arg Pro Val Phe Leu

-continued

```
225                 230                 235                 240

His Ala Phe Val Lys Cys Lys Cys Gly Ser Tyr His Trp Thr Val Gly
                245                 250                 255

Asp Trp Thr Ser Tyr Val Ser Thr Cys Cys Gly Phe Lys Cys Lys Pro
            260                 265                 270

Val Leu Val Ala Ser Cys Ser Ala Thr Pro Gly Ser Val Val Val Thr
        275                 280                 285

Arg Ala Gly Ala Gly Thr Gly Val Lys Tyr Tyr Asn Asn Met Phe Leu
    290                 295                 300

Arg His Val Ala Asp Ile Asp Gly Leu Ala Phe Trp Arg Ile Leu Lys
305                 310                 315                 320

Val Gln Ser Lys Asp Asp Leu Ala Cys Ser Gly Lys Phe Leu Glu His
                325                 330                 335

His Glu Glu Gly Phe Thr Asp Pro Cys Tyr Phe Leu Asn Asp Ser Ser
            340                 345                 350

Ile Ala Thr Lys Leu Lys Phe Asp Ile Leu Ser Gly Lys Phe Ser Asp
        355                 360                 365

Glu Val Lys Gln Ala Ile Phe Ala Gly His Val Val Val Gly Ser Ala
    370                 375                 380

Leu Val Asp Ile Val Asp Asp Ala Leu Gly Gln Pro Trp Phe Ile Arg
385                 390                 395                 400

Lys Leu Gly Asp Leu Ala Ser Ala Ala Trp Glu Gln Leu Lys Ala Val
                405                 410                 415

Val Arg Gly Leu Asn Leu Leu Ser Asp Glu Val Val Leu Phe Gly Lys
            420                 425                 430

Arg Leu Ser Cys Ala Thr Leu Ser Ile Val Asn Gly Val Phe Glu Phe
        435                 440                 445

Ile Ala Glu Val Pro Glu Lys Leu Ala Ala Ala Val Thr Val Phe Val
    450                 455                 460

Asn Phe Leu Asn Glu Leu Phe Glu Ser Ala Cys Asp Cys Leu Lys Val
465                 470                 475                 480

Gly Gly Lys Thr Phe Asn Lys Val Gly Ser Tyr Val Leu Phe Asp Asn
                485                 490                 495

Ala Leu Val Lys Leu Val Lys Ala Lys Val Arg Gly Pro Arg Gln Ala
            500                 505                 510

Gly Val Cys Glu Val Arg Tyr Thr Ser Leu Val Ile Gly Ser Thr Thr
        515                 520                 525

Lys Val Val Ser Lys Arg Val Glu Asn Ala Asn Val Asn Leu Val Val
    530                 535                 540

Val Asp Glu Asp Val Thr Leu Asn Thr Thr Gly Arg Thr Val Val Val
545                 550                 555                 560

Asp Gly Leu Ala Phe Phe Glu Ser Asp Gly Phe Tyr Arg His Leu Ala
                565                 570                 575

Asp Ala Asp Val Val Ile Glu His Pro Val Tyr Lys Ser Ala Cys Glu
            580                 585                 590

Leu Lys Pro Val Phe Glu Cys Asp Pro Ile Pro Asp Phe Pro Met Pro
        595                 600                 605

Val Ala Ala Ser Val Ala Glu Leu Cys Val Gln Thr Asp Leu Leu Leu
    610                 615                 620

Lys Asn Tyr Asn Thr Pro Tyr Lys Thr Tyr Ser Cys Val Val Arg Gly
625                 630                 635                 640

Asp Lys Cys Cys Ile Thr Cys Thr Leu His Phe Thr Ala Pro Ser Tyr
                645                 650                 655
```

-continued

```
Met Glu Ala Ala Ala Asn Phe Val Asp Leu Cys Thr Lys Asn Ile Gly
            660                 665                 670

Thr Ala Gly Phe His Glu Phe Tyr Ile Thr Ala His Glu Gln Gln Asp
        675                 680                 685

Leu Gln Gly Phe Val Thr Thr Cys Cys Thr Met Ser Gly Phe Glu Cys
    690                 695                 700

Phe Met Pro Ile Ile Pro Gln Cys Pro Ala Val Leu Glu Glu Ile Asp
705                 710                 715                 720

Gly Gly Ser Ile Trp Arg Ser Phe Ile Thr Gly Leu Asn Thr Met Trp
                725                 730                 735

Asp Phe Cys Lys His Leu Lys Val Ser Phe Gly Leu Asp Gly Ile Val
            740                 745                 750

Val Thr Val Ala Arg Lys Phe Lys Arg Leu Gly Ala Leu Leu Ala Glu
        755                 760                 765

Met Tyr Asn Thr Tyr Leu Ser Thr Val Val Glu Asn Leu Val Leu Ala
    770                 775                 780

Gly Val Ser Phe Lys Tyr Tyr Ala Thr Ser Val Pro Lys Ile Val Leu
785                 790                 795                 800

Gly Cys Cys Phe His Ser Val Lys Ser Val Leu Ala Ser Ala Phe Gln
                805                 810                 815

Ile Pro Val Gln Ala Gly Val Glu Lys Phe Lys Val Phe Leu Asn Cys
            820                 825                 830

Val His Pro Val Val Pro Arg Val Ile Glu Thr Ser Phe Val Glu Leu
        835                 840                 845

Glu Glu Thr Thr Phe Lys Pro Pro Ala Leu Asn Gly Ser Ile Ala Ile
    850                 855                 860

Val Asp Gly Phe Ala Phe Tyr Tyr Asp Gly Thr Leu Tyr Tyr Pro Thr
865                 870                 875                 880

Asp Gly Asn Ser Val Val Pro Ile Cys Phe Lys Lys Lys Gly Gly Gly
                885                 890                 895

Asp Val Lys Phe Ser Asp Glu Val Ser Val Lys Thr Ile Asp Pro Val
            900                 905                 910

Tyr Lys Val Ser Leu Glu Phe Glu Phe Glu Ser Glu Thr Ile Met Ala
        915                 920                 925

Val Leu Asn Lys Ala Val Gly Asn Cys Ile Lys Val Thr Gly Gly Trp
    930                 935                 940

Asp Asp Val Val Glu Tyr Ile Asn Val Ala Ile Glu Val Leu Lys Asp
945                 950                 955                 960

His Ile Asp Val Pro Lys Tyr Tyr Ile Tyr Asp Glu Glu Gly Gly Thr
                965                 970                 975

Asp Pro Asn Leu Pro Val Met Val Ser Gln Trp Pro Leu Asn Asp Asp
            980                 985                 990

Thr Ile Ser Gln Asp Leu Leu Asp  Val Glu Val Val Thr  Asp Ala Pro
        995                 1000                1005

Val Asp  Phe Glu Gly Asp Glu  Val Asp Ser Ser Asp  Pro Asp Lys
    1010                1015                1020

Val Ala  Asp Val Ala Asn Ser  Glu Pro Glu Asp Asp  Gly Leu Asn
    1025                1030                1035

Val Ala  Pro Glu Thr Asn Val  Glu Ser Glu Val Glu  Glu Val Ala
    1040                1045                1050

Ala Thr  Leu Ser Phe Ile Lys  Asp Thr Pro Ser Thr  Val Thr Lys
    1055                1060                1065
```

-continued

```
Asp Pro  Phe Ala Phe Asp Phe  Ala Ser Tyr Gly Gly  Leu Lys Val
    1070                 1075                 1080

Leu Arg  Gln Ser His Asn Asn  Cys Trp Val Thr Ser  Thr Leu Val
    1085                 1090                 1095

Gln Leu  Gln Leu Leu Gly Ile  Val Asp Asp Pro Ala  Met Glu Leu
    1100                 1105                 1110

Phe Ser  Ala Gly Arg Val Gly  Pro Met Val Arg Lys  Cys Tyr Glu
    1115                 1120                 1125

Ser Gln  Lys Ala Ile Leu Gly  Ser Leu Gly Asp Val  Ser Ala Cys
    1130                 1135                 1140

Leu Glu  Ser Leu Thr Lys Asp  Leu His Thr Leu Lys  Ile Thr Cys
    1145                 1150                 1155

Ser Val  Val Cys Gly Cys Gly  Thr Gly Glu Arg Ile  Tyr Asp Gly
    1160                 1165                 1170

Cys Ala  Phe Arg Met Thr Pro  Thr Leu Glu Pro Phe  Pro Tyr Gly
    1175                 1180                 1185

Ala Cys  Ala Gln Cys Ala Gln  Val Leu Met His Thr  Phe Lys Ser
    1190                 1195                 1200

Ile Val  Gly Thr Gly Ile Phe  Cys Arg Asp Thr Thr  Ala Leu Ser
    1205                 1210                 1215

Leu Asp  Ser Leu Val Val Lys  Pro Leu Cys Ala Ala  Ala Phe Ile
    1220                 1225                 1230

Gly Lys  Asp Ser Gly His Tyr  Val Thr Asn Phe Tyr  Asp Ala Ala
    1235                 1240                 1245

Met Ala  Ile Asp Gly Tyr Gly  Arg His Gln Ile Lys  Tyr Asp Thr
    1250                 1255                 1260

Leu Asn  Thr Ile Cys Val Lys  Asp Val Asn Trp Thr  Ala Pro Phe
    1265                 1270                 1275

Val Pro  Asp Val Glu Pro Val  Leu Glu Pro Val Val  Lys Pro Phe
    1280                 1285                 1290

Tyr Ser  Tyr Lys Asn Val Asp  Phe Tyr Gln Gly Asp  Phe Ser Asp
    1295                 1300                 1305

Leu Val  Lys Leu Pro Cys Asp  Phe Val Val Asn Ala  Ala Asn Glu
    1310                 1315                 1320

Asn Leu  Ser His Gly Gly Gly  Ile Ala Lys Ala Ile  Asp Val Tyr
    1325                 1330                 1335

Thr Lys  Gly Met Leu Gln Lys  Cys Ser Asn Asp Tyr  Ile Lys Ala
    1340                 1345                 1350

His Gly  Pro Ile Lys Val Gly  Arg Gly Val Met Leu  Glu Ala Leu
    1355                 1360                 1365

Gly Leu  Lys Val Phe Asn Val  Val Gly Pro Arg Lys  Gly Lys His
    1370                 1375                 1380

Ala Pro  Glu Leu Leu Val Lys  Ala Tyr Lys Ser Val  Phe Ala Asn
    1385                 1390                 1395

Ser Gly  Val Ala Leu Thr Pro  Leu Ile Ser Val Gly  Ile Phe Ser
    1400                 1405                 1410

Val Pro  Leu Glu Glu Ser Leu  Ser Ala Phe Leu Ala  Cys Val Gly
    1415                 1420                 1425

Asp Arg  His Cys Lys Cys Phe  Cys Tyr Ser Asp Lys  Glu Arg Glu
    1430                 1435                 1440

Ala Ile  Ile Asn Tyr Met Asp  Gly Leu Val Asp Ala  Ile Phe Lys
    1445                 1450                 1455

Asp Ala  Leu Val Asp Thr Thr  Pro Val Gln Glu Asp  Val Gln Gln
```

```
    1460                1465                1470

Val Ser  Gln Lys Pro Val Leu  Pro Asn Phe Glu Pro  Phe Arg Ile
    1475                1480                1485

Glu Gly  Ala His Ala Phe Tyr  Glu Cys Asn Pro Glu  Gly Leu Met
    1490                1495                1500

Ser Leu  Gly Ala Asp Lys Leu  Val Leu Phe Thr Asn  Ser Asn Leu
    1505                1510                1515

Asp Phe  Cys Ser Val Gly Lys  Cys Leu Asn Asn Val  Thr Gly Gly
    1520                1525                1530

Ala Leu  Leu Glu Ala Ile Asn  Val Phe Lys Lys Ser  Asn Lys Thr
    1535                1540                1545

Val Pro  Ala Gly Asn Cys Val  Thr Phe Glu Cys Ala  Asp Met Ile
    1550                1555                1560

Ser Ile  Thr Met Val Val Leu  Pro Ser Asp Gly Asp  Ala Asn Tyr
    1565                1570                1575

Asp Lys  Asn Tyr Ala Arg Ala  Val Val Lys Val Ser  Lys Leu Lys
    1580                1585                1590

Gly Lys  Leu Leu Leu Ala Val  Gly Asp Ala Met Leu  Tyr Ser Lys
    1595                1600                1605

Leu Ser  His Leu Ser Val Leu  Gly Phe Val Ser Thr  Pro Asp Asp
    1610                1615                1620

Val Glu  Arg Phe Tyr Ala Asn  Lys Ser Val Val Ile  Lys Val Thr
    1625                1630                1635

Glu Asp  Thr Arg Ser Val Lys  Thr Val Lys Val Glu  Ser Thr Val
    1640                1645                1650

Thr Tyr  Gly Gln Gln Ile Gly  Pro Cys Leu Val Asn  Asp Thr Val
    1655                1660                1665

Val Thr  Asp Asn Lys Pro Val  Val Ala Asp Val Val  Ala Lys Val
    1670                1675                1680

Val Pro  Ser Ala Asn Trp Asp  Ser His Tyr Gly Phe  Asp Lys Ala
    1685                1690                1695

Gly Glu  Phe His Met Leu Asp  His Thr Gly Phe Ala  Phe Pro Ser
    1700                1705                1710

Glu Val  Val Asn Gly Arg Arg  Val Leu Lys Thr Thr  Asp Asn Asn
    1715                1720                1725

Cys Trp  Val Asn Val Thr Cys  Leu Gln Leu Gln Phe  Ala Arg Phe
    1730                1735                1740

Arg Phe  Lys Ser Ala Gly Leu  Gln Ala Met Trp Glu  Ser Tyr Cys
    1745                1750                1755

Thr Gly  Asp Val Ala Met Phe  Val His Trp Leu Tyr  Trp Leu Thr
    1760                1765                1770

Gly Val  Asp Lys Gly Gln Pro  Ser Asp Ser Glu Asn  Ala Leu Asn
    1775                1780                1785

Met Leu  Ser Lys Tyr Ile Val  Pro Ala Gly Ser Val  Thr Ile Glu
    1790                1795                1800

Arg Val  Thr His Asp Gly Cys  Cys Cys Ser Lys Arg  Val Val Thr
    1805                1810                1815

Ala Pro  Val Val Asn Ala Ser  Val Leu Lys Leu Gly  Val Glu Asp
    1820                1825                1830

Gly Leu  Cys Pro His Gly Leu  Asn Tyr Ile Asp Lys  Val Val Val
    1835                1840                1845

Val Lys  Gly Thr Thr Ile Val  Val Asn Val Gly Lys  Pro Val Val
    1850                1855                1860
```

-continued

```
Ala Pro  Ser His Leu Phe Leu  Lys Gly Val Ser Tyr  Thr Thr Phe
    1865                 1870                 1875

Leu Asp  Asn Gly Asn Gly Val  Ala Gly His Tyr Thr  Val Phe Asp
    1880                 1885                 1890

His Asp  Thr Gly Met Val His  Asp Gly Asp Val Phe  Val Pro Gly
    1895                 1900                 1905

Asp Leu  Asn Val Ser Pro Val  Thr Asn Val Val Val  Ser Glu Gln
    1910                 1915                 1920

Thr Ala  Val Val Ile Lys Asp  Pro Val Lys Lys Val  Glu Leu Asp
    1925                 1930                 1935

Ala Thr  Lys Leu Leu Asp Thr  Met Asn Tyr Ala Ser  Glu Arg Phe
    1940                 1945                 1950

Phe Ser  Phe Gly Asp Phe Met  Ser Arg Asn Leu Ile  Thr Val Phe
    1955                 1960                 1965

Leu Tyr  Ile Leu Ser Ile Leu  Gly Leu Cys Phe Arg  Ala Phe Arg
    1970                 1975                 1980

Lys Arg  Asp Val Lys Val Leu  Ala Gly Val Pro Gln  Arg Thr Gly
    1985                 1990                 1995

Ile Ile  Leu Arg Lys Ser Val  Arg Tyr Asn Ala Lys  Ala Leu Gly
    2000                 2005                 2010

Val Phe  Phe Lys Leu Lys Leu  Tyr Trp Phe Lys Val  Leu Gly Lys
    2015                 2020                 2025

Phe Ser  Leu Gly Ile Tyr Ala  Leu Tyr Ala Leu Leu  Phe Met Thr
    2030                 2035                 2040

Ile Arg  Phe Thr Pro Ile Gly  Gly Pro Val Cys Asp  Asp Val Val
    2045                 2050                 2055

Ala Gly  Tyr Ala Asn Ser Ser  Phe Asp Lys Asn Glu  Tyr Cys Asn
    2060                 2065                 2070

Ser Val  Ile Cys Lys Val Cys  Leu Tyr Gly Tyr Gln  Glu Leu Ser
    2075                 2080                 2085

Asp Phe  Ser His Thr Gln Val  Val Trp Gln His Leu  Arg Asp Pro
    2090                 2095                 2100

Leu Ile  Gly Asn Val Met Pro  Phe Phe Tyr Leu Ala  Phe Leu Ala
    2105                 2110                 2115

Ile Phe  Gly Gly Val Tyr Val  Lys Ala Ile Thr Leu  Tyr Phe Ile
    2120                 2125                 2130

Phe Gln  Tyr Leu Asn Ile Leu  Gly Val Phe Leu Gly  Leu Gln Gln
    2135                 2140                 2145

Ser Ile  Trp Phe Leu Gln Leu  Val Pro Phe Asp Val  Phe Gly Asp
    2150                 2155                 2160

Glu Ile  Val Val Phe Phe Ile  Val Thr Arg Val Leu  Met Phe Leu
    2165                 2170                 2175

Lys His  Val Phe Leu Gly Cys  Asp Lys Ala Ser Cys  Val Ala Cys
    2180                 2185                 2190

Ser Lys  Ser Ala Arg Leu Lys  Arg Val Pro Val Gln  Thr Ile Phe
    2195                 2200                 2205

Gln Gly  Thr Ser Lys Ser Phe  Tyr Val His Ala Asn  Gly Gly Ser
    2210                 2215                 2220

Lys Phe  Cys Lys Lys His Asn  Phe Phe Cys Leu Asn  Cys Asp Ser
    2225                 2230                 2235

Tyr Gly  Pro Gly Cys Thr Phe  Ile Asn Asp Val Ile  Ala Thr Glu
    2240                 2245                 2250
```

```
Val Gly  Asn Val Val Lys Leu  Asn Val Gln Pro Thr  Gly Pro Ala
    2255                 2260                 2265

Thr Ile  Leu Ile Asp Lys Val  Glu Phe Ser Asn Gly  Phe Tyr Tyr
    2270                 2275                 2280

Leu Tyr  Ser Gly Asp Thr Phe  Trp Lys Tyr Asn Phe  Asp Ile Thr
    2285                 2290                 2295

Asp Asn  Lys Tyr Thr Cys Lys  Glu Ser Leu Lys Asn  Cys Ser Ile
    2300                 2305                 2310

Ile Thr  Asp Phe Ile Val Phe  Asn Asn Asn Gly Ser  Asn Val Asn
    2315                 2320                 2325

Gln Val  Lys Asn Ala Cys Val  Tyr Phe Ser Gln Met  Leu Cys Lys
    2330                 2335                 2340

Pro Val  Lys Leu Val Asp Ser  Ala Leu Leu Ala Ser  Leu Ser Val
    2345                 2350                 2355

Asp Phe  Gly Ala Ser Leu His  Ser Ala Phe Val Ser  Val Leu Ser
    2360                 2365                 2370

Asn Ser  Phe Gly Lys Asp Leu  Ser Ser Cys Asn Asp  Met Gln Asp
    2375                 2380                 2385

Cys Lys  Ser Thr Leu Gly Phe  Asp Asp Val Pro Leu  Asp Thr Phe
    2390                 2395                 2400

Asn Ala  Ala Val Ala Glu Ala  His Arg Tyr Asp Val  Leu Leu Thr
    2405                 2410                 2415

Asp Met  Ser Phe Asn Asn Phe  Thr Thr Ser Tyr Ala  Lys Pro Glu
    2420                 2425                 2430

Glu Lys  Leu Pro Val His Asp  Ile Ala Thr Cys Met  Arg Val Gly
    2435                 2440                 2445

Ala Lys  Ile Val Asn His Asn  Val Leu Val Lys Asp  Ser Ile Pro
    2450                 2455                 2460

Val Val  Trp Leu Val Arg Asp  Phe Ile Ala Leu Ser  Glu Glu Thr
    2465                 2470                 2475

Arg Lys  Tyr Ile Ile Arg Thr  Thr Lys Val Lys Gly  Ile Thr Phe
    2480                 2485                 2490

Met Leu  Thr Phe Asn Asp Cys  Arg Met His Thr Thr  Ile Pro Thr
    2495                 2500                 2505

Val Cys  Ile Ala Asn Lys Lys  Gly Ala Gly Leu Pro  Ser Phe Ser
    2510                 2515                 2520

Lys Val  Lys Lys Phe Phe Trp  Phe Leu Cys Leu Phe  Ile Val Ala
    2525                 2530                 2535

Val Phe  Phe Ala Leu Ser Phe  Phe Asp Phe Ser Thr  Gln Val Ser
    2540                 2545                 2550

Ser Asp  Ser Asp Tyr Asp Phe  Lys Tyr Ile Glu Ser  Gly Gln Leu
    2555                 2560                 2565

Lys Thr  Phe Asp Asn Pro Leu  Ser Cys Val His Asn  Val Phe Ser
    2570                 2575                 2580

Asn Phe  Asp Gln Trp His Asp  Ala Lys Phe Gly Phe  Thr Pro Val
    2585                 2590                 2595

Asn Asn  Pro Ser Cys Pro Ile  Val Val Gly Val Ser  Asp Glu Ala
    2600                 2605                 2610

Arg Thr  Val Pro Gly Ile Pro  Ala Gly Val Tyr Leu  Ala Gly Lys
    2615                 2620                 2625

Thr Leu  Val Phe Ala Ile Asn  Thr Ile Phe Gly Thr  Ser Gly Leu
    2630                 2635                 2640

Cys Phe  Asp Ala Ser Gly Val  Ala Asp Lys Gly Ala  Cys Ile Phe
```

```
    2645                2650                2655

Asn Ser Ala Cys Thr Thr Leu Ser Gly Leu Gly Gly Thr Ala Val
    2660                2665                2670

Tyr Cys Tyr Lys Asn Gly Leu Val Glu Gly Ala Lys Leu Tyr Ser
    2675                2680                2685

Glu Leu Ala Pro His Ser Tyr Tyr Lys Met Val Asp Gly Asn Ala
    2690                2695                2700

Val Ser Leu Pro Glu Ile Ile Ser Arg Gly Phe Gly Ile Arg Thr
    2705                2710                2715

Ile Arg Thr Lys Ala Met Thr Tyr Cys Arg Val Gly Gln Cys Val
    2720                2725                2730

Gln Ser Ala Glu Gly Val Cys Phe Gly Ala Asp Arg Phe Phe Val
    2735                2740                2745

Tyr Asn Ala Glu Ser Gly Ser Asp Phe Val Cys Gly Thr Gly Leu
    2750                2755                2760

Phe Thr Leu Leu Met Asn Val Ile Ser Val Phe Ser Lys Thr Val
    2765                2770                2775

Pro Val Thr Val Leu Ser Gly Gln Ile Leu Phe Asn Cys Ile Ile
    2780                2785                2790

Ala Phe Ala Ala Val Ala Val Cys Phe Leu Phe Thr Lys Phe Lys
    2795                2800                2805

Arg Met Phe Gly Asp Met Ser Val Gly Val Phe Thr Val Gly Ala
    2810                2815                2820

Cys Thr Leu Leu Asn Asn Val Ser Tyr Ile Val Thr Gln Asn Thr
    2825                2830                2835

Leu Gly Met Leu Gly Tyr Ala Thr Leu Tyr Phe Leu Cys Thr Lys
    2840                2845                2850

Gly Val Arg Tyr Met Trp Ile Trp His Leu Gly Phe Leu Ile Ser
    2855                2860                2865

Tyr Ile Leu Ile Ala Pro Trp Trp Val Leu Met Val Tyr Ala Phe
    2870                2875                2880

Ser Ala Ile Phe Glu Phe Met Pro Asn Leu Phe Lys Leu Lys Val
    2885                2890                2895

Ser Thr Gln Leu Phe Glu Gly Asp Lys Phe Val Gly Ser Phe Glu
    2900                2905                2910

Asn Ala Ala Ala Gly Thr Phe Val Leu Asp Met His Ala Tyr Glu
    2915                2920                2925

Arg Leu Ala Asn Ser Ile Ser Thr Glu Lys Leu Arg Gln Tyr Ala
    2930                2935                2940

Ser Thr Tyr Asn Lys Tyr Lys Tyr Tyr Ser Gly Ser Ala Ser Glu
    2945                2950                2955

Ala Asp Tyr Arg Leu Ala Cys Phe Ala His Leu Ala Lys Ala Met
    2960                2965                2970

Met Asp Tyr Ala Ser Asn His Asn Asp Thr Leu Tyr Thr Pro Pro
    2975                2980                2985

Thr Val Ser Tyr Asn Ser Thr Leu Gln Ala Gly Leu Arg Lys Met
    2990                2995                3000

Ala Gln Pro Ser Gly Val Val Glu Lys Cys Ile Val Arg Val Cys
    3005                3010                3015

Tyr Gly Asn Met Ala Leu Asn Gly Leu Trp Leu Gly Asp Thr Val
    3020                3025                3030

Ile Cys Pro Arg His Val Ile Ala Ser Ser Thr Thr Ser Thr Ile
    3035                3040                3045
```

```
Asp Tyr  Asp Tyr Ala Leu Ser  Val Leu Arg Leu His  Asn Phe Ser
    3050                 3055                 3060

Ile Ser  Ser Gly Asn Val Phe  Leu Gly Val Val Gly  Val Thr Met
    3065                 3070                 3075

Arg Gly  Ala Leu Leu Gln Ile  Lys Val Asn Gln Asn  Asn Val His
    3080                 3085                 3090

Thr Pro  Lys Tyr Thr Tyr Arg  Thr Val Arg Pro Gly  Glu Ser Phe
    3095                 3100                 3105

Asn Ile  Leu Ala Cys Tyr Asp  Gly Ser Ala Ala Gly  Val Tyr Gly
    3110                 3115                 3120

Val Asn  Met Arg Ser Asn Tyr  Thr Ile Arg Gly Ser  Phe Ile Asn
    3125                 3130                 3135

Gly Ala  Cys Gly Ser Pro Gly  Tyr Asn Ile Asn Asn  Gly Thr Val
    3140                 3145                 3150

Glu Phe  Cys Tyr Leu His Gln  Leu Glu Leu Gly Ser  Gly Cys His
    3155                 3160                 3165

Val Gly  Ser Asp Leu Asp Gly  Val Met Tyr Gly Gly  Tyr Glu Asp
    3170                 3175                 3180

Gln Pro  Thr Leu Gln Val Glu  Gly Ala Ser Ser Leu  Phe Thr Glu
    3185                 3190                 3195

Asn Val  Leu Ala Phe Leu Tyr  Ala Ala Leu Ile Asn  Gly Ser Thr
    3200                 3205                 3210

Trp Trp  Leu Ser Ser Ser Arg  Ile Ala Val Asp Arg  Phe Asn Glu
    3215                 3220                 3225

Trp Ala  Val His Asn Gly Met  Thr Thr Val Val Asn  Thr Asp Cys
    3230                 3235                 3240

Phe Ser  Ile Leu Ala Ala Lys  Thr Gly Val Asp Val  Gln Arg Leu
    3245                 3250                 3255

Leu Ala  Ser Ile Gln Ser Leu  His Lys Asn Phe Gly  Gly Lys Gln
    3260                 3265                 3270

Ile Leu  Gly Tyr Thr Ser Leu  Thr Asp Glu Phe Thr  Thr Gly Glu
    3275                 3280                 3285

Val Ile  Arg Gln Met Tyr Gly  Val Asn Leu Gln Ser  Gly Tyr Val
    3290                 3295                 3300

Ser Arg  Ala Cys Arg Asn Val  Leu Leu Val Gly Ser  Phe Leu Thr
    3305                 3310                 3315

Phe Phe  Trp Ser Glu Leu Val  Ser Tyr Thr Lys Phe  Phe Trp Val
    3320                 3325                 3330

Asn Pro  Gly Tyr Val Thr Pro  Met Phe Ala Cys Leu  Ser Leu Leu
    3335                 3340                 3345

Ser Ser  Leu Leu Met Phe Thr  Leu Lys His Lys Thr  Leu Phe Phe
    3350                 3355                 3360

Gln Val  Phe Leu Ile Pro Ala  Leu Ile Val Thr Ser  Cys Ile Asn
    3365                 3370                 3375

Leu Ala  Phe Asp Val Glu Val  Tyr Asn Tyr Leu Ala  Glu His Phe
    3380                 3385                 3390

Asp Tyr  His Val Ser Leu Met  Gly Phe Asn Ala Gln  Gly Leu Val
    3395                 3400                 3405

Asn Ile  Phe Val Cys Phe Val  Val Thr Ile Leu His  Gly Thr Tyr
    3410                 3415                 3420

Thr Trp  Arg Phe Phe Asn Thr  Pro Val Ser Ser Val  Thr Tyr Val
    3425                 3430                 3435
```

-continued

```
Val Ala  Leu Leu Thr Ala Ala  Tyr Asn Tyr Phe Tyr  Ala Ser Asp
    3440                 3445                 3450

Ile Leu  Ser Cys Ala Met Thr  Leu Phe Ala Ser Val  Thr Gly Asn
    3455                 3460                 3465

Trp Phe  Val Gly Ala Val Cys  Tyr Lys Ala Ala Val  Tyr Met Ala
    3470                 3475                 3480

Leu Arg  Phe Pro Thr Phe Val  Ala Ile Phe Gly Asp  Ile Lys Ser
    3485                 3490                 3495

Val Met  Phe Cys Tyr Leu Val  Leu Gly Tyr Phe Thr  Cys Cys Phe
    3500                 3505                 3510

Tyr Gly  Ile Leu Tyr Trp Phe  Asn Arg Phe Phe Lys  Val Ser Val
    3515                 3520                 3525

Gly Val  Tyr Asp Tyr Thr Val  Ser Ala Ala Glu Phe  Lys Tyr Met
    3530                 3535                 3540

Val Ala  Asn Gly Leu Arg Ala  Pro Thr Gly Thr Leu  Asp Ser Leu
    3545                 3550                 3555

Leu Leu  Ser Ala Lys Leu Ile  Gly Ile Gly Gly Glu  Arg Asn Ile
    3560                 3565                 3570

Lys Ile  Ser Ser Val Gln Ser  Lys Leu Thr Asp Ile  Lys Cys Ser
    3575                 3580                 3585

Asn Val  Val Leu Leu Gly Cys  Leu Ser Ser Met Asn  Val Ser Ala
    3590                 3595                 3600

Asn Ser  Thr Glu Trp Ala Tyr  Cys Val Asp Leu His  Asn Lys Ile
    3605                 3610                 3615

Asn Leu  Cys Asn Asp Pro Glu  Lys Ala Gln Glu Met  Leu Leu Ala
    3620                 3625                 3630

Leu Leu  Ala Phe Phe Leu Ser  Lys Asn Ser Ala Phe  Gly Leu Asp
    3635                 3640                 3645

Asp Leu  Leu Glu Ser Tyr Phe  Asn Asp Asn Ser Met  Leu Gln Ser
    3650                 3655                 3660

Val Ala  Ser Thr Tyr Val Gly  Leu Pro Ser Tyr Val  Ile Tyr Glu
    3665                 3670                 3675

Asn Ala  Arg Gln Gln Tyr Glu  Asp Ala Val Asn Asn  Gly Ser Pro
    3680                 3685                 3690

Pro Gln  Leu Val Lys Gln Leu  Arg His Ala Met Asn  Val Ala Lys
    3695                 3700                 3705

Ser Glu  Phe Asp Arg Glu Ala  Ser Thr Gln Arg Lys  Leu Asp Arg
    3710                 3715                 3720

Met Ala  Glu Gln Ala Ala Ala  Gln Met Tyr Lys Glu  Ala Arg Ala
    3725                 3730                 3735

Val Asn  Arg Lys Ser Lys Val  Val Ser Ala Met His  Ser Leu Leu
    3740                 3745                 3750

Phe Gly  Met Leu Arg Arg Leu  Asp Met Ser Ser Val  Asp Thr Ile
    3755                 3760                 3765

Leu Asn  Leu Ala Lys Asp Gly  Val Val Pro Leu Ser  Val Ile Pro
    3770                 3775                 3780

Ala Val  Ser Ala Thr Lys Leu  Asn Ile Val Thr Ser  Asp Ile Asp
    3785                 3790                 3795

Ser Tyr  Asn Arg Ile Gln Arg  Glu Gly Cys Val His  Tyr Ala Gly
    3800                 3805                 3810

Thr Ile  Trp Asn Ile Ile Asp  Ile Lys Asp Asn Asp  Gly Lys Val
    3815                 3820                 3825

Val His  Val Lys Glu Val Thr  Ala Gln Asn Ala Glu  Ser Leu Ser
```

-continued

```
    3830                3835                3840

Trp Pro Leu Val Leu Gly Cys Glu Arg Ile Val Lys Leu Gln Asn
    3845                3850                3855

Asn Glu Ile Ile Pro Gly Lys Leu Lys Gln Arg Ser Ile Lys Ala
    3860                3865                3870

Glu Gly Asp Gly Ile Val Gly Glu Gly Lys Ala Leu Tyr Asn Asn
    3875                3880                3885

Glu Gly Gly Arg Thr Phe Met Tyr Ala Phe Ile Ser Asp Lys Pro
    3890                3895                3900

Asp Leu Arg Val Val Lys Trp Glu Phe Asp Gly Gly Cys Asn Thr
    3905                3910                3915

Ile Glu Leu Glu Pro Pro Arg Lys Phe Leu Val Asp Ser Pro Asn
    3920                3925                3930

Gly Ala Gln Ile Lys Tyr Leu Tyr Phe Val Arg Asn Leu Asn Thr
    3935                3940                3945

Leu Arg Arg Gly Ala Val Leu Gly Tyr Ile Gly Ala Thr Val Arg
    3950                3955                3960

Leu Gln Ala Gly Lys Gln Thr Glu Gln Ala Ile Asn Ser Ser Leu
    3965                3970                3975

Leu Thr Leu Cys Ala Phe Ala Val Asp Pro Ala Lys Thr Tyr Ile
    3980                3985                3990

Asp Ala Val Lys Ser Gly His Lys Pro Val Gly Asn Cys Val Lys
    3995                4000                4005

Met Leu Ala Asn Gly Ser Gly Asn Gly Gln Ala Val Thr Asn Gly
    4010                4015                4020

Val Glu Ala Ser Thr Asn Gln Asp Ser Tyr Gly Gly Ala Ser Val
    4025                4030                4035

Cys Leu Tyr Cys Arg Ala His Val Glu His Pro Ser Met Asp Gly
    4040                4045                4050

Phe Cys Arg Leu Lys Gly Lys Tyr Val Gln Val Pro Leu Gly Thr
    4055                4060                4065

Val Asp Pro Ile Arg Phe Val Leu Glu Asn Asp Val Cys Lys Val
    4070                4075                4080

Cys Gly Cys Trp Leu Ala Asn Gly Cys Thr Cys Asp Arg Ser Ile
    4085                4090                4095

Met Gln Ser Thr Asp Tyr Gly Leu Phe Lys Arg Val Arg Gly Ser
    4100                4105                4110

Ser Ala Ala Arg Leu Glu Pro Cys Asn Gly Thr Asp Thr Gln His
    4115                4120                4125

Val Tyr Arg Ala Phe Asp Ile Tyr Asn Lys Asp Val Ala Cys Leu
    4130                4135                4140

Gly Lys Phe Leu Lys Val Asn Cys Val Arg Leu Lys Asn Leu Asp
    4145                4150                4155

Lys His Asp Ala Phe Tyr Val Val Lys Arg Cys Thr Lys Ser Ala
    4160                4165                4170

Met Glu His Glu Gln Ser Ile Tyr Ser Arg Leu Glu Lys Cys Gly
    4175                4180                4185

Ala Val Ala Glu His Asp Phe Phe Thr Trp Lys Asp Gly Arg Ala
    4190                4195                4200

Ile Tyr Gly Asn Val Cys Arg Lys Asp Leu Thr Glu Tyr Thr Met
    4205                4210                4215

Met Asp Leu Cys Tyr Ala Leu Arg Asn Phe Asp Glu Asn Asn Cys
    4220                4225                4230
```

```
Asp Val  Leu Lys Ser Ile Leu  Ile Lys Val Gly Ala  Cys Glu Glu
    4235                 4240                 4245

Ser Tyr  Phe Asn Asn Lys Val  Trp Phe Asp Pro Val  Glu Asn Glu
    4250                 4255                 4260

Asp Ile  His Arg Val Tyr Ala  Leu Leu Gly Thr Ile  Val Ser Arg
    4265                 4270                 4275

Ala Met  Leu Lys Cys Val Lys  Phe Cys Asp Ala Met  Val Glu Gln
    4280                 4285                 4290

Gly Ile  Val Gly Val Val Thr  Leu Asp Asn Gln Asp  Leu Asn Gly
    4295                 4300                 4305

Asp Phe  Tyr Asp Phe Gly Asp  Phe Thr Cys Ser Ile  Lys Gly Met
    4310                 4315                 4320

Gly Ile  Pro Ile Cys Thr Ser  Tyr Tyr Ser Tyr Met  Met Pro Val
    4325                 4330                 4335

Met Gly  Met Thr Asn Cys Leu  Ala Ser Glu Cys Phe  Val Lys Ser
    4340                 4345                 4350

Asp Ile  Phe Gly Glu Asp Phe  Lys Ser Tyr Asp Leu  Leu Glu Tyr
    4355                 4360                 4365

Asp Phe  Thr Glu His Lys Thr  Ala Leu Phe Asn Lys  Tyr Phe Lys
    4370                 4375                 4380

Tyr Trp  Gly Leu Gln Tyr His  Pro Asn Cys Val Asp  Cys Ser Asp
    4385                 4390                 4395

Glu Gln  Cys Ile Val His Cys  Ala Asn Phe Asn Thr  Leu Phe Ser
    4400                 4405                 4410

Thr Thr  Ile Pro Ile Thr Ala  Phe Gly Pro Leu Cys  Arg Lys Cys
    4415                 4420                 4425

Trp Ile  Asp Gly Val Pro Leu  Val Thr Thr Ala Gly  Tyr His Phe
    4430                 4435                 4440

Lys Gln  Leu Gly Ile Val Trp  Asn Asn Asp Leu Asn  Leu His Ser
    4445                 4450                 4455

Ser Arg  Leu Ser Ile Asn Glu  Leu Leu Gln Phe Cys  Ser Asp Pro
    4460                 4465                 4470

Ala Leu  Leu Ile Ala Ser Ser  Pro Ala Leu Val Asp  Gln Arg Thr
    4475                 4480                 4485

Val Cys  Phe Ser Val Ala Ala  Leu Gly Thr Gly Met  Thr Asn Gln
    4490                 4495                 4500

Thr Val  Lys Pro Gly His Phe  Asn Lys Glu Phe Tyr  Asp Phe Leu
    4505                 4510                 4515

Leu Glu  Gln Gly Phe Phe Ser  Glu Gly Ser Glu Leu  Thr Leu Lys
    4520                 4525                 4530

His Phe  Phe Phe Ala Gln Lys  Gly Asp Ala Ala Val  Lys Asp Phe
    4535                 4540                 4545

Asp Tyr  Tyr Arg Tyr Asn Arg  Pro Thr Val Leu Asp  Ile Cys Gln
    4550                 4555                 4560

Ala Arg  Val Val Tyr Gln Ile  Val Gln Arg Tyr Phe  Asp Ile Tyr
    4565                 4570                 4575

Glu Gly  Gly Cys Ile Thr Ala  Lys Glu Val Val Val  Thr Asn Leu
    4580                 4585                 4590

Asn Lys  Ser Ala Gly Tyr Pro  Leu Asn Lys Phe Gly  Lys Ala Gly
    4595                 4600                 4605

Leu Tyr  Tyr Glu Ser Leu Ser  Tyr Glu Glu Gln Asp  Glu Leu Tyr
    4610                 4615                 4620
```

-continued

Ala Tyr Thr Lys Arg Asn Ile Leu Pro Thr Met Thr Gln Leu Asn
4625 4630 4635

Leu Lys Tyr Ala Ile Ser Gly Lys Glu Arg Ala Arg Thr Val Gly
4640 4645 4650

Gly Val Ser Leu Leu Ser Thr Met Thr Thr Arg Gln Tyr His Gln
4655 4660 4665

Lys His Leu Lys Ser Ile Val Asn Thr Arg Gly Ala Ser Val Val
4670 4675 4680

Ile Gly Thr Thr Lys Phe Tyr Gly Gly Trp Asp Asn Met Leu Lys
4685 4690 4695

Asn Leu Ile Asp Gly Val Glu Asn Pro Cys Leu Met Gly Trp Asp
4700 4705 4710

Tyr Pro Lys Cys Asp Arg Ala Leu Pro Asn Met Ile Arg Met Ile
4715 4720 4725

Ser Ala Met Ile Leu Gly Ser Lys His Thr Thr Cys Cys Ser Ser
4730 4735 4740

Thr Asp Arg Phe Phe Arg Leu Cys Asn Glu Leu Ala Gln Val Leu
4745 4750 4755

Thr Glu Val Val Tyr Ser Asn Gly Gly Phe Tyr Leu Lys Pro Gly
4760 4765 4770

Gly Thr Thr Ser Gly Asp Ala Thr Thr Ala Tyr Ala Asn Ser Val
4775 4780 4785

Phe Asn Ile Phe Gln Ala Val Ser Ala Asn Val Asn Lys Leu Leu
4790 4795 4800

Ser Val Asp Ser Asn Val Cys His Asn Leu Glu Val Lys Gln Leu
4805 4810 4815

Gln Arg Lys Leu Tyr Glu Cys Cys Tyr Arg Ser Thr Thr Val Asp
4820 4825 4830

Asp Gln Phe Val Val Glu Tyr Tyr Gly Tyr Leu Arg Lys His Phe
4835 4840 4845

Ser Met Met Ile Leu Ser Asp Asp Gly Val Val Cys Tyr Asn Asn
4850 4855 4860

Asp Tyr Ala Ser Leu Gly Tyr Val Ala Asp Leu Asn Ala Phe Lys
4865 4870 4875

Ala Val Leu Tyr Tyr Gln Asn Asn Val Phe Met Ser Ala Ser Lys
4880 4885 4890

Cys Trp Ile Glu Pro Asp Ile Asn Lys Gly Pro His Glu Phe Cys
4895 4900 4905

Ser Gln His Thr Met Gln Ile Val Asp Lys Asp Gly Thr Tyr Tyr
4910 4915 4920

Leu Pro Tyr Pro Asp Pro Ser Arg Ile Leu Ser Ala Gly Val Phe
4925 4930 4935

Val Asp Asp Val Val Lys Thr Asp Ala Val Val Leu Leu Glu Arg
4940 4945 4950

Tyr Val Ser Leu Ala Ile Asp Ala Tyr Pro Leu Ser Lys His Glu
4955 4960 4965

Asn Pro Glu Tyr Lys Lys Val Phe Tyr Val Leu Leu Asp Trp Val
4970 4975 4980

Lys His Leu Tyr Lys Thr Leu Asn Ala Gly Val Leu Glu Ser Phe
4985 4990 4995

Ser Val Thr Leu Leu Glu Asp Ser Thr Ala Lys Phe Trp Asp Glu
5000 5005 5010

Ser Phe Tyr Ala Asn Met Tyr Glu Lys Ser Ala Val Leu Gln Ser

```
    5015                5020                5025

Ala Gly  Leu Cys Val Val Cys  Gly Ser Gln Thr Val  Leu Arg Cys
    5030                5035                5040

Gly Asp  Cys Leu Arg Arg Pro  Met Leu Cys Thr Lys  Cys Ala Tyr
    5045                5050                5055

Asp His  Val Ile Gly Thr Thr  His Lys Phe Ile Leu  Ala Ile Thr
    5060                5065                5070

Pro Tyr  Val Cys Cys Ala Ser  Asp Cys Gly Val Asn  Asp Val Thr
    5075                5080                5085

Lys Leu  Tyr Leu Gly Gly Leu  Ser Tyr Trp Cys His  Asp His Lys
    5090                5095                5100

Pro Arg  Leu Ala Phe Pro Leu  Cys Ser Ala Gly Asn  Val Phe Gly
    5105                5110                5115

Leu Tyr  Lys Asn Ser Ala Thr  Gly Ser Pro Asp Val  Glu Asp Phe
    5120                5125                5130

Asn Arg  Ile Ala Thr Ser Asp  Trp Thr Asp Val Ser  Asp Tyr Arg
    5135                5140                5145

Leu Ala  Asn Asp Val Lys Asp  Ser Leu Arg Leu Phe  Ala Ala Glu
    5150                5155                5160

Thr Ile  Lys Ala Lys Glu Glu  Ser Val Lys Ser Ser  Tyr Ala Cys
    5165                5170                5175

Ala Thr  Leu His Glu Val Val  Gly Pro Lys Glu Leu  Leu Leu Lys
    5180                5185                5190

Trp Glu  Val Gly Arg Pro Lys  Pro Pro Leu Asn Arg  Asn Ser Val
    5195                5200                5205

Phe Thr  Cys Tyr His Ile Thr  Lys Asn Thr Lys Phe  Gln Ile Gly
    5210                5215                5220

Glu Phe  Val Phe Glu Lys Ala  Glu Tyr Asp Asn Asp  Ala Val Thr
    5225                5230                5235

Tyr Lys  Thr Thr Ala Thr Thr  Lys Leu Val Pro Gly  Met Val Phe
    5240                5245                5250

Val Leu  Thr Ser His Asn Val  Gln Pro Leu Arg Ala  Pro Thr Ile
    5255                5260                5265

Ala Asn  Gln Glu Arg Tyr Ser  Thr Ile His Lys Leu  His Pro Ala
    5270                5275                5280

Phe Asn  Ile Pro Glu Ala Tyr  Ser Ser Leu Val Pro  Tyr Tyr Gln
    5285                5290                5295

Leu Ile  Gly Lys Gln Lys Ile  Thr Thr Ile Gln Gly  Pro Pro Gly
    5300                5305                5310

Ser Gly  Lys Ser His Cys Val  Ile Gly Leu Gly Leu  Tyr Tyr Pro
    5315                5320                5325

Gly Ala  Arg Ile Val Phe Thr  Ala Cys Ser His Ala  Ala Val Asp
    5330                5335                5340

Ser Leu  Cys Val Lys Ala Ser  Thr Ala Tyr Ser Asn  Asp Lys Cys
    5345                5350                5355

Ser Arg  Ile Ile Pro Gln Arg  Ala Arg Val Glu Cys  Tyr Asp Gly
    5360                5365                5370

Phe Lys  Ser Asn Asn Thr Ser  Ala Gln Tyr Leu Phe  Ser Thr Val
    5375                5380                5385

Asn Ala  Leu Pro Glu Cys Asn  Ala Asp Ile Val Val  Val Asp Glu
    5390                5395                5400

Val Ser  Met Cys Thr Asn Tyr  Asp Leu Ser Val Ile  Asn Gln Arg
    5405                5410                5415
```

```
Ile Ser  Tyr Arg His Val Val  Tyr Val Gly Asp Pro  Gln Gln Leu
    5420                 5425                 5430

Pro Ala  Pro Arg Val Met Ile  Ser Arg Gly Thr Leu  Glu Pro Lys
    5435                 5440                 5445

Asp Tyr  Asn Val Val Thr Gln  Arg Met Cys Ala Leu  Lys Pro Asp
    5450                 5455                 5460

Val Phe  Leu His Lys Cys Tyr  Arg Cys Pro Ala Glu  Ile Val Arg
    5465                 5470                 5475

Thr Val  Ser Glu Met Val Tyr  Glu Asn Gln Phe Ile  Pro Val His
    5480                 5485                 5490

Pro Asp  Ser Lys Gln Cys Phe  Lys Ile Phe Cys Lys  Gly Asn Val
    5495                 5500                 5505

Gln Val  Asp Asn Gly Ser Ser  Ile Asn Arg Arg Gln  Leu Asp Val
    5510                 5515                 5520

Val Arg  Met Phe Leu Ala Lys  Asn Pro Arg Trp Ser  Lys Ala Val
    5525                 5530                 5535

Phe Ile  Ser Pro Tyr Asn Ser  Gln Asn Tyr Val Ala  Ser Arg Met
    5540                 5545                 5550

Leu Gly  Leu Gln Ile Gln Thr  Val Asp Ser Ser Gln  Gly Ser Glu
    5555                 5560                 5565

Tyr Asp  Tyr Val Ile Tyr Thr  Gln Thr Ser Asp Thr  Ala His Ala
    5570                 5575                 5580

Cys Asn  Val Asn Arg Phe Asn  Val Ala Ile Thr Arg  Ala Lys Lys
    5585                 5590                 5595

Gly Ile  Leu Cys Ile Met Cys  Asp Arg Ser Leu Phe  Asp Val Leu
    5600                 5605                 5610

Lys Phe  Phe Glu Leu Lys Leu  Ser Asp Leu Gln Ala  Asn Glu Gly
    5615                 5620                 5625

Cys Gly  Leu Phe Lys Asp Cys  Ser Arg Gly Asp Asp  Leu Leu Pro
    5630                 5635                 5640

Pro Ser  His Ala Asn Thr Phe  Met Ser Leu Ala Asp  Asn Phe Lys
    5645                 5650                 5655

Thr Asp  Gln Asp Leu Ala Val  Gln Ile Gly Val Asn  Gly Pro Ile
    5660                 5665                 5670

Lys Tyr  Glu His Val Ile Ser  Phe Met Gly Phe Arg  Phe Asp Ile
    5675                 5680                 5685

Asn Ile  Pro Asn His His Thr  Leu Phe Cys Thr Arg  Asp Phe Ala
    5690                 5695                 5700

Met Arg  Asn Val Arg Gly Trp  Leu Gly Phe Asp Val  Glu Gly Ala
    5705                 5710                 5715

His Val  Val Gly Ser Asn Val  Gly Thr Asn Val Pro  Leu Gln Leu
    5720                 5725                 5730

Gly Phe  Ser Asn Gly Val Asp  Phe Val Val Arg Pro  Glu Gly Cys
    5735                 5740                 5745

Val Val  Thr Glu Ser Gly Asp  Tyr Ile Lys Pro Val  Arg Ala Arg
    5750                 5755                 5760

Ala Pro  Pro Gly Glu Gln Phe  Ala His Leu Leu Pro  Leu Leu Lys
    5765                 5770                 5775

Arg Gly  Gln Pro Trp Asp Val  Val Arg Lys Arg Ile  Val Gln Met
    5780                 5785                 5790

Cys Ser  Asp Tyr Leu Ala Asn  Leu Ser Asp Ile Leu  Ile Phe Val
    5795                 5800                 5805
```

```
Leu Trp Ala Gly Gly Leu Glu Leu Thr Thr Met Arg Tyr Phe Val
    5810                5815                5820

Lys Ile Gly Pro Ser Lys Ser Cys Asp Cys Gly Lys Val Ala Thr
    5825                5830                5835

Cys Tyr Asn Ser Ala Leu His Thr Tyr Cys Cys Phe Lys His Ala
    5840                5845                5850

Leu Gly Cys Asp Tyr Leu Tyr Asn Pro Tyr Cys Ile Asp Ile Gln
    5855                5860                5865

Gln Trp Gly Tyr Lys Gly Ser Leu Ser Leu Asn His His Glu His
    5870                5875                5880

Cys Asn Val His Arg Asn Glu His Val Ala Ser Gly Asp Ala Ile
    5885                5890                5895

Met Thr Arg Cys Leu Ala Ile His Asp Cys Phe Val Lys Asn Val
    5900                5905                5910

Asp Trp Ser Ile Thr Tyr Pro Phe Ile Gly Asn Glu Ala Val Ile
    5915                5920                5925

Asn Lys Ser Gly Arg Ile Val Gln Ser His Thr Met Arg Ser Val
    5930                5935                5940

Leu Lys Leu Tyr Asn Pro Lys Ala Ile Tyr Asp Ile Gly Asn Pro
    5945                5950                5955

Lys Gly Ile Arg Cys Ala Val Thr Asp Ala Lys Trp Phe Cys Phe
    5960                5965                5970

Asp Lys Asn Pro Thr Asn Ser Asn Val Lys Thr Leu Glu Tyr Asp
    5975                5980                5985

Tyr Ile Thr His Gly Gln Phe Asp Gly Leu Cys Leu Phe Trp Asn
    5990                5995                6000

Cys Asn Val Asp Met Tyr Pro Glu Phe Ser Val Val Cys Arg Phe
    6005                6010                6015

Asp Thr Arg Cys Arg Ser Pro Leu Asn Leu Glu Gly Cys Asn Gly
    6020                6025                6030

Gly Ser Leu Tyr Val Asn Asn His Ala Phe His Thr Pro Ala Phe
    6035                6040                6045

Asp Lys Arg Ala Phe Ala Lys Leu Lys Pro Met Pro Phe Phe Phe
    6050                6055                6060

Tyr Asp Asp Thr Glu Cys Asp Lys Leu Gln Asp Ser Ile Asn Tyr
    6065                6070                6075

Val Pro Leu Arg Ala Ser Asn Cys Ile Thr Lys Cys Asn Val Gly
    6080                6085                6090

Gly Ala Val Cys Ser Lys His Cys Ala Met Tyr His Ser Tyr Val
    6095                6100                6105

Asn Ala Tyr Asn Thr Phe Thr Ser Ala Gly Phe Thr Ile Trp Val
    6110                6115                6120

Pro Thr Ser Phe Asp Thr Tyr Asn Leu Trp Gln Thr Phe Ser Asn
    6125                6130                6135

Asn Leu Gln Gly Leu Glu Asn Ile Ala Phe Asn Val Val Lys Lys
    6140                6145                6150

Gly Ser Phe Val Gly Ala Glu Gly Glu Leu Pro Val Ala Val Val
    6155                6160                6165

Asn Asp Lys Val Leu Val Arg Asp Gly Thr Val Asp Thr Leu Val
    6170                6175                6180

Phe Thr Asn Lys Thr Ser Leu Pro Thr Asn Val Ala Phe Glu Leu
    6185                6190                6195

Tyr Ala Lys Arg Lys Val Gly Leu Thr Pro Pro Ile Thr Ile Leu
```

-continued

```
    6200                6205                6210

Arg Asn  Leu Gly Val Val Cys  Thr Ser Lys Cys Val  Ile Trp Asp
    6215                6220                6225

Tyr Glu  Ala Glu Arg Pro Leu  Thr Thr Phe Thr Lys  Asp Val Cys
    6230                6235                6240

Lys Tyr  Thr Asp Phe Glu Gly  Asp Val Cys Thr Leu  Phe Asp Asn
    6245                6250                6255

Ser Ile  Val Gly Ser Leu Glu  Arg Phe Ser Met Thr  Gln Asn Ala
    6260                6265                6270

Val Leu  Met Ser Leu Thr Ala  Val Lys Lys Leu Thr  Gly Ile Lys
    6275                6280                6285

Leu Thr  Tyr Gly Tyr Leu Asn  Gly Val Pro Val Asn  Thr His Glu
    6290                6295                6300

Asp Lys  Pro Phe Thr Trp Tyr  Ile Tyr Thr Arg Lys  Asn Gly Lys
    6305                6310                6315

Phe Glu  Asp His Pro Asp Gly  Tyr Phe Thr Gln Gly  Arg Thr Thr
    6320                6325                6330

Ala Asp  Phe Ser Pro Arg Ser  Asp Met Glu Lys Asp  Phe Leu Ser
    6335                6340                6345

Met Asp  Met Gly Leu Phe Ile  Asn Lys Tyr Gly Leu  Glu Asp Tyr
    6350                6355                6360

Gly Phe  Glu His Val Val Tyr  Gly Asp Val Ser Lys  Thr Thr Leu
    6365                6370                6375

Gly Gly  Leu His Leu Leu Ile  Ser Gln Val Arg Leu  Ala Cys Met
    6380                6385                6390

Gly Val  Leu Lys Ile Asp Glu  Phe Val Ser Ser Asn  Asp Ser Thr
    6395                6400                6405

Leu Lys  Ser Cys Thr Val Thr  Tyr Ala Asp Asn Pro  Ser Ser Lys
    6410                6415                6420

Met Val  Cys Thr Tyr Met Asp  Leu Leu Leu Asp Asp  Phe Val Ser
    6425                6430                6435

Ile Leu  Lys Ser Leu Asp Leu  Gly Val Val Ser Lys  Val His Glu
    6440                6445                6450

Val Met  Val Asp Cys Lys Met  Trp Arg Trp Met Leu  Trp Cys Lys
    6455                6460                6465

Asp His  Lys Leu Gln Thr Phe  Tyr Pro Gln Leu Gln  Ala Ser Glu
    6470                6475                6480

Trp Lys  Cys Gly Tyr Ser Met  Pro Ser Ile Tyr Lys  Ile Gln Arg
    6485                6490                6495

Met Cys  Leu Glu Pro Cys Asn  Leu Tyr Asn Tyr Gly  Ala Gly Ile
    6500                6505                6510

Lys Leu  Pro Asp Gly Ile Met  Phe Asn Val Val Lys  Tyr Thr Gln
    6515                6520                6525

Leu Cys  Gln Tyr Leu Asn Ser  Thr Thr Met Cys Val  Pro His His
    6530                6535                6540

Met Arg  Val Leu His Leu Gly  Ala Gly Ser Asp Lys  Gly Val Ala
    6545                6550                6555

Pro Gly  Thr Ala Val Leu Arg  Arg Trp Leu Pro Leu  Asp Ala Ile
    6560                6565                6570

Ile Val  Asp Asn Asp Ser Val  Asp Tyr Val Ser Asp  Ala Asp Tyr
    6575                6580                6585

Ser Val  Thr Gly Asp Cys Ser  Thr Leu Tyr Leu Ser  Asp Lys Phe
    6590                6595                6600
```

```
Asp Leu  Val Ile Ser Asp Met  Tyr Asp Gly Lys Ile  Lys Ser Cys
    6605                 6610                 6615

Asp Gly  Glu Asn Val Ser Lys  Glu Gly Phe Phe Pro  Tyr Ile Asn
    6620                 6625                 6630

Gly Val  Ile Thr Glu Lys Leu  Ala Leu Gly Gly Thr  Val Ala Ile
    6635                 6640                 6645

Lys Val  Thr Glu Phe Ser Trp  Asn Lys Lys Leu Tyr  Glu Leu Ile
    6650                 6655                 6660

Gln Arg  Phe Glu Tyr Trp Thr  Met Phe Cys Thr Ser  Val Asn Thr
    6665                 6670                 6675

Ser Ser  Ser Glu Ala Phe Leu  Ile Gly Val His Tyr  Leu Gly Asp
    6680                 6685                 6690

Phe Ala  Ser Gly Ala Val Ile  Asp Gly Asn Thr Met  His Ala Asn
    6695                 6700                 6705

Tyr Ile  Phe Trp Arg Asn Ser  Thr Ile Met Thr Met  Ser Tyr Asn
    6710                 6715                 6720

Ser Val  Leu Asp Leu Ser Lys  Phe Asn Cys Lys His  Lys Ala Thr
    6725                 6730                 6735

Val Val  Ile Asn Leu Lys Asp  Ser Ser Ile Ser Asp  Val Val Leu
    6740                 6745                 6750

Gly Leu  Leu Lys Asn Gly Lys  Leu Leu Val Arg Asn  Asn Asp Ala
    6755                 6760                 6765

Ile Cys  Gly Phe Ser Asn His  Leu Val Asn Val Asn  Lys
    6770                 6775                 6780


<210> SEQ ID NO 12
<211> LENGTH: 1386
<212> TYPE: PRT
<213> ORGANISM: artificial sequence
<220> FEATURE:
<223> OTHER INFORMATION: Spike (S1 and S2 domains) protein amino acid
      sequence

<400> SEQUENCE: 12

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
```

-continued

```
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590
```

-continued

```
Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
        995                 1000                1005
```

-continued

```
Asn Ile  Thr Ser Ala Phe Glu  Ser Val Lys Glu Ala  Ile Ser Gln
    1010                 1015                 1020

Thr Ser  Lys Gly Leu Asn Thr  Val Ala His Ala Leu  Thr Lys Val
    1025                 1030                 1035

Gln Glu  Val Val Asn Ser Gln  Gly Ala Ala Leu Thr  Gln Leu Thr
    1040                 1045                 1050

Val Gln  Leu Gln His Asn Phe  Gln Ala Ile Ser Ser  Ser Ile Asp
    1055                 1060                 1065

Asp Ile  Tyr Ser Arg Leu Asp  Ile Leu Ser Ala Asp  Val Gln Val
    1070                 1075                 1080

Asp Arg  Leu Ile Thr Gly Arg  Leu Ser Ala Leu Asn  Ala Phe Val
    1085                 1090                 1095

Ser Gln  Thr Leu Thr Lys Tyr  Thr Glu Val Gln Ala  Ser Arg Lys
    1100                 1105                 1110

Leu Ala  Gln Gln Lys Val Asn  Glu Cys Val Lys Ser  Gln Ser Gln
    1115                 1120                 1125

Arg Tyr  Gly Phe Cys Gly Gly  Asp Gly Glu His Ile  Phe Ser Leu
    1130                 1135                 1140

Val Gln  Ala Ala Pro Gln Gly  Leu Leu Phe Leu His  Thr Val Leu
    1145                 1150                 1155

Val Pro  Ser Asp Phe Val Asp  Val Ile Ala Ile Ala  Gly Leu Cys
    1160                 1165                 1170

Val Asn  Asp Glu Ile Ala Leu  Thr Leu Arg Glu Pro  Gly Leu Val
    1175                 1180                 1185

Leu Phe  Thr His Glu Leu Gln  Asn His Thr Ala Thr  Glu Tyr Phe
    1190                 1195                 1200

Val Ser  Ser Arg Arg Met Phe  Glu Pro Arg Lys Pro  Thr Val Ser
    1205                 1210                 1215

Asp Phe  Val Gln Ile Glu Ser  Cys Val Val Thr Tyr  Val Asn Leu
    1220                 1225                 1230

Thr Arg  Asp Gln Leu Pro Asp  Val Ile Pro Asp Tyr  Ile Asp Val
    1235                 1240                 1245

Asn Lys  Thr Leu Asp Glu Ile  Leu Ala Ser Leu Pro  Asn Arg Thr
    1250                 1255                 1260

Gly Pro  Ser Leu Pro Leu Asp  Val Phe Asn Ala Thr  Tyr Leu Asn
    1265                 1270                 1275

Leu Thr  Gly Glu Ile Ala Asp  Leu Glu Gln Arg Ser  Glu Ser Leu
    1280                 1285                 1290

Arg Asn  Thr Thr Glu Glu Leu  Gln Ser Leu Ile Tyr  Asn Ile Asn
    1295                 1300                 1305

Asn Thr  Leu Val Asp Leu Glu  Trp Leu Asn Arg Val  Glu Thr Tyr
    1310                 1315                 1320

Ile Lys  Trp Pro Trp Trp Val  Trp Leu Ile Ile Phe  Ile Val Leu
    1325                 1330                 1335

Ile Phe  Val Val Ser Leu Leu  Val Phe Cys Cys Ile  Ser Thr Gly
    1340                 1345                 1350

Cys Cys  Gly Cys Cys Gly Cys  Cys Cys Ala Cys Phe  Ser Gly Cys
    1355                 1360                 1365

Cys Arg  Gly Pro Arg Leu Gln  Pro Tyr Glu Val Phe  Glu Lys Val
    1370                 1375                 1380

His Val  Gln
    1385
```

<210> SEQ ID NO 13
<211> LENGTH: 224
<212> TYPE: PRT
<213> ORGANISM: artificial sequence
<220> FEATURE:
<223> OTHER INFORMATION: ORF3 Coronavirus NS3b amino acid sequence

<400> SEQUENCE: 13

```
Met Phe Leu Gly Leu Phe Gln Tyr Thr Ile Asp Thr Val Val Lys Asp
1               5                   10                  15

Val Ser Lys Ser Ala Asn Leu Ser Leu Asp Ala Val Gln Glu Leu Glu
            20                  25                  30

Leu Asn Val Val Pro Ile Arg Gln Ala Ser Asn Val Thr Gly Phe Leu
        35                  40                  45

Phe Thr Ser Val Phe Ile Tyr Phe Phe Ala Leu Phe Lys Ala Ser Ser
    50                  55                  60

Leu Arg Arg Asn Tyr Ile Met Leu Ala Ala Arg Phe Ala Val Ile Val
65                  70                  75                  80

Leu Tyr Cys Pro Leu Leu Tyr Tyr Cys Gly Ala Phe Leu Asp Ala Thr
                85                  90                  95

Ile Ile Cys Cys Thr Leu Ile Gly Arg Leu Cys Leu Val Cys Phe Tyr
            100                 105                 110

Ser Trp Arg Tyr Lys Asn Ala Leu Phe Ile Ile Phe Asn Thr Thr Thr
        115                 120                 125

Leu Ser Phe Leu Asn Gly Lys Ala Ala Tyr Tyr Asp Gly Lys Ser Ile
    130                 135                 140

Val Ile Leu Glu Gly Gly Asp His Tyr Ile Thr Phe Gly Asn Ser Phe
145                 150                 155                 160

Val Ala Phe Val Ser Ser Ile Asp Leu Tyr Leu Ala Ile Arg Gly Arg
                165                 170                 175

Gln Glu Ala Asp Leu Gln Leu Leu Arg Thr Val Glu Leu Leu Asp Gly
            180                 185                 190

Lys Lys Leu Tyr Val Phe Ser Gln His Gln Ile Val Gly Ile Thr Asn
        195                 200                 205

Ala Ala Phe Asp Ser Ile Gln Leu Asp Glu Tyr Ala Thr Ile Ser Glu
    210                 215                 220
```

<210> SEQ ID NO 14
<211> LENGTH: 76
<212> TYPE: PRT
<213> ORGANISM: artificial sequence
<220> FEATURE:
<223> OTHER INFORMATION: Envelope protein amino acid sequence

<400> SEQUENCE: 14

```
Met Leu Gln Leu Val Asn Asp Asn Gly Leu Val Val Asn Val Ile Leu
1               5                   10                  15

Trp Leu Phe Val Leu Phe Phe Leu Leu Ile Ile Ser Ile Thr Phe Val
            20                  25                  30

Gln Leu Val Asn Leu Cys Phe Thr Cys His Arg Leu Cys Asn Ser Ala
        35                  40                  45

Val Tyr Thr Pro Ile Gly Arg Leu Tyr Arg Val Tyr Lys Ser Tyr Met
    50                  55                  60

Gln Ile Asp Pro Leu Pro Ser Thr Val Ile Asp Val
65                  70                  75
```

<210> SEQ ID NO 15
<211> LENGTH: 226

```
<212> TYPE: PRT
<213> ORGANISM: artificial sequence
<220> FEATURE:
<223> OTHER INFORMATION: Membrane protein amino acid sequence

<400> SEQUENCE: 15

Met Ser Asn Gly Ser Ile Pro Val Asp Glu Val Ile Gln His Leu Arg
1               5                   10                  15

Asn Trp Asn Phe Thr Trp Asn Ile Ile Leu Thr Ile Leu Leu Val Val
            20                  25                  30

Leu Gln Tyr Gly His Tyr Lys Tyr Ser Ala Phe Leu Tyr Gly Val Lys
        35                  40                  45

Met Ala Ile Leu Trp Ile Leu Trp Pro Leu Val Leu Ala Leu Ser Leu
    50                  55                  60

Phe Asp Ala Trp Ala Ser Phe Gln Val Asn Trp Val Phe Phe Ala Phe
65                  70                  75                  80

Ser Ile Leu Met Ala Cys Ile Thr Leu Met Leu Trp Ile Met Tyr Phe
                85                  90                  95

Val Asn Ser Ile Arg Leu Trp Arg Arg Thr His Ser Trp Trp Ser Phe
            100                 105                 110

Asn Pro Glu Thr Asp Ala Leu Leu Thr Thr Ser Val Met Gly Arg Gln
        115                 120                 125

Val Cys Ile Pro Val Leu Gly Ala Pro Thr Gly Val Thr Leu Thr Leu
    130                 135                 140

Leu Ser Gly Thr Leu Leu Val Glu Gly Tyr Lys Val Ala Thr Gly Val
145                 150                 155                 160

Gln Val Ser Gln Leu Pro Asn Phe Val Thr Val Ala Lys Ala Thr Thr
                165                 170                 175

Thr Ile Val Tyr Gly Arg Val Gly Arg Ser Val Asn Ala Ser Ser Gly
            180                 185                 190

Thr Gly Trp Ala Phe Tyr Val Arg Ser Lys His Gly Asp Tyr Ser Ala
        195                 200                 205

Val Ser Asn Pro Ser Ser Val Leu Thr Asp Ser Glu Lys Val Leu His
    210                 215                 220

Leu Val
225


<210> SEQ ID NO 16
<211> LENGTH: 441
<212> TYPE: PRT
<213> ORGANISM: artificial sequence
<220> FEATURE:
<223> OTHER INFORMATION: Nucleoprotein amino acid sequence

<400> SEQUENCE: 16

Met Ala Ser Val Ser Phe Gln Asp Arg Gly Arg Lys Arg Val Pro Leu
1               5                   10                  15

Ser Leu Tyr Ala Pro Leu Arg Val Thr Asn Asp Lys Pro Leu Ser Lys
            20                  25                  30

Val Leu Ala Asn Asn Ala Val Pro Thr Asn Lys Gly Asn Lys Asp Gln
        35                  40                  45

Gln Ile Gly Tyr Trp Asn Glu Gln Ile Arg Trp Arg Met Arg Arg Gly
    50                  55                  60

Glu Arg Ile Glu Gln Pro Ser Asn Trp His Phe Tyr Tyr Leu Gly Thr
65                  70                  75                  80

Gly Pro His Ala Asp Leu Arg Tyr Arg Thr Arg Thr Glu Gly Val Phe
                85                  90                  95
```

```
Trp Val Ala Lys Glu Gly Ala Lys Thr Glu Pro Thr Asn Leu Gly Val
            100                 105                 110

Arg Lys Ala Ser Glu Lys Pro Ile Ile Pro Asn Phe Ser Gln Gln Leu
        115                 120                 125

Pro Ser Val Val Glu Ile Val Glu Pro Asn Thr Pro Pro Thr Ser Arg
    130                 135                 140

Ala Asn Ser Arg Ser Arg Ser Arg Gly Asn Gly Asn Asn Arg Ser Arg
145                 150                 155                 160

Ser Pro Ser Asn Asn Arg Gly Asn Asn Gln Ser Arg Gly Asn Ser Gln
                165                 170                 175

Asn Arg Gly Asn Asn Gln Gly Arg Gly Ala Ser Gln Asn Arg Gly Gly
            180                 185                 190

Asn Asn Asn Asn Asn Asn Lys Ser Arg Asn Gln Ser Lys Asn Arg Asn
        195                 200                 205

Gln Ser Asn Asp Arg Gly Gly Val Thr Ser Arg Asp Asp Leu Val Ala
    210                 215                 220

Ala Val Lys Asp Ala Leu Lys Ser Leu Gly Ile Gly Glu Asn Pro Asp
225                 230                 235                 240

Lys Leu Lys Gln Gln Gln Lys Pro Lys Gln Glu Arg Ser Asp Ser Ser
                245                 250                 255

Gly Lys Asn Thr Pro Lys Lys Asn Lys Ser Arg Ala Thr Ser Lys Glu
            260                 265                 270

Arg Asp Leu Lys Asp Ile Pro Glu Trp Arg Arg Ile Pro Lys Gly Glu
        275                 280                 285

Asn Ser Val Ala Ala Cys Phe Gly Pro Arg Gly Gly Phe Lys Asn Phe
    290                 295                 300

Gly Asp Ala Glu Phe Val Glu Lys Gly Val Asp Ala Ser Gly Tyr Ala
305                 310                 315                 320

Gln Ile Ala Ser Leu Ala Pro Asn Val Ala Ala Leu Leu Phe Gly Gly
                325                 330                 335

Asn Val Ala Val Arg Glu Leu Ala Asp Ser Tyr Glu Ile Thr Tyr Asn
            340                 345                 350

Tyr Lys Met Thr Val Pro Lys Ser Asp Pro Asn Val Glu Leu Leu Val
        355                 360                 365

Ser Gln Val Asp Ala Phe Lys Thr Gly Asn Ala Lys Pro Gln Arg Lys
    370                 375                 380

Lys Glu Lys Lys Asn Lys Arg Glu Thr Thr Gln Gln Leu Asn Glu Glu
385                 390                 395                 400

Ala Ile Tyr Asp Asp Val Gly Val Pro Ser Asp Val Thr His Ala Asn
                405                 410                 415

Leu Glu Trp Asp Thr Ala Val Asp Gly Gly Asp Thr Ala Val Glu Ile
            420                 425                 430

Ile Asn Glu Ile Phe Asp Thr Gly Asn
        435                 440
```

<210> SEQ ID NO 17
<211> LENGTH: 1035
<212> TYPE: PRT
<213> ORGANISM: artificial sequence
<220> FEATURE:
<223> OTHER INFORMATION: Truncated and fused S1 and S2 domains of the spike protein

<400> SEQUENCE: 17

```
Gly Glu Asp Gly Ile Ser Tyr Gln Pro Cys Thr Ala Asn Cys Ile Gly
```

-continued

```
1               5                   10                  15

Tyr Ala Ala Asn Val Phe Ala Thr Glu Pro Asn Gly His Ile Pro Glu
            20                  25                  30

Gly Phe Ser Phe Asn Asn Trp Phe Leu Leu Ser Asn Asp Ser Thr Leu
        35                  40                  45

Val His Gly Lys Val Val Ser Asn Gln Pro Leu Leu Val Asn Cys Leu
    50                  55                  60

Leu Ala Ile Pro Lys Ile Tyr Gly Leu Gly Gln Phe Phe Ser Phe Asn
65                  70                  75                  80

Gln Thr Ile Asp Gly Val Cys Asn Gly Ala Ala Val Gln Arg Ala Pro
                85                  90                  95

Glu Ala Leu Arg Phe Asn Ile Asn Asp Thr Ser Val Ile Leu Ala Glu
            100                 105                 110

Gly Ser Ile Val Leu His Thr Ala Leu Gly Thr Asn Phe Ser Phe Val
        115                 120                 125

Cys Ser Asn Ser Ser Asn Pro His Leu Ala Thr Phe Ala Ile Pro Leu
    130                 135                 140

Gly Ala Thr Gln Val Pro Tyr Tyr Cys Phe Leu Lys Val Asp Thr Tyr
145                 150                 155                 160

Asn Ser Thr Val Tyr Lys Phe Leu Ala Val Leu Pro Pro Thr Val Arg
                165                 170                 175

Glu Ile Val Ile Thr Lys Tyr Gly Asp Val Tyr Val Asn Gly Phe Gly
            180                 185                 190

Tyr Leu His Leu Gly Leu Leu Asp Ala Val Thr Ile Asn Phe Thr Gly
        195                 200                 205

His Gly Thr Asp Asp Asp Val Ser Gly Phe Trp Thr Ile Ala Ser Thr
    210                 215                 220

Asn Phe Val Asp Ala Leu Ile Glu Val Gln Gly Thr Ala Ile Gln Arg
225                 230                 235                 240

Ile Leu Tyr Cys Asp Asp Pro Val Ser Gln Leu Lys Cys Ser Gln Val
                245                 250                 255

Ala Phe Asp Leu Asp Asp Gly Phe Tyr Pro Ile Ser Ser Arg Asn Leu
            260                 265                 270

Leu Ser His Glu Gln Pro Ile Ser Phe Val Thr Leu Pro Ser Phe Asn
        275                 280                 285

Asp His Ser Phe Val Asn Ile Thr Val Ser Ala Ser Phe Gly Gly His
    290                 295                 300

Ser Gly Ala Asn Leu Ile Ala Ser Asp Thr Thr Ile Asn Gly Phe Ser
305                 310                 315                 320

Ser Phe Cys Val Asp Thr Arg Gln Phe Thr Ile Ser Leu Phe Tyr Asn
                325                 330                 335

Val Thr Asn Ser Tyr Gly Tyr Val Ser Lys Ser Gln Asp Ser Asn Cys
            340                 345                 350

Pro Phe Thr Leu Gln Ser Val Asn Asp Tyr Leu Ser Phe Ser Lys Phe
        355                 360                 365

Cys Val Ser Thr Ser Leu Leu Ala Ser Ala Cys Thr Ile Asp Leu Phe
    370                 375                 380

Gly Tyr Pro Glu Phe Gly Ser Gly Val Lys Phe Thr Ser Leu Tyr Phe
385                 390                 395                 400

Gln Phe Thr Lys Gly Glu Leu Ile Thr Gly Thr Pro Lys Pro Leu Glu
                405                 410                 415

Gly Val Thr Asp Val Ser Phe Met Thr Leu Asp Val Cys Thr Lys Tyr
            420                 425                 430
```

```
Thr Ile Tyr Gly Phe Lys Gly Glu Gly Ile Ile Thr Leu Thr Asn Ser
        435                 440                 445

Ser Phe Leu Ala Gly Val Tyr Tyr Thr Ser Asp Ser Gly Gln Leu Leu
    450                 455                 460

Ala Phe Lys Asn Val Thr Ser Gly Ala Val Tyr Ser Val Thr Pro Cys
465                 470                 475                 480

Ser Phe Ser Glu Gln Ala Ala Tyr Val Asp Asp Asp Ile Val Gly Val
                485                 490                 495

Ile Ser Ser Leu Ser Ser Ser Thr Phe Asn Ser Thr Arg Glu Leu Pro
            500                 505                 510

Gly Phe Phe Tyr His Ser Asn Asp Gly Ser Asn Cys Thr Glu Pro Val
        515                 520                 525

Leu Val Tyr Ser Asn Ile Gly Val Cys Lys Ser Gly Ser Ile Gly Tyr
    530                 535                 540

Val Pro Ser Gln Ser Gly Gln Val Lys Ile Ala Pro Thr Val Thr Gly
545                 550                 555                 560

Asn Ile Ser Ile Pro Thr Asn Phe Ser Ser Asn Gly Arg Ser Val Ala
                565                 570                 575

Asp Leu Val Cys Ala Gln Tyr Tyr Ser Gly Val Met Val Leu Pro Gly
            580                 585                 590

Val Val Asp Ala Glu Lys Leu His Met Tyr Ser Ala Ser Leu Ile Gly
        595                 600                 605

Gly Met Val Leu Gly Gly Phe Thr Ser Ala Ala Ala Leu Pro Phe Ser
    610                 615                 620

Tyr Ala Val Gln Ala Arg Leu Asn Tyr Leu Ala Leu Gln Thr Asp Val
625                 630                 635                 640

Leu Gln Arg Asn Gln Gln Leu Leu Ala Glu Ser Phe Asn Ser Ala Ile
                645                 650                 655

Gly Asn Ile Thr Ser Ala Phe Glu Ser Val Lys Glu Ala Ile Ser Gln
            660                 665                 670

Thr Ser Lys Gly Leu Asn Thr Val Ala His Ala Leu Thr Lys Val Gln
        675                 680                 685

Glu Val Val Asn Ser Gln Gly Ala Ala Leu Thr Gln Leu Thr Val Gln
    690                 695                 700

Leu Gln His Asn Phe Gln Ala Ile Ser Ser Ser Ile Asp Asp Ile Tyr
705                 710                 715                 720

Ser Arg Leu Asp Ile Leu Ser Ala Asp Val Gln Val Asp Arg Leu Ile
                725                 730                 735

Thr Gly Arg Leu Ser Ala Leu Asn Ala Phe Val Ala Gln Thr Leu Thr
            740                 745                 750

Lys Tyr Thr Glu Val Gln Ala Ser Arg Lys Leu Ala Gln Gln Lys Val
        755                 760                 765

Asn Glu Cys Val Lys Ser Gln Ser Gln Arg Tyr Gly Phe Cys Gly Gly
    770                 775                 780

Asp Gly Glu His Ile Phe Ser Leu Val Gln Ala Ala Pro Gln Gly Leu
785                 790                 795                 800

Leu Phe Leu His Thr Val Leu Val Pro Ser Asp Phe Val Asp Val Ile
                805                 810                 815

Ala Ile Ala Gly Leu Cys Val Asn Asp Glu Ile Ala Leu Thr Leu Arg
            820                 825                 830

Glu Pro Gly Leu Val Leu Phe Thr His Glu Leu Gln Asn His Thr Ala
        835                 840                 845
```

-continued

```
Thr Glu Tyr Phe Val Ser Ser Arg Arg Met Phe Glu Pro Arg Lys Pro
    850                 855                 860

Thr Val Ser Asp Phe Val Gln Ile Glu Ser Cys Val Val Thr Tyr Val
865                 870                 875                 880

Asn Leu Thr Arg Asp Gln Leu Pro Asp Val Ile Pro Asp Tyr Ile Asp
                885                 890                 895

Val Asn Lys Thr Leu Asp Glu Ile Leu Ala Ser Leu Pro Asn Arg Thr
            900                 905                 910

Gly Pro Ser Leu Pro Leu Asp Val Phe Asn Ala Thr Tyr Leu Asn Leu
        915                 920                 925

Thr Gly Glu Ile Ala Asp Leu Glu Gln Arg Ser Glu Ser Leu Arg Asn
    930                 935                 940

Thr Thr Glu Glu Leu Gln Ser Leu Ile Tyr Asn Ile Asn Asn Thr Leu
945                 950                 955                 960

Val Asp Leu Glu Trp Leu Asn Arg Val Glu Thr Tyr Ile Lys Trp Pro
                965                 970                 975

Trp Trp Val Trp Leu Ile Ile Phe Ile Val Leu Ile Phe Val Val Ser
            980                 985                 990

Leu Leu Val Phe Cys Cys Ile Ser  Thr Gly Cys Cys Gly  Cys Cys Gly
        995                 1000                1005

Cys Cys  Cys Ala Cys Phe Ser  Gly Cys Cys Arg Gly  Pro Arg Leu
    1010                1015                1020

Gln Pro  Tyr Glu Val Phe Glu  Lys Val His Val Gln
    1025                1030                1035
```

<210> SEQ ID NO 18
<211> LENGTH: 3111
<212> TYPE: DNA
<213> ORGANISM: artificial sequence
<220> FEATURE:
<223> OTHER INFORMATION: Codon optimized nucleotide sequence of the truncated and fused S1 and S2 domains of the spike protein

<400> SEQUENCE: 18

```
atgggtgaag acggaatctc ctaccaacct tgtactgcta actgcatcgg atacgccgcc     60

aacgtgttcg ccactgagcc aaacggacac atccccgagg gattctcttt caacaactgg    120

ttcctgctca gcaacgactc aaccctcgtg cacggcaagg tggtcagcaa ccaacccttg    180

ctggtcaact gtctcttggc tatccctaag atctacggac tgggccagtt cttctccttc    240

aaccaaacta tcgacggagt ttgcaacggt gctgctgtgc agagggctcc tgaggctttg    300

agattcaaca tcaacgatac ctctgtgatc ctggctgaag gaagcatcgt cttgcacacc    360

gccctgggta ctaacttctc attcgtgtgt tcgaactcct ctaacccaca cttggccaca    420

ttcgctatcc cactgggtgc tacccaggtt ccgtactact gcttcctgaa ggtggacaca    480

tacaactcca ccgtctacaa gttcttggcc gttctgcccc ctactgtccg tgagatcgtt    540

atcacaaagt acggagacgt ctacgttaac ggcttcggat acttgcacct gggtctgctc    600

gatgctgtga ctatcaactt cacaggtcac ggcaccgacg atgacgtctc aggcttctgg    660

actatcgctt cgacaaactt cgtggacgcc ctgatcgagg tccagggaac cgctatccaa    720

aggatcctgt actgtgatga cccagtctcg cagctcaagt gctcccaagt tgccttcgac    780

ttggatgacg gcttctaccc gatcagctca agaaacttgc tgtcccacga acagcccatc    840

tctttcgtga cactgccttc tttcaacgat cacagcttcg tgaacatcac tgtctccgcc    900

tctttcggtg gccactccgg tgctaacctc atcgcctctg acaccactat caacggcttc    960
```

-continued

```
tcgtccttct gtgtcgatac ccgccagttc actatctccc tgttctacaa cgtcaccaac   1020
tcttacggtt acgttagcaa gtcacaagac agcaactgcc cattcactct ccagtcagtg   1080
aacgattact tgtcgttctc caagttctgt gtctctacta gcctcttggc cagcgcttgc   1140
acaatcgact tgttcggcta ccccgagttc ggaagcggtg tgaagttcac ctcactgtac   1200
ttccagttca ctaagggcga gctcatcact ggaacaccaa agccgttgga aggtgtgaca   1260
gacgtctcct tcatgaccct ggatgtctgc acaaagtaca ccatctacgg cttcaagggc   1320
gagggaatca tcaccttgac taactctagc ttcctggctg gcgtgtacta cacctcagac   1380
tcgggacaac tgctcgcttt caagaacgtc acctcaggag ccgtttactc ggtgactccc   1440
tgctccttct ctgaacaggc tgcctacgtg gatgacgata tcgtgggtgt catctcatcg   1500
ctctcctcta gcacattcaa ctccaccagg gagttgcccg gtttcttcta ccactccaac   1560
gacggctcta actgtactga acctgttctg gtgtactcta acatcggcgt ttgcaagagc   1620
ggttcaatcg gctacgtgcc ttcgcagtcc ggccaagtta agatcgctcc aacagtgacc   1680
ggaaacatct ccatcccgac caacttctca tcgaacggaa gatctgttgc tgacctggtg   1740
tgcgcccagt actacagcgg tgtcatggtt ctgcccggcg ttgtggatgc tgagaagctc   1800
cacatgtact ctgccagcct catcggtggt atggtgttgg gcggattcac cagcgctgcc   1860
gctttgcctt tctcatacgc cgtgcaggct cgtctgaact acctcgcctt gcagactgac   1920
gtcctccaac gcaaccagca attgctggct gagtcgttca actccgccat cggaaacatc   1980
accagcgctt tcgagtcagt gaaggaagcc atctctcaga ctagcaaggg tctgaacaca   2040
gtggcccacg ctctcaccaa ggtccaggaa gtcgttaact cccaaggcgc cgctctcact   2100
cagttgacag tccagctgca acacaacttc caagctatct cctctagcat cgacgatatc   2160
tactcgaggc tggacatcct ctccgccgac gtgcaggtcg ataggctgat caccggtaga   2220
ttgtcagccc tgaacgcttt cgtcgcccaa actctgacaa agtacactga ggttcaggct   2280
tctaggaagc tcgcccagca aaaggtcaac gaatgtgtta agtcacagtc gcaaagatac   2340
ggattctgcg gtggcgacgg cgagcacatc ttcagcctgg tgcaggccgc tccacaaggc   2400
ctcttgttcc tccacaccgt tttggtgccg tccgacttcg tcgatgttat cgccatcgct   2460
ggcctctgcg tgaacgacga gatcgctctg acactccgcg aacctggatt ggtcctgttc   2520
acccacgagc tgcagaacca caccgccact gaatacttcg tgtcatcgcg tcgcatgttc   2580
gagccccgta agcctaccgt gtcggacttc gtccaaatcg aatcatgcgt ggtcacttac   2640
gtcaacctga cacgcgacca gctccccgat gttatccctg actacatcga tgtgaacaag   2700
actctggacg agatcctcgc ttccttgcca aaccgtacag gtccatctct cccgttggac   2760
gtgttcaacg ctacctacct gaacctcact ggcgaaatcg ccgatttgga gcaacgttcc   2820
gaatctctgc gcaacacaac cgaggaactg cagtctctca tctacaacat caacaacacc   2880
ttggtggacc tggagtggct caaccgcgtc gaaacttaca tcaagtggcc ttggtgggtc   2940
tggctgatca tcttcatcgt tctcatcttc gttgtgagcc tgctcgtctt ctgctgtatc   3000
tcaaccggat gctgtggttg ctgtggctgc tgttgcgctt gcttctccgg ttgttgtaga   3060
ggtcccagac tccagccata cgaggtgttc gagaaggtcc acgtccaata a            3111
```

```
<210> SEQ ID NO 19
<211> LENGTH: 1036
<212> TYPE: PRT
<213> ORGANISM: artificial sequence
<220> FEATURE:
<223> OTHER INFORMATION: Codon optimized amino acid sequence of the
```

-continued truncated and fused S1 and S2 domains of the spike protein

<400> SEQUENCE: 19

```
Met Gly Glu Asp Gly Ile Ser Tyr Gln Pro Cys Thr Ala Asn Cys Ile
1               5                   10                  15

Gly Tyr Ala Ala Asn Val Phe Ala Thr Glu Pro Asn Gly His Ile Pro
            20                  25                  30

Glu Gly Phe Ser Phe Asn Asn Trp Phe Leu Leu Ser Asn Asp Ser Thr
        35                  40                  45

Leu Val His Gly Lys Val Val Ser Asn Gln Pro Leu Leu Val Asn Cys
    50                  55                  60

Leu Leu Ala Ile Pro Lys Ile Tyr Gly Leu Gly Gln Phe Phe Ser Phe
65                  70                  75                  80

Asn Gln Thr Ile Asp Gly Val Cys Asn Gly Ala Ala Val Gln Arg Ala
                85                  90                  95

Pro Glu Ala Leu Arg Phe Asn Ile Asn Asp Thr Ser Val Ile Leu Ala
            100                 105                 110

Glu Gly Ser Ile Val Leu His Thr Ala Leu Gly Thr Asn Phe Ser Phe
        115                 120                 125

Val Cys Ser Asn Ser Ser Asn Pro His Leu Ala Thr Phe Ala Ile Pro
    130                 135                 140

Leu Gly Ala Thr Gln Val Pro Tyr Tyr Cys Phe Leu Lys Val Asp Thr
145                 150                 155                 160

Tyr Asn Ser Thr Val Tyr Lys Phe Leu Ala Val Leu Pro Pro Thr Val
                165                 170                 175

Arg Glu Ile Val Ile Thr Lys Tyr Gly Asp Val Tyr Val Asn Gly Phe
            180                 185                 190

Gly Tyr Leu His Leu Gly Leu Leu Asp Ala Val Thr Ile Asn Phe Thr
        195                 200                 205

Gly His Gly Thr Asp Asp Asp Val Ser Gly Phe Trp Thr Ile Ala Ser
    210                 215                 220

Thr Asn Phe Val Asp Ala Leu Ile Glu Val Gln Gly Thr Ala Ile Gln
225                 230                 235                 240

Arg Ile Leu Tyr Cys Asp Asp Pro Val Ser Gln Leu Lys Cys Ser Gln
                245                 250                 255

Val Ala Phe Asp Leu Asp Asp Gly Phe Tyr Pro Ile Ser Ser Arg Asn
            260                 265                 270

Leu Leu Ser His Glu Gln Pro Ile Ser Phe Val Thr Leu Pro Ser Phe
        275                 280                 285

Asn Asp His Ser Phe Val Asn Ile Thr Val Ser Ala Ser Phe Gly Gly
    290                 295                 300

His Ser Gly Ala Asn Leu Ile Ala Ser Asp Thr Thr Ile Asn Gly Phe
305                 310                 315                 320

Ser Ser Phe Cys Val Asp Thr Arg Gln Phe Thr Ile Ser Leu Phe Tyr
                325                 330                 335

Asn Val Thr Asn Ser Tyr Gly Tyr Val Ser Lys Ser Gln Asp Ser Asn
            340                 345                 350

Cys Pro Phe Thr Leu Gln Ser Val Asn Asp Tyr Leu Ser Phe Ser Lys
        355                 360                 365

Phe Cys Val Ser Thr Ser Leu Leu Ala Ser Ala Cys Thr Ile Asp Leu
    370                 375                 380

Phe Gly Tyr Pro Glu Phe Gly Ser Gly Val Lys Phe Thr Ser Leu Tyr
385                 390                 395                 400
```

```
Phe Gln Phe Thr Lys Gly Glu Leu Ile Thr Gly Thr Pro Lys Pro Leu
                405                 410                 415

Glu Gly Val Thr Asp Val Ser Phe Met Thr Leu Asp Val Cys Thr Lys
            420                 425                 430

Tyr Thr Ile Tyr Gly Phe Lys Gly Glu Gly Ile Ile Thr Leu Thr Asn
        435                 440                 445

Ser Ser Phe Leu Ala Gly Val Tyr Tyr Thr Ser Asp Ser Gly Gln Leu
    450                 455                 460

Leu Ala Phe Lys Asn Val Thr Ser Gly Ala Val Tyr Ser Val Thr Pro
465                 470                 475                 480

Cys Ser Phe Ser Glu Gln Ala Ala Tyr Val Asp Asp Asp Ile Val Gly
                485                 490                 495

Val Ile Ser Ser Leu Ser Ser Ser Thr Phe Asn Ser Thr Arg Glu Leu
            500                 505                 510

Pro Gly Phe Phe Tyr His Ser Asn Asp Gly Ser Asn Cys Thr Glu Pro
        515                 520                 525

Val Leu Val Tyr Ser Asn Ile Gly Val Cys Lys Ser Cys Ser Phe Ser
    530                 535                 540

Glu Gln Ala Ala Tyr Val Asp Asp Asp Ile Val Gly Val Ile Ser Ser
545                 550                 555                 560

Leu Ser Ser Ser Thr Phe Asn Ser Thr Arg Glu Leu Pro Gly Phe Phe
                565                 570                 575

Tyr His Ser Asn Asp Gly Ser Asn Cys Thr Glu Pro Val Leu Val Tyr
            580                 585                 590

Ser Asn Ile Gly Val Cys Lys Ser Gly Ser Ile Gly Tyr Val Pro Ser
        595                 600                 605

Gln Ser Gly Gln Val Lys Ile Ala Pro Thr Val Thr Gly Asn Ile Ser
    610                 615                 620

Ile Pro Thr Asn Phe Ser Ser Asn Gly Arg Ser Val Ala Asp Leu Val
625                 630                 635                 640

Cys Ala Gln Tyr Tyr Ser Gly Val Met Val Leu Pro Gly Val Val Asp
                645                 650                 655

Ala Glu Lys Leu His Met Tyr Ser Ala Ser Leu Ile Gly Gly Met Val
            660                 665                 670

Leu Gly Gly Phe Thr Ser Ala Ala Ala Leu Pro Phe Ser Tyr Ala Val
        675                 680                 685

Gln Ala Arg Leu Asn Tyr Leu Ala Leu Gln Thr Asp Val Leu Gln Arg
    690                 695                 700

Asn Gln Gln Leu Leu Ala Glu Ser Phe Asn Ser Ala Ile Gly Asn Ile
705                 710                 715                 720

Thr Ser Ala Phe Glu Ser Val Lys Glu Ala Ile Ser Gln Thr Ser Lys
                725                 730                 735

Gly Leu Asn Thr Val Ala His Ala Leu Thr Lys Val Gln Glu Val Val
            740                 745                 750

Asn Ser Gln Gly Ala Ala Leu Thr Gln Leu Thr Val Gln Leu Gln His
        755                 760                 765

Asn Phe Gln Ala Ile Ser Ser Ser Ile Asp Asp Ile Tyr Ser Arg Leu
    770                 775                 780

Asp Ile Leu Ser Ala Asp Val Gln Val Asp Arg Leu Ile Thr Gly Arg
785                 790                 795                 800

Leu Ser Ala Leu Asn Ala Phe Val Ala Gln Thr Leu Thr Lys Tyr Thr
                805                 810                 815

Glu Val Gln Ala Ser Arg Lys Leu Ala Gln Gln Lys Val Asn Glu Cys
```

-continued

```
            820                 825                 830

Val Lys Ser Gln Ser Gln Arg Tyr Gly Phe Cys Gly Gly Asp Gly Glu
        835                 840                 845

His Ile Phe Ser Leu Val Gln Ala Ala Pro Gln Gly Leu Leu Phe Leu
    850                 855                 860

His Thr Val Leu Val Pro Ser Asp Phe Val Asp Val Ile Ala Ile Ala
865                 870                 875                 880

Gly Leu Cys Val Asn Asp Glu Ile Ala Leu Thr Leu Arg Glu Pro Gly
                885                 890                 895

Leu Val Leu Phe Thr Leu Asp Glu Ile Leu Ala Ser Leu Pro Asn Arg
            900                 905                 910

Thr Gly Pro Ser Leu Pro Leu Asp Val Phe Asn Ala Thr Tyr Leu Asn
        915                 920                 925

Leu Thr Gly Glu Ile Ala Asp Leu Glu Gln Arg Ser Glu Ser Leu Arg
    930                 935                 940

Asn Thr Thr Glu Glu Leu Gln Ser Leu Ile Tyr Asn Ile Asn Asn Thr
945                 950                 955                 960

Leu Val Asp Leu Glu Trp Leu Asn Arg Val Glu Thr Tyr Ile Lys Trp
                965                 970                 975

Pro Trp Trp Val Trp Leu Ile Ile Phe Ile Val Leu Ile Phe Val Val
            980                 985                 990

Ser Leu Leu Val Phe Cys Cys Ile  Ser Thr Gly Cys Cys  Gly Cys Cys
        995                 1000                 1005

Gly Cys  Cys Cys Ala Cys Phe  Ser Gly Cys Cys Arg  Gly Pro Arg
    1010                 1015                 1020

Leu Gln  Pro Tyr Glu Val Phe  Glu Lys Val His Val  Gln
    1025                 1030                 1035
```

<210> SEQ ID NO 20
<211> LENGTH: 3096
<212> TYPE: DNA
<213> ORGANISM: artificial sequence
<220> FEATURE:
<223> OTHER INFORMATION: Final nucleotide sequence for cloning into vector showing N-terminal gp67 signal peptide sequence

<400> SEQUENCE: 20

```
atgctactag taaatcagtc acaccaaggc ttcaataagg aacacacaag caagatggta     60

agcgctattg ttttatatgt gcttttggcg gcggcggcgc attctgcctt tgcggcggat    120

cttggatctg aattcatggg tgaagacgga atctcctacc aaccttgtac tgctaactgc    180

atcggatacg ccgccaacgt gttcgccact gagccaaacg gacacatccc cgagggattc    240

tctttcaaca actggttcct gctcagcaac gactcaaccc tcgtgcacgg caaggtggtc    300

agcaaccaac ccttgctggt caactgtctc ttggctatcc ctaagatcta cggactgggc    360

cagttcttct ccttcaacca aactatcgac ggagtttgca acggtgctgc tgtgcagagg    420

gctcctgagg ctttgagatt caacatcaac gatacctctg tgatcctggc tgaaggaagc    480

atcgtcttgc acaccgccct gggtactaac ttctcattcg tgtgttcgaa ctcctctaac    540

ccacacttgg ccacattcgc tatcccactg ggtgctaccc aggttccgta ctactgcttc    600

ctgaaggtgg acacatacaa ctccaccgtc tacaagttct tggccgttct gccccctact    660

gtccgtgaga tcgttatcac aaagtacgga gacgtctacg ttaacggctt cggatacttg    720

cacctgggtc tgctcgatgc tgtgactatc aacttcacag gtcacggcac cgacgatgac    780

gtctcaggct tctggactat cgcttcgaca aacttcgtgg acgccctgat cgaggtccag    840
```

```
ggaaccgcta tccaaaggat cctgtactgt gatgacccag tctcgcagct caagtgctcc    900
caagttgcct tcgacttgga tgacggcttc tacccgatca gctcaagaaa cttgctgtcc    960
cacgaacagc ccatctcttt cgtgacactg ccttctttca acgatcacag cttcgtgaac   1020
atcactgtct ccgcctcttt cggtggccac tccggtgcta acctcatcgc ctctgacacc   1080
actatcaacg gcttctcgtc cttctgtgtc gatacccgcc agttcactat ctccctgttc   1140
tacaacgtca ccaactctta cggttacgtt agcaagtcac aagacagcaa ctgcccattc   1200
actctccagt cagtgaacga ttacttgtcg ttctccaagt tctgtgtctc tactagcctc   1260
ttggccagcg cttgcacaat cgacttgttc ggctaccccg agttcggaag cggtgtgaag   1320
ttcacctcac tgtacttcca gttcactaag ggcgagctca tcactggaac accaaagccg   1380
ttggaaggtg tgacagacgt ctccttcatg accctggatg tctgcacaaa gtacaccatc   1440
tacggcttca agggcgaggg aatcatcacc ttgactaact ctagcttcct ggctggcgtg   1500
tactacacct cagactcggg acaactgctc gctttcaaga acgtcacctc aggagccgtt   1560
tactcggtga ctccctgctc cttctctgaa caggctgcct acgtggatga cgatatcgtg   1620
ggtgtcatct catcgctctc ctctagcaca ttcaactcca ccagggagtt gcccggtttc   1680
ttctaccact ccaacgacgg ctctaactgt actgaacctg ttctggtgta ctctaacatc   1740
ggcgtttgca agagcggttc aatcggctac gtgccttcgc agtccggcca agttaagatc   1800
gctccaacag tgaccggaaa catctccatc ccgaccaact tctcatcgaa cggaagatct   1860
gttgctgacc tggtgtgcgc ccagtactac agcggtgtca tggttctgcc cggcgttgtg   1920
gatgctgaga agctccacat gtactctgcc agcctcatcg gtggtatggt gttgggcgga   1980
ttcaccagcg ctgccgcttt gcctttctca tacgccgtgc aggctcgtct gaactacctc   2040
gccttgcaga ctgacgtcct ccaacgcaac cagcaattgc tggctgagtc gttcaactcc   2100
gccatcggaa acatcaccag cgctttcgag tcagtgaagg aagccatctc tcagactagc   2160
aagggtctga acacagtggc ccacgctctc accaaggtcc aggaagtcgt taactcccaa   2220
ggcgccgctc tcactcagtt gacagtccag ctgcaacaca acttccaagc tatctcctct   2280
agcatcgacg atatctactc gaggctggac atcctctccg ccgacgtgca ggtcgatagg   2340
ctgatcaccg gtagattgtc agccctgaac gctttcgtcg cccaaactct gacaaagtac   2400
actgaggttc aggcttctag gaagctcgcc cagcaaaagg tcaacgaatg tgttaagtca   2460
cagtcgcaaa gatacggatt ctgcggtggc gacggcgagc acatcttcag cctggtgcag   2520
gccgctccac aaggcctctt gttcctccac accgttttgg tgccgtccga cttcgtcgat   2580
gttatcgcca tcgctggcct ctgcgtgaac gacgagatcg ctctgacact ccgcgaacct   2640
ggattggtcc tgttcaccca cgagctgcag aaccacaccg ccactgaata cttcgtgtca   2700
tcgcgtcgca tgttcgagcc ccgtaagcct accgtgtcgg acttcgtcca aatcgaatca   2760
tgcgtggtca cttacgtcaa cctgacacgc gaccagctcc ccgatgttat ccctgactac   2820
atcgatgtga acaagactct ggacgagatc ctcgcttcct tgccaaaccg tacaggtcca   2880
tctctcccgt tggacgtgtt caacgctacc tacctgaacc tcactggcga aatcgccgat   2940
ttggagcaac gttccgaatc tctgcgcaac acaaccgagg aactgcagtc tctcatctac   3000
aacatcaaca acaccttggt ggacctggag tggctcaacc gcgtcgaaac ttacatcaag   3060
tggcctcacc accaccacca ccactaatga aagctt                             3096
```

<210> SEQ ID NO 21

<211> LENGTH: 1028
<212> TYPE: PRT
<213> ORGANISM: artificial sequence
<220> FEATURE:
<223> OTHER INFORMATION: Final amino acid sequence showing N-terminal gp67 signal peptide sequence and histidine tag

<400> SEQUENCE: 21

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Leu Gly Ser Glu Phe Met Gly Glu
        35                  40                  45

Asp Gly Ile Ser Tyr Gln Pro Cys Thr Ala Asn Cys Ile Gly Tyr Ala
    50                  55                  60

Ala Asn Val Phe Ala Thr Glu Pro Asn Gly His Ile Pro Glu Gly Phe
65                  70                  75                  80

Ser Phe Asn Asn Trp Phe Leu Leu Ser Asn Asp Ser Thr Leu Val His
                85                  90                  95

Gly Lys Val Val Ser Asn Gln Pro Leu Leu Val Asn Cys Leu Leu Ala
            100                 105                 110

Ile Pro Lys Ile Tyr Gly Leu Gly Gln Phe Phe Ser Phe Asn Gln Thr
        115                 120                 125

Ile Asp Gly Val Cys Asn Gly Ala Ala Val Gln Arg Ala Pro Glu Ala
    130                 135                 140

Leu Arg Phe Asn Ile Asn Asp Thr Ser Val Ile Leu Ala Glu Gly Ser
145                 150                 155                 160

Ile Val Leu His Thr Ala Leu Gly Thr Asn Phe Ser Phe Val Cys Ser
                165                 170                 175

Asn Ser Ser Asn Pro His Leu Ala Thr Phe Ala Ile Pro Leu Gly Ala
            180                 185                 190

Thr Gln Val Pro Tyr Tyr Cys Phe Leu Lys Val Asp Thr Tyr Asn Ser
        195                 200                 205

Thr Val Tyr Lys Phe Leu Ala Val Leu Pro Pro Thr Val Arg Glu Ile
    210                 215                 220

Val Ile Thr Lys Tyr Gly Asp Val Tyr Val Asn Gly Phe Gly Tyr Leu
225                 230                 235                 240

His Leu Gly Leu Leu Asp Ala Val Thr Ile Asn Phe Thr Gly His Gly
                245                 250                 255

Thr Asp Asp Asp Val Ser Gly Phe Trp Thr Ile Ala Ser Thr Asn Phe
            260                 265                 270

Val Asp Ala Leu Ile Glu Val Gln Gly Thr Ala Ile Gln Arg Ile Leu
        275                 280                 285

Tyr Cys Asp Asp Pro Val Ser Gln Leu Lys Cys Ser Gln Val Ala Phe
    290                 295                 300

Asp Leu Asp Asp Gly Phe Tyr Pro Ile Ser Ser Arg Asn Leu Leu Ser
305                 310                 315                 320

His Glu Gln Pro Ile Ser Phe Val Thr Leu Pro Ser Phe Asn Asp His
                325                 330                 335

Ser Phe Val Asn Ile Thr Val Ser Ala Ser Phe Gly Gly His Ser Gly
            340                 345                 350

Ala Asn Leu Ile Ala Ser Asp Thr Thr Ile Asn Gly Phe Ser Ser Phe
        355                 360                 365

Cys Val Asp Thr Arg Gln Phe Thr Ile Ser Leu Phe Tyr Asn Val Thr

```
    370                 375                 380

Asn Ser Tyr Gly Tyr Val Ser Lys Ser Gln Asp Ser Asn Cys Pro Phe
385                 390                 395                 400

Thr Leu Gln Ser Val Asn Asp Tyr Leu Ser Phe Ser Lys Phe Cys Val
                405                 410                 415

Ser Thr Ser Leu Leu Ala Ser Ala Cys Thr Ile Asp Leu Phe Gly Tyr
            420                 425                 430

Pro Glu Phe Gly Ser Gly Val Lys Phe Thr Ser Leu Tyr Phe Gln Phe
        435                 440                 445

Thr Lys Gly Glu Leu Ile Thr Gly Thr Pro Lys Pro Leu Glu Gly Val
    450                 455                 460

Thr Asp Val Ser Phe Met Thr Leu Asp Val Cys Thr Lys Tyr Thr Ile
465                 470                 475                 480

Tyr Gly Phe Lys Gly Glu Gly Ile Ile Thr Leu Thr Asn Ser Ser Phe
                485                 490                 495

Leu Ala Gly Val Tyr Tyr Thr Ser Asp Ser Gly Gln Leu Leu Ala Phe
            500                 505                 510

Lys Asn Val Thr Ser Gly Ala Val Tyr Ser Val Thr Pro Cys Ser Phe
        515                 520                 525

Ser Glu Gln Ala Ala Tyr Val Asp Asp Asp Ile Val Gly Val Ile Ser
    530                 535                 540

Ser Leu Ser Ser Ser Thr Phe Asn Ser Thr Arg Glu Leu Pro Gly Phe
545                 550                 555                 560

Phe Tyr His Ser Asn Asp Gly Ser Asn Cys Thr Glu Pro Val Leu Val
                565                 570                 575

Tyr Ser Asn Ile Gly Val Cys Lys Ser Gly Ser Ile Gly Tyr Val Pro
            580                 585                 590

Ser Gln Ser Gly Gln Val Lys Ile Ala Pro Thr Val Thr Gly Asn Ile
        595                 600                 605

Ser Ile Pro Thr Asn Phe Ser Ser Asn Gly Arg Ser Val Ala Asp Leu
    610                 615                 620

Val Cys Ala Gln Tyr Tyr Ser Gly Val Met Val Leu Pro Gly Val Val
625                 630                 635                 640

Asp Ala Glu Lys Leu His Met Tyr Ser Ala Ser Leu Ile Gly Gly Met
                645                 650                 655

Val Leu Gly Gly Phe Thr Ser Ala Ala Ala Leu Pro Phe Ser Tyr Ala
            660                 665                 670

Val Gln Ala Arg Leu Asn Tyr Leu Ala Leu Gln Thr Asp Val Leu Gln
        675                 680                 685

Arg Asn Gln Gln Leu Leu Ala Glu Ser Phe Asn Ser Ala Ile Gly Asn
    690                 695                 700

Ile Thr Ser Ala Phe Glu Ser Val Lys Glu Ala Ile Ser Gln Thr Ser
705                 710                 715                 720

Lys Gly Leu Asn Thr Val Ala His Ala Leu Thr Lys Val Gln Glu Val
                725                 730                 735

Val Asn Ser Gln Gly Ala Ala Leu Thr Gln Leu Thr Val Gln Leu Gln
            740                 745                 750

His Asn Phe Gln Ala Ile Ser Ser Ser Ile Asp Asp Ile Tyr Ser Arg
        755                 760                 765

Leu Asp Ile Leu Ser Ala Asp Val Gln Val Asp Arg Leu Ile Thr Gly
    770                 775                 780

Arg Leu Ser Ala Leu Asn Ala Phe Val Ala Gln Thr Leu Thr Lys Tyr
785                 790                 795                 800
```

Thr Glu Val Gln Ala Ser Arg Lys Leu Ala Gln Gln Lys Val Asn Glu
805 810 815

Cys Val Lys Ser Gln Ser Gln Arg Tyr Gly Phe Cys Gly Gly Asp Gly
820 825 830

Glu His Ile Phe Ser Leu Val Gln Ala Ala Pro Gln Gly Leu Leu Phe
835 840 845

Leu His Thr Val Leu Val Pro Ser Asp Phe Val Asp Val Ile Ala Ile
850 855 860

Ala Gly Leu Cys Val Asn Asp Glu Ile Ala Leu Thr Leu Arg Glu Pro
865 870 875 880

Gly Leu Val Leu Phe Thr His Glu Leu Gln Asn His Thr Ala Thr Glu
885 890 895

Tyr Phe Val Ser Ser Arg Arg Met Phe Glu Pro Arg Lys Pro Thr Val
900 905 910

Ser Asp Phe Val Gln Ile Glu Ser Cys Val Val Thr Tyr Val Asn Leu
915 920 925

Thr Arg Asp Gln Leu Pro Asp Val Ile Pro Asp Tyr Ile Asp Val Asn
930 935 940

Lys Thr Leu Asp Glu Ile Leu Ala Ser Leu Pro Asn Arg Thr Gly Pro
945 950 955 960

Ser Leu Pro Leu Asp Val Phe Asn Ala Thr Tyr Leu Asn Leu Thr Gly
965 970 975

Glu Ile Ala Asp Leu Glu Gln Arg Ser Glu Ser Leu Arg Asn Thr Thr
980 985 990

Glu Glu Leu Gln Ser Leu Ile Tyr Asn Ile Asn Asn Thr Leu Val Asp
995 1000 1005

Leu Glu Trp Leu Asn Arg Val Glu Thr Tyr Ile Lys Trp Pro His
1010 1015 1020

His His His His His
1025

<210> SEQ ID NO 22
<211> LENGTH: 18
<212> TYPE: PRT
<213> ORGANISM: artificial sequence
<220> FEATURE:
<223> OTHER INFORMATION: 22 - Antigenicity index of a portion of native spike (S1 domain) protein

<400> SEQUENCE: 22

Lys Phe Asn Val Gln Ala Pro Ala Val Val Val Leu Gly Gly Tyr Leu
1 5 10 15

Pro Ile

<210> SEQ ID NO 23
<211> LENGTH: 38
<212> TYPE: PRT
<213> ORGANISM: artificial sequence
<220> FEATURE:
<223> OTHER INFORMATION: 23 - (Antigenicity index of a portion of native spike (S1 domain) protein)

<400> SEQUENCE: 23

Trp Phe Leu Leu Ser Asn Asp Ser Thr Leu Val His Gly Lys Val Val
1 5 10 15

Ser Asn Gln Pro Leu Leu Val Asn Cys Leu Leu Ala Ile Pro Lys Ile
20 25 30

```
Tyr Gly Leu Gly Gln Phe
        35


<210> SEQ ID NO 24
<211> LENGTH: 71
<212> TYPE: PRT
<213> ORGANISM: artificial sequence
<220> FEATURE:
<223> OTHER INFORMATION: 24 - (Antigenicity index of a portion of native
      spike (S1 domain) protein)

<400> SEQUENCE: 24

Pro His Leu Ala Thr Phe Ala Ile Pro Leu Gly Ala Thr Gln Val Pro
1               5                   10                  15

Tyr Tyr Cys Phe Leu Lys Val Asp Thr Tyr Asn Ser Thr Val Tyr Lys
            20                  25                  30

Phe Leu Ala Val Leu Pro Pro Thr Val Arg Glu Ile Val Ile Thr Lys
        35                  40                  45

Tyr Gly Asp Val Tyr Val Asn Gly Phe Gly Tyr Leu His Leu Gly Leu
    50                  55                  60

Leu Asp Ala Val Thr Ile Asn
65                  70


<210> SEQ ID NO 25
<211> LENGTH: 33
<212> TYPE: PRT
<213> ORGANISM: artificial sequence
<220> FEATURE:
<223> OTHER INFORMATION: 25 - Antigenicity index of a portion of native
      spike (S1 domain) protein

<400> SEQUENCE: 25

Ser Gly Ala Val Tyr Ser Val Thr Pro Cys Ser Phe Ser Glu Gln Ala
1               5                   10                  15

Ala Tyr Val Asp Asp Asp Ile Val Gly Val Ile Ser Ser Leu Ser Ser
            20                  25                  30

Ser


<210> SEQ ID NO 26
<211> LENGTH: 23
<212> TYPE: PRT
<213> ORGANISM: artificial sequence
<220> FEATURE:
<223> OTHER INFORMATION: 26 - Antigenicity index of a portion of native
      spike (S1 domain) protein

<400> SEQUENCE: 26

Leu Thr Tyr Phe Trp Leu Phe Leu Pro Val Leu Ser Thr Leu Ser Leu
1               5                   10                  15

Pro Gln Asp Val Thr Arg Cys
            20


<210> SEQ ID NO 27
<211> LENGTH: 33
<212> TYPE: PRT
<213> ORGANISM: artificial sequence
<220> FEATURE:
<223> OTHER INFORMATION: 27 - Antigenicity index of a portion of native
      spike (S1 domain) protein

<400> SEQUENCE: 27

Thr Glu Pro Val Leu Val Tyr Ser Asn Ile Gly Val Cys Lys Ser Gly
1               5                   10                  15
```

-continued

Ser Ile Gly Tyr Val Pro Ser Gln Ser Gly Gln Val Lys Ile Ala Pro
20 25 30

Thr

<210> SEQ ID NO 28
<211> LENGTH: 39
<212> TYPE: PRT
<213> ORGANISM: artificial sequence
<220> FEATURE:
<223> OTHER INFORMATION: 28 - Antigenicity index of a portion of native spike (S1 domain) protein

<400> SEQUENCE: 28

Asp Ser Asn Cys Pro Phe Thr Leu Gln Ser Val Asn Asp Tyr Leu Ser
1 5 10 15

Phe Ser Lys Phe Cys Val Ser Thr Ser Leu Leu Ala Ser Ala Cys Thr
20 25 30

Ile Asp Leu Phe Gly Tyr Pro
35

<210> SEQ ID NO 29
<211> LENGTH: 15
<212> TYPE: PRT
<213> ORGANISM: artificial sequence
<220> FEATURE:
<223> OTHER INFORMATION: 29 - Antigenicity index of a portion of native spike (S1 domain) protein

<400> SEQUENCE: 29

Thr Ser Val Ile Leu Ala Glu Gly Ser Ile Val Leu His Thr Ala
1 5 10 15

<210> SEQ ID NO 30
<211> LENGTH: 22
<212> TYPE: PRT
<213> ORGANISM: artificial sequence
<220> FEATURE:
<223> OTHER INFORMATION: 30 - Antigenicity index of a portion of native spike (S1 domain) protein

<400> SEQUENCE: 30

Ile Gln Arg Ile Leu Tyr Cys Asp Asp Pro Val Ser Gln Leu Lys Cys
1 5 10 15

Ser Gln Val Ala Phe Asp
20

<210> SEQ ID NO 31
<211> LENGTH: 17
<212> TYPE: PRT
<213> ORGANISM: artificial sequence
<220> FEATURE:
<223> OTHER INFORMATION: 31 - Antigenicity index of a portion of native spike (S1 domain) protein

<400> SEQUENCE: 31

Cys Ala Met Gln Tyr Val Tyr Glu Pro Thr Tyr Tyr Met Leu Asn Val
1 5 10 15

Thr

<210> SEQ ID NO 32
<211> LENGTH: 23
<212> TYPE: PRT
<213> ORGANISM: artificial sequence
<220> FEATURE:
<223> OTHER INFORMATION: 32 - Antigenicity index of a portion of native spike (S1 domain) protein

<400> SEQUENCE: 32

```
Ser Thr Trp Tyr Cys Ala Gly Gln His Pro Thr Ala Ser Gly Val His
1               5                   10                  15

Gly Ile Phe Val Ser His Ile
            20
```

<210> SEQ ID NO 33
<211> LENGTH: 10
<212> TYPE: PRT
<213> ORGANISM: artificial sequence
<220> FEATURE:
<223> OTHER INFORMATION: 33- Antigenicity index of a portion of native spike (S1 domain) protein

<400> SEQUENCE: 33

```
Ser Ser Phe Leu Ala Gly Val Tyr Tyr Thr
1               5                   10
```

<210> SEQ ID NO 34
<211> LENGTH: 15
<212> TYPE: PRT
<213> ORGANISM: artificial sequence
<220> FEATURE:
<223> OTHER INFORMATION: 34 - Antigenicity index of a portion of native spike (S1 domain) protein

<400> SEQUENCE: 34

```
Asp Gly Val Cys Asn Gly Ala Ala Val Gln Arg Ala Pro Glu Ala
1               5                   10                  15
```

<210> SEQ ID NO 35
<211> LENGTH: 13
<212> TYPE: PRT
<213> ORGANISM: artificial sequence
<220> FEATURE:
<223> OTHER INFORMATION: 35 - Antigenicity index of a portion of native spike (S1 domain) protein

<400> SEQUENCE: 35

```
Thr Asn Phe Val Asp Ala Leu Ile Glu Val Gln Gly Thr
1               5                   10
```

<210> SEQ ID NO 36
<211> LENGTH: 13
<212> TYPE: PRT
<213> ORGANISM: artificial sequence
<220> FEATURE:
<223> OTHER INFORMATION: 36 - Antigenicity index of a portion of native spike (S1 domain) protein

<400> SEQUENCE: 36

```
Phe Met Thr Leu Asp Val Cys Thr Lys Tyr Thr Ile Tyr
1               5                   10
```

<210> SEQ ID NO 37
<211> LENGTH: 14
<212> TYPE: PRT
<213> ORGANISM: artificial sequence
<220> FEATURE:
<223> OTHER INFORMATION: 37 - Antigenicity index of a portion of native spike (S1 domain) protein

<400> SEQUENCE: 37

```
Arg Leu Arg Ile Cys Gln Phe Pro Ser Ile Lys Thr Leu Gly
1               5                   10
```

<210> SEQ ID NO 38
<211> LENGTH: 9
<212> TYPE: PRT
<213> ORGANISM: artificial sequence
<220> FEATURE:
<223> OTHER INFORMATION: 38 - Antigenicity index of a portion of native spike (S1 domain) protein

<400> SEQUENCE: 38

Phe Ser Ser Phe Cys Val Asp Thr Arg
1 5

<210> SEQ ID NO 39
<211> LENGTH: 10
<212> TYPE: PRT
<213> ORGANISM: artificial sequence
<220> FEATURE:
<223> OTHER INFORMATION: 39 - Antigenicity index of a portion of native spike (S1 domain) protein

<400> SEQUENCE: 39

Pro Ser Gly Tyr Gln Leu Tyr Leu His Lys
1 5 10

<210> SEQ ID NO 40
<211> LENGTH: 23
<212> TYPE: PRT
<213> ORGANISM: artificial sequence
<220> FEATURE:
<223> OTHER INFORMATION: 40 - Antigenicity index of a portion of native spike (S1 domain) protein

<400> SEQUENCE: 40

Gly Phe Tyr Pro Ile Ser Ser Arg Asn Leu Leu Ser His Glu Gln Pro
1 5 10 15

Ile Ser Phe Val Thr Leu Pro
20

<210> SEQ ID NO 41
<211> LENGTH: 9
<212> TYPE: PRT
<213> ORGANISM: artificial sequence
<220> FEATURE:
<223> OTHER INFORMATION: 41 - Antigenicity index of a portion of native spike (S1 domain) protein

<400> SEQUENCE: 41

Thr Ile Ser Leu Phe Tyr Asn Val Thr
1 5

<210> SEQ ID NO 42
<211> LENGTH: 7
<212> TYPE: PRT
<213> ORGANISM: artificial sequence
<220> FEATURE:
<223> OTHER INFORMATION: 42 - Antigenicity index of a portion of native spike (S1 domain) protein

<400> SEQUENCE: 42

Glu His Ser Val Val Gly Ile
1 5

<210> SEQ ID NO 43
<211> LENGTH: 19
<212> TYPE: PRT
<213> ORGANISM: artificial sequence
<220> FEATURE:
<223> OTHER INFORMATION: 43 - Antigenicity index of a portion of native spike (S1 domain) protein

<400> SEQUENCE: 43

Ser Tyr Gln Pro Cys Thr Ala Asn Cys Ile Gly Tyr Ala Ala Asn Val
1 5 10 15

Phe Ala Thr

<210> SEQ ID NO 44
<211> LENGTH: 9
<212> TYPE: PRT
<213> ORGANISM: artificial sequence
<220> FEATURE:
<223> OTHER INFORMATION: 44 - Antigenicity index of a portion of native spike (S1 domain) protein

<400> SEQUENCE: 44

Asn Phe Ser Phe Val Cys Ser Asn Ser
1 5

<210> SEQ ID NO 45
<211> LENGTH: 14
<212> TYPE: PRT
<213> ORGANISM: artificial sequence
<220> FEATURE:
<223> OTHER INFORMATION: 45 - Antigenicity index of a portion of native spike (S1 domain) protein

<400> SEQUENCE: 45

Arg Val Thr Val Phe Ser Asp Lys Ile Tyr Tyr Phe Tyr Phe
1 5 10

<210> SEQ ID NO 46
<211> LENGTH: 8
<212> TYPE: PRT
<213> ORGANISM: artificial sequence
<220> FEATURE:
<223> OTHER INFORMATION: 46 - Antigenicity index of a portion of native spike (S1 domain) protein

<400> SEQUENCE: 46

Gly Gln Leu Leu Ala Phe Lys Asn
1 5

<210> SEQ ID NO 47
<211> LENGTH: 13
<212> TYPE: PRT
<213> ORGANISM: artificial sequence
<220> FEATURE:
<223> OTHER INFORMATION: 47 - Antigenicity index of a portion of native spike (S1 domain) protein

<400> SEQUENCE: 47

Gly Ser Gly Val Lys Phe Thr Ser Leu Tyr Phe Gln Phe
1 5 10

<210> SEQ ID NO 48
<211> LENGTH: 10
<212> TYPE: PRT
<213> ORGANISM: artificial sequence
<220> FEATURE:
<223> OTHER INFORMATION: 48 - Antigenicity index of a portion of native spike (S1 domain) protein

<400> SEQUENCE: 48

Arg Val Ala Thr Lys Cys Tyr Asn Ser Gly 1 5 10

<210> SEQ ID NO 49
<211> LENGTH: 13
<212> TYPE: PRT
<213> ORGANISM: artificial sequence
<220> FEATURE:
<223> OTHER INFORMATION: 49 - Antigenicity index of a portion of native spike (S1 domain) protein

<400> SEQUENCE: 49

His Ser Phe Val Asn Ile Thr Val Ser Ala Ser Phe Gly
1 5 10

<210> SEQ ID NO 50
<211> LENGTH: 14
<212> TYPE: PRT
<213> ORGANISM: artificial sequence
<220> FEATURE:
<223> OTHER INFORMATION: 50 - Antigenicity index of a portion of native spike (S1 domain) protein

<400> SEQUENCE: 50

Gly Arg Asn Cys Leu Phe Asn Lys Ala Ile Pro Ala His Met
1 5 10

<210> SEQ ID NO 51
<211> LENGTH: 6
<212> TYPE: PRT
<213> ORGANISM: artificial sequence
<220> FEATURE:
<223> OTHER INFORMATION: 51 - Antigenicity index of a portion of native spike (S1 domain) protein

<400> SEQUENCE: 51

Pro Gly Phe Phe Tyr His
1 5

<210> SEQ ID NO 52
<211> LENGTH: 8
<212> TYPE: PRT
<213> ORGANISM: artificial sequence
<220> FEATURE:
<223> OTHER INFORMATION: 52 - Antigenicity index of a portion of native spike (S1 domain) protein

<400> SEQUENCE: 52

Ser Tyr Gly Tyr Val Ser Lys Ser
1 5

<210> SEQ ID NO 53
<211> LENGTH: 7
<212> TYPE: PRT
<213> ORGANISM: artificial sequence
<220> FEATURE:
<223> OTHER INFORMATION: 53 - Antigenicity index of a portion of native spike (S1 domain) protein

<400> SEQUENCE: 53

Leu Glu Gly Val Thr Asp Val
1 5

<210> SEQ ID NO 54
<211> LENGTH: 7
<212> TYPE: PRT
<213> ORGANISM: artificial sequence
<220> FEATURE:
<223> OTHER INFORMATION: Antigenicity index of a portion of native spike (S2 domain) protein

<400> SEQUENCE: 54

Ala Asn Leu Ile Ala Ser Asp
1               5

<210> SEQ ID NO 55
<211> LENGTH: 55
<212> TYPE: PRT
<213> ORGANISM: artificial sequence
<220> FEATURE:
<223> OTHER INFORMATION: 55 - Antigenicity index of a portion of native
      spike (S2 domain) protein

<400> SEQUENCE: 55

Trp Val Trp Leu Ile Ile Phe Ile Val Leu Ile Phe Val Val Ser Leu
1               5                   10                  15

Leu Val Phe Cys Cys Ile Ser Thr Gly Cys Cys Gly Cys Cys Gly Cys
            20                  25                  30

Cys Cys Ala Cys Phe Ser Gly Cys Cys Arg Gly Pro Arg Leu Gln Pro
        35                  40                  45

Tyr Glu Val Phe Glu Lys Val
    50                  55

<210> SEQ ID NO 56
<211> LENGTH: 21
<212> TYPE: PRT
<213> ORGANISM: artificial sequence
<220> FEATURE:
<223> OTHER INFORMATION: 56 - Antigenicity index of a portion of native
      spike (S2 domain) protein

<400> SEQUENCE: 56

Lys Pro Thr Val Ser Asp Phe Val Gln Ile Glu Ser Cys Val Val Thr
1               5                   10                  15

Tyr Val Asn Leu Thr
            20

<210> SEQ ID NO 57
<211> LENGTH: 11
<212> TYPE: PRT
<213> ORGANISM: artificial sequence
<220> FEATURE:
<223> OTHER INFORMATION: 57 - Antigenicity index of a portion of native
      spike (S2 domain) protein

<400> SEQUENCE: 57

Thr Asn Val Leu Gly Val Ser Val Tyr Asp Pro
1               5                   10

<210> SEQ ID NO 58
<211> LENGTH: 38
<212> TYPE: PRT
<213> ORGANISM: artificial sequence
<220> FEATURE:
<223> OTHER INFORMATION: 58 - Antigenicity index of a portion of native
      spike (S2 domain) protein

<400> SEQUENCE: 58

Ile Phe Ser Leu Val Gln Ala Ala Pro Gln Gly Leu Leu Phe Leu His
1               5                   10                  15

Thr Val Leu Val Pro Ser Asp Phe Val Asp Val Ile Ala Ile Ala Gly
            20                  25                  30

Leu Cys Val Asn Asp Glu

35

<210> SEQ ID NO 59
<211> LENGTH: 38
<212> TYPE: PRT
<213> ORGANISM: artificial sequence
<220> FEATURE:
<223> OTHER INFORMATION: 59 - Antigenicity index of a portion of native spike (S2 domain) protein

<400> SEQUENCE: 59

Ile Phe Ser Leu Val Gln Ala Ala Pro Gln Gly Leu Leu Phe Leu His
1 5 10 15

Thr Val Leu Val Pro Ser Asp Phe Val Asp Val Ile Ala Ile Ala Gly
20 25 30

Leu Cys Val Asn Asp Glu
35

<210> SEQ ID NO 60
<211> LENGTH: 23
<212> TYPE: PRT
<213> ORGANISM: artificial sequence
<220> FEATURE:
<223> OTHER INFORMATION: 60 - Antigenicity index of a portion of native spike (S2 domain) protein

<400> SEQUENCE: 60

Thr Glu Tyr Leu Gln Leu Tyr Asn Thr Pro Val Ser Val Asp Cys Ala
1 5 10 15

Thr Tyr Val Cys Asn Gly Asn
20

<210> SEQ ID NO 61
<211> LENGTH: 12
<212> TYPE: PRT
<213> ORGANISM: artificial sequence
<220> FEATURE:
<223> OTHER INFORMATION: 61 - Antigenicity index of a portion of native spike (S2 domain) protein

<400> SEQUENCE: 61

Ile Glu Asp Leu Leu Phe Asn Lys Val Val Thr Asn
1 5 10

<210> SEQ ID NO 62
<211> LENGTH: 35
<212> TYPE: PRT
<213> ORGANISM: artificial sequence
<220> FEATURE:
<223> OTHER INFORMATION: 62 - Antigenicity index of a portion of native spike (S2 domain) protein

<400> SEQUENCE: 62

Ser Ala Ala Ala Leu Pro Phe Ser Tyr Ala Val Gln Ala Arg Leu Asn
1 5 10 15

Tyr Leu Ala Leu Gln Thr Asp Val Leu Gln Arg Asn Gln Gln Leu Leu
20 25 30

Ala Glu Ser
35

<210> SEQ ID NO 63
<211> LENGTH: 59
<212> TYPE: PRT
<213> ORGANISM: artificial sequence
<220> FEATURE:

<223> OTHER INFORMATION: 63 - Antigenicity index of a portion of native spike (S2 domain) protein

<400> SEQUENCE: 63

Leu Asn Thr Val Ala His Ala Leu Thr Lys Val Gln Glu Val Val Asn
1 5 10 15

Ser Gln Gly Ala Ala Leu Thr Gln Leu Thr Val Gln Leu Gln His Asn
20 25 30

Phe Gln Ala Ile Ser Ser Ser Ile Asp Asp Ile Tyr Ser Arg Leu Asp
35 40 45

Ile Leu Ser Ala Asp Val Gln Val Asp Arg Leu
50 55

<210> SEQ ID NO 64
<211> LENGTH: 16
<212> TYPE: PRT
<213> ORGANISM: artificial sequence
<220> FEATURE:
<223> OTHER INFORMATION: 64 - Antigenicity index of a portion of native spike (S2 domain) protein

<400> SEQUENCE: 64

Pro Ser Leu Pro Leu Asp Val Phe Asn Ala Thr Tyr Leu Asn Leu Thr
1 5 10 15

<210> SEQ ID NO 65
<211> LENGTH: 14
<212> TYPE: PRT
<213> ORGANISM: artificial sequence
<220> FEATURE:
<223> OTHER INFORMATION: 65 - Antigenicity index of a portion of native spike (S2 domain) protein

<400> SEQUENCE: 65

Ala Leu Thr Leu Arg Glu Pro Gly Leu Val Leu Phe Thr His
1 5 10

<210> SEQ ID NO 66
<211> LENGTH: 12
<212> TYPE: PRT
<213> ORGANISM: artificial sequence
<220> FEATURE:
<223> OTHER INFORMATION: 66 - Antigenicity index of a portion of native spike (S2 domain) protein

<400> SEQUENCE: 66

Leu Pro Asp Val Ile Pro Asp Tyr Ile Asp Val Asn
1 5 10

<210> SEQ ID NO 67
<211> LENGTH: 33
<212> TYPE: PRT
<213> ORGANISM: artificial sequence
<220> FEATURE:
<223> OTHER INFORMATION: 67 - Antigenicity index of a portion of native spike (S2 domain) protein

<400> SEQUENCE: 67

Cys Lys Gln Leu Leu Thr Gln Tyr Thr Ala Ala Cys Lys Thr Ile Glu
1 5 10 15

Ser Ala Leu Gln Leu Ser Ala Arg Leu Glu Ser Val Glu Val Asn Ser
20 25 30

Met

```
<210> SEQ ID NO 68
<211> LENGTH: 23
<212> TYPE: PRT
<213> ORGANISM: artificial sequence
<220> FEATURE:
<223> OTHER INFORMATION: 68 - Antigenicity index of a portion of native
      spike (S2 domain) protein

<400> SEQUENCE: 68

Tyr Thr Glu Val Gln Ala Ser Arg Lys Leu Ala Gln Gln Lys Val Asn
1               5                   10                  15

Glu Cys Val Lys Ser Gln Ser
            20


<210> SEQ ID NO 69
<211> LENGTH: 16
<212> TYPE: PRT
<213> ORGANISM: artificial sequence
<220> FEATURE:
<223> OTHER INFORMATION: 69 - Antigenicity index of a portion of native
      spike (S2 domain) protein

<400> SEQUENCE: 69

Thr Gly Arg Leu Ser Ala Leu Asn Ala Phe Val Ala Gln Thr Leu Thr
1               5                   10                  15


<210> SEQ ID NO 70
<211> LENGTH: 7
<212> TYPE: PRT
<213> ORGANISM: artificial sequence
<220> FEATURE:
<223> OTHER INFORMATION: 70 - Antigenicity index of a portion of native
      spike (S2 domain) protein

<400> SEQUENCE: 70

Asn Thr Leu Val Asp Leu Glu
1               5


<210> SEQ ID NO 71
<211> LENGTH: 11
<212> TYPE: PRT
<213> ORGANISM: artificial sequence
<220> FEATURE:
<223> OTHER INFORMATION: 71 - Antigenicity index of a portion of native
      spike (S2 domain) protein

<400> SEQUENCE: 71

Ser Glu Glu Ala Leu Gln Leu Ala Thr Ile Ser
1               5                   10


<210> SEQ ID NO 72
<211> LENGTH: 7
<212> TYPE: PRT
<213> ORGANISM: artificial sequence
<220> FEATURE:
<223> OTHER INFORMATION: 72 - Antigenicity index of a portion of native
      spike (S2 domain) protein

<400> SEQUENCE: 72

Leu Gln Ser Leu Ile Tyr Asn
1               5


<210> SEQ ID NO 73
<211> LENGTH: 8
<212> TYPE: PRT
<213> ORGANISM: artificial sequence
<220> FEATURE:
<223> OTHER INFORMATION: 73 - Antigenicity index of a portion of native
```

spike (S2 domain) protein

<400> SEQUENCE: 73

Ser Gly Arg Val Val Gln Lys Arg
1 5

<210> SEQ ID NO 74
<211> LENGTH: 7
<212> TYPE: PRT
<213> ORGANISM: artificial sequence
<220> FEATURE:
<223> OTHER INFORMATION: 74 - Antigenicity index of a portion of native spike (S2 domain) protein

<400> SEQUENCE: 74

Asp Glu Ile Leu Ala Ser Leu
1 5

<210> SEQ ID NO 75
<211> LENGTH: 12
<212> TYPE: PRT
<213> ORGANISM: artificial sequence
<220> FEATURE:
<223> OTHER INFORMATION: 75 - Antigenicity index of a portion of native spike (S2 domain) protein

<400> SEQUENCE: 75

Leu His Met Tyr Ser Ala Ser Leu Ile Gly Gly Met
1 5 10

<210> SEQ ID NO 76
<211> LENGTH: 8
<212> TYPE: PRT
<213> ORGANISM: artificial sequence
<220> FEATURE:
<223> OTHER INFORMATION: 76 - Antigenicity index of a portion of native spike (S2 domain) protein

<400> SEQUENCE: 76

Thr Glu Tyr Phe Val Ser Ser Arg
1 5

<210> SEQ ID NO 77
<211> LENGTH: 8
<212> TYPE: PRT
<213> ORGANISM: artificial sequence
<220> FEATURE:
<223> OTHER INFORMATION: 77 - Antigenicity index of a portion of native spike (S2 domain) protein

<400> SEQUENCE: 77

Ala Phe Glu Ser Val Lys Glu Ala
1 5

<210> SEQ ID NO 78
<211> LENGTH: 3111
<212> TYPE: DNA
<213> ORGANISM: artificial sequence
<220> FEATURE:
<223> OTHER INFORMATION: Original non-truncated non-fused NPL-PEDV spike (S domain) nucleotide sequence

<400> SEQUENCE: 78
atgggtgagg atggtatttc ttatcaaccc tgtacagcta attgcattgg ttatgctgcc 60
aatgtatttg ctactgagcc caatggccac ataccagaag gttttagttt taataattgg 120
tttcttttgt ccaatgattc cactttggtg catggtaagg tggtttccaa ccaaccattg 180

```
ttggtcaatt gtcttttggc cattcctaag atttatggac taggccaatt tttctccttt    240
aatcaaacga tcgatggtgt ttgtaatgga gctgctgtgc agcgtgcacc agaggctctg    300
aggtttaata ttaatgacac ctctgtcatt cttgctgaag gctcaattgt acttcatact    360
gctttaggaa caaatttttc ttttgtttgc agtaattcct caaatcctca cttagccacc    420
ttcgccatac ctctgggtgc tacccaagta ccttattatt gttttcttaa agtggatact    480
tacaactcca ctgtttataa atttttggct gttttacctc ctaccgtcag ggaaattgtc    540
atcaccaagt atggtgatgt ttatgtcaat gggtttggat acttgcatct cggtttgttg    600
gatgctgtca caattaattt cactggtcat ggcactgacg atgatgtttc tggtttttgg    660
accatagcat cgactaattt tgttgatgca ctcatcgaag ttcaaggaac cgccattcag    720
cgtattcttt attgtgatga tcctgttagc caactcaagt gttctcaggt tgcttttgac    780
cttgacgatg gtttttaccc tatttcttct agaaaccttc tgagtcatga acagccaatt    840
tcttttgtta ctctgccatc atttaatgat cattcttttg ttaacattac tgtatctgct    900
tcctttggtg gtcatagtgg tgccaacctt attgcatctg acactactat caatgggttt    960
agttctttct gtgttgacac tagacaattt accatttcac tgttttataa cgttacaaac   1020
agttatggtt atgtgtctaa atcacaggac agtaattgcc ctttcacctt gcaatctgtt   1080
aatgattacc tgtcttttag caaattttgt gtttccacca gccttttggc tagtgcctgt   1140
accatagatc tttttggtta ccctgagttt ggtagtggtg ttaagtttac gtccctttac   1200
tttcaattca caaagggtga gttgattact ggcacgccta aaccacttga aggtgtcacg   1260
gacgtttctt ttatgactct ggatgtgtgt accaagtata ctatctatgg ctttaaaggt   1320
gagggtatca ttacccttac aaattctagc tttttggcag gtgtttatta cacatctgat   1380
tctggacagt tgttagcctt taagaatgtc actagtggtg ctgtttattc tgttacgcca   1440
tgttcttttt cagagcaggc tgcatatgtt gatgatgata tagtgggtgt tatttctagt   1500
ttgtctagct ccacttttaa cagtactagg gagttgcctg gtttcttcta ccattctaat   1560
gatggctcta attgtacaga gcctgtgttg gtgtatagta acataggtgt ttgtaaatct   1620
ggcagtattg gctacgtccc atctcagtct ggccaagtca agattgcacc cacggttact   1680
gggaatatta gtattcccac caactttagt tctaatggtc gctctgtggc agatctagtc   1740
tgtgcacagt attactctgg tgtcatggta ctacctggtg ttgttgacgc tgagaagctt   1800
cacatgtata gtgcgtctct catcggtggt atggtgctag gaggttttac ttctgcagcg   1860
gcattgcctt ttagctatgc tgttcaagct agactcaatt atcttgctct acagacggat   1920
gttctacagc ggaaccagca attgcttgct gagtctttta actctgctat tggtaatata   1980
acttcagcct ttgagagtgt taaagaggct attagtcaaa cttccaaggg tttgaacact   2040
gtggctcatg cgcttactaa ggttcaagag gttgttaact cgcagggtgc agctttgact   2100
caacttaccg tacagctgca acacaacttc caagccattt ctagttctat tgatgacatt   2160
tactctcgac tggacattct ttcagccgat gttcaggttg accgtctcat caccggcaga   2220
ttatcagcac ttaatgcttt tgttgctcaa accctcacta agtatactga ggttcaggct   2280
agcaggaagt tagcacagca aaaggttaat gagtgcgtta aatcgcaatc tcagcgttat   2340
ggtttttgtg gtggtgatgg cgagcacatt ttctctctgg tacaggcagc acctcagggc   2400
ctgctgtttt tacatacagt acttgtaccg agtgattttg tagatgttat tgccatcgct   2460
ggcttatgcg ttaacgatga aattgccttg actctacgtg agcctggctt agtcttgttt   2520
```

acgcatgaac ttcaaaatca tactgcgacg gaatattttg tttcatcgcg acgtatgttt 2580
gaacctagaa aacctaccgt tagtgatttt gttcaaattg agagttgtgt ggtcacctat 2640
gtcaatttga ctagagacca actaccagat gtaatcccag attacatcga tgttaacaaa 2700
acacttgatg agattttagc ttctctgccc aatagaactg gtccaagtct tcctttagat 2760
gtttttaatg ccacttatct taatctcact ggtgaaattg cagatttaga gcagcgttca 2820
gagtctctcc gtaatactac agaggagctc caaagtctta tatataatat caacaacaca 2880
ctagttgacc ttgagtggct caaccgagtt gagacatata tcaagtggcc gtggtgggtt 2940
tggttgatta ttttcattgt tctcatcttt gttgtgtcat tactagtgtt ctgctgcatt 3000
tccacgggtt gttgtggatg ctgcggctgc tgctgtgctt gtttctcagg ttgttgtagg 3060
ggtcctagac ttcaacctta cgaagttttt gaaaaggtcc acgtgcagtg a 3111

<210> SEQ ID NO 79
<211> LENGTH: 1036
<212> TYPE: PRT
<213> ORGANISM: artificial sequence
<220> FEATURE:
<223> OTHER INFORMATION: Original non-truncated non-fused NPL-PEDV spike (S domain) protein sequence

<400> SEQUENCE: 79

Met Gly Glu Asp Gly Ile Ser Tyr Gln Pro Cys Thr Ala Asn Cys Ile
1 5 10 15

Gly Tyr Ala Ala Asn Val Phe Ala Thr Glu Pro Asn Gly His Ile Pro
20 25 30

Glu Gly Phe Ser Phe Asn Asn Trp Phe Leu Leu Ser Asn Asp Ser Thr
35 40 45

Leu Val His Gly Lys Val Val Ser Asn Gln Pro Leu Leu Val Asn Cys
50 55 60

Leu Leu Ala Ile Pro Lys Ile Tyr Gly Leu Gly Gln Phe Phe Ser Phe
65 70 75 80

Asn Gln Thr Ile Asp Gly Val Cys Asn Gly Ala Ala Val Gln Arg Ala
85 90 95

Pro Glu Ala Leu Arg Phe Asn Ile Asn Asp Thr Ser Val Ile Leu Ala
100 105 110

Glu Gly Ser Ile Val Leu His Thr Ala Leu Gly Thr Asn Phe Ser Phe
115 120 125

Val Cys Ser Asn Ser Ser Asn Pro His Leu Ala Thr Phe Ala Ile Pro
130 135 140

Leu Gly Ala Thr Gln Val Pro Tyr Tyr Cys Phe Leu Lys Val Asp Thr
145 150 155 160

Tyr Asn Ser Thr Val Tyr Lys Phe Leu Ala Val Leu Pro Pro Thr Val
165 170 175

Arg Glu Ile Val Ile Thr Lys Tyr Gly Asp Val Tyr Val Asn Gly Phe
180 185 190

Gly Tyr Leu His Leu Gly Leu Leu Asp Ala Val Thr Ile Asn Phe Thr
195 200 205

Gly His Gly Thr Asp Asp Asp Val Ser Gly Phe Trp Thr Ile Ala Ser
210 215 220

Thr Asn Phe Val Asp Ala Leu Ile Glu Val Gln Gly Thr Ala Ile Gln
225 230 235 240

Arg Ile Leu Tyr Cys Asp Asp Pro Val Ser Gln Leu Lys Cys Ser Gln
245 250 255

-continued

```
Val Ala Phe Asp Leu Asp Asp Gly Phe Tyr Pro Ile Ser Ser Arg Asn
            260                 265                 270

Leu Leu Ser His Glu Gln Pro Ile Ser Phe Val Thr Leu Pro Ser Phe
        275                 280                 285

Asn Asp His Ser Phe Val Asn Ile Thr Val Ser Ala Ser Phe Gly Gly
    290                 295                 300

His Ser Gly Ala Asn Leu Ile Ala Ser Asp Thr Thr Ile Asn Gly Phe
305                 310                 315                 320

Ser Ser Phe Cys Val Asp Thr Arg Gln Phe Thr Ile Ser Leu Phe Tyr
                325                 330                 335

Asn Val Thr Asn Ser Tyr Gly Tyr Val Ser Lys Ser Gln Asp Ser Asn
            340                 345                 350

Cys Pro Phe Thr Leu Gln Ser Val Asn Asp Tyr Leu Ser Phe Ser Lys
        355                 360                 365

Phe Cys Val Ser Thr Ser Leu Leu Ala Ser Ala Cys Thr Ile Asp Leu
    370                 375                 380

Phe Gly Tyr Pro Glu Phe Gly Ser Gly Val Lys Phe Thr Ser Leu Tyr
385                 390                 395                 400

Phe Gln Phe Thr Lys Gly Glu Leu Ile Thr Gly Thr Pro Lys Pro Leu
                405                 410                 415

Glu Gly Val Thr Asp Val Ser Phe Met Thr Leu Asp Val Cys Thr Lys
            420                 425                 430

Tyr Thr Ile Tyr Gly Phe Lys Gly Glu Gly Ile Ile Thr Leu Thr Asn
        435                 440                 445

Ser Ser Phe Leu Ala Gly Val Tyr Tyr Thr Ser Asp Ser Gly Gln Leu
    450                 455                 460

Leu Ala Phe Lys Asn Val Thr Ser Gly Ala Val Tyr Ser Val Thr Pro
465                 470                 475                 480

Cys Ser Phe Ser Glu Gln Ala Ala Tyr Val Asp Asp Asp Ile Val Gly
                485                 490                 495

Val Ile Ser Ser Leu Ser Ser Ser Thr Phe Asn Ser Thr Arg Glu Leu
            500                 505                 510

Pro Gly Phe Phe Tyr His Ser Asn Asp Gly Ser Asn Cys Thr Glu Pro
        515                 520                 525

Val Leu Val Tyr Ser Asn Ile Gly Val Cys Lys Ser Gly Ser Ile Gly
    530                 535                 540

Tyr Val Pro Ser Gln Ser Gly Gln Val Lys Ile Ala Pro Thr Val Thr
545                 550                 555                 560

Gly Asn Ile Ser Ile Pro Thr Asn Phe Ser Ser Asn Gly Arg Ser Val
                565                 570                 575

Ala Asp Leu Val Cys Ala Gln Tyr Tyr Ser Gly Val Met Val Leu Pro
            580                 585                 590

Gly Val Val Asp Ala Glu Lys Leu His Met Tyr Ser Ala Ser Leu Ile
        595                 600                 605

Gly Gly Met Val Leu Gly Gly Phe Thr Ser Ala Ala Ala Leu Pro Phe
    610                 615                 620

Ser Tyr Ala Val Gln Ala Arg Leu Asn Tyr Leu Ala Leu Gln Thr Asp
625                 630                 635                 640

Val Leu Gln Arg Asn Gln Gln Leu Leu Ala Glu Ser Phe Asn Ser Ala
                645                 650                 655

Ile Gly Asn Ile Thr Ser Ala Phe Glu Ser Val Lys Glu Ala Ile Ser
            660                 665                 670

Gln Thr Ser Lys Gly Leu Asn Thr Val Ala His Ala Leu Thr Lys Val
```

-continued

```
        675                 680                 685

Gln Glu Val Val Asn Ser Gln Gly Ala Ala Leu Thr Gln Leu Thr Val
    690                 695                 700

Gln Leu Gln His Asn Phe Gln Ala Ile Ser Ser Ser Ile Asp Asp Ile
705                 710                 715                 720

Tyr Ser Arg Leu Asp Ile Leu Ser Ala Asp Val Gln Val Asp Arg Leu
                725                 730                 735

Ile Thr Gly Arg Leu Ser Ala Leu Asn Ala Phe Val Ala Gln Thr Leu
            740                 745                 750

Thr Lys Tyr Thr Glu Val Gln Ala Ser Arg Lys Leu Ala Gln Gln Lys
        755                 760                 765

Val Asn Glu Cys Val Lys Ser Gln Ser Gln Arg Tyr Gly Phe Cys Gly
    770                 775                 780

Gly Asp Gly Glu His Ile Phe Ser Leu Val Gln Ala Ala Pro Gln Gly
785                 790                 795                 800

Leu Leu Phe Leu His Thr Val Leu Val Pro Ser Asp Phe Val Asp Val
                805                 810                 815

Ile Ala Ile Ala Gly Leu Cys Val Asn Asp Glu Ile Ala Leu Thr Leu
            820                 825                 830

Arg Glu Pro Gly Leu Val Leu Phe Thr His Glu Leu Gln Asn His Thr
        835                 840                 845

Ala Thr Glu Tyr Phe Val Ser Ser Arg Arg Met Phe Glu Pro Arg Lys
    850                 855                 860

Pro Thr Val Ser Asp Phe Val Gln Ile Glu Ser Cys Val Val Thr Tyr
865                 870                 875                 880

Val Asn Leu Thr Arg Asp Gln Leu Pro Asp Val Ile Pro Asp Tyr Ile
                885                 890                 895

Asp Val Asn Lys Thr Leu Asp Glu Ile Leu Ala Ser Leu Pro Asn Arg
            900                 905                 910

Thr Gly Pro Ser Leu Pro Leu Asp Val Phe Asn Ala Thr Tyr Leu Asn
        915                 920                 925

Leu Thr Gly Glu Ile Ala Asp Leu Glu Gln Arg Ser Glu Ser Leu Arg
    930                 935                 940

Asn Thr Thr Glu Glu Leu Gln Ser Leu Ile Tyr Asn Ile Asn Asn Thr
945                 950                 955                 960

Leu Val Asp Leu Glu Trp Leu Asn Arg Val Glu Thr Tyr Ile Lys Trp
                965                 970                 975

Pro Trp Trp Val Trp Leu Ile Ile Phe Ile Val Leu Ile Phe Val Val
            980                 985                 990

Ser Leu Leu Val Phe Cys Cys Ile  Ser Thr Gly Cys Cys  Gly Cys Cys
        995                 1000                1005

Gly Cys  Cys Cys Ala Cys Phe  Ser Gly Cys Cys Arg  Gly Pro Arg
    1010                1015                1020

Leu Gln  Pro Tyr Glu Val Phe  Glu Lys Val His Val  Gln
    1025                1030                1035
```

<210> SEQ ID NO 80
<211> LENGTH: 23
<212> TYPE: DNA
<213> ORGANISM: artificial sequence
<220> FEATURE:
<223> OTHER INFORMATION: 80 -PEDF1

<400> SEQUENCE: 80
acttaaagag atttctatc tac 23

<210> SEQ ID NO 81
<211> LENGTH: 22
<212> TYPE: DNA
<213> ORGANISM: artificial sequence
<220> FEATURE:
<223> OTHER INFORMATION: PEDF2 - 81

<400> SEQUENCE: 81
aggttgcacg tactccaaag at 22

<210> SEQ ID NO 82
<211> LENGTH: 22
<212> TYPE: DNA
<213> ORGANISM: artificial sequence
<220> FEATURE:
<223> OTHER INFORMATION: PEDF3 - 82

<400> SEQUENCE: 82
gcattggtta agcttgtcaa gg 22

<210> SEQ ID NO 83
<211> LENGTH: 23
<212> TYPE: DNA
<213> ORGANISM: artificial sequence
<220> FEATURE:
<223> OTHER INFORMATION: PEDF4- SEQ ID NO:83

<400> SEQUENCE: 83
cttcaagtat tatgccacca gtg 23

<210> SEQ ID NO 84
<211> LENGTH: 23
<212> TYPE: DNA
<213> ORGANISM: artificial sequence
<220> FEATURE:
<223> OTHER INFORMATION: PEDF5- SEQ ID NO:84

<400> SEQUENCE: 84
tgactttgca agctatggag gac 23

<210> SEQ ID NO 85
<211> LENGTH: 20
<212> TYPE: DNA
<213> ORGANISM: artificial sequence
<220> FEATURE:
<223> OTHER INFORMATION: PEDF6- SEQ ID NO:85

<400> SEQUENCE: 85
gcatgcacct gagcttcttg 20

<210> SEQ ID NO 86
<211> LENGTH: 23
<212> TYPE: DNA
<213> ORGANISM: artificial sequence
<220> FEATURE:
<223> OTHER INFORMATION: PEDF7- SEQ ID NO:86

<400> SEQUENCE: 86
gttgtagcta aggttgtacc aag 23

<210> SEQ ID NO 87
<211> LENGTH: 22
<212> TYPE: DNA
<213> ORGANISM: artificial sequence
<220> FEATURE:

<223> OTHER INFORMATION: PEDF8- SEQ ID NO:87

<400> SEQUENCE: 87
acgtactggt attatattgc gt 22

<210> SEQ ID NO 88
<211> LENGTH: 23
<212> TYPE: DNA
<213> ORGANISM: artificial sequence
<220> FEATURE:
<223> OTHER INFORMATION: PEDF9- SEQ ID NO:88

<400> SEQUENCE: 88
cttaatgtgc aaccgacagg tcc 23

<210> SEQ ID NO 89
<211> LENGTH: 22
<212> TYPE: DNA
<213> ORGANISM: artificial sequence
<220> FEATURE:
<223> OTHER INFORMATION: PEDF10- SEQ ID NO:89

<400> SEQUENCE: 89
gacaatccac ttagttgtgt gc 22

<210> SEQ ID NO 90
<211> LENGTH: 23
<212> TYPE: DNA
<213> ORGANISM: artificial sequence
<220> FEATURE:
<223> OTHER INFORMATION: PEDF11- SEQ ID NO:90

<400> SEQUENCE: 90
cacagaacac acttggcatg ttg 23

<210> SEQ ID NO 91
<211> LENGTH: 22
<212> TYPE: DNA
<213> ORGANISM: artificial sequence
<220> FEATURE:
<223> OTHER INFORMATION: PEDF12- SEQ ID NO:91

<400> SEQUENCE: 91
atgatggttc tgcagctggt gt 22

<210> SEQ ID NO 92
<211> LENGTH: 22
<212> TYPE: DNA
<213> ORGANISM: artificial sequence
<220> FEATURE:
<223> OTHER INFORMATION: PEDF13- SEQ ID NO:92

<400> SEQUENCE: 92
tgcacaaggt cttgttaaca tc 22

<210> SEQ ID NO 93
<211> LENGTH: 23
<212> TYPE: DNA
<213> ORGANISM: artificial sequence
<220> FEATURE:
<223> OTHER INFORMATION: PEDF14- SEQ ID NO:93

<400> SEQUENCE: 93
gatgctgtta ataatggttc tcc 23

<210> SEQ ID NO 94
<211> LENGTH: 23
<212> TYPE: DNA
<213> ORGANISM: artificial sequence
<220> FEATURE:
<223> OTHER INFORMATION: PEDF15- SEQ ID NO:94

<400> SEQUENCE: 94
gccactgtac gcttgcaggc tgg 23

<210> SEQ ID NO 95
<211> LENGTH: 23
<212> TYPE: DNA
<213> ORGANISM: artificial sequence
<220> FEATURE:
<223> OTHER INFORMATION: PEDF16- SEQ ID NO:95

<400> SEQUENCE: 95
gaagacattc atcgtgtcta tgc 23

<210> SEQ ID NO 96
<211> LENGTH: 24
<212> TYPE: DNA
<213> ORGANISM: artificial sequence
<220> FEATURE:
<223> OTHER INFORMATION: PEDF17- SEQ ID NO:96

<400> SEQUENCE: 96
gtggttgtat cactgctaaa gagg 24

<210> SEQ ID NO 97
<211> LENGTH: 24
<212> TYPE: DNA
<213> ORGANISM: artificial sequence
<220> FEATURE:
<223> OTHER INFORMATION: PED18- SEQ ID NO:97

<400> SEQUENCE: 97
tcgagcctga cattaataaa ggtc 24

<210> SEQ ID NO 98
<211> LENGTH: 22
<212> TYPE: DNA
<213> ORGANISM: artificial sequence
<220> FEATURE:
<223> OTHER INFORMATION: PEDF19- SEQ ID NO:98

<400> SEQUENCE: 98
cacttgttat catataacga ag 22

<210> SEQ ID NO 99
<211> LENGTH: 24
<212> TYPE: DNA
<213> ORGANISM: artificial sequence
<220> FEATURE:
<223> OTHER INFORMATION: PEDF20- SEQ ID NO:99

<400> SEQUENCE: 99
actgtgtctg agatggtcta tgaa 24

<210> SEQ ID NO 100
<211> LENGTH: 23
<212> TYPE: DNA
<213> ORGANISM: artificial sequence
<220> FEATURE:
<223> OTHER INFORMATION: PEDF21- SEQ ID NO:100

<400> SEQUENCE: 100
cgtcagagct cgtgctccac cag 23

<210> SEQ ID NO 101
<211> LENGTH: 23
<212> TYPE: DNA
<213> ORGANISM: artificial sequence
<220> FEATURE:
<223> OTHER INFORMATION: PEDF22- SEQ ID NO:101

<400> SEQUENCE: 101
atgatgatac tgagtgtgac aag 23

<210> SEQ ID NO 102
<211> LENGTH: 23
<212> TYPE: DNA
<213> ORGANISM: artificial sequence
<220> FEATURE:
<223> OTHER INFORMATION: PEDF23- SEQ ID NO:102

<400> SEQUENCE: 102
caagtacgga cttgaagatt agc 23

<210> SEQ ID NO 103
<211> LENGTH: 23
<212> TYPE: DNA
<213> ORGANISM: artificial sequence
<220> FEATURE:
<223> OTHER INFORMATION: PEDF24- SEQ ID NO:103

<400> SEQUENCE: 103
ctgatatgta tgatggtaag att 23

<210> SEQ ID NO 104
<211> LENGTH: 24
<212> TYPE: DNA
<213> ORGANISM: artificial sequence
<220> FEATURE:
<223> OTHER INFORMATION: PEDF25- SEQ ID NO:104

<400> SEQUENCE: 104
ctagtggtta ccagctttat ttac 24

<210> SEQ ID NO 105
<211> LENGTH: 24
<212> TYPE: DNA
<213> ORGANISM: artificial sequence
<220> FEATURE:
<223> OTHER INFORMATION: PEDF26- SEQ ID NO:105

<400> SEQUENCE: 105
ccactgttta taaattcttg gctg 24

<210> SEQ ID NO 106
<211> LENGTH: 23
<212> TYPE: DNA
<213> ORGANISM: artificial sequence
<220> FEATURE:
<223> OTHER INFORMATION: PED27- SEQ ID NO:106

<400> SEQUENCE: 106
gtcactagtg gtgctgttta ttc 23

<210> SEQ ID NO 107
<211> LENGTH: 24

<212> TYPE: DNA
<213> ORGANISM: artificial sequence
<220> FEATURE:
<223> OTHER INFORMATION: PEDF28- SEQ ID NO:107

<400> SEQUENCE: 107
ctctgctatt ggtaatataa cttc 24

<210> SEQ ID NO 108
<211> LENGTH: 25
<212> TYPE: DNA
<213> ORGANISM: artificial sequence
<220> FEATURE:
<223> OTHER INFORMATION: PEDF29- SEQ ID NO:108

<400> SEQUENCE: 108
gttgaccttg agtggctcaa ccgag 25

<210> SEQ ID NO 109
<211> LENGTH: 23
<212> TYPE: DNA
<213> ORGANISM: artificial sequence
<220> FEATURE:
<223> OTHER INFORMATION: PEDF30- SEQ ID NO:109

<400> SEQUENCE: 109
tggtctagta gttaatgtta tac 23

<210> SEQ ID NO 110
<211> LENGTH: 25
<212> TYPE: DNA
<213> ORGANISM: artificial sequence
<220> FEATURE:
<223> OTHER INFORMATION: PEDF31- SEQ ID NO:110

<400> SEQUENCE: 110
gtggccgcaa acgggtgcca ttatc 25

<210> SEQ ID NO 111
<211> LENGTH: 24
<212> TYPE: DNA
<213> ORGANISM: artificial sequence
<220> FEATURE:
<223> OTHER INFORMATION: PEDF32- SEQ ID NO:111

<400> SEQUENCE: 111
tagcgtagca gcttgcttcg gacc 24

<210> SEQ ID NO 112
<211> LENGTH: 22
<212> TYPE: DNA
<213> ORGANISM: artificial sequence
<220> FEATURE:
<223> OTHER INFORMATION: PEDR1- SEQ ID NO:112

<400> SEQUENCE: 112
atctttggag tacgtgcaac ct 22

<210> SEQ ID NO 113
<211> LENGTH: 22
<212> TYPE: DNA
<213> ORGANISM: artificial sequence
<220> FEATURE:
<223> OTHER INFORMATION: PEDR2- SEQ ID NO:113

<400> SEQUENCE: 113
ccttgacaag cttaaccaat gc 22

<210> SEQ ID NO 114
<211> LENGTH: 23
<212> TYPE: DNA
<213> ORGANISM: artificial sequence
<220> FEATURE:
<223> OTHER INFORMATION: PEDR3- SEQ ID NO:114

<400> SEQUENCE: 114
cactggtggc ataatacttg aag 23

<210> SEQ ID NO 115
<211> LENGTH: 23
<212> TYPE: DNA
<213> ORGANISM: artificial sequence
<220> FEATURE:
<223> OTHER INFORMATION: PEDR4- SEQ ID NO:115

<400> SEQUENCE: 115
gtcctccata gcttgcaaag tca 23

<210> SEQ ID NO 116
<211> LENGTH: 22
<212> TYPE: DNA
<213> ORGANISM: artificial sequence
<220> FEATURE:
<223> OTHER INFORMATION: PEDR5- SEQ ID NO:116

<400> SEQUENCE: 116
caagaagctc aggtgcatgc tt 22

<210> SEQ ID NO 117
<211> LENGTH: 23
<212> TYPE: DNA
<213> ORGANISM: artificial sequence
<220> FEATURE:
<223> OTHER INFORMATION: PEDR6- SEQ ID NO:117

<400> SEQUENCE: 117
cttggtacaa ccttagctac aac 23

<210> SEQ ID NO 118
<211> LENGTH: 22
<212> TYPE: DNA
<213> ORGANISM: artificial sequence
<220> FEATURE:
<223> OTHER INFORMATION: PEDR7- SEQ ID NO:118

<400> SEQUENCE: 118
acgcaatata ataccagtac gt 22

<210> SEQ ID NO 119
<211> LENGTH: 23
<212> TYPE: DNA
<213> ORGANISM: artificial sequence
<220> FEATURE:
<223> OTHER INFORMATION: PEDR8- SEQ ID NO:119

<400> SEQUENCE: 119
ggacctgtcg gttgcacatt aag 23

<210> SEQ ID NO 120
<211> LENGTH: 22
<212> TYPE: DNA
<213> ORGANISM: artificial sequence

<220> FEATURE:
<223> OTHER INFORMATION: PEDR9- SEQ ID NO:120

<400> SEQUENCE: 120
gcacacaact aagtggattg tc 22

<210> SEQ ID NO 121
<211> LENGTH: 23
<212> TYPE: DNA
<213> ORGANISM: artificial sequence
<220> FEATURE:
<223> OTHER INFORMATION: PEDR10- SEQ ID NO:121

<400> SEQUENCE: 121
caacatgcca agtgtgttct gtg 23

<210> SEQ ID NO 122
<211> LENGTH: 22
<212> TYPE: DNA
<213> ORGANISM: artificial sequence
<220> FEATURE:
<223> OTHER INFORMATION: PEDR11- SEQ ID NO:122

<400> SEQUENCE: 122
acaccagctg cagaaccatc at 22

<210> SEQ ID NO 123
<211> LENGTH: 22
<212> TYPE: DNA
<213> ORGANISM: artificial sequence
<220> FEATURE:
<223> OTHER INFORMATION: PEDR12- SEQ ID NO:123

<400> SEQUENCE: 123
gatgttaaca agaccttgtg ca 22

<210> SEQ ID NO 124
<211> LENGTH: 23
<212> TYPE: DNA
<213> ORGANISM: artificial sequence
<220> FEATURE:
<223> OTHER INFORMATION: PEDR13- SEQ ID NO:124

<400> SEQUENCE: 124
ggagaaccat tattaacagc atc 23

<210> SEQ ID NO 125
<211> LENGTH: 23
<212> TYPE: DNA
<213> ORGANISM: artificial sequence
<220> FEATURE:
<223> OTHER INFORMATION: PEDR14- SEQ ID NO:125

<400> SEQUENCE: 125
ccagcctgca agcgtacagt ggc 23

<210> SEQ ID NO 126
<211> LENGTH: 23
<212> TYPE: DNA
<213> ORGANISM: artificial sequence
<220> FEATURE:
<223> OTHER INFORMATION: PEDR15- SEQ ID NO:126

<400> SEQUENCE: 126
gcatagacac gatgaatgtc ttc 23

<210> SEQ ID NO 127
<211> LENGTH: 24
<212> TYPE: DNA
<213> ORGANISM: artificial sequence
<220> FEATURE:
<223> OTHER INFORMATION: PEDR16- SEQ ID NO:127

<400> SEQUENCE: 127
cctctttagc agtgttacaa ccac 24

<210> SEQ ID NO 128
<211> LENGTH: 24
<212> TYPE: DNA
<213> ORGANISM: artificial sequence
<220> FEATURE:
<223> OTHER INFORMATION: PEDR17- SEQ ID NO:128

<400> SEQUENCE: 128
gacctttatt aatgtcaggc tcga 24

<210> SEQ ID NO 129
<211> LENGTH: 22
<212> TYPE: DNA
<213> ORGANISM: artificial sequence
<220> FEATURE:
<223> OTHER INFORMATION: PEDR18- SEQ ID NO:129

<400> SEQUENCE: 129
cttcgttata tgataacaag tg 22

<210> SEQ ID NO 130
<211> LENGTH: 23
<212> TYPE: DNA
<213> ORGANISM: artificial sequence
<220> FEATURE:
<223> OTHER INFORMATION: PEDR19- SEQ ID NO:130

<400> SEQUENCE: 130
tcatagacca tctcagacac agt 23

<210> SEQ ID NO 131
<211> LENGTH: 23
<212> TYPE: DNA
<213> ORGANISM: artificial sequence
<220> FEATURE:
<223> OTHER INFORMATION: PEDR20- SEQ ID NO:131

<400> SEQUENCE: 131
ctggtggagc acgagctctg agc 23

<210> SEQ ID NO 132
<211> LENGTH: 23
<212> TYPE: DNA
<213> ORGANISM: artificial sequence
<220> FEATURE:
<223> OTHER INFORMATION: PEDR21- SEQ ID NO:132

<400> SEQUENCE: 132
cttgtcacac tcagtatcat cat 23

<210> SEQ ID NO 133
<211> LENGTH: 23
<212> TYPE: DNA
<213> ORGANISM: artificial sequence
<220> FEATURE:
<223> OTHER INFORMATION: PEDR22- SEQ ID NO:133

<400> SEQUENCE: 133
cgtaatcttc aagtccgtac ttg 23

<210> SEQ ID NO 134
<211> LENGTH: 23
<212> TYPE: DNA
<213> ORGANISM: artificial sequence
<220> FEATURE:
<223> OTHER INFORMATION: PEDR23- SEQ ID NO:134

<400> SEQUENCE: 134
aatcttacca tcatacatat cag 23

<210> SEQ ID NO 135
<211> LENGTH: 23
<212> TYPE: DNA
<213> ORGANISM: artificial sequence
<220> FEATURE:
<223> OTHER INFORMATION: PEDR24- SEQ ID NO:135

<400> SEQUENCE: 135
gtaaataagc tggtaaccac tag 23

<210> SEQ ID NO 136
<211> LENGTH: 24
<212> TYPE: DNA
<213> ORGANISM: artificial sequence
<220> FEATURE:
<223> OTHER INFORMATION: PEDR25- SEQ ID NO:136

<400> SEQUENCE: 136
cagccaagaa tttataaaca gtgg 24

<210> SEQ ID NO 137
<211> LENGTH: 23
<212> TYPE: DNA
<213> ORGANISM: artificial sequence
<220> FEATURE:
<223> OTHER INFORMATION: PEDR26- SEQ ID NO:137

<400> SEQUENCE: 137
gaataaacag caccactagt gac 23

<210> SEQ ID NO 138
<211> LENGTH: 24
<212> TYPE: DNA
<213> ORGANISM: artificial sequence
<220> FEATURE:
<223> OTHER INFORMATION: PEDR27- SEQ ID NO:138

<400> SEQUENCE: 138
gaagttatat taccaatagc agag 24

<210> SEQ ID NO 139
<211> LENGTH: 25
<212> TYPE: DNA
<213> ORGANISM: artificial sequence
<220> FEATURE:
<223> OTHER INFORMATION: PEDR28- SEQ ID NO:139

<400> SEQUENCE: 139
ctcggttgag ccactcaagg tcaac 25

<210> SEQ ID NO 140

<211> LENGTH: 23
<212> TYPE: DNA
<213> ORGANISM: artificial sequence
<220> FEATURE:
<223> OTHER INFORMATION: PERR29- SEQ ID NO:140

<400> SEQUENCE: 140
gtataacatt aactactaga cca 23

<210> SEQ ID NO 141
<211> LENGTH: 25
<212> TYPE: DNA
<213> ORGANISM: artificial sequence
<220> FEATURE:
<223> OTHER INFORMATION: PEDR30- SEQ ID NO:141

<400> SEQUENCE: 141
gataatggca cccgtttgcg gccac 25

<210> SEQ ID NO 142
<211> LENGTH: 24
<212> TYPE: DNA
<213> ORGANISM: artificial sequence
<220> FEATURE:
<223> OTHER INFORMATION: PEDR31- SEQ ID NO:142

<400> SEQUENCE: 142
ggtccgaagc aagctgctac gcta 24

<210> SEQ ID NO 143
<211> LENGTH: 24
<212> TYPE: DNA
<213> ORGANISM: artificial sequence
<220> FEATURE:
<223> OTHER INFORMATION: PEDR32- SEQ ID NO:143

<400> SEQUENCE: 143
gtgtatccat atcaacaccg tcag 24

<210> SEQ ID NO 144
<211> LENGTH: 23
<212> TYPE: DNA
<213> ORGANISM: artificial sequence
<220> FEATURE:
<223> OTHER INFORMATION: Reseq1F - SEQ ID NO: 144

<400> SEQUENCE: 144
atcactggtc ttaatacaat gtg 23

<210> SEQ ID NO 145
<211> LENGTH: 25
<212> TYPE: DNA
<213> ORGANISM: artificial sequence
<220> FEATURE:
<223> OTHER INFORMATION: Reseq1R- SEQ ID NO: 145

<400> SEQUENCE: 145
caatactacc attgagtgct ggtgg 25

<210> SEQ ID NO 146
<211> LENGTH: 23
<212> TYPE: DNA
<213> ORGANISM: artificial sequence
<220> FEATURE:
<223> OTHER INFORMATION: Reseq2F- SEQ ID NO: 146

<400> SEQUENCE: 146
tgcagaagtg ctcgaatgat tac 23

<210> SEQ ID NO 147
<211> LENGTH: 24
<212> TYPE: DNA
<213> ORGANISM: artificial sequence
<220> FEATURE:
<223> OTHER INFORMATION: Reseq2R- SEQ ID NO: 147

<400> SEQUENCE: 147
cttgttgaac atcttcctgg acag 24

<210> SEQ ID NO 148
<211> LENGTH: 21
<212> TYPE: DNA
<213> ORGANISM: artificial sequence
<220> FEATURE:
<223> OTHER INFORMATION: Reseq3F- SEQ ID NO: 148

<400> SEQUENCE: 148
ttgtgattct tatggtccag g 21

<210> SEQ ID NO 149
<211> LENGTH: 23
<212> TYPE: DNA
<213> ORGANISM: artificial sequence
<220> FEATURE:
<223> OTHER INFORMATION: Reseq3R- SEQ ID NO: 149

<400> SEQUENCE: 149
ctggccaaca acgctgagtc cac 23

<210> SEQ ID NO 150
<211> LENGTH: 23
<212> TYPE: DNA
<213> ORGANISM: artificial sequence
<220> FEATURE:
<223> OTHER INFORMATION: Reseq4F- SEQ ID NO: 150

<400> SEQUENCE: 150
ctgctctgat tgttacatct tgc 23

<210> SEQ ID NO 151
<211> LENGTH: 23
<212> TYPE: DNA
<213> ORGANISM: artificial sequence
<220> FEATURE:
<223> OTHER INFORMATION: Reseq4R- SEQ ID NO: 151

<400> SEQUENCE: 151
tagccacaaa agtaggaaat ctc 23

<210> SEQ ID NO 152
<211> LENGTH: 21
<212> TYPE: DNA
<213> ORGANISM: artificial sequence
<220> FEATURE:
<223> OTHER INFORMATION: Reseq5F- SEQ ID NO: 152

<400> SEQUENCE: 152
gttgacttgc ataacaagat c 21

<210> SEQ ID NO 153
<211> LENGTH: 23
<212> TYPE: DNA

<213> ORGANISM: artificial sequence
<220> FEATURE:
<223> OTHER INFORMATION: Reseq5R- SEQ ID NO: 153

<400> SEQUENCE: 153
agcagtgaat gcatagcact tac 23

<210> SEQ ID NO 154
<211> LENGTH: 22
<212> TYPE: DNA
<213> ORGANISM: artificial sequence
<220> FEATURE:
<223> OTHER INFORMATION: Reseq6F- SEQ ID NO: 154

<400> SEQUENCE: 154
acaattgcga tgttcttaag ag 22

<210> SEQ ID NO 155
<211> LENGTH: 21
<212> TYPE: DNA
<213> ORGANISM: artificial sequence
<220> FEATURE:
<223> OTHER INFORMATION: Reseq6R- SEQ ID NO: 155

<400> SEQUENCE: 155
tcctcaccaa atatatcact c 21

<210> SEQ ID NO 156
<211> LENGTH: 24
<212> TYPE: DNA
<213> ORGANISM: artificial sequence
<220> FEATURE:
<223> OTHER INFORMATION: Reseq7F- SEQ ID NO: 156

<400> SEQUENCE: 156
cagactgtta aacctggcca tttc 24

<210> SEQ ID NO 157
<211> LENGTH: 21
<212> TYPE: DNA
<213> ORGANISM: artificial sequence
<220> FEATURE:
<223> OTHER INFORMATION: Reseq7R- SEQ ID NO: 157

<400> SEQUENCE: 157
aggttgagct gtgtcatagt g 21

<210> SEQ ID NO 158
<211> LENGTH: 19
<212> TYPE: DNA
<213> ORGANISM: artificial sequence
<220> FEATURE:
<223> OTHER INFORMATION: Reseq8F- SEQ ID NO: 158

<400> SEQUENCE: 158
tatggttact tgcgtaaac 19

<210> SEQ ID NO 159
<211> LENGTH: 21
<212> TYPE: DNA
<213> ORGANISM: artificial sequence
<220> FEATURE:
<223> OTHER INFORMATION: Reseq8R- SEQ ID NO: 159

<400> SEQUENCE: 159
ctctaacaca ccagcattaa g 21

<210> SEQ ID NO 160
<211> LENGTH: 22
<212> TYPE: DNA
<213> ORGANISM: artificial sequence
<220> FEATURE:
<223> OTHER INFORMATION: Reseq9F- SEQ ID NO: 160

<400> SEQUENCE: 160
tctgactaca ggttggcaaa tg 22

<210> SEQ ID NO 161
<211> LENGTH: 22
<212> TYPE: DNA
<213> ORGANISM: artificial sequence
<220> FEATURE:
<223> OTHER INFORMATION: Reseq9R- SEQ ID NO: 161

<400> SEQUENCE: 161
gcactaagct agaataagct tc 22

<210> SEQ ID NO 162
<211> LENGTH: 22
<212> TYPE: DNA
<213> ORGANISM: artificial sequence
<220> FEATURE:
<223> OTHER INFORMATION: Reseq10F- SEQ ID NO: 162

<400> SEQUENCE: 162
tggatgaggt ctctatgtgc ac 22

<210> SEQ ID NO 163
<211> LENGTH: 20
<212> TYPE: DNA
<213> ORGANISM: artificial sequence
<220> FEATURE:
<223> OTHER INFORMATION: Reseq10R- SEQ ID NO: 163

<400> SEQUENCE: 163
ccacaaccct cattagcctg 20

<210> SEQ ID NO 164
<211> LENGTH: 22
<212> TYPE: DNA
<213> ORGANISM: artificial sequence
<220> FEATURE:
<223> OTHER INFORMATION: Reseq11F- SEQ ID NO: 164

<400> SEQUENCE: 164
actgatcaag atcttgctgt tc 22

<210> SEQ ID NO 165
<211> LENGTH: 20
<212> TYPE: DNA
<213> ORGANISM: artificial sequence
<220> FEATURE:
<223> OTHER INFORMATION: Reseq11R- SEQ ID NO: 165

<400> SEQUENCE: 165
gctaagtgat cccttgtatc 20

<210> SEQ ID NO 166
<211> LENGTH: 21
<212> TYPE: DNA
<213> ORGANISM: artificial sequence
<220> FEATURE:

<223> OTHER INFORMATION: Reseq12F- SEQ ID NO: 166

<400> SEQUENCE: 166
ctaatgtcaa gacattggag t 21

<210> SEQ ID NO 167
<211> LENGTH: 22
<212> TYPE: DNA
<213> ORGANISM: artificial sequence
<220> FEATURE:
<223> OTHER INFORMATION: Reseq12R- SEQ ID NO: 167

<400> SEQUENCE: 167
tacgacattg aaagcaatgt tc 22

<210> SEQ ID NO 168
<211> LENGTH: 21
<212> TYPE: DNA
<213> ORGANISM: artificial sequence
<220> FEATURE:
<223> OTHER INFORMATION: Reseq13F- SEQ ID NO: 168

<400> SEQUENCE: 168
tggtatattt acactaggaa g 21

<210> SEQ ID NO 169
<211> LENGTH: 21
<212> TYPE: DNA
<213> ORGANISM: artificial sequence
<220> FEATURE:
<223> OTHER INFORMATION: Reseq13R- SEQ ID NO: 169

<400> SEQUENCE: 169
gcaggagatc catatacgta c 21

<210> SEQ ID NO 170
<211> LENGTH: 21
<212> TYPE: DNA
<213> ORGANISM: artificial sequence
<220> FEATURE:
<223> OTHER INFORMATION: Reseq14F- SEQ ID NO: 170

<400> SEQUENCE: 170
tgccactgga tgccattata g 21

<210> SEQ ID NO 171
<211> LENGTH: 23
<212> TYPE: DNA
<213> ORGANISM: artificial sequence
<220> FEATURE:
<223> OTHER INFORMATION: Reseq14R- SEQ ID NO: 171

<400> SEQUENCE: 171
ctaaatagtg aacaccaatt aag 23

<210> SEQ ID NO 172
<211> LENGTH: 21
<212> TYPE: DNA
<213> ORGANISM: artificial sequence
<220> FEATURE:
<223> OTHER INFORMATION: Reseq15F- SEQ ID NO: 172

<400> SEQUENCE: 172
tcaacttggt actgtgctgg c 21

<210> SEQ ID NO 173
<211> LENGTH: 21
<212> TYPE: DNA
<213> ORGANISM: artificial sequence
<220> FEATURE:
<223> OTHER INFORMATION: Reseq15R- SEQ ID NO: 173

<400> SEQUENCE: 173
gacagtgaca cgatcattat c 21

<210> SEQ ID NO 174
<211> LENGTH: 21
<212> TYPE: DNA
<213> ORGANISM: artificial sequence
<220> FEATURE:
<223> OTHER INFORMATION: Reseq16F- SEQ ID NO: 174

<400> SEQUENCE: 174
gtgagttgat tactggcacg c 21

<210> SEQ ID NO 175
<211> LENGTH: 22
<212> TYPE: DNA
<213> ORGANISM: artificial sequence
<220> FEATURE:
<223> OTHER INFORMATION: Reseq16R- SEQ ID NO: 175

<400> SEQUENCE: 175
tgtcctaata ctcatactaa ag 22

<210> SEQ ID NO 176
<211> LENGTH: 22
<212> TYPE: DNA
<213> ORGANISM: artificial sequence
<220> FEATURE:
<223> OTHER INFORMATION: Reseq17F- SEQ ID NO: 176

<400> SEQUENCE: 176
tcgctctgtg gcagatctag tc 22

<210> SEQ ID NO 177
<211> LENGTH: 24
<212> TYPE: DNA
<213> ORGANISM: artificial sequence
<220> FEATURE:
<223> OTHER INFORMATION: Reseq17R- SEQ ID NO: 177

<400> SEQUENCE: 177
tgaggtgctg cctgtaccag agag 24

<210> SEQ ID NO 178
<211> LENGTH: 20
<212> TYPE: DNA
<213> ORGANISM: artificial sequence
<220> FEATURE:
<223> OTHER INFORMATION: Reseq18F- SEQ ID NO: 178

<400> SEQUENCE: 178
cagattacat cgatgttaac 20

<210> SEQ ID NO 179
<211> LENGTH: 23
<212> TYPE: DNA
<213> ORGANISM: artificial sequence
<220> FEATURE:
<223> OTHER INFORMATION: Reseq18R- SEQ ID NO: 179

-continued

```
<400> SEQUENCE: 179

gacaagttag cagactttga gac                                               23


<210> SEQ ID NO 180
<211> LENGTH: 20
<212> TYPE: DNA
<213> ORGANISM: artificial sequence
<220> FEATURE:
<223> OTHER INFORMATION: Reseq19F- SEQ ID NO: 180

<400> SEQUENCE: 180

gctgacctac agctgttgcg                                                   20
```

RECOMBINANT SPIKE PROTEIN SUBUNIT BASED VACCINE FOR PORCINE EPIDEMIC DIARRHEA VIRUS (PEDV)

INCORPORATION BY REFERENCE

This application claims priority to provisional application U.S. Ser. No. 62/000,240, filed on 19 May 2014, and incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is Recombinant_PEDV_Paul_Lawrence_ST25. The text file is 192 KB; it was created on 14 May 2015; and it is being submitted electronically via EFS-Web, concurrent with the filing of the specification.

FIELD OF THE INVENTION

The present disclosure relates generally to vaccines and more specifically to a recombinant subunit vaccine to prevent or reduce the chance of infection of pigs by porcine epidemic diarrhea virus (PEDV).

BACKGROUND

Porcine epidemic diarrhea Virus (PEDV) is a severe and highly contagious swine disease. While older pigs have a chance of survival, 80 to 100 percent of the PEDV-infected piglets die within 24 hours of being infected. PEDV spreads primarily through fecal-oral contact (Pospischil et al., 2002; Song and Park, 2012). Once internalized it destroys the inner lining of piglets' intestines, making them incapable of digesting and deriving nutrition from milk and feed (Pospischil et al., 2002). The virus causes diarrhea, vomiting and death from severe dehydration and starvation in piglets. Moreover, the infected piglets shed virus for seven to ten days (Song and Park, 2012).

Porcine Epidemic Diarrhea was first reported as a clinical entity in England in 1971 and was determined to be separate from porcine transmissible gastroenteritis virus (TGEV) (Wood, 1977). The infectious agent was further characterized and identified as a coronavirus-like particle in Belgium in 1978 (Pensaert and de Bouck, 1978). Since then, PEDV has been reported in many European and Asian countries including the Czech Republic, Hungary, Italy, Germany, Spain, Korea, the Philippines, China, Thailand and Japan (Song and Park, 2012; Pospischil et al., 2002). In contrast to infections in Asia, severe PEDV outbreaks with high mortality are rare in Europe. Within Asia, China has seen a large increase in outbreaks since 2010, which has been attributed to the emerging of new strains (Li et al., 2012). In contrast, PEDV has not been detected or reported from Central America or South America countries to date.

PEDV was first reported in the United States in May 2013 in Iowa. Since then, the PEDV has spread rapidly nationwide (The Pig Site, 2013; Promed 2013). The number of confirmed cases of PEDV increased by 296 during March, thus bringing the total number reported to 4,757, since the outbreak according to the U.S. Department of Agriculture's National Animal Health Laboratory Network (NAHLN). Twenty seven U.S states have reported PEDV infection as of March, 2014. However, one case can represent an individual animal or an entire herd at a single site. The hog industry analysts estimate that PEDV has killed approximately 5 million U.S. hogs alone since May 2013. Although highly infectious in pigs, PEDV does not affect humans and is not a food safety risk.

PEDV is a member of the Coronavirinae family and belongs to alphacoronavirus genera. These viruses are enveloped, positive-sense, single-stranded RNA and with a nucleocapsid of helical symmetry of 130 nm in diameter (Pensaert and de Bouck, 1978; Spaan et al., 1988; Kocherhans et al., 2001). Their genomic size ranges from an approximately 26 to 32 Kb, relatively large for an RNA virus. Coronavirus are the largest viruses that are known to infect humans, other mammals, and birds, usually causing subclinical respiratory or gastrointestinal diseases. The PEDV subgenomic mRNAs, which are transcribed from the genome, produce viral protein subunits, such as the spike (S, ~180-220 kDa), envelope (E, ~8.8 kDa), membrane (M, 27-32 kDa), nucleoprotein (N, 55-58 kDa), and several other proteins of unknown function (Kocherhans et al., 2001; Li et al., 2012).

About two-thirds of the 5' end of the genome encodes a replicase protein. These proteins are encoded by two slightly overlapping open reading frames (ORF), ORF1a and ORF1b (Bridgen et al., 1988; Kocherhans et al., 2001). These two ORF subunits are connected by a ribosomal frame shift site in all the coronaviruses. This regulates the ratio of the two polypeptides encoded by ORF1a and the read-through product ORF1ab. About 70-80% of the translation products are terminated at the end of ORF1a, and the remaining 20-30% continues to transcribe until the end of ORF1b. The polypeptides are posttranslationally processed by viral encoded proteases (Bridgen et al., 1988; Park et al., 2012; Park et al., 2013). These proteases are encoded within ORF1a and the polymerase-/helicase-function are encoded by ORF1b. The analysis and amino acid alignment of N, M, E, ORF3 and S gene sequences of the highly virulent PEDV strain CV777 shows that PEDV occupies an intermediate position between the two well-characterized members of the group I corona viruses, TGEV and human coronavirus (HCoV-229E) (Pratelli 2011).

The nucleoprotein (N) subunit is a RNA-binding protein, and plays an important role in both virus RNA synthesis and modulating host cell processes. Phosphorylation and dephosphorylation may regulate these processes by exposing various functional motifs (Spencer et al., 2008; Hsieh et al., 2005). The N protein subunit has been implicated in various functions throughout the coronavirus life cycle including encapsulation, packaging, correct folding of the RNA molecule, the deregulation of the host cell cycle (Surjit, et al., 2006; Masters and Sturman, 1990), inhibition of interferon production, up-regulation of COX2 production, up-regulation of AP1 activity, induction of apoptosis, association with host cell proteins, and RNA chaperone activity (Stohlman et al., 1988; Tang et al., 2005; Nelson et al., 2000).

The PEDV E protein subunit is a homooligomer which interacts with the membrane (M) protein subunit in the budding compartment of the host cell, which is located between the endoplasmic reticulum (ER) and the Golgi complex (Duarte et al., 1994; Bridgen et al., 1998). The E protein subunit is a component of the viral envelope that plays a central role in virus morphogenesis and assembly. It also acts as a viroporin, inducing the formation of hydrophilic pores in cellular membranes and is sufficient to form virus-like particles (Madan et al., 2005). The PEDV E protein subunit has no effect on the intestinal epithelial cells (IEC) growth, cell cycle and cyclin-A expression. In contrast, the cells expressing PEDV E protein induce higher levels of IL-8 than control cells (Xu et al., 2013). Studies have shown that PEDV E protein induces ER-stress and activates transcription factor NF-κB, which is responsible for the up-regulation of interleukin 8 (IL-8) and Bcl-2 expression (Liao et al., 2006; Liao et al., 2004; Xu et al., 2013).

The M protein subunit of PEDV is the most abundant component of the viral envelope. In silico analysis of the M protein subunit shows that it consists of a triple-transmembrane segment flanked by a short amino-terminal domain on the exterior of the virion and a long carboxy-tail located inside the virion. The M protein subunit of coronaviruses is indispensable in the assembly process and budding of virions (Zhang et al., 2012). The immune reaction to the M protein of coronaviruses plays an important role in the induction of protection and in mediating the course of the disease (Zhang et al., 2012). Monoclonal antibodies against the M protein subunit of coronaviruses have virus-neutralizing activity in the presence of complement (Qian et al., 2006). Furthermore, the M protein subunit of coronavirus can also stimulate the production of alpha-interferon (α-IFN) which can inhibit viral replication (Xing et al., 2009).

The function of the PEDV ORF3 product subunit remains enigmatic, however computational modeling of PEDV OFR3 protein subunit shows that it may function as an ion channel and regulate virus production (Wang et al., 2012). Small interfering RNA (siRNA) knockdown of ORF3 gene in PEDV infected cells reduces the number of particles released from the cells (Wang et al., 2012). Passing PEDV in cell culture leads to the truncation or loss of ORF3 (Schmitz et al., 1998; Utiger et al., 1995). Homologues of the ORF3 protein subunit are found in all other alphacoronaviruses. The ORF3 protein of hCoV-NL63 was shown to be N-glycosylated at the amino terminus and incorporated into virions. However, deletion of the ORF3 gene from the viral genome had little effect on virus replication in vitro (Donaldson et al., 2008). Similar to other alphacoronaviruses (TGEV and, HCoV-229E) loss of PEDV ORF3 does not affect its replication in vitro (Dijkman et al., 2006; Woods, 2001). Despite a non-essential role in cell culture, the maintenance of the ORF3 gene in alphacoronavirus field strains strongly points to an important role of the ORF3 protein in natural infection in the animal host. Consistently, the loss of virulence of live-attenuated PEDV vaccine strains has been associated with mutations in the ORF3 gene resulting from cell culture adaptation (Song et al., 2007). However, this loss of virulence can also be attributed to concomitant mutations in other genes such as the spike protein gene (Park et al., 2008; Sato et al., 2012). The specific function of the ORF3 protein (and other viral proteins in the 3' genome region) in PEDV replication and pathogenesis can now be investigated using the reverse genetics system (Li et al., 2013).

The spike protein of the PEDV is a large glycoprotein of ~180 to 200 kDa, and belongs to the class I fusion proteins (Bosch et al., 2003). The functional S protein subunit forms a homotrimer on the virion surface. The coronavirus S proteins consists of two subunits and are cleaved by host proteases into the N-terminal S1 subunit and the C-terminal membrane-anchored S2 subunit. The S1 subunit binds to its receptor on the host cell, while the S2 subunit is responsible for fusion activity (Park et al., 2007; de Haan et al., 2004). This cleavage initiates the cell-to-cell fusion and virus entry into cells (Spaan et al., 2008; Simmons et al., 2004). Various proteases are known to be utilized for cleavage of the S protein subunit of each coronavirus. For example, in murine coranavirus mouse hepatitis virus (MHV), the basic amino acid cluster in the middle of the S protein is cleaved by a protease, furin, during its biogenesis. The cleaved S protein subunit is retained on the virion and infected-cell surfaces, inducing cell-to-cell fusion (Spaan et al., 2008). In contrast, S proteins of severe acute respiratory syndrome coronavirus (SARS-CoV), nonfusogenic MHV-2, and HCoV-229E, have no furin recognition site, therefore these S proteins are not cleaved during their biogenesis (Simmons et al., 2004; Matsuyama et al., 2004; Yoshikura et al., 1988; Shirato et al., 2011). These S proteins without a furin recognition site are cleaved by endosomal proteases, such as cathepsins, and other proteases activated by the low-pH environment (Shirato et al., 2011). These coronaviruses, once bound to the receptor, are transported to the endosome, where the S protein subunit is cleaved and activated for fusion, which, in turn, results in the release of the virus genome into the cytoplasm from the endosome (Shirato et al., 2011). Thus, these coranavirus fail to induce syncytia in infected cells, and the S protein on the virion is not in a cleaved form (Shirato et al., 2011). Furthermore, the efficiency of infection of these coronavirus is not influenced by exogenous proteases. Similarly, PEDV has uncleaved S protein and PEDV-infected cells produce syncytia only after treatment with an exogenous protease, features similar to those of the coronavirus described above (Duarte et al., 1994; Durante and Laude, 1994). However, without the exogenous protease treatment, PEDV cannot grow efficiently in vitro (Park et al., 2007; Shirato et al., 2011). This explains the need for protease mediated cleavage of PEDV S protein subunit for virulence and in vitro propagation.

The complete genomic sequences of PEDV isolated from outbreaks in Minnesota and Iowa are available in the GenBank (Colorado, USA: USA/Colorado/2013, accession no. KF272920; 13-019349, accession no. KF267450 and ISU13-19338E-IN-homogenate, accession number KF650370). The genetic and phylogenetic analysis of the three U.S. strains reveals a close relationship with Chinese PEDV strains and possible Chinese origin. The U.S. PEDV strains underwent evolutionary divergence, and are classified into two sublineages. The three emergent U.S. strains are most closely related to a strain isolated in 2012 from Anhui Province in China, which might be the result of multiple recombination events between different genetic lineages or sublineages of PEDV. Molecular clock analysis of the PEDV strain-divergence based on the complete genomic sequences shows an approximately 2 to 3 years' time-frame between the Chinese (December 2010) and the U.S (May 2013) outbreaks [US-USDA, Technical note, PED. Fort Collins (Colo.): USDA; 2013]. The finding that the emergent U.S. PEDV strains share unique genetic features at the 5'-untranslated region with a bat coronavirus provided further support of the evolutionary origin of PEDV from bats and potential cross-species transmission (Graham and Baric 2010; Wang et al., 2014).

All the isolates from recent studies have shown that all PEDV strains in the U.S. are clustered together in one clade within the subgenogroup 2a and are closely related to a strain from China, AH2012 (Sun et al., 2012; Park et al. 2012; Park et al., 2013). However, in February 2014, the Animal Disease Diagnostic Laboratory of the Ohio Department of Agriculture announced that it identified a variant PED strain OH851 which showed 99% and 97% nucleotide identity to PEDVs currently circulating in the United States (Colorado, Iowa, Indiana, and Minnesota) for the whole genome and the full-length spike gene, respectively (Wang et al., 2014). By distinct contrast, the strain OH851 showed only 89% or even lower nucleotide identity to PEDVs currently circulating in the United States in the first 1,170 nt of the S1 region. In that region, nucleotide similarity to that of a PEDV strain from China (CH/HBQX/10, JS120103) was 99%, suggesting that strain OH851 is a new PEDV variant. Phylogenetic analysis of the complete genome indicated that the novel OH851 PEDV is clustered with other strains of PEDV currently circulating in the US, including another strain from Ohio, OH1414. However, phylogenetic analysis of the full-length S gene showed that strain OH851 is clustered with other strains of PEDV from China and most closely related to a PEDV strain from China, CH/HBQX/10, but distantly related to other PEDV strains currently circulating in the US and strain AH2012 (Zheng et al., 2013). These finding strongly suggests that strain OH851 is a variant PEDV. In comparison with the S gene of other strains from the US, the S gene of strain OH851 has 3 deletions (a 1-nt deletion at position 167, a 11-nt deletion at position 176, and a 3-nt deletion at position 416), a 6-nt insertion between positions 474 and 475, and several mutations mainly located in the first 1,170 nt of the S1 region (Zheng et al., 2013).

Due to these sequence deletions, insertion, and mutations the strain OH851 may have been attenuated. Since this strain does not cause severe clinical disease, including death, the novel virus is a potential vaccine candidate that could help protect the US swine industry from the infection caused by the virulent strains of PEDV currently circulating in the US. Furthermore, this analysis also indicates that the US PEDV strains are still evolving.

Over the years numerous PEDV vaccines have been developed and tried without much success. Although vaccines for PEDV exist in China, Japan and South Korea, there is no approved vaccine in the US or Europe (USDA 2013). There are two types of vaccines against PEDV that are currently available in the market—killed or live attenuated. Several Japanese, Chinese and South Korean companies manufacture PEDV vaccines, however, the efficacy and protection by PEDV vaccines is not promising or adequate for the global swine industry. On the other hand, piglets can obtain immunity from their mothers if the sow has an adequate amount of antibodies to pass immunity through colostrum (Geiger et al., 2013). Due to the lack of any efficacious vaccine in the US, one of the common practices followed by the veterinarians to protect the herd is via feedback, which is unacceptable. Recently an alphavirus based PEDV vaccine developed, licensed and distributed by a US company has failed to provide adequate protection.

The available evidence clearly indicates that PEDV is still evolving in the US and there is an immediate need to develop a more effective large scale vaccine. To achieve this, Newport Laboratories Inc., sequenced a PEDV strain isolated from the Midwest region to study its genetics, diversity and develop a subunit or attenuated vaccine.

SUMMARY OF THE INVENTION

In one aspect, the invention is a recombinant subunit vaccine comprising protein of a subunit of porcine epidemic diarrhea virus. The subunit protein may include, for example, protein of the S1 and S2 domains of the S protein gene (i.e., spike or S domain protein) of porcine epidemic diarrhea virus. In another embodiment, the subunit protein may further include the nucleoprotein (N) region of the N subunit gene of porcine epidemic diarrhea virus. In yet another embodiment, the subunit protein may include protein of the E region of the E subunit gene of porcine epidemic diarrhea virus. In yet another embodiment, the subunit protein may include protein of the M region of the M subunit gene of porcine epidemic diarrhea virus. In yet another embodiment, the subunit protein may include protein of the ORF regions of the ORF subunit genes of porcine epidemic diarrhea virus. The above embodiments may further include a suitable adjuvant.

In another aspect, the invention is a recombinant porcine epidemic diarrhea virus protein produced by an expression of a recombinant DNA construct. The construct may include a baculovirus vector and a porcine epidemic diarrhea virus DNA fragment. In one embodiment, the porcine epidemic diarrhea virus DNA fragment is all or part of the nucleoprotein (N) sequence. In another embodiment, the porcine epidemic diarrhea virus DNA fragment is all or part of the E sequence. In yet another embodiment, the porcine epidemic diarrhea virus DNA fragment is all or part of the M sequence. In yet another embodiment, the porcine epidemic diarrhea virus DNA fragment is all or part of the ORF sequence. In yet another embodiment, the porcine epidemic diarrhea virus DNA fragment is all or part of the spike protein (S1 and S2 domains) sequence. Any of the embodiments may further include at least one additional antigen or a combination of PEDV infective or non-infective DNA fragments.

In another aspect, the invention is isolated or purified virus-like particles comprising porcine epidemic diarrhea virus M protein. In one embodiment, the isolated or purified virus-like particles of the porcine epidemic diarrhea virus M protein may be used to create an immunoprotective vaccine with a pharmaceutically acceptable carrier. In another embodiment, the vaccine may include one or more other antigens.

In yet another aspect, the invention is isolated or purified virus-like particles including porcine epidemic diarrhea virus E protein. In one embodiment, the isolated or purified virus-like particles of the porcine epidemic diarrhea virus E protein may be used to create an immunoprotective vaccine with a pharmaceutically acceptable carrier. In another embodiment, the vaccine may include one or more other antigens.

BRIEF DESCRIPTION OF THE DRAWINGS

The figures are aligned with the sequences according to Table 1.

TABLE 1

Figure 6B:
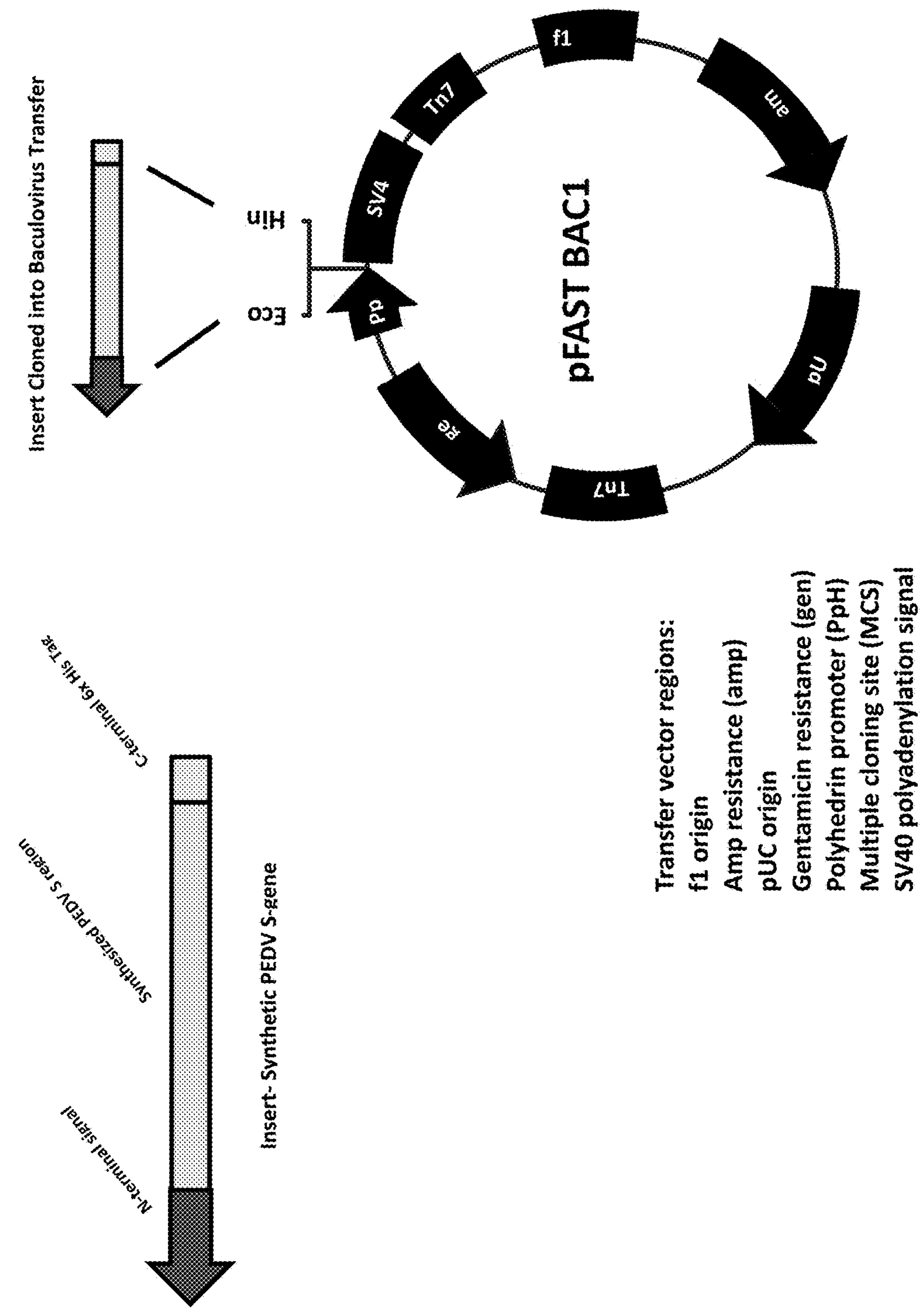

| SEQ ID NO | TYPE | Description |
|---|---|---|
| 1 | DNA | 5' UTR nucleotide sequence of Newport Labs PEDV isolate |
| 2 | DNA | Polyprotein nucleotide sequence ORF1a and ORF1b |
| 3 | DNA | Spike (S domain) nucleotide sequence |
| 4 | DNA | ORF3 Coronavirus NS3b nucleotide sequence |
| 5 | DNA | Envelope protein |
| 6 | DNA | Reseq19R reverse gap fill primer |
| 7 | DNA | Membrane protein nucleotide sequence |
| 8 | DNA | Intergenic region B |
| 9 | DNA | Nucleoprotein nucleotide sequence |
| 10 | DNA | 3' UTR nucleotide sequence of Newport Labs PEDV isolate |
| 11 | protein | ORF1a/ORF1b amino acid sequence |
| 12 | protein | Spike (S1 and S2domains) protein amino acid sequence |
| 13 | protein | ORF3 Coronavirus NS3b amino acid sequence |

TABLE 1-continued

| SEQ ID NO | TYPE | Description |
|---|---|---|
| 14 | protein | Envelope protein amino acid sequence |
| 15 | protein | Membrane protein amino acid sequence |
| 16 | protein | Nucleoprotein amino acid sequence |
| 17 | protein | Truncated and fused S1 and S2 domains of the spike protein |
| 18 | DNA | Codon optimized nucleotide sequence of the truncated and fused S1 and S2 domains of the spike protein |
| 19 | protein | Codon optimized amino acid sequence of the truncated and fused S1 and S2 domains of the spike protein |
| 20 | DNA | Final nucleotide sequence for cloning into vector showing N-terminal gp67 signal peptide sequence |
| 21 | protein | Final amino acid sequence showing N-terminal gp67 signal peptide sequence and histidine tag |
| 22 | protein | Antigenicity index of a portion of native spike (S1 domain) protein |
| 23 | protein | Antigenicity index of a portion of native spike (S1 domain) protein |
| 24 | protein | Antigenicity index of a portion of native spike (S1 domain) protein |
| 25 | protein | Antigenicity index of a portion of native spike (S1 domain) protein |
| 26 | protein | Antigenicity index of a portion of native spike (S1 domain) protein |
| 27 | protein | Antigenicity index of a portion of native spike (S1 domain) protein |
| 28 | protein | Antigenicity index of a portion of native spike (S1 domain) protein |
| 29 | protein | Antigenicity index of a portion of native spike (S1 domain) protein |
| 30 | protein | Antigenicity index of a portion of native spike (S1 domain) protein |
| 31 | protein | Antigenicity index of a portion of native spike (S1 domain) protein |
| 32 | protein | Antigenicity index of a portion of native spike (S1 domain) protein |
| 33 | protein | Antigenicity index of a portion of native spike (S1 domain) protein |
| 34 | protein | Antigenicity index of a portion of native spike (S1 domain) protein |
| 35 | protein | Antigenicity index of a portion of native spike (S1 domain) protein |
| 36 | protein | Antigenicity index of a portion of native spike (S1 domain) protein |
| 37 | protein | Antigenicity index of a portion of native spike (S1 domain) protein |
| 38 | protein | Antigenicity index of a portion of native spike (S1 domain) protein |
| 39 | protein | Antigenicity index of a portion of native spike (S1 domain) protein |
| 40 | protein | Antigenicity index of a portion of native spike (S1 domain) protein |
| 41 | protein | Antigenicity index of a portion of native spike (S1 domain) protein |
| 42 | protein | Antigenicity index of a portion of native spike (S1 domain) protein |
| 43 | protein | Antigenicity index of a portion of native spike (S1 domain) protein |
| 44 | protein | Antigenicity index of a portion of native spike (S1 domain) protein |
| 45 | protein | Antigenicity index of a portion of native spike (S1 domain) protein |
| 46 | protein | Antigenicity index of a portion of native spike (S1 domain) protein |
| 47 | protein | Antigenicity index of a portion of native spike (S1 domain) protein |
| 48 | protein | Antigenicity index of a portion of native spike (S1 domain) protein |
| 49 | protein | Antigenicity index of a portion of native spike (S1 domain) protein |
| 50 | protein | Antigenicity index of a portion of native spike (S1 domain) protein |
| 51 | protein | Antigenicity index of a portion of native spike (S1 domain) protein |
| 52 | protein | Antigenicity index of a portion of native spike (S1 domain) protein |

TABLE 1-continued

| SEQ ID NO | TYPE | Description |
|---|---|---|
| 53 | protein | Antigenicity index of a portion of native spike (S1 domain) protein |
| 54 | protein | Antigenicity index of a portion of native spike (S1 domain) protein |
| 55 | protein | Antigenicity index of a portion of native spike (S2 domain) protein |
| 56 | protein | Antigenicity index of a portion of native spike (S2 domain) protein |
| 57 | protein | Antigenicity index of a portion of native spike (S2 domain) protein |
| 58 | protein | Antigenicity index of a portion of native spike (S2 domain) protein |
| 59 | protein | Antigenicity index of a portion of native spike (S2 domain) protein |
| 60 | protein | Antigenicity index of a portion of native spike (S2 domain) protein |
| 61 | protein | Antigenicity index of a portion of native spike (S2 domain) protein |
| 62 | protein | Antigenicity index of a portion of native spike (S2 domain) protein |
| 63 | protein | Antigenicity index of a portion of native spike (S2 domain) protein |
| 64 | protein | Antigenicity index of a portion of native spike (S2 domain) protein |
| 65 | protein | Antigenicity index of a portion of native spike (S2 domain) protein |
| 66 | protein | Antigenicity index of a portion of native spike (S2 domain) protein |
| 67 | protein | Antigenicity index of a portion of native spike (S2 domain) protein |
| 68 | protein | Antigenicity index of a portion of native spike (S2 domain) protein |
| 69 | protein | Antigenicity index of a portion of native spike (S2 domain) protein |
| 70 | protein | Antigenicity index of a portion of native spike (S2 domain) protein |
| 71 | protein | Antigenicity index of a portion of native spike (S2 domain) protein |
| 72 | protein | Antigenicity index of a portion of native spike (S2 domain) protein |
| 73 | protein | Antigenicity index of a portion of native spike (S2 domain) protein |
| 74 | protein | Antigenicity index of a portion of native spike (S2 domain) protein |
| 75 | protein | Antigenicity index of a portion of native spike (S2 domain) protein |
| 76 | protein | Antigenicity index of a portion of native spike (S2 domain) protein |
| 77 | protein | Antigenicity index of a portion of native spike (S2 domain) protein |
| 78 | DNA | Original non-truncated non-fused NPL-PEDV spike (S domain) nucleotide sequence |
| 79 | protein | Original non-truncated non-fused NPL-PEDV spike (S domain) protein sequence |
| 80 | DNA | PEDF1 forward primer |
| 81 | DNA | PEDF2 forward primer |
| 82 | DNA | PEDF3 forward primer |
| 83 | DNA | PEDF4 forward primer |
| 84 | DNA | PEDF5 forward primer |
| 85 | DNA | PEDF6 forward primer |
| 86 | DNA | PEDF7 forward primer |
| 87 | DNA | PEDF8 forward primer |
| 88 | DNA | PEDF9 forward primer |
| 89 | DNA | PEDF10 forward primer |
| 90 | DNA | PEDF11 forward primer |
| 91 | DNA | PEDF12 forward primer |
| 92 | DNA | PEDF13 forward primer |
| 93 | DNA | PEDF14 forward primer |
| 94 | DNA | PEDF15 forward primer |
| 95 | DNA | PEDF16 forward primer |
| 96 | DNA | PEDF17 forward primer |
| 97 | DNA | PED18 forward primer |
| 98 | DNA | PEDF19 forward primer |
| 99 | DNA | PEDF20 forward primer |
| 100 | DNA | PEDF21 forward primer |
| 101 | DNA | PEDF22 forward primer |
| 102 | DNA | PEDF23 forward primer |

TABLE 1-continued

| SEQ ID NO | TYPE | Description |
|---|---|---|
| 103 | DNA | PEDF24 forward primer |
| 104 | DNA | PEDF25 forward primer |
| 105 | DNA | PEDF26 forward primer |
| 106 | DNA | PED27 forward primer |
| 107 | DNA | PEDF28 forward primer |
| 108 | DNA | PEDF29 forward primer |
| 109 | DNA | PEDF30 forward primer |
| 110 | DNA | PEDF31 forward primer |
| 111 | DNA | PEDF32 forward primer |
| 112 | DNA | PEDR1 reverse primer |
| 113 | DNA | PEDR2 reverse primer |
| 114 | DNA | PEDR3 reverse primer |
| 115 | DNA | PEDR4 reverse primer |
| 116 | DNA | PEDR5 reverse primer |
| 117 | DNA | PEDR6 reverse primer |
| 118 | DNA | PEDR7 reverse primer |
| 119 | DNA | PEDR8 reverse primer |
| 120 | DNA | PEDR9 reverse primer |
| 121 | DNA | PEDR10 reverse primer |
| 122 | DNA | PEDR11 reverse primer |
| 123 | DNA | PEDR12 reverse primer |
| 124 | DNA | PEDR13 reverse primer |
| 125 | DNA | PEDR14 reverse primer |
| 126 | DNA | PEDR15 reverse primer |
| 127 | DNA | PEDR16 reverse primer |
| 128 | DNA | PEDR17 reverse primer |
| 129 | DNA | PEDR18 reverse primer |
| 130 | DNA | PEDR19 reverse primer |
| 131 | DNA | PEDR20 reverse primer |
| 132 | DNA | PEDR21 reverse primer |
| 133 | DNA | PEDR22 reverse primer |
| 134 | DNA | PEDR23 reverse primer |
| 135 | DNA | PEDR24 reverse primer |
| 136 | DNA | PEDR25 reverse primer |
| 137 | DNA | PEDR26 reverse primer |
| 138 | DNA | PEDR27 reverse primer |
| 139 | DNA | PEDR28 reverse primer |
| 140 | DNA | PERR29 reverse primer |
| 141 | DNA | PEDR30 reverse primer |
| 142 | DNA | PEDR31 reverse primer |
| 143 | DNA | PEDR32 reverse primer |
| 144 | DNA | Reseq1F forward gap fill primer |
| 145 | DNA | Reseq1R reverse gap fill primer |
| 146 | DNA | Reseq2F forward gap fill primer |
| 147 | DNA | Reseq2R reverse gap fill primer |
| 148 | DNA | Reseq3F forward gap fill primer |
| 149 | DNA | Reseq3R reverse gap fill primer |
| 150 | DNA | Reseq4F forward gap fill primer |
| 151 | DNA | Reseq4R reverse gap fill primer |
| 152 | DNA | Reseq5F forward gap fill primer |
| 153 | DNA | Reseq5R reverse gap fill primer |
| 154 | DNA | Reseq6F forward gap fill primer |
| 155 | DNA | Reseq6R reverse gap fill primer |
| 156 | DNA | Reseq7F forward gap fill primer |
| 157 | DNA | Reseq7R reverse gap fill primer |
| 158 | DNA | Reseq8F forward gap fill primer |
| 159 | DNA | Reseq8R reverse gap fill primer |
| 160 | DNA | Reseq9F forward gap fill primer |
| 161 | DNA | Reseq9R reverse gap fill primer |
| 162 | DNA | Reseq10F forward gap fill primer |
| 163 | DNA | Reseq10R reverse gap fill primer |
| 164 | DNA | Reseq11F forward gap fill primer |
| 165 | DNA | Reseq11R reverse gap fill primer |
| 166 | DNA | Reseq12F forward gap fill primer |
| 167 | DNA | Reseq12R reverse gap fill primer |
| 168 | DNA | Reseq13F forward gap fill primer |
| 169 | DNA | Reseq13R reverse gap fill primer |
| 170 | DNA | Reseq14F forward gap fill primer |
| 171 | DNA | Reseq14R reverse gap fill primer |
| 172 | DNA | Reseq15F forward gap fill primer |
| 173 | DNA | Reseq15R reverse gap fill primer |
| 174 | DNA | Reseq16F forward gap fill primer |
| 175 | DNA | Reseq16R reverse gap fill primer |
| 176 | DNA | Reseq17F forward gap fill primer |
| 177 | DNA | Reseq17R reverse gap fill primer |
| 178 | DNA | Reseq18F forward gap fill primer |

TABLE 1-continued

| SEQ ID NO | TYPE | Description |
|---|---|---|
| 179 | DNA | Reseq18R reverse gap fill primer |
| 180 | DNA | Reseq19F forward gap fill primer |

A full and enabling description of the present invention is set forth in the remainder of the specification, including reference to the accompanying figures, wherein:

FIGS. 1A-1N are the whole genome sequence of NPL-PED (i.e., Newport Laboratories Porcine Epidemic Diarrhea Virus) with designated open reading frames (ORFs).

FIGS. 1O-1S are the derived amino acid sequence for each individual open reading frame as indicated.

FIGS. 2A-2C are the combined nucleotide and amino acid sequence of the native spike (S domain) isolate.

FIGS. 3A-3M are the antigenicity index of the S domain of NPL-PEDV.

FIGS. 3N-3P illustrate a truncated and full length NPL-PEDV spike (S domain; S1 and S2) amino acid sequence.

FIG. 3Q illustrates truncated and fused S1 and S2 domains of the spike protein of PEDV.

FIGS. 4A-4E are the truncated and fused spike protein nucleotide sequence from 3B codon optimized for an insect cell system. Optimized sequences are shown in gray.

FIGS. 4F-4G are the truncated and fused spike protein from 3C codon optimized for an insect cell system with a gp67 signal peptide at the N-terminus.

FIGS. 5A-5B: Amino acid sequence for subcloning of truncated, fused, codon optimized NPL-PEDV spike (S domain).

FIG. 5C: Nucleotide sequence for subcloning of truncated, fused, codon optimized NPL-PEDV spike (S domain).

FIG. 6A: Overview of steps involved in generating recombinant PEDV spike protein.

FIG. 6B: Cloning of PEDV spike protein gene into transfer vector.

Figure 6C:
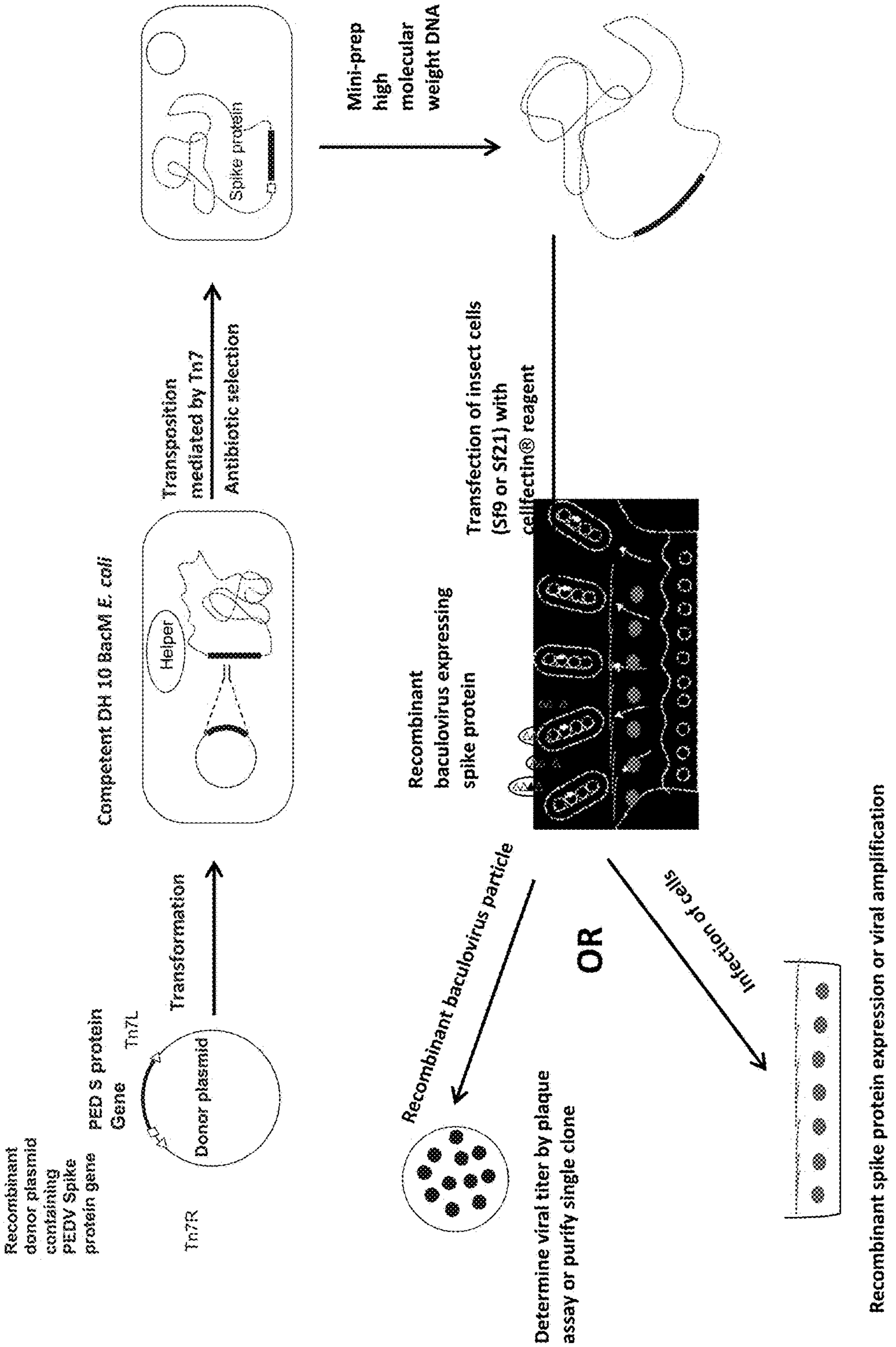

FIG. 6C: Generation of recombinant PEDV spike protein.

Figure 6D:
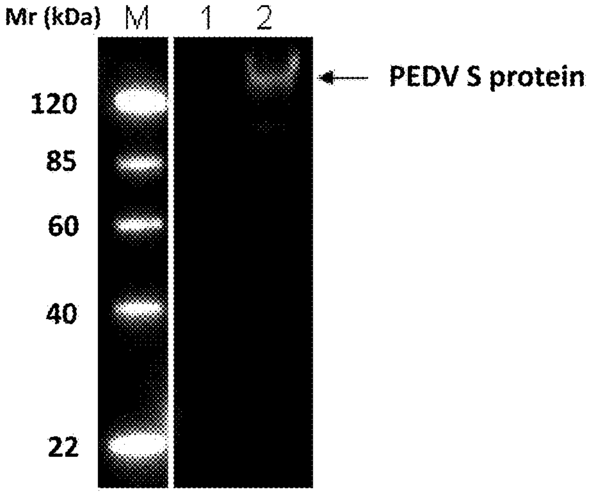

FIG. 6D: Western blot analysis of PEDV spike protein.

DETAILED DESCRIPTION OF THE INVENTION

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The antigenic polypeptides of the invention are capable of protecting against porcine epidemic diarrhea virus (PEDV). That is, they are capable of stimulating an immune response in an animal. By "antigen" or "immunogen" means a substance that induces a specific immune response in a host animal. The antigen of the instant invention is a subunit or portion of an organism; a recombinant vector containing an insert with immunogenic properties; a piece or fragment of DNA capable of inducing an immune response upon presentation to a host animal; a polypeptide, an epitope, a hapten, or any combination thereof.

The term "immunogenic protein, polypeptide, or peptide" as used herein includes polypeptides that are immunologically active in the sense that once administered to the host, it is able to evoke an immune response of the humoral and/or cellular type directed against the protein. A protein fragment according to the invention has at least one epitope or antigenic determinant. An "immunogenic" protein or polypeptide, as used herein, includes the full-length sequence of the protein, analogs thereof, or immunogenic fragments thereof.

As discussed the invention encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it has nucleotides encoding an epitope or antigenic determinant of a PEDV polypeptide. A polynucleotide encoding a fragment of a PEDV polypeptide may have a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" or "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a PEDV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. That is the polypeptide is separated from cellular components. By "substantially purified" it is intended that such that the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are PEDV antigenic polypeptides that are produced in insect cells. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the NPL-PEDV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for PEDV polypeptides, the DNA sequence of the PEDV gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of PEDV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the PEDV polypeptide encoded by the nucleotide sequence is functionally unchanged.

The invention further encompasses the PEDV polynucleotides contained in a vector molecule or an expression vector and operably linked to a promoter element and optionally to an enhancer. A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semi-synthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to porcine vaccines or pharmaceutical or immunological compositions which may comprise an effective amount of a recombinant PEDV antigens and a pharmaceutically or veterinarily acceptable carrier, excipient, or vehicle.

The subject matter described herein is directed in part, to compositions and methods related to the PEDV antigen prepared in an insect expression system that was highly immunogenic and protected animals against challenge from PEDV strains.

Newport Laboratories Inc., received small intestine and colon samples from 0-7 day old piglets in May 2013. The piglets were exhibiting vomiting and diarrhea. PEDV is related to transmissible gastroenteritis virus (TGEV) and causes enteric disease clinically indistinguishable from TGEV. There is little to no cross protection afforded by immunity developed to one virus against the other. Similarly, diagnostic tests designed to detect TGEV will not detect PEDV or vice versa. However, we detected PEDV by qPCR using multiplex real-time RT-PCR technique (Kim et al., 2007). In addition, the samples were negative for TGEV or rotavirus group ABC. The samples were then used to extract viral RNA and the complete genome of the NPL-PEDV (i.e., Newport Laboratories Porcine Epidemic Diarrhea Virus). The strain was sequenced using a primer walking technique, assembled and annotated. Complete in silico genome analysis was performed and the spike protein was selected to develop a first generation recombinant vaccine.

PEDV spike protein plays an important role in viral infection and pathogenesis. Mutation of spike protein can cause attenuation and antibodies against spike protein can reduce PEDV infection. In addition, the spike protein gene is highly conserved across pathogenic PEDV strains. Therefore, development of a subunit vaccine containing spike protein may afford broader protection. With this objective a recombinant spike protein gene was codon optimized and synthesized from the NPL-PEDV genome sequence information and expressed in a baculovirus expression system. The next generation of vaccines may include other possible PEDV target antigens such as M and N proteins and possibly portions of ORF1ab. Baculovirus expression systems could also be used to create virus-like particle (VLP) vaccines. This information will also be used to develop attenuated PEDV strains by directed mutagenesis for live vaccination program.

Methods and Results

Isolation of Viral RNA and Whole Genome Sequencing

The intestinal samples were pooled into two sets and were used for total nucleic acid extraction independently. Briefly, 200 μL of PEDV pools 1 and 2 were treated with a DNAse/RNAse cocktail [Epicentre Biotechnologies, WI, USA] using 2 U of enzyme/microliter of suspension after adding $MgCl_2$ to a final concentration of 5 mM. Each sample was incubated for one hour at 37° C. in order to completely digest exogenous host DNA and RNA. After treatment, RNA was purified from the samples using Trizol LS reagent according to the manufacturer's recommendation [Life Technologies, NY, USA]. The precipitated RNA was resuspended in 50 μL of 10 mM Tris buffer and frozen at −80° C. until cDNA conversion. The cDNA conversion was performed using the Maxima H Minus Double-stranded cDNA synthesis kit [Thermo Fisher Scientific, MA, USA] according to the manufacturer's instructions. For each sample 2 μg of input RNA was used in conjunction with random hexamer primers at a 100 pmol concentration. Following cDNA synthesis, samples were treated with RNAse according to the kit instructions to eliminate any residual RNA from the sample preparation. Following treatment samples were immediately frozen and stored at −20° C.

The double stranded DNA was used in polymerase chain reaction using a set of 32 primer pairs spanning the entire PEDV genome. See Table 2.

TABLE 2

| Primer name | Primer sequence 5' → 3' |
|---|---|
| PEDF1 - SEQ ID NO: 80 | ACTTAAAGAGATTTTCTATCTAC |
| PEDF2 - SEQ ID NO: 81 | AGGTTGCACGTACTCCAAAGAT |
| PEDF3 - SEQ ID NO: 82 | GCATTGGTTAAGCTTGTCAAGG |
| PEDF4 - SEQ ID NO: 83 | CTTCAAGTATTATGCCACCAGTG |
| PEDF5 - SEQ ID NO: 84 | TGACTTTGCAAGCTATGGAGGAC |
| PEDF6 - SEQ ID NO: 85 | GCATGCACCTGAGCTTCTTG |
| PEDF7 - SEQ ID NO: 86 | GTTGTAGCTAAGGTTGTACCAAG |
| PEDF8 - SEQ ID NO: 87 | ACGTACTGGTATTATATTGCGT |
| PEDF9 - SEQ ID NO: 88 | CTTAATGTGCAACCGACAGGTCC |
| PEDF10 - SEQ ID NO: 89 | GACAATCCACTTAGTTGTGTGC |
| PEDF11 - SEQ ID NO: 90 | CACAGAACACACTTGGCATGTTG |
| PEDF12 - SEQ ID NO: 91 | ATGATGGTTCTGCAGCTGGTGT |
| PEDF13 - SEQ ID NO: 92 | TGCACAAGGTCTTGTTAACATC |
| PEDF14 - SEQ ID NO: 93 | GATGCTGTTAATAATGGTTCTCC |
| PEDF15 - SEQ ID NO: 94 | GCCACTGTACGCTTGCAGGCTGG |
| PEDF16 - SEQ ID NO: 95 | GAAGACATTCATCGTGTCTATGC |
| PEDF17 - SEQ ID NO: 96 | GTGGTTGTATCACTGCTAAAGAGG |
| PED18 - SEQ ID NO: 97 | TCGAGCCTGACATTAATAAAGGTC |
| PEDF19 - SEQ ID NO: 98 | CACTTGTTATCATATAACGAAG |
| PEDF20 - SEQ ID NO: 99 | ACTGTGTCTGAGATGGTCTATGAA |
| PEDF21 - SEQ ID NO: 100 | CGTCAGAGCTCGTGCTCCACCAG |
| PEDF22 - SEQ ID NO: 101 | ATGATGATACTGAGTGTGACAAG |
| PEDF23 - SEQ ID NO: 102 | CAAGTACGGACTTGAAGATTAGC |
| PEDF24 - SEQ ID NO: 103 | CTGATATGTATGATGGTAAGATT |
| PEDF25 - SEQ ID NO: 104 | CTAGTGGTTACCAGCTTTATTTAC |

TABLE 2-continued

| Primer name | Primer sequence 5' → 3' |
|---|---|
| PEDF26 - SEQ ID NO: 105 | CCACTGTTTATAAATTCTTGGCTG |
| PED27 - SEQ ID NO: 106 | GTCACTAGTGGTGCTGTTTATTC |
| PEDF28 - SEQ ID NO: 107 | CTCTGCTATTGGTAATATAACTTC |
| PEDF29 - SEQ ID NO: 108 | GTTGACCTTGAGTGGCTCAACCGAG |
| PEDF30 - SEQ ID NO: 109 | TGGTCTAGTAGTTAATGTTATAC |
| PEDF31 - SEQ ID NO: 110 | GTGGCCGCAAACGGGTGCCATTATC |
| PEDF32 - SEQ ID NO: 111 | TAGCGTAGCAGCTTGCTTCGGACC |
| PEDR1 - SEQ ID NO: 112 | ATCTTTGGAGTACGTGCAACCT |
| PEDR2 - SEQ ID NO: 113 | CCTTGACAAGCTTAACCAATGC |
| PEDR3 - SEQ ID NO: 114 | CACTGGTGGCATAATACTTGAAG |
| PEDR4 - SEQ ID NO: 115 | GTCCTCCATAGCTTGCAAAGTCA |
| PEDR5 - SEQ ID NO: 116 | CAAGAAGCTCAGGTGCATGCTT |
| PEDR6 - SEQ ID NO: 117 | CTTGGTACAACCTTAGCTACAAC |
| PEDR7 - SEQ ID NO: 118 | ACGCAATATAATACCAGTACGT |
| PEDR8 - SEQ ID NO: 119 | GGACCTGTCGGTTGCACATTAAG |
| PEDR9 - SEQ ID NO: 120 | GCACACAACTAAGTGGATTGTC |
| PEDR10 - SEQ ID NO: 121 | CAACATGCCAAGTGTGTTCTGTG |
| PEDR11 - SEQ ID NO: 122 | ACACCAGCTGCAGAACCATCAT |
| PEDR12 - SEQ ID NO: 123 | GATGTTAACAAGACCTTGTGCA |
| PEDR13 - SEQ ID NO: 124 | GGAGAACCATTATTAACAGCATC |
| PEDR14 - SEQ ID NO: 125 | CCAGCCTGCAAGCGTACAGTGGC |
| PEDR15 - SEQ ID NO: 126 | GCATAGACACGATGAATGTCTTC |
| PEDR16 - SEQ ID NO: 127 | CCTCTTTAGCAGTGTTACAACCAC |
| PEDR17 - SEQ ID NO: 128 | GACCTTTATTAATGTCAGGCTCGA |
| PEDR18 - SEQ ID NO: 129 | CTTCGTTATATGATAACAAGTG |
| PEDR19 - SEQ ID NO: 130 | TCATAGACCATCTCAGACACAGT |
| PEDR20 - SEQ ID NO: 131 | CTGGTGGAGCACGAGCTCTGAGC |
| PEDR21 - SEQ ID NO: 132 | CTTGTCACACTCAGTATCATCAT |
| PEDR22 - SEQ ID NO: 133 | CGTAATCTTCAAGTCCGTACTTG |
| PEDR23 - SEQ ID NO: 134 | AAT CTT ACC ATC ATA CAT ATC AG |
| PEDR24 - SEQ ID NO: 135 | GTA AAT AA GCTGGTAACCACT AG |
| PEDR25 - SEQ ID NO: 136 | CAGCCAAGAATTTATAAACAGTGG |
| PEDR26 - SEQ ID NO: 137 | GAATAAACAGCACCACTAGTGAC |
| PEDR27 - SEQ ID NO: 138 | GAAGTTATATTACCAATAGCAGAG |
| PEDR28 - SEQ ID NO: 139 | CTCGGTTGAGCCACTCAAGGTCAAC |
| PERR29 - SEQ ID NO: 140 | GTATAACATTAACTACTAGACCA |
| PEDR30 - SEQ ID NO: 141 | GATAATGGCACCCGTTTGCGGCCAC |
| PEDR31 - SEQ ID NO: 142 | GGTCCGAAGCAAGCTGCTACGCTA |
| PEDR32 - SEQ ID NO: 143 | GTGTATCCATATCAACACCGTCAG |

The primers were designed based on the consensus-genome sequences of two U.S. PEDV strains—USA/Colorado/2013 (GenBank accession no. KF272920) and 13-019349 (GenBank accession no. KF267450). Primer sets 1-32 were used to amplify segments of the PEDV genome. The letter “F” in the primer name denotes a forward primer. The letter “R” in the primer name denotes a reverse primer. Each reaction was performed using Phire Green Hot-Start II DNA polymerase [Thermo Fisher Scientific, MA, USA] according to the manufacturer’s instructions. About 1-10 ng of the DNA template was used in a 50 µl cocktail and the reaction was performed according to the manufacturer’s protocol. The amplified products ranging from 900-1000 bp were run on an agarose gel to confirm their size. The PCR cycling conditions were as follows: initial denaturation at 98° C. for 30 sec, followed by 35 cycles: 98° C.—15 sec, 50° C.—15 sec, 72° C.—45 sec and a final extension at 72° C. for 1 min.

The PCR products were purified from each reaction using an IBI Gel/PCR product purification kit [IBI Scientific, IA, USA] according to the manufacturer’s recommendation. The final elution was performed using 30 µL of elution buffer. About 15 µL of each purified product was sent to Eurofins/Operon [Eurofins MWG Operon, Ala., USA] for bi-directional sequencing using the amplification primers specific for each product as listed in Table 2.

Sequence Assembly and Analysis

The raw sequence data was assembled using USA/Colorado/2013 (GenBank accession no. KF272920) as reference sequence, using the Geneious assembler [Biomatters LTD., CA, USA]. After assembling the whole NPL-PED genome to the reference genome the gaps and ambiguous regions in NPL-PED genome were closed using a second set of internal primers disclosed in Table 3 following the same PCR and sequencing technique.

TABLE 3

| Primer name | Primer sequence 5' → 3' |
|---|---|
| Reseq1F - SEQ ID NO: 144 | ATCACTGGTCTTAATACAATGTG |
| Reseq1R - SEQ ID NO: 145 | CAATACTACCATTGAGTGCTGGTGG |
| Reseq2F - SEQ ID NO: 146 | TGCAGAAGTGCTCGAATGATTAC |
| Reseq2R - SEQ ID NO: 147 | CTTGTTGAACATCTTCCTGGACAG |
| Reseq3F - SEQ ID NO: 148 | TTGTGATTCTTATGGTCCAGG |
| Reseq3R - SEQ ID NO: 149 | CTGGCCAACAACGCTGAGTCCAC |
| Reseq4F - SEQ ID NO: 150 | CTGCTCTGATTGTTACATCTTGC |
| Reseq4R - SEQ ID NO: 151 | TAGCCACAAAAGTAGGAAATCTC |
| Reseq5F - SEQ ID NO: 152 | GTTGACTTGCATAACAAGATC |
| Reseq5R - SEQ ID NO: 153 | AGCAGTGAATGCATAGCACTTAC |
| Reseq6F - SEQ ID NO: 154 | ACAATTGCGATGTTCTTAAGAG |
| Reseq6R - SEQ ID NO: 155 | TCCTCACCAAATATATCACTC |

TABLE 3-continued

| Primer name | Primer sequence 5' → 3' |
|---|---|
| Reseq7F - SEQ ID NO: 156 | CAGACTGTTAAACCTGGCCATTTC |
| Reseq7R - SEQ ID NO: 157 | AGGTTGAGCTGTGTCATAGTG |
| Reseq8F - SEQ ID NO: 158 | TATGGTTACTTGCGTAAAC |
| Reseq8R - SEQ ID NO: 159 | CTCTAACACACCAGCATTAAG |
| Reseq9F - SEQ ID NO: 160 | TCTGACTACAGGTTGGCAAATG |
| Reseq9R - SEQ ID NO: 161 | GCACTAAGCTAGAATAAGCTTC |
| Reseq10F - SEQ ID NO: 162 | TGGATGAGGTCTCTATGTGCAC |
| Reseq10R - SEQ ID NO: 163 | CCACAACCCTCATTAGCCTG |
| Reseq11F - SEQ ID NO: 164 | ACTGATCAAGATCTTGCTGTTC |
| Reseq11R - SEQ ID NO: 165 | GCTAAGTGATCCCTTGTATC |
| Reseq12F - SEQ ID NO: 166 | CTAATGTCAAGACATTGGAGT |
| Reseq12R - SEQ ID NO: 167 | TACGACATTGAAAGCAATGTTC |
| Reseq13F - SEQ ID NO: 168 | TGGTATATTTACACTAGGAAG |
| Reseq13R - SEQ ID NO: 169 | GCAGGAGATCCATATACGTAC |
| Reseq14F - SEQ ID NO: 170 | TGCCACTGGATGCCATTATAG |
| Reseq14R - SEQ ID NO: 171 | CTAAATAGTGAACACCAATTAAG |
| Reseq15F - SEQ ID NO: 172 | TCAACTTGGTACTGTGCTGGC |
| Reseq15R - SEQ ID NO: 173 | GACAGTGACACGATCATTATC |
| Reseq16F - SEQ ID NO: 174 | GTGAGTTGATTACTGGCACGC |
| Reseq16R - SEQ ID NO: 175 | TGTCCTAATACTCATACTAAAG |
| Reseq17F - SEQ ID NO: 176 | TCGCTCTGTGGCAGATCTAGTC |
| Reseq17R - SEQ ID NO: 177 | TGAGGTGCTGCCTGTACCAGAGAG |
| Reseq18F - SEQ ID NO: 178 | CAGATTACATCGATGTTAAC |
| Reseq18R - SEQ ID NO: 179 | GACAAGTTAGCAGACTTTGAGAC |
| Reseq19F - SEQ ID NO: 180 | GCTGACCTACAGCTGTTGCG |
| Reseq19R - SEQ ID NO: 6 | TCATCAACGGGAATAGAACCG |

The complete sequence of the two NPL PEDV isolates were assembled as one large contig and annotated. Further global BLAST analysis and alignment was done using the web based software from NCBI, to identify indels/point mutations with reference to US and other PEDV isolates in the GenBank. The whole genome sequence of NPL-PED (FIG. 1A, SEQ ID NOs 1, 2, 3, 4, 5, 6, 7, 8, 9 and 10) contains 28,064 nucleotides (nt), including a 5' and 3' UTR. The derived amino acid sequence is also provided (FIG. 1B, SEQ ID NOs: 11, 12, 13, 14, 15 and 16).

The NPL-PEDV genome shares 99% identity with the all the U.S. isolates sequenced to date and many Chinese isolates as well (except for the strain OH851). The top three BLAST hits were against U.S. isolates, USA/Colorado/2013 (KF272920), IA1 (KF468753.1) and Iowa isolate 13-019349 (KF267450.1). NPL-PEDV also shares 99% identity with the Chinese outbreak isolate AH2012 (KC210145). When compared to KF272920, NPL-PEDV has insertions between 20634-20637nt, 25455-25474nt, a nucleotide substitution at 278 (T→C) which falls in the 5' UTR, an insertion at 9645nt (C) and a deletion at 9648nt.

Analysis of Spike Protein

The spike coding region (S domain) is highly conserved across PEDV strains. The spike protein is composed of two domains: S1 and S2. FIG. 2 shows the amino acid sequence for S1 and S2 (SEQ ID NO: 12) as well as the nucleotide sequence for S1 and S2 (SEQ ID NO: 3). BLAST analysis of the NPL-PEDV strain shows that it shares 99% homology with PEDV isolates from USA and China. Internet based software was used to analyze the antigenicity index (EMBOSS programs). Based on the antigenicity index of the S domain (FIG. 3A), the amino acid sequences showing the highest antigenic index were chosen and fused. The truncated S1 and S2 subunit domains were joined together as indicated in FIG. 3B (SEQ ID NO. 17) and FIG. 3C (SEQ ID NO: 17), deleting intervening amino acids. Deleted regions are indicated with a dash "-" and regions retained for expression are indicated with an asterisk "*" in FIG. 3B. The truncated and fused PEDV spike protein sequence (SEQ ID NO: 17) is shown in FIG. 3C.

The nucleotide sequence of the truncated and fused spike protein was codon optimized for an insect cell system. FIG. 4A shows the original nucleotide sequence of the truncated and fused spike region (S domain, SEQ ID NO: 78) compared with the codon optimized spike region (S domain codon optimized, SEQ ID NO: 18). FIG. 4B shows the original amino acid sequence of the truncated and fused spike region (S domain, SEQ ID NO: 79) compared with the codon optimized spike region (S domain codon optimized, SEQ ID NO: 19).

Gene Synthesis, Cloning into Baculovirus Expression System and Detection of Recombinant Spike The complete nucleotide sequence of the synthesized spike protein gene is shown in FIG. 5A (SEQ ID NO: 20). The gene was synthesized [GenScript Corporation, NJ, U.S.A] with an engineered 5' Eco RI site immediately after the signal peptide sequence and an 3' Hin dIII site to facilitate cloning. This gene was cloned into Bac-to-Bac® Baculovirus Expression System [Life Technologies, NY, U.S.A] according to the manufacturer's instruction and expressed in Sf21, Sf9 or high five cells. FIG. 5B shows the synthesized spike (S domain) amino acid sequence (SEQ ID NO: 21). A C-terminal His tag and an N-terminal signal peptide sequence was engineered to selectively purify the protein from a nickel column and to detect the protein by monoclonal antibody on a Western blot, respectively.

The overall cloning, protein expression and detection is explained in FIGS. 6A-D. FIG. 6A is an overview of the process. The synthetic spike protein gene was generated and cloned into transfer vector as indicated in FIG. 6B. The integrity of the cloned gene was confirmed by bi-directional sequencing. After confirming the sequence the transfer vector was introduced into competent *E. coli* cells containing a helper plasmid. The *E. coli* was selected on Luria-Bertani (LB) plates containing 100 μg/ml ampicillin. Transposition mediated by Tn results in the integration of the spike gene into the bacmid. The resultant bacmid DNA was extracted using Qiagen Plasmid preparation kit (Qiagen, Calif., USA) and transfected into Sf9 of Sf21 cells using Cellfectin® reagent following the manufacturer's instructions. Once P1 clones were generated plaque assay and qPCR were used to determine the PFU/ml. Plaque assay was used to isolate single clones (FIG. 6C). The P1 stock was used to generate P2 stock and for confirmation of protein expression Sf9 or Sf21 cells according to the manufacturer's recommendation [Life Technologies, NY, USA]. Once expressed the cell lysate and the supernatant were analyzed for protein expression on a SDS-PAGE gel and transferred onto PVFD membrane. The PVDF membrane was blocked with blocking buffer and probed with mouse anti-His Antibody coupled to HRP (Cat. No. A00612; GenScript Corporation, NJ, USA, FIG. 6D).

The recombinant spike protein was expressed in high five cells and used for vaccination studies in pigs.

In an embodiment, the invention is an immunogenic composition comprising a recombinant polypeptide sequence of the S1 and S2 domains of the S subunit of porcine epidemic diarrhea virus according to SEQ ID NO. 19 and a pharmaceutically or veterinary acceptable vehicle, diluent or excipient. The invention may further include a suitable adjuvant. The adjuvant may be an oil, emulsion, a metal salt (e.g. $Al(OH)_3$), or combinations thereof. In an embodiment, the adjuvant is TRIGEN® or ULTRAGEN® or PrimaVant® (TRIGEN+Quil A), TS6 (described in U.S. Pat. No. 7,371,395 US to Merial), LR4 (described in U.S. Pat. No. 7,691,368, to Merial), or any formulation described in US 2011-0129494 A1 (to Merial).

In another embodiment, the immunogenic composition is a recombinant nucleotide sequence 80% or greater in sequence identity to SEQ ID NO. 18.

In another aspect, the invention is a method of vaccinating a host susceptible to PEDV comprising at least one administration of a recombinant polypeptide sequence of the S1 and S2 domains of the S subunit of porcine epidemic diarrhea virus according to SEQ ID NO. 19 and a pharmaceutically or veterinary acceptable vehicle, diluent or excipient. An adjuvant may also be included.

In another aspect, the invention is a recombinant subunit vaccine for use against porcine epidemic diarrhea virus comprising a porcine epidemic diarrhea virus DNA fragment according to SEQ ID NO. 18 in a baculovirus expression system. In an embodiment, the invention is a recombinant subunit vaccine comprising the amino acid sequence according to SEQ ID NO. 19. In yet another embodiment, the invention is a recombinant subunit vaccine comprising the amino acid sequence according to SEQ ID NO. 20. In yet another embodiment, the invention is a recombinant subunit vaccine comprising the amino acid sequence according to SEQ ID NO. 21. In yet another embodiment, the invention is an immunogenic composition comprising a recombinant polypeptide sequence of the S1 and S2 domains of the S subunit of porcine epidemic diarrhea virus according to SEQ ID NO. 19 and a pharmaceutically or veterinary acceptable vehicle, diluent or excipient and at least one additional antigen associated with a pathogen other than porcine epidemic diarrhea virus.

In yet another embodiment, the invention is an isolated polypeptide sequence, wherein the polypeptide sequence is 80% or greater in sequence identity to SEQ ID NO. 17. In yet another embodiment, the invention is an isolated polypeptide sequence, wherein the polypeptide sequence is 80% or greater in sequence identity to SEQ ID NO:19.

The genome sequence of PEDV can also be used to generate virus-like particles (VLPs) using structural genes or other non-infectious components of PEDV. Examples are virus-like particles made from the E and M subunit genes of PEDV.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, polymers of crosslinked acrylic or methacrylic acid, e.g., crosslinked by polyalkenyl ethers of sugars or polyalcohols, are appropriate. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, or no more than eight such groups, the hydrogen atoms of at least three hydroxyl groups being replaced by unsaturated, aliphatic radicals having at least two carbon atoms. Some radicals are those containing 2 to 4 carbon atoms, e.g., vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, the EMA (Monsanto) are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are formed by basic units having the following formula:

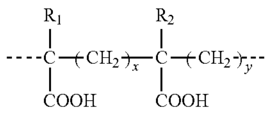

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNγ), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TFGβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a porcine cytokine for preparations to be administered to swine).

REFERENCES

Bai B., Hu Q., Hu H., Zhou P., Shi Z., Meng J., Lu B., Huang Y., Mao P., Wang H. 2008. Virus-like particles of SARS-like coronavirus formed by membrane proteins from different origins demonstrate stimulating activity in human dendritic cells.

PLoS One. 3(7):e2685. doi: 10.1371/journal-.pone.0002685.

Bosch B J., van der Zee R., de Haan C A., Rottier P J. 2003. The coronavirus spike protein is a class I virus fusion protein: structural and functional characterization of the fusion core complex. J. Virol. 77:8801-8811.

Bridgen A., Kocherhans R., Tobler K., Carvajal A., Ackermann M. 1998. Further analysis of the genome of porcine epidemic diarrhea virus. Adv. Exp. Med. Biol. 440:781-786.

de Haan C A., Stadler K., Godeke G J., Bosch B J., Rottier P J. 2004. Cleavage inhibition of the murine coronavirus spike protein by a furin-like enzyme affects cell-cell but not virus-cell fusion. J. Virol. 78 (11):6048-6054.

Donaldson E F., Yount B., Sims A C., Burkett S., Pickles R J., Baric R S. 2008. Systematic assembly of a full-length infectious clone of human coronavirus NL63. J Virol 82: 11948-11957.

Dijkman R., Jebbink M F., Wilbrink B., Pyrc K., Zaaijer H L., Minor P D., Franklin S., Berkhout B., Thiel V., van der Hoek L. 2006. Human coronavirus 229E encodes a single ORF4 protein between the spike and the envelope genes. Virol J 3: 106.

Duarte M., Tobler K., Bridgen A., Rasschaert D., Ackermann M., Laude H. 1994. Sequence analysis of the porcine epidemic diarrhea virus genome between the nucleocapsid and spike protein genes reveals a polymorphic ORF. Virology 198:466-476.

Duarte M., Laude H. 1994. Sequence of the spike protein of the porcine epidemic diarrhoea virus. J. Gen. Virol. 75 (Pt 5):1195-1200.

Geiger J O, Connor J F. 2013. Porcine epidemic diarrhea, diagnosis, and elimination. Perry: American Association of Swine Practitioners: 1-4.

Graham R L., Baric R S. 2010. Recombination, reservoirs, and the modular spike: mechanisms of coronavirus cross-species transmission. J. Virol. 84:3134-3146.

Hsieh P K., Chang S C., Huang C C., Lee T T., Hsiao C W., Kou Y H., Chen I Y., Chang C K., Huang T H., Chang M F. 2005. Assembly of severe acute respiratory syndrome coronavirus RNA packaging signal into virus-like particles is nucleocapsid dependent J. Virol. 79:13848-13855.

Kim S H., Kim I J., Pyo H M., Tark D S., Song J Y., Hyun B H. 2007. Multiplex real-time RT-PCR for the simultaneous detection and quantification of transmissible gastroenteritis virus and porcine epidemic diarrhea virus. J Virol Methods. 146 (1-2):172-177.

Kocherhans R., Bridgen A., Ackermann M., Tobler K. 2001. Completion of the porcine epidemic diarrhoea coronavirus (PEDV) genome sequence. Virus Genes. 23(2):137-44.

Li C., Li Z., Zou Y., Wicht O., van Kuppeveld F J., Rottier P J., Bosch B J. 2013. Manipulation of the porcine epidemic diarrhea virus genome using targeted RNA recombination. PLoS One. August 2; 8(8):e69997.

Li, W., Li, H., Liu, Y., Pan, Y., Deng, F., Song, Y., Tang, X., He, Q. 2012. New variants of porcine epidemic diarrhea virus, China, 2011. Emerging infectious diseases 18, 1350-1353.

Liao Y., Q. Yuan Q., J. Torres, J., Tam J P., Liu D X. 2006. Biochemical and functional characterization of the membrane association and membrane permeabilizing activity of the severe acute respiratory syndrome coronavirus envelope protein Virology, 349, 264-275.

Liao Y., Lescar J., Tam J P., Liu D X. 2004. Expression of SARS-coronavirus envelope protein in *Escherichia coli* cells alters membrane permeability Biochem. Biophys. Res. Commu 325 374-380.

Madan V., Garcia Mde, J., Sanz M A., Carrasco L. 2005. Viroporin activity of murine hepatitis virus E protein FEBS Lett., 579: 3607-3612.

Masters P S., Sturman L S. 1990. Background paper. Functions of the coronavirus nucleocapsid protein Adv. Exp. Med. Biol. 276:235-238.

Matsuyama S., Ujike M., Morikawa S., Tashiro M., Taguchi F. 2005. Protease-mediated enhancement of severe acute respiratory syndrome coronavirus infection. Proc. Natl. Acad. Sci. U.S.A. 102:12543-12547.

Nelson G W., Stohlman S A., Tahara S M. 2000. High affinity interaction between nucleocapsid protein and leader/intergenic sequence of mouse hepatitis virus RNA. J. Gen. Virol. 81:181-188.

Park S J., Song D. S., Park B. K., 2013. Molecular epidemiology and phylogenetic analysis of porcine epidemic diarrhea virus (PED) field isolates in Korea. Archives of Virology. 158(7):1533-1541.

Park S J, Kim H K, Song D S, An D J, Park B K. 2012. Complete genome sequences of a Korean virulent porcine epidemic diarrhea virus and its attenuated counterpart. J. Virol. 86:5964-5964.5964.10.1128/JVI.00557-12.

Park S J., Moon H J., Luo Y., Kim H K., Kim E M., Yang J S., Song D S., Kang B K., Lee C S., Park B K. 2008. Cloning and further sequence analysis of the ORF3 gene of wild- and attenuated-type porcine epidemic diarrhea viruses Virus Genes, 36: 95-104.

Park S J., Song D S., Ha G W., Park B K. 2007. Cloning and further sequence analysis of the spike gene of attenuated porcine epidemic diarrhea virus DR13. Virus Genes 35: 55-64.

Pensaert M., de Bouck, P. 1978. A New Coronavirus-like Particle Associated with Diarrhea in Swine. Archives of virology 58: 243-247.

Pospischil A., Stuedli A., Kiupel M. 2002. Diagnostic Notes Update on porcine epidemic diarrhea. J Swine Health Prod 10: 81-85.

Pratelli A. 2011. The evolutionary processes of canine coronaviruses. Adv Virol. Volume 2011 (2011), Article ID 562831 2011: 562831.

ProMed, 2013. Porcine Epidemic Diarrhea-USA (Iowa) First Report. International Society for Infectious Diseases.

Qian C., Din D., Tang Q., Zeng Y., Tang G X., Lu C. 2006. Identification of a B-cell antigenic epitope at the N-terminus of SARS-CoV M protein and characterization of monoclonal antibody against the protein. Virus Genes. 33:147-156.

Sato T., Takeyama N., Katsumata A., Tuchiya K., Kodama T., Kusanagi K. 2011. Mutations in the spike gene of porcine epidemic diarrhea virus associated with growth adaptation in vitro and attenuation of virulence in vivo. Virus Genes 43: 72-78.

Schmitz A., Tobler K., Suter M., Ackermann M. 1998. Prokaryotic expression of porcine epidemic diarrhoea virus ORF3 Adv. Exp. Med. Biol. 440:775-780.

Shirato K., Matsuyama S., Ujike M, Taguchi F. 2011. Role of proteases in the release of porcine epidemic diarrhea virus from infected cells. J Virol. 85 (15):7872-7880.

Simmons G., Reeves J D., Rennekamp A J., Amberg S M., Piefer A J., Bates P. 2004. Characterization of severe acute respiratory syndrome-associated coronavirus (SARS-CoV) spike glycoprotein-mediated viral entry. Proc. Natl. Acad. Sci. U.S.A. 101:4240-4245.

Song D, Park B, 2012. Porcine epidemic diarrhoea virus: a comprehensive review of molecular epidemiology, diagnosis, and vaccines. Virus genes 44:167-175.

Song D S., Oh J S., Kang B K., Yang J S., Moon H J., Yoo H S., Jang Y S., Park B K. 2007. Oral efficacy of vero cell attenuated porcine epidemic diarrhea virus DR13 strain. Res Vet Sci 82: 134-140.

Spaan W., Cavanagh D., Horzinek M. C. 1988. Coronaviruses: structure and genome expression. J. Gen. Virol. 69(Pt 12):2939-2952.

Spencer K A., Dee M., Britton P., Hiscox J A. 2008. Role of phosphorylation clusters in the biology of the coronavirus infectious bronchitis virus nucleocapsid protein. Virology. 370 (2):373-381.

Stohlman S A., Baric R S., Nelson G N., Soe L H., Welter L M., Deans R J. 1988. Specific interaction between coronavirus leader RNA and nucleocapsid protein J. Virol. 62: 4288-4295.

Surjit, M., Liu, B., Chow, V. T., Lal, S. K. 2006. The nucleocapsid protein of severe acute respiratory syndrome-coronavirus inhibits the activity of cyclin-cyclin-dependent kinase complex and blocks S phase progression in mammalian cells J. Biol. Chem. 281:10669-10681.

Sun R Q, Cai R J, Chen Y Q, Liang P S, Chen D K, Song C X. 2012. Outbreak of porcine epidemic diarrhea in suckling piglets, china. Emerg Infect Dis 18: 161-163.

Tang T K., Wu M P., Chen S T., Hou M H., Hong M H., Pan F M., Yu H M., Chen J H., Yao C W., Wang A H. 2005. Biochemical and immunological studies of nucleocapsid proteins of severe acute respiratory syndrome and 229E human coronaviruses Proteomics, 5: 925-937.

The Center for Food Security and Public Health, 2013. Vaccines: Porcine Epidemic Diarrhea. Iowa State University.

Turgeon D C., Morin M., Jolette J., Higgins R., Marsolais G., DiFranco E. 1980. Coronavirus-like particles associated with diarrhea in baby pigs in Quebec. Can Vet J. 21(3):100-xxiii.

U.S. Department of Agriculture (US) [USDA]. Technical note, Porcine epidemic diarrhea (PED). Fort Collins (Colo.): USDA; 2013. p 4 p. Available from http://www.aphis.usda-.gov/animal_health/animal_dis_spec/swine/downloads/ped_tech_note.pdf.

USDA-APHIS-VS-CEAH National Surveillance Unit, 2013. Case definition for porcine epidemic diarrhea. Date accessed: May 21, 2013.

Utiger A., Tobler K., Bridgen A., Suter M., Singh M., Ackermann M. 1995. Identification of proteins specified by porcine epidemic diarrhoea virus Adv. Exp. Med. Biol. 380:287-290.

Wang K., Lu W., Chen J., Xie S., Shi H., Hsu H., Yu W., Xu K., Bian C., Fischer W B., Schwarz W., Feng L., Sun B. 2012. PEDV ORF3 encodes an ion channel protein and regulates virus production. FEBS Lett. 586:384-391.

Wang L., Byrum B., Zhang Y. 2014. New Variant of Porcine Epidemic Diarrhea Virus, United States. Emerging Infectious Diseases. Vol 20, Number 5—May 2014.

Wood E N. 1977. An apparently new syndrome of porcine epidemic diarrhoea. The Veterinary record 100: 243-244.

Woods R D. 2001. Efficacy of a transmissible gastroenteritis coronavirus with an altered ORF-3 gene. Can J Vet Res 65: 28-32.

Xing J J., Liu S W., Han Z X., Shao Y H., Li H X., Kong X G. 2009. Identification of a novel B-cell epitope in the M protein of Avian Infectious Bronchitis Coronaviruses. J Microbiol. 47:589-599.

Xu X., Zhang H., Zhang Q., Dong J., Liang Y., Huang Y., Liu H J., Tong D. 2013. Porcine epidemic diarrhea virus E protein causes endoplasmic reticulum stress and up-regulates interleukin-8 expression. Virol J. 10:26.

Yoshikura H., Tejima S. 1981. Role of protease in mouse hepatitis virus-induced cell fusion. Studies with a cold-sensitive mutant isolated from a persistent infection. Virology 113: 503-511.

Zhang Z., Chen J., Shi H., Chen X., Shi D., Feng L., Yang B. 2012. Identification of a conserved linear B-cell epitope in the M protein of porcine epidemic diarrhea virus. Virol J. 9:225.

Zheng F M, Huo J Y, Zhao J, Chang H T, Wang X M, Chen L, 2013. Molecular characterization and phylogenetic analysis of porcine epidemic diarrhea virus field strains in central China during 2010-2012 outbreaks. Bing Du Xue Bao. (2):197-205.

The invention claimed is:

1. An immunogenic composition comprising a recombinant spike polypeptide of porcine epidemic diarrhea virus comprising SEQ ID NO:19 and a pharmaceutically or veterinary acceptable vehicle, diluent or excipient, and wherein the recombinant spike polypeptide is expressed in a baculovirus expression system.

2. The immunogenic composition of claim further comprising a suitable adjuvant.

3. The immunogenic composition of claim 1, wherein the recombinant spike polypeptide is encoded by a nucleotide comprising the sequence of SEQ ID NO:18.

4. A method of vaccinating a host susceptible to PEDV comprising at least one administration of a vaccine according to claim 2.

5. The composition of claim 2, further comprising at least one additional antigen associated with a pathogen other than porcine epidemic diarrhea virus.

* * * * *